US012577565B2

(12) United States Patent
Zhang et al.

(10) Patent No.: US 12,577,565 B2
(45) Date of Patent: Mar. 17, 2026

(54) NUCLEIC ACID, PHARMACEUTICAL COMPOSITION, CONJUGATE, PREPARATION METHOD, AND USE

(71) Applicant: SUZHOU RIBO LIFE SCIENCE CO., LTD., Suzhou (CN)

(72) Inventors: Hongyan Zhang, Suzhou (CN); Shan Gao, Suzhou (CN); Daiwu Kang, Suzhou (CN)

(73) Assignee: SUZHOU RIBO LIFE SCIENCE CO., LTD., Suzhou (CN)

( * ) Notice: Subject to any disclaimer, the term of this patent is extended or adjusted under 35 U.S.C. 154(b) by 1111 days.

(21) Appl. No.: 17/595,594

(22) PCT Filed: May 21, 2020

(86) PCT No.: PCT/CN2020/091649
§ 371 (c)(1),
(2) Date: Nov. 19, 2021

(87) PCT Pub. No.: WO2020/238766
PCT Pub. Date: Dec. 3, 2020

(65) Prior Publication Data
US 2022/0235359 A1    Jul. 28, 2022

(30) Foreign Application Priority Data
May 24, 2019    (CN) ......................... 201910441714.9

(51) Int. Cl.
*C07H 21/02*     (2006.01)
*A61K 31/713*    (2006.01)
*A61K 47/50*     (2017.01)
*C12N 15/113*    (2010.01)

(52) U.S. Cl.
CPC ........ *C12N 15/1137* (2013.01); *A61K 31/713* (2013.01); *A61K 47/50* (2017.08); *C12N 2310/14* (2013.01); *C12N 2310/315* (2013.01); *C12N 2310/351* (2013.01)

(58) Field of Classification Search
CPC .......................... C12N 15/113; C12N 2310/14
See application file for complete search history.

(56) References Cited

U.S. PATENT DOCUMENTS

| | | | |
|---|---|---|---|
| 8,030,474 | B2 | 10/2011 | Khvorova et al. |
| 8,106,022 | B2 | 1/2012 | Manoharan et al. |
| 8,334,372 | B2 | 12/2012 | Freier et al. |
| 8,344,125 | B2 | 1/2013 | Manoharan et al. |
| 9,428,751 | B2 | 8/2016 | Macdonald et al. |
| 9,670,492 | B2 | 6/2017 | Freier et al. |
| 10,130,651 | B2 | 11/2018 | Wooddell et al. |
| 10,246,708 | B2 | 4/2019 | Kasperkovitz et al. |
| 10,294,477 | B2 | 5/2019 | Swayze |
| 10,370,453 | B2 | 8/2019 | Sexton et al. |
| 10,934,544 | B2 | 3/2021 | Akinc et al. |
| 11,084,884 | B2 | 8/2021 | Sexton et al. |
| 11,414,661 | B2 | 8/2022 | Zhang et al. |
| 11,414,665 | B2 | 8/2022 | Zhang et al. |
| 11,492,620 | B2 | 11/2022 | Zhang et al. |
| 11,918,600 | B2 | 3/2024 | Zhang et al. |
| 2003/0206887 | A1 | 11/2003 | Morrissey et al. |
| 2004/0266707 | A1 | 12/2004 | Leake et al. |
| 2005/0245475 | A1 | 11/2005 | Khvorova et al. |
| 2005/0246794 | A1 | 11/2005 | Khvorova et al. |
| 2005/0255487 | A1 | 11/2005 | Khvorova et al. |
| 2008/0113351 | A1 | 5/2008 | Naito et al. |
| 2008/0146788 | A1 | 6/2008 | Bhat et al. |
| 2010/0063132 | A1 | 3/2010 | Kim et al. |
| 2010/0137414 | A1 | 6/2010 | Freier et al. |
| 2011/0015252 | A1 | 1/2011 | Fitzgerald et al. |
| 2011/0039914 | A1 | 2/2011 | Pavco et al. |
| 2011/0054005 | A1 | 3/2011 | Naito et al. |
| 2012/0052487 | A9 | 3/2012 | Khvorova et al. |
| 2012/0108803 | A1 | 5/2012 | Han et al. |
| 2012/0172412 | A1 | 7/2012 | Rozema et al. |
| 2012/0184595 | A1 | 7/2012 | Macdonald et al. |
| 2012/0201756 | A1 | 8/2012 | Sexton |
| 2012/0227119 | A1 | 9/2012 | Doran et al. |
| 2013/0005793 | A1 | 1/2013 | Chin et al. |
| 2013/0023579 | A1 | 1/2013 | Crooke et al. |
| 2013/0041133 | A1 | 2/2013 | Aaronson et al. |

(Continued)

FOREIGN PATENT DOCUMENTS

| | | |
|---|---|---|
| AU | 2014208251 A1 | 8/2014 |
| CA | 2930393 A1 | 6/2009 |

(Continued)

OTHER PUBLICATIONS

Elbashir et al. (The EMBO Journal, vol. 20, No. 23, pp. 6877-6888, 2001).*
Fujita et al. (Int. J. Mol. Sci. 2015, 16, 5254-5270).*
Qui, S. et al., "Dickkopf 3 attenuates xanthine dehydrogenase expression to prevent oxidative stress-induced apoptosis," Genes to Cells, 2017, vol. 22, pp. 406-417. (cited in Extended European Search Report issued on Jan. 30, 2024, in European Patent Application No. 20813863.6).
Yasuda, T. et al., "Anti-Gout Agent Allopurinol Exerts Cytotoxicity to Human Hormone-Refractory Prostate Cancer Cells in Combination with Tumor Necrosis Factor-Related Apoptosis-Inducing Ligand," Mol Cancer Res, Dec. 2008, vol. 6, No. 12, pp. 1852-1860. (cited in Extended European Search Report issued on Jan. 30, 2024, in European Patent Application No. 20813863.6).

(Continued)

*Primary Examiner* — Amy Rose Hudson
(74) *Attorney, Agent, or Firm* — Panitch Schwarze Belisario & Nadel LLLP

(57) ABSTRACT

An siRNA inhibiting xanthine oxidase (XO) gene expression, a pharmaceutical composition containing the siRNA, a siRNA conjugate, and an application of the siRNA in the preparation of drugs for treating and/or preventing uric acid metabolism disorder or diseases or physical conditions caused by uric acid metabolism disorder. Each nucleotide in the siRNA is an independent modified or unmodified nucleotide, and the siRNA contains a sense strand and an antisense strand.

20 Claims, 4 Drawing Sheets

Specification includes a Sequence Listing.

(56)     References Cited

U.S. PATENT DOCUMENTS

| | | | |
|---|---|---|---|
| 2013/0096288 A1 | 4/2013 | Han et al. | |
| 2013/0123482 A1 | 5/2013 | Xi et al. | |
| 2013/0158021 A1 | 6/2013 | Dong et al. | |
| 2013/0190484 A1 | 7/2013 | Rozema et al. | |
| 2014/0099666 A1 | 4/2014 | Rossomando et al. | |
| 2014/0128453 A1 | 5/2014 | Mullick et al. | |
| 2014/0179768 A1 | 6/2014 | Bettencourt et al. | |
| 2014/0194489 A1 | 7/2014 | Bumcrot et al. | |
| 2014/0343123 A1 | 11/2014 | Prakash et al. | |
| 2015/0093444 A1 | 4/2015 | Zhang et al. | |
| 2015/0152436 A1 | 6/2015 | Musunuru et al. | |
| 2015/0174260 A1 | 6/2015 | Yang et al. | |
| 2015/0191726 A1 | 7/2015 | Manoharan et al. | |
| 2015/0247143 A1 | 9/2015 | Fitzgerald et al. | |
| 2015/0263948 A1 | 9/2015 | Jan et al. | |
| 2015/0291958 A1 | 10/2015 | Albaek et al. | |
| 2015/0315584 A1 | 11/2015 | Macdonald et al. | |
| 2015/0315594 A1 | 11/2015 | Prakash et al. | |
| 2016/0017335 A1 | 1/2016 | Borodovsky et al. | |
| 2016/0186180 A1 | 6/2016 | Bettencourt et al. | |
| 2016/0237438 A1 | 8/2016 | Brown et al. | |
| 2016/0283653 A1 | 9/2016 | Staudt et al. | |
| 2016/0354404 A1 | 12/2016 | Hinkle et al. | |
| 2017/0000815 A1 | 1/2017 | Fitzgerald et al. | |
| 2017/0002094 A1 | 1/2017 | Sexton et al. | |
| 2017/0114341 A1 | 4/2017 | Bradshaw et al. | |
| 2018/0087054 A1 | 3/2018 | Querbes et al. | |
| 2018/0148722 A1 | 5/2018 | Fitzgerald et al. | |
| 2018/0216114 A1* | 8/2018 | Fitzgerald ............ A61K 9/0019 |
| 2018/0245077 A1 | 8/2018 | Chiu et al. | |
| 2019/0062749 A1 | 2/2019 | Zhang | |
| 2019/0078088 A1 | 3/2019 | Li et al. | |
| 2019/0202855 A1 | 7/2019 | Sakamuri et al. | |
| 2019/0255091 A1 | 8/2019 | Li et al. | |
| 2019/0292547 A1 | 9/2019 | Li et al. | |
| 2020/0199591 A1 | 6/2020 | Fitzgerald et al. | |
| 2020/0338201 A1 | 10/2020 | Zhang et al. | |
| 2020/0360522 A1 | 11/2020 | Zhang et al. | |
| 2021/0032623 A1 | 2/2021 | Zhang et al. | |
| 2021/0275564 A1 | 9/2021 | Zhang et al. | |
| 2021/0277400 A1 | 9/2021 | Zhang et al. | |
| 2021/0401994 A1 | 12/2021 | Zhang et al. | |
| 2022/0049249 A1 | 2/2022 | Zhang et al. | |
| 2022/0062427 A1 | 3/2022 | Zhang et al. | |
| 2022/0186221 A1 | 6/2022 | Zhang et al. | |
| 2022/0235359 A1 | 7/2022 | Zhang et al. | |
| 2022/0315929 A1 | 10/2022 | Zhang et al. | |
| 2022/0356474 A1 | 11/2022 | Zhang et al. | |
| 2022/0389428 A1 | 12/2022 | Zhang et al. | |
| 2022/0395526 A1 | 12/2022 | Zhang et al. | |
| 2023/0076803 A1 | 3/2023 | Zhang et al. | |
| 2023/0132756 A1 | 5/2023 | Zhang et al. | |
| 2023/0193277 A1 | 6/2023 | Zhang et al. | |
| 2023/0257827 A1 | 8/2023 | Zhang et al. | |
| 2023/0313195 A1 | 10/2023 | Zhang et al. | |
| 2024/0200060 A1 | 6/2024 | Zhang et al. | |
| 2024/0200076 A1 | 6/2024 | Zhang et al. | |
| 2025/0057870 A1 | 2/2025 | Liang et al. | |

FOREIGN PATENT DOCUMENTS

| | | | |
|---|---|---|---|
| CA | 2 677 068 A1 | 3/2011 |
| CN | 101603042 A | 12/2009 |
| CN | 102006890 A | 4/2011 |
| CN | 102016036 A | 4/2011 |
| CN | 102124107 A | 7/2011 |
| CN | 102140458 A | 8/2011 |
| CN | 102140459 A | 8/2011 |
| CN | 102140460 A | 8/2011 |
| CN | 102140461 A | 8/2011 |
| CN | 102344477 A | 2/2012 |
| CN | 102439148 A | 5/2012 |
| CN | 102719434 A | 10/2012 |
| CN | 102753186 A | 10/2012 |
| CN | 102869774 A | 1/2013 |
| CN | 103380113 A | 10/2013 |
| CN | 102083983 B | 4/2014 |
| CN | 103890000 A | 6/2014 |
| CN | 104107437 A | 10/2014 |
| CN | 104232644 A | 12/2014 |
| CN | 104328121 A | 2/2015 |
| CN | 104717982 A | 6/2015 |
| CN | 104854242 A | 8/2015 |
| CN | 104922141 A | 9/2015 |
| CN | 105324485 A | 2/2016 |
| CN | 105378082 A | 3/2016 |
| CN | 105392488 A | 3/2016 |
| CN | 105452465 A | 3/2016 |
| CN | 105517556 A | 4/2016 |
| CN | 105713092 A | 6/2016 |
| CN | 105814204 A | 7/2016 |
| CN | 106132442 A | 11/2016 |
| CN | 106146591 A | 11/2016 |
| CN | 106232831 A | 12/2016 |
| CN | 106255755 A | 12/2016 |
| CN | 106460025 A | 2/2017 |
| CN | 107075516 A | 8/2017 |
| CN | 107109405 A | 8/2017 |
| CN | 107250362 A | 10/2017 |
| CN | 107854478 A | 3/2018 |
| CN | 108271386 A | 3/2018 |
| CN | 108064294 A | 5/2018 |
| CN | 108064313 A | 5/2018 |
| CN | 108220293 A | 6/2018 |
| CN | 108239644 A | 7/2018 |
| CN | 108265052 A | 7/2018 |
| CN | 108348541 A | 7/2018 |
| CN | 110945131 A | 3/2020 |
| CN | 110959011 A | 4/2020 |
| CN | 111050807 A | 4/2020 |
| CN | 111973617 A | 11/2020 |
| CN | 111973618 A | 11/2020 |
| CN | 111973619 A | 11/2020 |
| CN | 111979237 A | 11/2020 |
| CN | 112423795 A | 2/2021 |
| CN | 113330117 A | 8/2021 |
| EP | 1 752 536 A1 | 2/2007 |
| EP | 2 194 128 A1 | 6/2010 |
| EP | 2 213 738 A2 | 8/2010 |
| EP | 2 376 641 | 10/2011 |
| EP | 2 669 377 A2 | 12/2013 |
| EP | 2 990 410 A1 | 3/2016 |
| EP | 3 312 281 A2 | 4/2018 |
| EP | 3 315 608 A1 | 5/2018 |
| EP | 3 335 715 A2 | 6/2018 |
| EP | 3409780 A1 | 12/2018 |
| EP | 3 719 128 A1 | 10/2020 |
| EP | 3 862 024 A1 | 8/2021 |
| JP | 2013523149 A | 6/2013 |
| JP | 2013537423 A | 10/2013 |
| JP | 2016501195 A | 1/2016 |
| JP | 2016523087 A | 8/2016 |
| JP | 2017521045 A | 8/2017 |
| JP | 2017534290 A | 11/2017 |
| RU | 2013 134 745 A | 2/2015 |
| RU | 2 558 258 C2 | 7/2015 |
| RU | 2015 133 167 A | 3/2017 |
| TW | 201925471 A | 7/2019 |
| TW | 201929905 A | 8/2019 |
| WO | 00/27795 A1 | 5/2000 |
| WO | 2004/045543 A2 | 6/2004 |
| WO | 2004/078181 A1 | 9/2004 |
| WO | 2005/116204 A1 | 12/2005 |
| WO | 2006/006948 A2 | 1/2006 |
| WO | 2006/096018 A1 | 9/2006 |
| WO | 2007/134161 A2 | 11/2007 |
| WO | 2008/011431 A2 | 1/2008 |
| WO | 2008/109472 A2 | 9/2008 |
| WO | 2009/073809 A2 | 6/2009 |
| WO | 2009/082607 A2 | 7/2009 |
| WO | 2009/134487 A2 | 11/2009 |
| WO | 2010/012244 A1 | 2/2010 |
| WO | 2010/045509 A2 | 4/2010 |
| WO | 2010/068978 A1 | 6/2010 |

(56)                 References Cited

FOREIGN PATENT DOCUMENTS

| WO | 2010/083615 A1 | 7/2010 |
| WO | 2010/101951 A1 | 9/2010 |
| WO | 2010/121074 A1 | 10/2010 |
| WO | 2010/131916 A2 | 11/2010 |
| WO | 2010/147992 A1 | 12/2010 |
| WO | 2011005793 A1 | 1/2011 |
| WO | 2011/028938 A1 | 3/2011 |
| WO | 2011/085271 A2 | 7/2011 |
| WO | 2011/104169 A1 | 9/2011 |
| WO | 2011126974 A1 | 10/2011 |
| WO | 2011/139702 A2 | 11/2011 |
| WO | 2011/154331 A1 | 12/2011 |
| WO | 2012/013127 A1 | 2/2012 |
| WO | 2012/024170 A2 | 2/2012 |
| WO | 2012/037254 A1 | 3/2012 |
| WO | 2012/068176 A1 | 5/2012 |
| WO | 2012/083185 A2 | 6/2012 |
| WO | 2012/089352 A1 | 7/2012 |
| WO | 2012/130086 A1 | 10/2012 |
| WO | 2012/139081 A2 | 10/2012 |
| WO | 2012/139469 A1 | 10/2012 |
| WO | 2012/177784 A2 | 12/2012 |
| WO | 2013/060261 A1 | 5/2013 |
| WO | 2013/070771 A1 | 5/2013 |
| WO | 2013061295 A1 | 5/2013 |
| WO | 2013/166155 A1 | 11/2013 |
| WO | 2014/025805 A1 | 2/2014 |
| WO | 2014076195 A1 | 5/2014 |
| WO | 2014/089313 A1 | 6/2014 |
| WO | 2014/118267 A2 | 11/2014 |
| WO | 2014/179626 A2 | 11/2014 |
| WO | 2014/179627 A2 | 11/2014 |
| WO | 2014/179629 A2 | 11/2014 |
| WO | 2014205451 A1 | 12/2014 |
| WO | 2015/006498 A2 | 1/2015 |
| WO | 2015/006740 A2 | 1/2015 |
| WO | 2015/015496 A1 | 2/2015 |
| WO | 2015/031679 A2 | 3/2015 |
| WO | 2015/051366 A2 | 4/2015 |
| WO | 2015/100394 A1 | 7/2015 |
| WO | 2015/113922 A1 | 8/2015 |
| WO | 2015/148580 A2 | 10/2015 |
| WO | 2015/168532 A2 | 11/2015 |
| WO | 2015168589 A1 | 11/2015 |
| WO | 2015/188197 A2 | 12/2015 |
| WO | 2016/077321 A2 | 12/2015 |
| WO | 2015188194 A1 | 12/2015 |
| WO | 2015/011123 A1 | 1/2016 |
| WO | 2016/028649 A1 | 2/2016 |
| WO | 2016/040589 A1 | 3/2016 |
| WO | 2016/081444 A1 | 5/2016 |
| WO | 2016077349 A1 | 5/2016 |
| WO | 2016/099982 A2 | 6/2016 |
| WO | 2016/149331 A2 | 9/2016 |
| WO | 2016/154127 A2 | 9/2016 |
| WO | 2016/168286 A1 | 10/2016 |
| WO | 2016/179342 A2 | 11/2016 |
| WO | 2016/188473 A1 | 12/2016 |
| WO | 2016/201301 A1 | 12/2016 |
| WO | 2016/206626 A1 | 12/2016 |
| WO | 2017/015175 A1 | 1/2017 |
| WO | 2017/019660 A1 | 2/2017 |
| WO | 2017/019891 A2 | 2/2017 |
| WO | 2017/035340 A1 | 3/2017 |
| WO | 2017/055627 A1 | 4/2017 |
| WO | 2017/100542 A1 | 6/2017 |
| WO | 2017/120397 A1 | 7/2017 |
| WO | 2017131236 A1 | 8/2017 |
| WO | 2017/184689 A1 | 10/2017 |
| WO | 2017/189813 A1 | 11/2017 |
| WO | 2018/027106 A2 | 2/2018 |
| WO | 2018/035380 A1 | 2/2018 |
| WO | 2018/044350 A1 | 3/2018 |
| WO | 2018/075658 A1 | 4/2018 |
| WO | 2018/140920 A1 | 8/2018 |
| WO | 2018/191278 A2 | 10/2018 |
| WO | 2018/209848 A1 | 11/2018 |
| WO | 2018/223073 A1 | 12/2018 |
| WO | 2019/105403 A1 | 6/2019 |
| WO | 2019/105404 A1 | 6/2019 |
| WO | 2019/105418 A1 | 6/2019 |
| WO | 2019/105419 A1 | 6/2019 |
| WO | 2019/105435 A1 | 6/2019 |
| WO | 2019/105437 A1 | 6/2019 |
| WO | 2019/128611 A1 | 7/2019 |
| WO | 2020038377 A1 | 2/2020 |
| WO | 2020/063198 A1 | 4/2020 |
| WO | 2020/093053 A1 | 5/2020 |
| WO | 2020/135581 A1 | 7/2020 |
| WO | 2020/147847 A1 | 7/2020 |
| WO | 2020233651 A1 | 11/2020 |
| WO | 2020233655 A1 | 11/2020 |
| WO | 2020233680 A1 | 11/2020 |
| WO | 2020238763 A1 | 12/2020 |
| WO | 2020238766 A1 | 12/2020 |

OTHER PUBLICATIONS

Hashimoto, K. et al., "Sulfotransferase-1A1-dependent bioactivation of aristolochic acid I and N-hydroxyaristolactam I in human cells," Carcinogenesis, 2016, vol. 37, No. 7, pp. 647-655. (cited in Extended European Search Report issued on Jan. 30, 2024, in European Patent Application No. 20813863.6).

Fedin A.I. et al., "Review of clinical recommendations for treatment and prevention of ischemic stroke", S. S. Korsakov Journal of Neurology and Psychiatry, 2019, vol. 119, No. 8, pp. 91-96, doi: 10.17116/jnevro201911908291, with English abstract. (Cited in Office Action issued on Mar. 6, 2024, in corresponding Russian Application No. 2021130601) (6 pages).

Meijers J.C. et al., "High levels of coagulation factor XI as a risk factor for venous thrombosis", N. Engl. J. Med., 2000, vol. 342, No. 10, pp. 696-701, doi: 10.1056/NEJM200003093421004. (Cited in Office Action issued on Mar. 6, 2024, in corresponding Russian Application No. 2021130601) (6 pages).

Soodabeh S. et al., "From in vitro Experiments to in vivo and Clinical Studies; Pros and Cons", Curr. Drug Discov. Technol., 2015, vol. 12, No. 4, pp. 218-224. (Cited in Office Action issued on Mar. 6, 2024, in corresponding Russian Application No. 2021130601) (7 pages).

Shafer A.I. et al., "Thrombotic Disorders Diagnosis and Treatment", Am. Soc. Hematol. Educ. Program, 2003, v. 1, pp. 520-539, doi 10.1182asheducation-2003.1.520. (Cited in Office Action issued on Mar. 6, 2024, in corresponding Russian Application No. 2021130601) (20 pages).

Sehgal, Alfica et al., "Liver as a target for oligonucleotide therapeutics", Journal of hepatology, 2013, vol. 59, pp. 1354-1359. (Cited in Office Action issued on Mar. 11, 2024, in corresponding Taiwanese Patent Application No. 109116935) (6 pages).

Diaz-Torné, Cesar et al., "New medications in development for the treatment of hyperuricemia of gout", Current opinion in rheumatology. 2015, vol. 27, No. 2, pp. 164-169. (Cited in Office Action issued on Mar. 11, 2024, in corresponding Taiwanese Patent Application No. 109116934) (6 pages).

Kojima, S. et al., "Tumour suppressors miR-1 and miR-133a target the oncogenic function ofphosphorylase (PNP) in prostate cancer", Br. J. Cancer, 2012, vol. 106(2), pp. 405-413. (Cited in Office Action issued on May 21, 2024, in corresponding Japanese Patent Application No. JP2021-569112) (9 pages).

Durnov, et al., "Children's Oncology", Paediatric Oncology, Second Edition, Moscow Publishing House Medicine, 2002, p. 139 and its English translation. Cited in Office Action issued on Oct. 10, 2022 in Russian Application No. 2020121741). (4 pages).

Dysop, "Chemistry of Synthetic Drugs", Publishing House MIR, 1964, pp. 12-19 and its English translation. Cited in Office Action issued on Oct. 10, 2022 in Russian Application No. 2020121741). (18 pages).

Belikov, V.G., "Pharmaceutical Chemistry", textbook, Moscow, 11th Edition, MEDpress-inform, 2007, pp. 27-29 and its English translation. (Cited in Office Action issued on Oct. 10, 2022 in Russian Application No. 2020121741). (8 pages).

(56)                     References Cited

OTHER PUBLICATIONS

Bertrand, et al., "Comparison of antisense oligonucleotides and siRNAs in cell culture and in vivo," Biochemical and Biophysical Research Communications, 2002, vol. 296, Issue 4, pp. 1000-1004, ISSN 0006-291X.

Examination Report No. 2 issued on Feb. 3, 2023, by the Australian Government IP Australia in Australian Patent Application No. 2018394875 (4 pages).

Ren et al., "Synthesis of Galactosyl Compounds for Targeted Gene Delivery", Bioorganic & Medicinal Chemistry, 2001, 9(11), pp. 2969-2978.

Extended European Search Report issued on Mar. 27, 2023, by the European Patent Office in European Patent Application No. 19902173.4 (11 pages).

Li et al., "The silencing of ApoC3 suppresses oxidative stress and inflammatory responses in placenta cells from mice with preeclampsia via inhibition of the NF-B signaling pathway", Biomedicine & Pharmacotherapy, Aug. 31, 2018, vol. 107, pp. 1377-1384.

Notice of Reasons for Refusal issued on Jun. 1, 2023, by the Japanese Patent Office in Japanese Patent Application No. 2021-537877, with an English translation of the Notice (6 pages).

Kanasty et al., "Delivery materials for siRNA therapeutics", Nature Materials, Nov. 2023, vol. 12, pp. 967-977.

Notice of Reasons for Refusal issued on Jun. 6, 2023, by the Japanese Patent Office in Japanese Patent Application No. 2021-509880, with an English translation of the Notice (6 pages).

Chen et al., "Proof-of-concept Studies for siRNA-mediated Gene Silencing for Coagulation Factors in Rat and Rabbit", Molecular Therapy—Nucleic Acids, Jan. 27, 2015, vol. 4, No. 1, p. e224.

Ferrone et al., "Ionis-PKK Rx a Novel Antisense Inhibitor of Prekallikrein and Bradykinin Production", Nucleic Acid Therapeutics, Apr. 1, 2019, vol. 29, No. 2, pp. 82-91.

Ghosh et al., "Effectiveness and Safety of Inclisiran, a Novel Long-Acting RNA Therapeutic Inhibitor of Proprotein Convertase Subtilisin/Kexin 9", American Journal of Cardiology, Cahners Publishing Co., Newton, MA, US, Jul. 3, 2018, vol. 122, No. 7, pp. 1272-1277.

Joshi et al., "siRNA: novel therapeutics from functional genomics", Biotechnology and Genetic Engineering Reviews, Jan. 2, 2014, vol. 30, No. 1, pp. 1-30.

Pawluczyk et al., "*Kallikrein* gene 'knock-down' by small interfering RNA transfection induces a profibrotic phenotype in rat mesangial cells", Journal of Hypertension, Lippincott Williams & Wilkens, Ltd., Jan. 1, 2008, vol. 26, No. 1, pp. 93-101.

Revenko et al., "Selective depletion of plasma prekallikrein or coagulation factor XII inhibits thrombosis in mice without increased risk of bleeding", Blood, American Society of Hematology, Nov. 10, 2011, vol. 118, No. 19, pp. 5302-5311.

Yamasaki et al., "Novel molecular targets regulated by tumor suppressors microRNA-1 and microRNA-133a in bladder cancer", International Journal of Oncology, Feb. 29, 2012, vol. 40, pp. 1821-1830.

Supplementary European Search Report issued on Jun. 14, 2023, by the European Patent Office in European Patent Application No. 20809702.2 (12 pages).

Supplementary European Search Report issued on Jun. 16, 2023, by the European Patent Office in European Patent Application No. 20814338.8 (10 pages).

Partial Supplementary European Search Report issued on Jul. 5, 2023, by the European Patent Office in European Patent Application No. 20810635.1 (13 pages).

Partial Supplementary European Search Report issued on Jul. 10, 2023, by the European Patent Office in European Patent Application No. 20815633.1 (17 pages).

The First Office Action issued on Jan. 30, 2022, by the State Intellectual Property Office of the People's Republic of China in Chinese Patent Application No. 201880049520.8 and an English translation of the Action. (11 pages).

Decision of Rejection issued on Mar. 3, 2022, by the State Intellectual Property Office of the People's Republic of China in Chinese Patent Application No. 202010426194.7 and an English translation of the Action. (20 pages).

The Second Office Action issued on Mar. 16, 2022, by the State Intellectual Property Office of the People's Republic of China in Chinese Patent Application No. 201980046892.X and an English translation of the Action. (24 pages).

The Second Office Action issued on Mar. 21, 2022, by the State Intellectual Property Office of the People's Republic of China in Chinese Patent Application No. 201980046893.4 and an English translation of the Action. (19 pages).

The First Office Action issued on May 7, 2022, by the State Intellectual Property Office of the People's Republic of China in Chinese Patent Application No. 201980010095.6 and an English translation of the Action. (27 pages).

The First Office Action issued on May 7, 2022, by the State Intellectual Property Office of the People's Republic of China in Chinese Patent Application No. 201980010175.1 and an English translation of the Action. (30 pages).

The First Office Action issued on May 7, 2022, by the State Intellectual Property Office of the People's Republic of China in Chinese Patent Application No. 201880049190.2 and an English translation of the Action. (31 pages).

The First Office Action issued on May 7, 2022, by the State Intellectual Property Office of the People's Republic of China in Chinese Patent Application No. 201880049191.7 and an English translation of the Action. (30 pages).

The First Office Action issued on May 7, 2022, by the State Intellectual Property Office of the People's Republic of China in Chinese Patent Application No. 202080007282.1 and an English translation of the Action. (33 pages).

The First Office Action issued on May 7, 2022, by the State Intellectual Property Office of the People's Republic of China in Chinese Patent Application No. 201880049564.0 and an English translation of the Action. (29 pages).

The First Office Action issued on May 7, 2022, by the State Intellectual Property Office of the People's Republic of China in Chinese Patent Application No. 201880049586.7 and an English translation of the Action. (33 pages).

The First Office Action issued on May 7, 2022, by the State Intellectual Property Office of the People's Republic of China in Chinese Patent Application No. 201880048597.3 and an English translation of the Action. (34 pages).

The First Office Action issued on May 7, 2022, by the State Intellectual Property Office of the People's Republic of China in Chinese Patent Application No. 201880048600.1 and an English translation of the Action. (34 pages).

The First Office Action issued on May 7, 2022, by the State Intellectual Property Office of the People's Republic of China in Chinese Patent Application No. 202080009787.1 and an English translation of the Action. (50 pages).

The First Office Action issued on May 7, 2022, by the State Intellectual Property Office of the People's Republic of China in Chinese Patent Application No. 201880048949.5 and an English translation of the Action. (33 pages).

The First Office Action issued on May 20, 2021, by the State Intellectual Property Office of the People's Republic of China in Chinese Patent Application No. 202010426194.7 and an English translation of the Action. (20 pages).

The First Office Action issued on Jun. 23, 2021, by the State Intellectual Property Office of the People's Republic of China in Chinese Patent Application No. 201980046892.X and an English translation of the Action. (13 pages).

The First Office Action issued on Jun. 23, 2021, by the State Intellectual Property Office of the People's Republic of China in Chinese Patent Application No. 201980046893.4 and an English translation of the Action. (12 pages).

The First Office Action issued on Jun. 29, 2022, by the State Intellectual Property Office of the People's Republic of China in Chinese Patent Application No. 201980046892.X and an English translation of the Action. (8 pages).

(56)                    References Cited

OTHER PUBLICATIONS

The First Office Action issued on Jun. 29, 2022, by the State Intellectual Property Office of the People's Republic of China in Chinese Patent Application No. 201980046893.4 and an English translation of the Action. (8 pages).

The First Office Action issued on Oct. 25, 2021, by the State Intellectual Property Office of the People's Republic of China in Chinese Patent Application No. 202010426196.6 and an English translation of the Action. (16 pages).

The Second Office Action issued on Nov. 12, 2021, by the State Intellectual Property Office of the People's Republic of China in Chinese Patent Application No. 202010426194.7 and an English translation of the Action. (16 pages).

The Extended European Search Report issued on Jun. 9, 2022, by the European Patent Office in European Patent Application Publication No. 19851738.5. (64 pages).

The Extended European Search Report issued on Jul. 19, 2022, by the European Patent Office in European Patent Application No. 19867686.8. (12 pages).

The Extended European Search Report and Supplementary European Search Report issued on Aug. 9, 2021, by the European Patent Office in European Patent Application Publication No. 18883362.8. (9 pages).

The Extended European Search Report issued on Sep. 16, 2021, by the European Patent Office in European Patent Application No. 18883803.1. (10 pages).

Extended European Search Report dated Sep. 17, 2021, issued by the European Patent Office in corresponding European Application No. 18883982.3. (9 pages).

Extended European Search Report dated Sep. 29, 2021, issued by the European Patent Office in corresponding European Application No. 18884492.2. (45 pages).

The Extended European Search Report issued on Oct. 7, 2021, by the European Patent Office in European Patent Application Publication No. 18896766.5. (19 pages).

Invitation to remedy deficiencies pursuant to Rule 30(3) EPC / Rule 163(3) EPC issued on Feb. 22, 2022, by the European Patent Office in European Patent Application No. 20809029.0. (2 pages).

Communication pursuant to Rule 159 and Rule 58 EPC Invitation to remedy deficiencies in the application documents issued on Jan. 24, 2022, by the European Patent Office in European Patent Application No. 20815633.1 (2 pages).

Supplementary European Search Report issued on Jul. 27, 2021, by the European Patent Office in European Patent Application No. 18883153. (7 pages).

Notification of Substantive Examination Result issued on Aug. 24, 2021, by the Intellectual Property Office of the Republic of Indonesia in Indonesian Patent Application No. P00202003131 and an English translation of the Notification. (6 pages).

Notification of Substantive Examination Result issued on Dec. 2, 2021, by the Intellectual Property Office of the Republic of Indonesia in Indonesian Patent Application No. P00202003125 and an English translation of the Notification. (6 pages).

Examination report under sections 12 & 13 of the Patents Act, 1970 and the Patents Rules, 2003 issued on Nov. 24, 2021, by the Intellectual Property Office of India in Indian Patent Application No. 202047017398 and English translation of the Report. (7 pages).

International Preliminary Report on Patentability issued on Jun. 11, 2020, by the International Bureau of WIPO in International Patent Application No. PCT/CN2018/118191. (7 pages).

International Preliminary Report on Patentability issued on Jul. 2, 2020, by the International Bureau of WIPO in International Patent Application No. PCT/CN2018/118232 and English translation of the Report. (14 pages).

International Preliminary Report on Patentability issued on Jul. 8, 2021, by the International Bureau of WIPO in International Patent Application No. PCT/CN2019/128686 and English translation of the Report. (17 pages).

International Preliminary Report on Patentability issued on Sep. 3, 2021, by the State Intellectual Property Office of the People's Republic of China in International Patent Application No. PCT/CN2020/091489 and English translation of the Report. (12 pages).

Written Opinion of the International Searching Authority and International Search Report issued on Feb. 20, 2019, by the State Intellectual Property Office of the People's Republic of China in International Patent Application No. PCT/CN2018/118107 and English translation. (22 pages).

Written Opinion of the International Searching Authority and International Search Report issued on Feb. 25, 2019, by the State Intellectual Property Office of the People's Republic of China in International Patent Application No. PCT/CN2018/118212 and English translation. (23 pages).

English translation of the Written Opinion of the International Searching Authority and International Search Report issued on Feb. 27, 2019, by the State Intellectual Property Office of the People's Republic of China in International Patent Application No. PCT/CN2018/118224. (13 pages).

Written Opinion of the International Searching Authority and International Search Report issued on Feb. 28, 2019, by the State Intellectual Property Office of the People's Republic of China in International Patent Application No. PCT/CN2018/118300 and English translation. (20 pages).

Written Opinion of the International Searching Authority and International Search Report issued on Mar. 6, 2019, by the State Intellectual Property Office of the People's Republic of China in International Patent Application No. PCT/CN2018/118106 and English translation. (20 pages).

Written Opinion of the International Searching Authority and International Search Report issued on Mar. 6, 2019, by the State Intellectual Property Office of the People's Republic of China in International Application No. PCT/CN2018/118191 and English translation. (17 pages).

Written Opinion of the International Searching Authority and International Search Report issued on Mar. 7, 2019, by the State Intellectual Property Office of the People's Republic of China in International Patent Application No. PCT/CN2018/118303 and English translation. (22 pages).

Written Opinion of the International Searching Authority and International Search Report issued on Mar. 7, 2019, by the State Intellectual Property Office of the People's Republic of China in International Patent Application No. PCT/CN2018/118232 and English translation. (24 pages).

Written Opinion of the International Searching Authority and International Search Report issued on Mar. 26, 2020, by the State Intellectual Property Office of the People's Republic of China in International Patent Application No. PCT/CN2019/129016 and English translation. (27 pages).

Written Opinion of the International Searching Authority and International Search Report issued on Mar. 26, 2020, by the State Intellectual Property Office of the People's Republic of China in International Patent Application No. PCT/CN2019/128686 and English translation. (27 pages).

Written Opinion of the International Searching Authority and International Search Report issued on Aug. 19, 2020, by the State Intellectual Property Office of the People's Republic of China in International Patent Application No. PCT/CN2020/091489 and English translation. (26 pages).

Written Opinion of the International Searching Authority and International Search Report issued on Aug. 21, 2020, by the State Intellectual Property Office of the People's Republic of China in International Patent Application No. PCT/CN2020/091484 and English translation. (29 pages).

Written Opinion of the International Searching Authority and International Search Report issued on Aug. 21, 2020, by the State Intellectual Property Office of the People's Republic of China in International Patent Application No. PCT/CN2020/091614 and English translation. (24 pages).

Written Opinion of the International Searching Authority and International Search Report issued on Aug. 24, 2020, by the State Intellectual Property Office of the People's Republic of China in International Patent Application No. PCT/CN2020/091624 and English translation. (26 pages).

(56)     References Cited

OTHER PUBLICATIONS

Written Opinion of the International Searching Authority and International Search Report issued on Aug. 25, 2020, by the State Intellectual Property Office of the People's Republic of China in International Patent Application No. PCT/CN2020/091485 and English translation. (30 pages).

Written Opinion of the International Searching Authority and International Search Report issued on Aug. 28, 2020, by the State Intellectual Property Office of the People's Republic of China in International Patent Application No. PCT/CN2020/091649 and English translation. (25 pages).

Written Opinion of the International Searching Authority and International Search Report issued on Sep. 2, 2020, by the State Intellectual Property Office of the People's Republic of China in International Patent Application No. PCT/CN2020/091606 and English translation. (28 pages).

Written Opinion of the International Searching Authority and International Search Report issued on Nov. 21, 2019, by the State Intellectual Property Office of the People's Republic of China in International Patent Application No. PCT/CN2019/101653 and English translation. (23 pages).

Written Opinion of the International Searching Authority and International Search Report issued on Nov. 28, 2019, by the State Intellectual Property Office of the People's Republic of China in International Patent Application No. PCT/CN2019/101656 and English translation. (21 pages).

Written Opinion of the International Searching Authority and International Search Report issued on Apr. 17, 2020, by the State Intellectual Property Office of the People's Republic of China in International Patent Application No. PCT/CN2020/072813 and English translation. (32 pages).

Office Action issued on Mar. 9, 2022, by the Russian Agency for Patents and Trademarks in Russian Patent Application No. 2020118025/10(030488) and English translation of the Action. (14 pages).

Office Action issued on May 11, 2022, by the Russian Agency for Patents and Trademarks in Russian Patent Application No. 2020121741/04(037329) and English translation of the Action. (18 pages).

Office Action issued on Jan. 28, 2022, by the U.S. Patent and Trademark Office in U.S. Appl. No. 16/758,532. (28 pages).

Office Action issued on Mar. 11, 2022, by the U.S. Patent and Trademark Office in U.S. Appl. No. 16/758,720. (21 pages).

Notice of Allowance issued on Mar. 31, 2022, by the U.S. Patent and Trademark Office in U.S. Appl. No. 16/764,307. (7 pages).

Notice of Allowance issued on Apr. 5, 2022, by the U.S. Patent and Trademark Office in U.S. Appl. No. 16/763,058. (7 pages).

Office Action issued on May 27, 2022, by the U.S. Patent and Trademark Office in U.S. Appl. No. 16/758,532. (8 pages).

Notice of Allowance issued on Jul. 25, 2022, by the U.S. Patent and Trademark Office in U.S. Appl. No. 16/758,720. (5 pages).

Office Action issued on Aug. 24, 2022, by the U.S. Patent and Trademark Office in U.S. Appl. No. 16/758,532. (13 pages).

Office Action issued on Oct. 29, 2021, by the U.S. Patent and Trademark Office in U.S. Appl. No. 16/764,307. (17 pages).

Office Action issued on Nov. 16, 2021, by the U.S. Patent and Trademark Office in U.S. Appl. No. 16/763,058. (26 pages).

Office Action issued Aug. 14, 2020, by the Intellectual Property Office of Vietnam in Vietnamese Patent Application No. 1-2020-03065 and an English translation of the Action. (3 pages).

Office Action issued Aug. 28, 2020, by the Intellectual Property Office of Vietnam in Vietnamese Patent Application No. 1-2020-03777 and an English translation of the Action. (3 pages).

Payment and Certificate of Renewal issued on May 30, 2022 by the Patent Office of South Africa in South African Patent Application No. 2020/03833. (1 page).

Ahmad Dar et al., "siRNAmod: A database of experimentally validated chemically modified SiRNAs," Scientific Reports, Jan. 28, 2016, vol. 6, No. 1. (8 pages).

Beaucage et al., "Advances in the Synthesis of Oligonucleotides by the Phosphoramidite Approach", Tetrahedron, 1992, vol. 48, No. 12, pp. 2223-2311.

Behlke, Mark A., "Chemical Modification of siRNAs for In Vivo Use," Oligonucleotides, 2008, vol. 18, pp. 305-320.

Berthold et al., "Cellular Delivery and Antisense Effects of Peptide Nucleic Acid Conjugated to Polyethyleneimine via Disulfide Linkers," Bioconjugate Chemistry, 2010, vol. 21, No. 10, pp. 1933-1938.

Chen et al., "Research progress on factor XI as a novel target for antithrombotic therapy," Chinese Pharmacological Bulletin, Apr. 15, 2015, vol. 31, No. 5, with English abstract, pp. 619-622.

Dai et al., "A vital role for AngpII3 in the PAN-induced podocyte loss by affecting detachment and apoptosis in vitro," BMC Nephrology, 2015, vol. 16, No. 1. (10 pages).

Ding et al., "Limited role of kininogen in the host response during gram-negative pneumonia derived sepsis," American Journal of Physiology Lung Cellular and Molecular Physiology, Nov. 9, 2017. (33 pages).

Dong et al., "Lipopeptide nanoparticles for potent and selective siRNA delivery in rodents and nonhuman primates", Proceedings of the National Academy of Sciences, Feb. 2014, www.pnas.org/cgi/doi/10.1073/pnas.1322937111 (6 pages).

Dong et al., "A novel packaging system of recombinant AAV5/5 vector," Chinese Journal of Biotechnology, May 25, 2010, vol. 26, No. 5, pp. 679-686.

Common knowledge "RNAi technology," 2005, with English translation. (5 pages).

Foster et al., "Advanced siRNA Designs Further Improve In Vivo Performance of GalNAc-SiRNA Conjugates," Molecular Therapy, Mar. 2018, vol. 26, No. 3, pp. 708-717.

Greene et al., "Protection for the Hydroxyl Group, Including 1,2- and 1,3-Diols", Protective Groups in Organic Synthesis, Third Edition, 1999 John Wiley & Sons, Inc. pp. 17-245, (229 pages).

"*Homo sapiens* Kininogen 1 (KNG1), Transcript Variant 1, mRNA" GenBank, May 2, 2018, NM 00102416.2. (8 pages).

Khaitmetova et al., "Synthesis and Study of the Properties of Polymer Complexes of Ethacizin with Carboxymethylcellulose," Chemistry of Plant Raw Materials, 2017, No. 4, with English translation. (18 pages).

Khan et al., "High-Molecular-Weight Kininogen Fragments Stimulate the Secretion of Cytokines and Chemokines Through uPAR, Mac-1, and gC1qR in Monocytes," Arteriosclerosis, Thrombosis, and Vascular Biology, Oct. 2006, vol. 26, No. 10, pp. 2260-2266.

Khvorova et al., "The chemical evolution of oligonucleotide therapies of clinical utility", Nature Biotechnology Advance Online Publication, Feb. 27, 2017; doi:10.1038/nbt.3765, (11 pages).

Kim et al., "Bifunctional compounds for targeted hepatic gene delivery," Gene Therapy, 2007, vol. 14, pp. 704-708.

Liu et al., "Determination of Human Plasma Pre-Kallikrein," Journal of China Medical University, 1988, vol. 17, No. 6, with English abstract, pp. 432-436.

Liu et al., "Coagulation factor XI induces Ca2+ response and accelerates cell migration in vascular smooth muscle cells via proteinase-activated receptor 1," American Journal of Physiology, Cell Physiology, Mar. 1, 2019, vol. 316, No. 3, pp. C377-C392.

Love et al., "Lipid-like materials for low-dose, in vivo gene silencing", Proceedings of the National Academy of Sciences, Feb. 2, 2010, vol. 107, No. 5, pp. 1864-1869. (7 pages).

Matsuda et al., "siRNA Conjugates Carrying Sequentially Assembled Trivalent N-Acetylgalactosamine Linked Through Nucleosides Elicit Robust Gene Silencing In Vivo in Hepatocytes", ACS Chemical Biology, 2015, DOI: 10.1021/cb501028c. (7 pages).

Montagne et al., "Pericyte degeneration causes white matter dysfunction in the mouse CNS," Nature Medicine, 2018, vol. 24, vol. 3, pp. 326-337.

Nair et al., "Multivalent N-Acetylgalactosamine-Conjugated siRNA Localizes in Hepatocytes and Elicits Robust RNAi-Mediated Gene Silencing", Journal of the American Chemical Society, 2014, vol. 136, pp. 16958-16961.

Nakagawa et al., "The RNAi-Mediated Silencing of Xanthine Dehydrogenase Impairs Growth and Fertility and Accelerates Leaf Senescence in Transgenic *Arabidopsis* Plants," Plant & Cell Physiology, 2007, vol. 48, No. 10, pp. 1484-1495.

Nakamoto et al., "Enhanced Intercellular Delivery of cRGD-siRNA Conjugates by an Additional Oligospermine Modification," ACS Omega, 2018, vol. 3, pp. 8226-8232. (7 pages).

(56)            References Cited

OTHER PUBLICATIONS

Norata et al., "Gene silencing approaches for the management of dyslipidaemia," Trends in Pharmacological Sciences, Apr. 13, 2013, vol. 34, No. 4, pp. 198-205.

Nordestgaard et al., "Advances in lipid-lowering therapy through gene-silencing technologies," Nature Reviews, Feb. 8, 2018, vol. 15. (12 pages).

Nothisen et al., "Cationic siRNAs Provide Carrier-Free Gene Silencing in Animal Cells," Journal of the American Chemical Society, 2009, vol. 131, No. 29, pp. 17730-17731. (2 pages).

Papulov, Yu. G., "Relationship between Properties of Compounds with Their Structures: Math Modeling," Advances in Modern Natural Sciences, 2006, with English translation, pp. 75-76.

Paris et al., "Conjugating Phosphospermines to siRNAs for Improved Stability in Serum, Intracellular Delivery and RNAi-Mediated Gene Silencing," Molecular Pharmaceutics, 2012, vol. 9, No. 12, pp. 3464-3475.

Peña-Altamira, et al., "Release of soluble and vesicular purine nucleoside phosphorylase from rat astrocytes and microglia induced by pro-inflammatory stimulation with extracellular ATP via P2X7 receptors," Neurochemistry International, May 31, 2018, vol. 115, pp. 37-49.

Pessentheiner et al., "ANGPTL3 targeting: The power of versatile lipid-lowering," Atherosclerosis, Jan. 2018, vol. 268, pp. 185-187.

Prakash et al., "Comprehensive Structure-Activity Relationship of Triantennary N-Acetylgalactosamine Conjugated Antisense Oligonucleotides for Targeted Delivery to Hepatocytes," Journal of Medicinal Chemistry, 2016, vol. 59, pp. 2718-2733.

Rajeev et al., "Hepatocyte-Specific Delivery of siRNAs Conjugated to Novel Non-nucleosidic Trivalent N-Acetylgalactosamine Elicits Robust Gene Silencing in Vivo" ChemBioChem, 2015, vol. 16, pp. 903-908.

Ren et al., "Synthesis of bifunctional cationic compound for gene delivery," Tetrahedron Letters, 2001, vol. 42, pp. 1007-1010.

Ren et al., "Gene Expression Profile of Transgenic Mouse Kidney Reveals Pathogenesis of Hepatitis B Virus Associated Nephropathy," Journal of Medical Virology, 2006, vol. 78, pp. 551-560.

Ren et al., "Stable Inhibition of Hepatitis B Virus Expression and Replication by Expressed siRNA", Biochemical and Biophysical Research Communications, Oct. 7, 2005, vol. 335, No. 4, with English abstract, pp. 1051-1058.

Springer et al., "GalNAc-siRNA Conjugates: Leading the Way for Delivery of RNAi Therapeutics," Nucleic Acid Therapeutics, May 2018, vol. 28, No. 3, pp. 109-118.

Su et al., "Progress on the Inhibition of Hepatitis B virus by siRNA Strategy," China Biotechnology, 2014, vol. 34, No. 9, with English abstract, pp. 102-107.

Tangkijvanich et al., "Low pretreatment serum HBsAg level and viral mutations as predictors of response to PEG-interferon alpha-2b therapy in chronic hepatitis B," Journal of Clinical Virology, vol. 46, 2009, pp. 117-123.

Ui-Tei et al., "Functional dissection of siRNA sequence by systematic DNA substitution: modified siRNA with a DNA seed arm is a powerful tool for mammalian gene silencing with significantly reduced off-target effect", Nucleic Acids Research, 2008, vol. 36, No. 7, pp. 2136-2151.

Watts et al., "Chemically modified siRNA: tools and applications," Drug Discovery Today, Oct. 2008, vol. 13, Nos. 19/20, pp. 842-855.

Wooddell et al., "Hepatocyte-targeted RNAi Therapeutics for the Treatment of Chronic Hepatitis B Virus Infection," The American Society of Gene & Cell Therapy, 2013, doi:10.1038/mt.2013.31. (13 pages).

Wu et al., "Cleaved high molecular weight kininogen inhibits tube formation of endothelial progenitor cells via suppression of matrix metalloproteinase 2," Journal of Thrombosis and Haemostasis, 2010, vol. 8, pp. 185-193.

Wu et al., "Contact pathway of coagulation and inflammation," Thrombosis Journal, 2015, pp. 13-17.

Xu et al., "Role of angiopoielin-like 3 (ANGPTL3) in regulating plasma level of low-density lipoprotein cholesterol," Atherosclerosis, 2018, vol. 268, pp. 196-206.

Yang et al., "A critical role for plasma kallikrein in the pathogenesis of autoantibody-induced arthritis," Federation of American Societies for Experimental Biology, Nov. 2017, vol. 31, No. 12, pp. 5419-5431.

Yang et al., "An essential role of high-molecular-weight kininogen in endotoxemia," Journal of Experimental Medicine, Sep. 4, 2017, vol. 214, No. 9, pp. 2649-2670.

Dana et al., "Molecular Mechanisms and Biological Functions of siRNA," International Journal of Biomedical Science, vol. 13, No. 2, pp. 48-57 (2017).

Elbashir et al., "Functional anatomy of siRNAs for mediating efficient RNAi in Drosophila melanogaster embryo lysate," The EMBO Journal, vol. 20, No. 23, pp. 6877-6888 (2001).

Fakhr et al., "Precise and efficient siRNA design: a key point in competent gene silencing," Cancer Gene Therapy, vol. 23, pp. 73-82 (2016).

Girardet et al., "Urate Crystal Deposition Disease and Gout—New Therapies for an Old Problem," Annual Reports in Medicinal Chemistry, vol. 49, pp. 151-164 (2014).

Kliuchnikov et al., "Improving the potency prediction for chemically modified siRNAs through insights from molecular modeing of individual sequence positions," Molecular Therapy: Nucleic Acids, vol. 36, pp. 1-14 (2025).

Lorenzer et al., "Going beyond the liver: Progress and Challenges of Targeted Delivery of siRNA Therapeutics," Journal of Controlled Release, vol. 203, pp. 1-15 (2015).

Willoughby et al., "Evaluation of GalNAc-siRNA Conjugate Activity in Pre-clinical Animal Models with Reduced Asialoglycoprotein Receptor Expression," Molecular Therapy, vol. 26, No. 1, pp. 105-114 (2018).

* cited by examiner

NUCLEIC ACID, PHARMACEUTICAL COMPOSITION, CONJUGATE, PREPARATION METHOD, AND USE

TECHNICAL FIELD

The present disclosure relates to a nucleic acid capable of inhibiting expression of a xanthine oxidase (XO) gene, and a pharmaceutical composition and an siRNA conjugate containing the nucleic acid. The present disclosure also relates to a preparation method and use of the nucleic acid, the pharmaceutical composition and the siRNA conjugate.

BACKGROUND

Gout is a disease directly related to hyperuricemia caused by purine metabolism disorder and/or uric acid excretion decrease. Gout has been a common disease in developed countries such as Europe and America since ancient times. After the Second World War, with the economic development of various countries, the prevalence rate of gout has been increasing year by year in the world, and has been gradually increased with the trend of patients being young. At present, there are 12 million patients suffering from gout in China.

Xanthine oxidase (XO) is one of the key targets for treating gout. By inhibiting the expression of XO, the production of hypoxanthine and guanine can be effectively inhibited, and then the production of uric acid can be reduced, thus achieving the purpose of relieving the progress of gout and reversing the disease. By inhibiting the expression of the XO gene, diseases caused by abnormal uric acid metabolism, especially hyperuricemia and gout, can be prevented and treated at the cellular level. Small interfering RNA (siRNA), based on the mechanism of RNA interference (RNAi), can inhibit or block the expression of interested target genes in a sequence-specific way, thus achieving the purpose of treating diseases.

One of the keys to develop siRNA drugs for inhibiting the expression of the XO gene and treating the disease caused by the abnormal uric acid metabolism lies in finding a suitable siRNA and modification and an effective delivery system thereof.

SUMMARY OF THE INVENTION

The inventors of the present disclosure have surprisingly found that the following siRNA and modification sequence thereof provided by the present disclosure can specifically inhibit the expression of the XO gene, and the pharmaceutical composition or the siRNA conjugate can specifically target the liver, thereby inhibiting the expression of the XO gene in the liver and realizing the treatment or prevention of the disease caused by the abnormal uric acid metabolism, thus completing the present disclosure.

In some embodiments, the present disclosure provides an siRNA capable of inhibiting expression of an XO gene. The siRNA comprises a sense strand and an antisense strand, each nucleotide in the siRNA is independently a modified or unmodified nucleotide, wherein the sense strand comprises a nucleotide sequence I, and the antisense strand comprises a nucleotide sequence II; the nucleotide sequence I and the nucleotide sequence II are at least partly reverse complementary to form a double-stranded region; and the nucleotide sequence I and the nucleotide sequence II are selected from a group of sequences shown in the following i)-xii):

i) the nucleotide sequence I has the same length and no more than three nucleotides difference from the nucleotide sequence shown in SEQ ID NO: 1; and the nucleotide sequence II has the same length and no more than three nucleotides difference from the nucleotide sequence shown in SEQ ID NO: 2:

```
                                    (SEQ ID NO: 1)
    5'-GAGAUGAAGUUCAAGAAUZ₁-3';

(SEQ ID NO: 2)
    5'-Z₂AUUCUUGAACUUCAUCUC-3',
``` wherein, $Z_1$ is A, $Z_2$ is U, the nucleotide sequence I comprises a nucleotide $Z_3$ at a corresponding site to $Z_1$, the nucleotide sequence II comprises a nucleotide $Z_4$ at a corresponding site to $Z_2$, and $Z_4$ is the first nucleotide from the 5' terminal of the antisense strand;

ii) the nucleotide sequence I has the same length and no more than three nucleotides differences from the nucleotide sequence shown in SEQ ID NO: 61; and the nucleotide sequence II has the same length and no more than three nucleotides differences from the nucleotide sequence shown in SEQ ID NO: 62:

```
                                    (SEQ ID NO: 61)
    5'-CAUAACUGGAAUUUGUAAZ₅-3';

(SEQ ID NO: 62)
    5'-Z₆UUACAAAUUCCAGUUAUG-3',
``` wherein, $Z_5$ is U, $Z_6$ is A, the nucleotide sequence I comprises a nucleotide $Z_7$ at a corresponding site to $Z_5$, the nucleotide sequence II comprises a nucleotide $Z_8$ at a corresponding site to $Z_6$, and $Z_8$ is the first nucleotide from the 5' terminal of the antisense strand;

iii) the nucleotide sequence I has the same length and no more than three nucleotides differences from the nucleotide sequence shown in SEQ ID NO: 121; and the nucleotide sequence II has the same length and no more than three nucleotides differences from the nucleotide sequence shown in SEQ ID NO: 122:

```
                                    (SEQ ID NO: 121)
    5'-CAUUAUCACAAUUGAGGAZ₉-3';

(SEQ ID NO: 122)
    5'-Z₁₀UCCUCAAUUGUGAUAAUG-3',
``` wherein, $Z_9$ is U, $Z_{10}$ is A, the nucleotide sequence I comprises a nucleotide $Z_{11}$ at a corresponding site to $Z_9$, the nucleotide sequence II comprises a nucleotide $Z_{12}$ at a corresponding site to $Z_{10}$, and $Z_{12}$ is the first nucleotide from the 5' terminal of the antisense strand;

iv) the nucleotide sequence I has the same length and no more than three nucleotides differences from the nucleotide sequence shown in SEQ ID NO: 181; and the nucleotide sequence II has the same length and no more than three nucleotides differences from the nucleotide sequence shown in SEQ ID NO: 182:

```
                                    (SEQ ID NO: 181)
    5'-GGAUCUCUCUCAGAGUAUZ₁₃-3';

(SEQ ID NO: 182)
    5'-Z₁₄AUACUCUGAGAGAGAUCC-3',
``` wherein, $Z_{13}$ is U, $Z_{14}$ is A, the nucleotide sequence I comprises a nucleotide $Z_{15}$ at a corresponding site to $Z_{13}$, the nucleotide sequence II comprises a nucleotide $Z_{16}$ at a corresponding site to $Z_{14}$, and $Z_{16}$ is the first nucleotide from the 5' terminal of the antisense strand;

v) the nucleotide sequence I has the same length and no more than three nucleotides differences from the nucleotide sequence shown in SEQ ID NO: 241; and the nucleotide sequence II has the same length and no more than three nucleotides differences from the nucleotide sequence shown in SEQ ID NO: 242:

(SEQ ID NO: 241)
5'-ACAUGGACAACUGCUAUAZ$_{17}$-3';

(SEQ ID NO: 242)
5'-Z$_{18}$UAUAGCAGUUGUCCAUGU-3', wherein, $Z_{17}$ is A, $Z_{18}$ is U, the nucleotide sequence I comprises a nucleotide $Z_{19}$ at a corresponding site to $Z_{17}$, the nucleotide sequence II comprises a nucleotide $Z_{20}$ at a corresponding site to $Z_{18}$, and $Z_{20}$ is the first nucleotide from the 5' terminal of the antisense strand;

vi) the nucleotide sequence I has the same length and no more than three nucleotides differences from the nucleotide sequence shown in SEQ ID NO: 301; and the nucleotide sequence II has the same length and no more than three nucleotides differences from the nucleotide sequence shown in SEQ ID NO: 302:

(SEQ ID NO: 301)
5'-UAGCAAGCUCUCAGUAUCZ$_{21}$-3';

(SEQ ID NO: 302)
5'-Z$_{22}$GAUACUGAGAGCUUGCUA-3', wherein, $Z_{21}$ is A, $Z_{22}$ is U, the nucleotide sequence I comprises a nucleotide $Z_{23}$ at a corresponding site to $Z_{21}$, the nucleotide sequence II comprises a nucleotide $Z_{24}$ at a corresponding site to $Z_{22}$, and $Z_{24}$ is the first nucleotide from the 5' terminal of the antisense strand;

vii) the nucleotide sequence I has the same length and no more than three nucleotides differences from the nucleotide sequence shown in SEQ ID NO: 361; and the nucleotide sequence II has the same length and no more than three nucleotides differences from the nucleotide sequence shown in SEQ ID NO: 362:

(SEQ ID NO: 361)
5'-AUAAGGUUACUUGUGUUGZ$_{25}$-3';

5'-Z$_{26}$CAACACAAGUAACCUUAU-3',
(SEQ ID NO: 362)

wherein, $Z_{25}$ is $Z_{26}$ is C, the nucleotide sequence I comprises a nucleotide $Z_{27}$ at a corresponding site to $Z_{25}$, the nucleotide sequence II comprises a nucleotide $Z_{28}$ at a corresponding site to $Z_{26}$, and $Z_{28}$ is the first nucleotide from the 5' terminal of the antisense strand;

viii) the nucleotide sequence I has the same length and no more than three nucleotides differences from the nucleotide sequence shown in SEQ ID NO: 421; and the nucleotide sequence II has the same length and no more than three nucleotides differences from the nucleotide sequence shown in SEQ ID NO: 422:

(SEQ ID NO: 421)
5'-GAAAAUCACCUAUGAAGAZ$_{29}$-3';

(SEQ ID NO: 422)
5'-Z$_{30}$UCUUCAUAGGUGAUUUUC-3', wherein, $Z_{29}$ is A, $Z_{30}$ is U, the nucleotide sequence I comprises a nucleotide $Z_{31}$ at a corresponding site to $Z_{29}$, the nucleotide sequence II comprises a nucleotide $Z_{32}$ at a corresponding site to $Z_{30}$, and $Z_{32}$ is the first nucleotide from the 5' terminal of the antisense strand;

ix) the nucleotide sequence I has the same length and no more than three nucleotides differences from the nucleotide sequence shown in SEQ ID NO: 481; and the nucleotide sequence II has the same length and no more than three nucleotides differences from the nucleotide sequence shown in SEQ ID NO: 482:

(SEQ ID NO: 481)
5'-GAUGCUAUAAAGAACAACZ$_{33}$-3';

(SEQ ID NO: 482)
5'-Z$_{34}$GUUGUUCUUUAUAGCAUC-3', wherein, $Z_{33}$ is U, $Z_{34}$ is A, the nucleotide sequence I comprises a nucleotide $Z_{35}$ at a corresponding site to $Z_{33}$, the nucleotide sequence II comprises a nucleotide $Z_{36}$ at a corresponding site to $Z_{34}$, and $Z_{36}$ is the first nucleotide from the 5' terminal of the antisense strand;

x) the nucleotide sequence I has the same length and no more than three nucleotides differences from the nucleotide sequence shown in SEQ ID NO: 541; and the nucleotide sequence II has the same length and no more than three nucleotides differences from the nucleotide sequence shown in SEQ ID NO: 542:

(SEQ ID NO: 541)
5'-GAACAACUCCUUUUAUGGZ$_{37}$-3';

(SEQ ID NO: 542)
5'-Z$_{38}$CCAUAAAAGGAGUUGUUC-3', wherein, $Z_{37}$ is A, $Z_{38}$ is U, the nucleotide sequence I comprises a nucleotide $Z_{39}$ at a corresponding site to $Z_{37}$, the nucleotide sequence II comprises a nucleotide $Z_{40}$ at a corresponding site to $Z_{38}$, and $Z_{40}$ is the first nucleotide from the 5' terminal of the antisense strand;

xi) the nucleotide sequence I has the same length and no more than three nucleotides differences from the nucleotide sequence shown in SEQ ID NO: 601; and the nucleotide sequence II has the same length and no more than three nucleotides differences from the nucleotide sequence shown in SEQ ID NO: 602:

(SEQ ID NO: 601)
5'-CUUGCUCUGAAGUAGAAAZ$_{41}$-3';

(SEQ ID NO: 602)
5'-Z$_{42}$AUUUCUACUUCAGAGCAAG-3', wherein, $Z_{41}$ is U, $Z_{42}$ is A, the nucleotide sequence I comprises a nucleotide $Z_{43}$ at a corresponding site to $Z_{41}$, the nucleotide sequence II comprises a nucleotide $Z_{44}$ at a corresponding site to $Z_{42}$, and $Z_{44}$ is the first nucleotide from the 5' terminal of the antisense strand; and xii) the nucleotide sequence I has the same length and no more than three nucleotides differences from the nucleotide sequence shown in SEQ ID NO: 661; and the nucleotide sequence II has the same length and no more than three nucleotides differences from the nucleotide sequence shown in SEQ ID NO: 662:

$$5'\text{-CUUCUUUGCCAUCAAAGAZ}_{45}\text{-3';}$$
(SEQ ID NO: 661)

$$5'\text{-Z}_{46}\text{UCUUUGAUGGCAAAGAAG-3',}$$
(SEQ ID NO: 662)

wherein, $Z_{45}$ is U, $Z_{46}$ is A, the nucleotide sequence I comprises a nucleotide $Z_{47}$ at a corresponding site to $Z_{45}$, the nucleotide sequence II comprises a nucleotide $Z_{48}$ at a corresponding site to $Z_{46}$, and $Z_{48}$ is the first nucleotide from the 5' terminal of the antisense strand.

In some embodiments, the present disclosure provides a pharmaceutical composition, wherein the pharmaceutical composition comprises the siRNA of the present disclosure and a pharmaceutically acceptable carrier.

In some embodiments, the present disclosure provides an siRNA conjugate, wherein the siRNA conjugate comprises the siRNA provided by the present disclosure and a conjugating group conjugatively linked to the siRNA.

In some embodiments, the present disclosure provides use of the siRNA and/or the pharmaceutical composition and/or the siRNA conjugate according to the present disclosure in the manufacture of a medicament for treating and/or preventing abnormal uric acid metabolism or a disease or a physiological condition caused by abnormal uric acid metabolism.

In some embodiments, the present disclosure provides a method for treating and/or preventing abnormal uric acid metabolism or a disease or a physiological condition caused by abnormal uric acid metabolism, wherein the method comprises administering an effective amount of the siRNA and/or the pharmaceutical composition and/or the siRNA conjugate of the present disclosure to a subject in need.

In some embodiments, the present disclosure provides a method for inhibiting expression of an XO gene in a hepatocyte, wherein the method comprises contacting an effective amount of the siRNA and/or the pharmaceutical composition and/or the siRNA conjugate of the present disclosure to the hepatocyte.

In some embodiments, the present disclosure provides a kit, wherein the kit comprises the siRNA and/or the pharmaceutical composition and/or the siRNA conjugate of the present disclosure.

INCORPORATED BY REFERENCE

All publications, patents and patent applications mentioned in this specification are incorporated herein by reference to the same extent as each individual publication, patent or patent application is specifically and individually incorporated herein by reference.

Advantageous Effects

In some embodiments, the siRNA, the pharmaceutical composition and the siRNA conjugate provided by the present disclosure have better stability, higher XO mRNA inhibitory activity and lower off-target effect, and/or can significantly treat or relieve abnormal uric acid metabolism or a disease or a physiological condition caused by abnormal uric acid metabolism, especially hyperuricemia and/or gout symptom.

In some embodiments, the siRNA, the pharmaceutical composition or the siRNA conjugate provided by the present disclosure exhibits excellent target gene inhibitory activity in cell experiments in vitro. In some embodiments, the siRNA, the pharmaceutical composition or the siRNA conjugate provided by the present disclosure exhibits an inhibition percentage to target gene expression in hepatocytes of at least 20%, 30%, 40%, 50%, 60%, 70%, 80%, 90%, or 95%. In some embodiments, the siRNA provided by the present disclosure has high inhibitory activity on XO mRNA in an in vitro psiCHECK system, and has certain inhibitory effects on XO target sequences at different siRNA concentrations, and in particular, the inhibitory rate on target sequences at 0.1 nM concentration is at least 61.39%, even as high as 85.43%. In some embodiments, the siRNA provided by the present disclosure exhibits higher inhibitory activity in CAL-27 cells, and the $IC_{50}$ for XO mRNA is between 0.037 µM and 0.3277 µM. In some embodiments, the siRNA conjugate provided by the present disclosure shows high inhibitory activity in primary hepatocytes of mice, and the inhibition percentage to XO mRNA is at least 78.95%, even as high as 88.07% under the siRNA concentration of 20 nM.

In some embodiments, the siRNA, the pharmaceutical composition or the siRNA conjugate provided by the present disclosure may exhibit higher stability and/or higher activity in vivo. In some embodiments, the siRNA, the pharmaceutical composition or the siRNA conjugate provided by the present disclosure exhibits an inhibition percentage to target gene expression in hepatocytes of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to XO gene expression in hepatocytes of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to XO gene expression in liver of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to XO gene expression in liver in animal models of at least 20%, 30%, 40%, 50%, 60%, 70%, 80%, 90%, or 95% in vivo. In some embodiments, the siRNA, the pharmaceutical composition or the siRNA conjugate provided by the present disclosure exhibits an inhibition percentage to XO gene expression in liver in human subjects of at least 20%, 30%, 40%, 50%, 60%, 70%, 80%, 90%, or 95% in vivo. In some embodiments, under the siRNA concentration of 3 mg/kg, the inhibition percentage of the siRNA conjugate provided by the present disclosure to XO mRNA expression in mice is between 70.9% and 76.2%.

In some embodiments, the siRNA, the pharmaceutical composition or the siRNA conjugate provided by the present disclosure exhibits no significant off-target effect. An off-target effect may be, for example, inhibition on normal expression of a gene which is not the target gene. It is considered insignificant if the binding/inhibition of off-target gene expression is at a level of lower than 50%, 40%, 30%, 20%, or 10% of the on-target effect.

In this way, it is indicated that the siRNA, the pharmaceutical composition and the siRNA conjugate provided by the present disclosure can inhibit the expression of XO gene, can effectively treat and/or prevent abnormal uric acid metabolism or the disease or physiological condition caused by abnormal uric acid metabolism, and have good application prospects.

Other features and advantages of the present disclosure will be described in detail in the detailed description section that follows.

DETAILED DESCRIPTION OF THE INVENTION

Figure 1A:
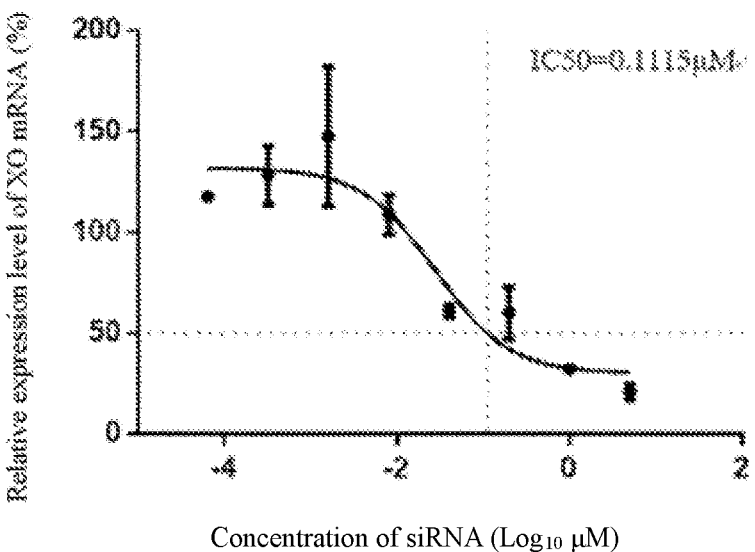
FIGS. 1A-1F are dose-response curves fitted according to relative expression levels of XO mRNA in CAL-27 cells in vitro after transfection of different siRNAs.
Figure 1B:
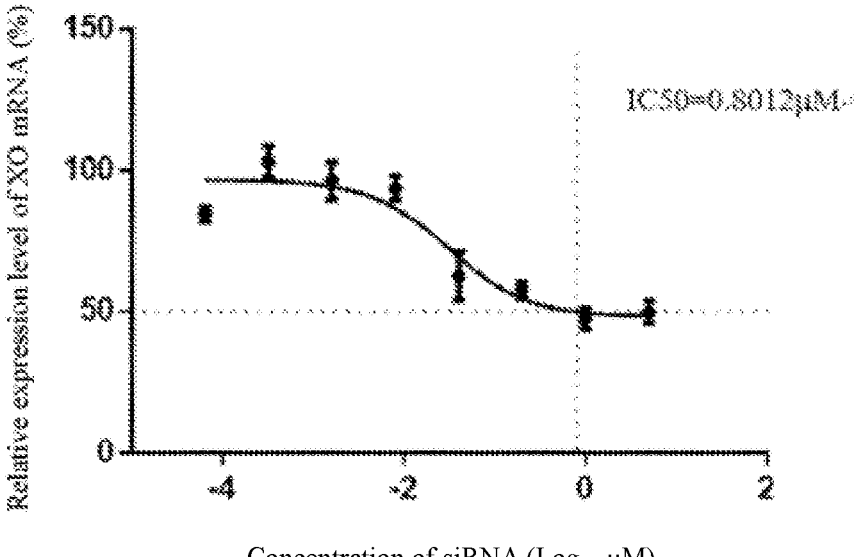
Figure 1C:
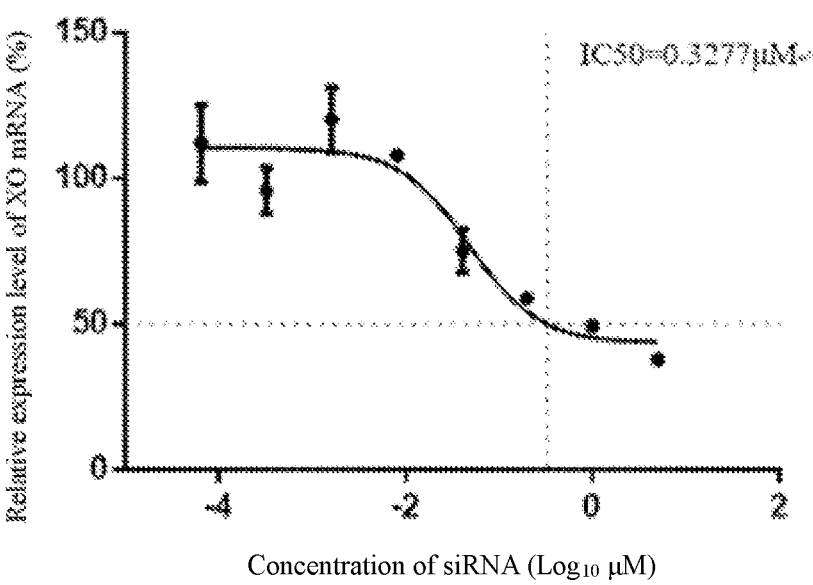
Figure 1D:
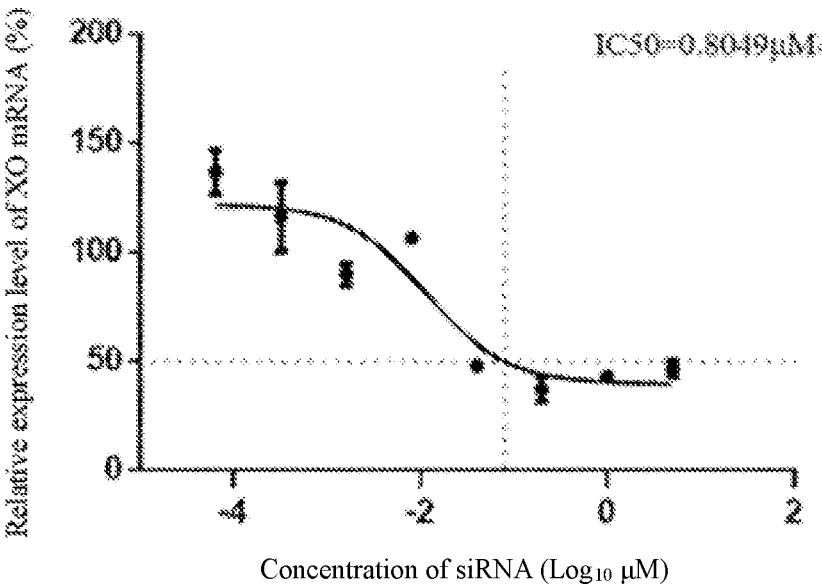
Figure 1E:
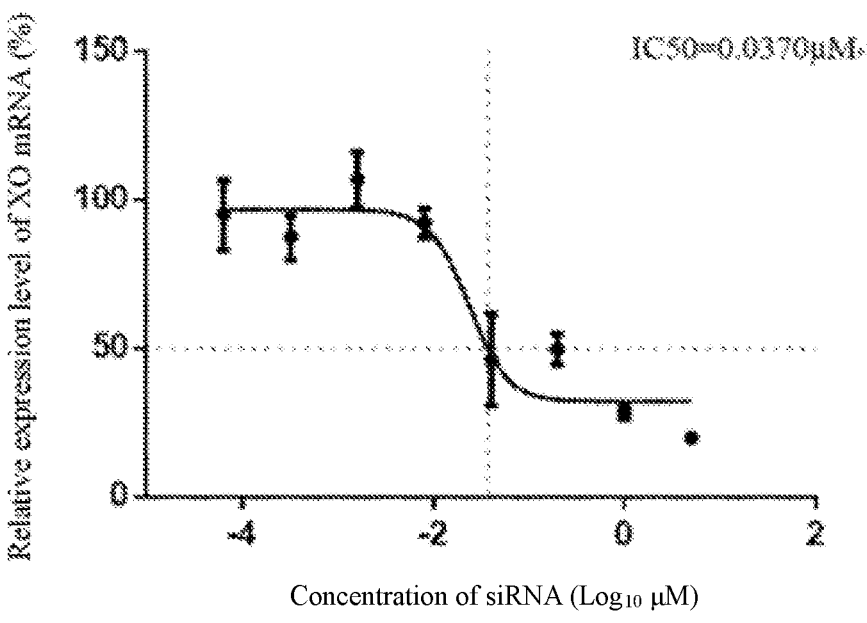
Figure 1F:
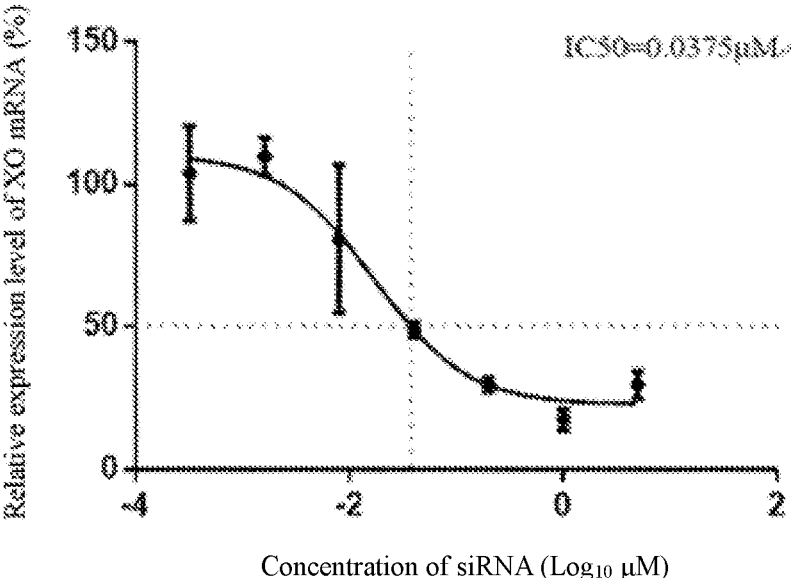

The specific embodiments of the present disclosure are described in detail as below. It should be understood that the specific embodiments described herein are only for the purpose of illustration and explanation of the present disclosure and are not intended to limit the present disclosure.

In the present disclosure, XO mRNA refers to the mRNA with the sequence shown in Genbank registration number NM_000379.3. Furthermore, unless otherwise stated, the term "target gene" used in the present disclosure refers to a gene capable of transcribing the above XO mRNA, and the term "target mRNA" refers to the above XO mRNA.

Definitions

In the context of the present disclosure, unless otherwise specified, capital letters C, G, U, and A indicate the base composition of the nucleotides; the lowercase m indicates that the nucleotide adjacent to the left side of the letter m is a methoxy modified nucleotide; the lowercase f indicates that the nucleotide adjacent to the left side of the letter f is a fluoro modified nucleotide; the lowercase letter s indicates that the two nucleotides adjacent to the left and right of the letter s are linked by phosphorothioate; P1 represents that the nucleotide adjacent to the right side of P1 is a 5'-phosphate nucleotide or a 5'-phosphate analogue modified nucleotide, the letter combination VP represents that the nucleotide adjacent to the right side of the letter combination VP is a vinyl phosphate modified nucleotide, the letter combination Ps represents that the nucleotide adjacent to the right side of the letter combination Ps is a phosphorothioate modified nucleotide, and the capital letter P represents that the nucleotide adjacent to the right side of the letter P is a 5'-phosphate nucleotide.

In the context of the present disclosure, the "fluoro modified nucleotide" refers to a nucleotide formed by substituting a 2'-hydroxy of a ribose group of the nucleotide with a fluoro, and the "non-fluoro modified nucleotide" refers to a nucleotide formed by substituting the 2'-hydroxy of the ribose group of the nucleotide with a non-fluoro group, or a nucleotide analogue. The "nucleotide analogue" refers to a group that can replace a nucleotide in a nucleic acid, while structurally differs from an adenine ribonucleotide, a guanine ribonucleotide, a cytosine ribonucleotide, a uracil ribonucleotide or a thymidine deoxyribonucleotide, such as an isonucleotide, a bridged nucleic acid (BNA)

nucleotide or an acyclic nucleotide. The "methoxy modified nucleotide" refers to a nucleotide formed by substituting the 2'-hydroxy of the ribose group with a methoxy group.

In the context of the present disclosure, expressions "complementary" and "reverse complementary" can be interchangeably used, and have a well-known meaning in the art, namely, the bases in one strand are complementarily paired with those in the other strand of a double-stranded nucleic acid molecule. In DNA, a purine base adenine (A) is always paired with a pyrimidine base thymine (T) (or uracil (U) in RNAs); and a purine base guanine (G) is always paired with a pyrimidine base cytosine (C). Each base pair comprises a purine and a pyrimidine. While adenines in one strand are always paired with thymines (or uracils) in another strand, and guanines are always paired with cytosines, these two strands are considered as being complementary each other; and the sequence of a strand may be deduced from the sequence of its complementary strand. Correspondingly, a "mispairing" means that in a double-stranded nucleic acid, the bases at corresponding sites are not presented in a manner of being complementarily paired.

In the context of the present disclosure, unless otherwise specified, "basically reverse complementary" means that there are no more than 3 base mispairings between two nucleotide sequences. "Substantially reverse complementary" means that there is no more than 1 base mispairing between two nucleotide sequences. "Completely complementary" means that there is no based mispairing between two nucleotide sequences.

In the context of the present disclosure, when a nucleotide sequence has "nucleotide difference" from another nucleotide sequence, the bases of the nucleotides at the same position therebetween are changed. For example, if a nucleotide base in the second sequence is A and the nucleotide base at the same position in the first sequence is U, C, G or T, these two nucleotide sequences are considered as having a nucleotide difference at this position. In some embodiments, if a nucleotide at a position is replaced with an abasic nucleotide or a nucleotide analogue, it is also considered that there is a nucleotide difference at the position.

In the context of the present disclosure, particularly in the description of the method for preparing the siRNA, the pharmaceutical composition or the siRNA conjugate of the present disclosure, unless otherwise specified, the nucleoside monomer refers to, according to the kind and sequence of the nucleotides in the siRNA or siRNA conjugate to be prepared, unmodified or modified RNA phosphoramidites used in a solid phase phosphoramidite synthesis (the RNA phosphoramidites are also called as Nucleoside phosphoramidites elsewhere). Solid phase phosphoramidite synthesis is a well-known method used in RNA synthesis to those skilled in the art. Nucleoside monomers used in the present disclosure can all be commercially available.

In the context of the present disclosure, unless otherwise stated, "conjugating" refers to two or more chemical moieties each with specific function being linked to each other via a covalent linkage. Correspondingly, a "conjugate" refers to a compound formed by covalent linkage of individual chemical moieties. Further, an "siRNA conjugate" represents a compound formed by covalently linking one or more chemical moieties with specific functions to siRNA. Hereinafter, the siRNA conjugate of the present disclosure is sometimes abbreviated as "conjugate". The siRNA conjugate should be understood according to the context as the generic term of the siRNA conjugates or the generic term of the siRNA conjugates as shown by Formula (305) and Formula (307), or the siRNA conjugates as shown by Formula (305), Formula (307), and Formula (308). In the context of the present disclosure, a "conjugating molecule" should be understood as a specific compound capable of being conjugated to an siRNA via reactions, thus finally forming the siRNA conjugate of the present disclosure.

As used herein, "optional" or "optionally" means that the subsequently described event or condition may or may not occur, and that the description includes instances wherein the event or condition may or may not occur. For example, "optionally substituted" "alkyl" encompasses both "alkyl" and "substituted alkyl" as defined below. Those skilled in the art would understand, with respect to any group containing one or more substituents, that such groups are not intended to introduce any substitution or substitution patterns that are sterically impractical, synthetically infeasible and/or inherently unstable.

As used herein, "alkyl" refers to straight chain and branched chain having the indicated number of carbon atoms, usually 1 to 20 carbon atoms, for example 1 to 10 carbon atoms, such as 1 to 8 or 1 to 6 carbon atoms. For example, $C_1$-$C_6$ alkyl encompasses both straight and branched chain alkyl of 1 to 6 carbon atoms. When naming an alkyl residue having a specific number of carbon atoms, all branched and straight chain forms having that number of carbon atoms are intended to be encompassed; thus, for example, "butyl" is meant to include n-butyl, sec-butyl, isobutyl and t-butyl; and "propyl" includes n-propyl and isopropyl. Alkylene is a subset of alkyl, referring to the same residues as alkyl, but having two attachment positions.

As used herein, "alkenyl" refers to an unsaturated branched or linear alkyl having at least one carbon-carbon double bond which is obtained by respectively removing one hydrogen molecule from two adjacent carbon atoms of the parent alkyl. The group may be in either cis or trans configuration of the double bond. Typical alkenyl groups include, but not limited to, ethenyl; propenyls such as prop-1-en-1-yl, prop-1-en-2-yl, prop-2-en-1-yl (allyl), and prop-2-en-2-yl; and butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, and the like. In certain embodiments, an alkenyl group has 2 to 20 carbon atoms, and in other embodiments, 2 to 10, 2 to 8, or 2 to 6 carbon atoms. Alkenylene is a subset of alkenyl, referring to the same residues as alkenyl, but having two attachment positions.

As used herein, "alkynyl" refers to an unsaturated branched or linear alkyl having at least one carbon-carbon triple bond which is obtained by respectively removing two hydrogen molecules from two adjacent carbon atoms of the parent alkyl. Typical alkynyl groups include, but not limited to, ethynyl; propynyls such as prop-1-yn-1-yl, and prop-2-yn-1-yl; and butynyls such as but-1-yn-1-yl, but-1-yn-3-yl, but-3-yn-1-yl, and the like. In certain embodiments, an alkynyl group has 2 to 20 carbon atoms, and in other embodiments, 2 to 10, 2 to 8, or 2 to 6 carbon atoms. Alkynylene is a subset of alkynyl, referring to the same residues as alkynyl, but having two attachment positions.

As used herein, "alkoxy" refers to an alkyl group of the indicated number of carbon atoms attached through an oxygen bridge, such as, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. An alkoxy usually has 1 to 10, 1 to 8, 1 to 6, or 1 to 4 carbon atoms attached through oxygen bridge.

As used herein, "aryl" refers to a group derived from an aromatic monocyclic or multicyclic hydrocarbon ring system by removing a hydrogen atom from a ring carbon atom. The aromatic monocyclic or multicyclic hydrocarbon ring system contains only hydrogen and 6 to 18 carbon atoms, wherein at least one ring in the ring system is fully unsaturated, i.e., containing a cyclic, delocalized $(4n+2)\pi$-electron system in accordance with the Hückel theory. Aryl groups include, but not limited to, phenyl, fluorenyl, naphthyl and the like. Arylene is a subset of aryl, referring to the same residues as aryl, but having two attachment positions.

As used herein, "halo substituent" or "halogen" refers to fluoro, chloro, bromo, and iodo, and the term "halogen" includes fluorine, chlorine, bromine, or iodine.

As used herein, "haloalkyl" refers to the alkyl as defined above with the specified number of carbon atoms being substituted with one or more halogen atoms, up to the maximum allowable number of halogen atoms. Examples of haloalkyl include, but not limited to, trifluoromethyl, difluoromethyl, 2-fluoroethyl, and pentafluoroethyl.

"Heterocyclyl" refers to a stable 3- to 18-membered non-aromatic ring radical that comprises 2-12 carbon atoms and 1-6 heteroatoms selected from nitrogen, oxygen or sulfur. Unless stated otherwise in the description, heterocyclyl is a monocyclic, bicyclic, tricyclic, or tetracyclic ring system, which may include fused or bridged ring systems. The heteroatoms in the heterocyclyl may be optionally oxidized. One or more nitrogen atoms, if present, are optionally quaternized. The heterocyclyl is partially or fully saturated. The heterocyclyl may be linked to the rest of the molecule through any atom of the ring. Examples of such heterocyclyl include, but not limited to, dioxanyl, thienyl[1,3]disulfonyl, decahydroisoquinolyl, imidazolinyl, imidazolidinyl, isothiazolidinyl, isoxazolidinyl, morpholinyl, octahydroindolyl, octahydroisoindolyl, 2-oxapiperazinyl, 2-oxapiperidinyl, 2-oxapyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

"Heteroaryl" refers to a group derived from a 3- to 18-membered aromatic ring radical that comprises 2 to 17 carbon atoms and 1 to 6 heteroatoms selected from nitrogen, oxygen and sulfur. As used herein, the heteroaryl may be a monocyclic, bicyclic, tricyclic or tetracyclic ring system, wherein at least one ring in the ring system is fully unsaturated, i.e., containing a cyclic, delocalized $(4n+2)\pi$-electron system in accordance with the Hückel theory. The heteroaryl includes fused or bridged ring systems. The heteroatoms in the heteroaryl are optionally oxidized. One or more nitrogen atoms, if present, are optionally quaternized. The heteroaryl may be linked to the rest of the molecule through any atom of the ring. Examples of such heteroaryl include, but not limited to, azepinyl, acridinyl, benzimidazolyl, benzindolyl, 1,3-benzodioxazolyl, benzofuranyl, benzoxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl, benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothienyl, furanyl, furanonyl, furo[3,2-c]pyridinyl, 5,6,7,8,9,10-hexahydrocycloocta[d] pyrimidinyl, 5,6,7,8,9,10-hexahydrocycloocta[d]pyridazinyl, 5,6,7,
8,9,10-hexahydrocycloocta[d]pyridinyl, isothiazolyl,
imidazolyl, indazolyl, indolyl, isoindolyl, indolinyl, isoin-
dolinyl, isoquinolyl, indolizinyl, isoxazolyl, 5,8-methano-5,
6,7,8-tetrahydroquinazolinyl, naphthyridinyl, 1,6-naphthyri-
dinonyl, oxadiazolyl, 2-oxoazepinyl, oxazolyl, oxiranyl, 5,6,
6a,7,8,9,10,10a-octahydrobenzo[h]quinazolinyl, 1-phenyl-
1H-pyrrolyl, phenazinyl, phenothiazinyl, phenoxazinyl,
phthalazinyl, pteridinyl, purinyl, pyrrolyl, pyrazolyl, pyra-
zolo[3,4-d]pyrimidinyl, pyridinyl, pyrido[3,2-d]pyrimidi-
nyl, pyrido[3,4-d]pyrimidinyl, pyrazinyl, pyrimidinyl,
pyridazinyl, pyrrolyl, quinazolinyl, quinoxalinyl, quinolinyl,
tetrahydroquinolinyl, 5,6,7,8-tetrahydroquinazolinyl, 5,6,7,
8-tetrahydrobenzo[4,5]thieno[2,3-d]pyrimidinyl, 6,7,8,9-
tetrahydro-5H-cyclohepta[4,5]thieno[2,3-d]pyrimidinyl,
5,6,7,8-tetrahydropyrido[4,5-c]pyridazinyl, thiazolyl, thia-
diazolyl, triazolyl, tetrazolyl, triazinyl, thieno[2,3-d]pyrim-
idinyl, thieno[3,2-d]pyrimidinyl, thieno[2,3-c]pridinyl, and
thiophenyl/thienyl.

Various hydroxy protecting groups may be used in the
present disclosure. In general, protecting groups render
chemical functionalities inert to specific reaction conditions,
and may be attached to and removed from such function-
alities in a molecule without substantially damaging the
remainder of the molecule. Representative hydroxy protect-
ing groups are disclosed in Tetrahedron 1992, 48, 2223-2311
written by Beaucage, et al., and also in Greene and Wuts,
Protective Groups in Organic Synthesis, Chapter 2, 2d ed,
John Wiley & Sons, New York, 1991, each of which is
hereby incorporated by reference in their entirety. In some
embodiments, the protecting group is stable under basic
conditions but can be removed under acidic conditions. In
some embodiments, non-exclusive examples of the hydroxy
protecting groups used herein include dimethoxytrityl
(DMT), monomethoxytrityl, 9-phenylxanthen-9-yl (Pixyl),
or 9-(p-methoxyphenyl)xanthen-9-yl (Mox). In some
embodiments, non-exclusive examples of the hydroxy pro-
tecting groups used herein include Tr(trityl), MMTr(4-
methoxytrityl), DMTr(4,4'-dimethoxytrityl), or TMTr(4,4',
4''-trimethoxytrityl).

The term "subject", as used herein, refers to any animal,
e.g., mammal or marsupial. The subject of the present
disclosure includes, but not limited to, human, non-human
primate (e.g., rhesus or other kinds of macaque), mouse, pig,
horse, donkey, cow, sheep, rat or any kind of poultry.

As used herein, "treatment" refers to a method for obtain-
ing advantageous or desired result, including but not limited
to, therapeutic benefit. "Therapeutic benefit" means eradi-
cation or improvement of potential disorder to be treated.
Moreover, the therapeutic benefit is achieved by eradicating
or ameliorating one or more of physiological symptoms
associated with the potential disorder such that an improve-
ment is observed in the subject, notwithstanding that the
subject may still be afflicted with the potential disorder.

As used herein, "prevention" refers to a method for
obtaining advantageous or desired result, including but not
limited to, prophylactic benefit. For obtaining the "prophy-
lactic benefit", the siRNA, the siRNA conjugate or the
pharmaceutical composition may be administered to the
subject at risk of developing a particular disease, or to the
subject reporting one or more physiological symptoms of a
disease, even though the diagnosis of this disease may not
have been made.

In one aspect, the present disclosure provides first to
twelfth siRNAs capable of inhibiting expression of an XO
gene. The siRNAs will be described in detail hereinafter.

The siRNA of the present disclosure comprises nucleo-
tides as basic structural units. It is well-known to those
skilled in the art that the nucleotide comprises a phosphate
group, a ribose group and a base. Detailed illustrations
relating to such groups are omitted herein.

The First siRNA

According to the present disclosure, the siRNA may be
the first siRNA.

The first siRNA comprises a sense strand and an antisense
strand. Each nucleotide in the first siRNA is independently
a modified or unmodified nucleotide, wherein the sense
strand comprises a segment of nucleotide sequence I, the
antisense strand comprises a segment of nucleotide sequence
II, and the nucleotide sequence I and the nucleotide
sequence II are at least partly reverse complementary to
form a double-stranded region, wherein the nucleotide
sequence I has the same length and no more than three
nucleotide differences from the nucleotide sequence shown
in SEQ ID NO: 1; and the nucleotide sequence II has the
same length and no more than three nucleotide differences
from the nucleotide sequence shown in SEQ ID NO: 2:

$$\text{(SEQ ID NO: 1)}$$
$$5'-\text{GAGAUGAAGUUCAAGAAUZ}_1\text{-}3';$$

$$\text{(SEQ ID NO: 2)}$$
$$5'-\text{Z}_2\text{AUUCUUGAACUUCAUCUC-}3',$$

wherein, $Z_1$ is A, $Z_2$ is U, the nucleotide sequence I
comprises a nucleotide $Z_3$ at a corresponding site to $Z_1$, the
nucleotide sequence II comprises a nucleotide $Z_4$ at a cor-
responding site to $Z_2$, and $Z_4$ is the first nucleotide from the
5' terminal of the antisense strand.

In this context, the term "corresponding site" means being
at the same site in the nucleotide sequence by counting from
the same terminal of the nucleotide sequence. For example,
the first nucleotide at the 3' terminal of the nucleotide
sequence I is a nucleotide at the corresponding site to the
first nucleotide at the 3' terminal of SEQ ID NO: 1.

In some embodiments, the sense strand exclusively com-
prises the nucleotide sequence I, and the antisense strand
exclusively comprises the nucleotide sequence II.

In some embodiments, the nucleotide sequence I has no
more than one nucleotide difference from the nucleotide
sequence shown in SEQ ID NO: 1, and/or the nucleotide
sequence II has no more than one nucleotide difference from
the nucleotide sequence shown in SEQ ID NO: 2.

In some embodiments, the nucleotide difference between
the nucleotide sequence II and the nucleotide sequence
shown in SEQ ID NO: 2 comprises a difference at the site
of $Z_4$, and $Z_4$ is selected from A, C or G. In some embodi-
ments, the nucleotide difference is a difference at the site of
$Z_4$, and $Z_4$ is selected from A, C or G. In some embodiments,
$Z_3$ is a nucleotide complementary to $Z_4$. The siRNAs having
the above nucleotide difference has higher ability to inhibit
the target mRNA, and these siRNAs are also within the
scope of the present disclosure.

In some embodiments, the nucleotide sequence I is basi-
cally reverse complementary, substantially reverse comple-
mentary, or completely reverse complementary to the
nucleotide sequence II. The basically reverse complemen-
tary refers to no more than three base mispairings between
two nucleotide sequences; the substantially reverse comple-
mentary refers to no more than one base mispairing between
two nucleotide sequences; and the completely reverse
complementary refers to no base mispairing between two
nucleotide sequences.

13

14

In some embodiments, the nucleotide sequence I is the nucleotide sequence shown in SEQ ID NO: 3, and the nucleotide sequence II is the nucleotide sequence shown in SEQ ID NO: 4:

(SEQ ID NO: 3)
5'-GAGAUGAAGUUCAAGAAUZ$_3$-3';

(SEQ ID NO: 4)
5'-Z$_4$AUUCUUGAACUUCAUCUC-3', wherein, Z$_4$ is the first nucleotide from 5' terminal of the antisense strand; Z$_4$ is selected from A, U, G or C; and Z$_3$ is a nucleotide complementary to Z$_4$; and in some embodiments, Z$_3$ is A, and Z$_4$ is U.

Moreover, lengths of the sense strand and the antisense strand are the same or different, the length of the sense strand is 19-23 nucleotides, and the length of the antisense strand is 19-26 nucleotides. In this way, a length ratio of the sense strand to the antisense strand of the siRNA provided by the present disclosure may be 19/19, 19/20, 19/21, 19/22, 19/23, 19/24, 19/25, 19/26, 20/20, 20/21, 20/22, 20/23, 20/24, 20/25, 20/26, 21/20, 21/21, 21/22, 21/23, 21/24, 21/25, 21/26, 22/20, 22/21, 22/22, 22/23, 22/24, 22/25, 22/26, 23/20, 23/21, 23/22, 23/23, 23/24, 23/25 or 23/26. In some embodiments, the length ratio of the sense strand to the antisense strand of the siRNA is 19/21, 21/23 or 23/25.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. In some embodiments, the nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 1 in the target mRNA and having the same length as the nucleotide sequence IV.

In some embodiments, the nucleotide sequence III and the nucleotide sequence IV both have a length of one nucleotide. The base of the nucleotide sequence III is U, and the base of the nucleotide sequence IV is A; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is UU, and the base composition of the nucleotide sequence IV is AA; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is AUU, and the base composition of the nucleotide sequence IV is AAU; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is CAUU, and the base composition of the nucleotide sequence IV is AAUG; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is UU, and the base composition of the nucleotide sequence IV is AA; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Second siRNA

According to the present disclosure, the siRNA may be the second siRNA.

The second siRNA comprises a sense strand and an antisense strand. Each nucleotide in the second siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 61; and the nucleotide sequence II has the same length and no more than three nucleotide differences from the nucleotide sequence shown in SEQ ID NO: 62:

(SEQ ID NO: 61)
5'-CAUAACUGGAAUUUGUAAZ$_5$-3';

(SEQ ID NO: 62)
5'-Z$_6$UUACAAAUUCCAGUUAUG-3', wherein, Z$_5$ is U, Z$_6$ is A, the nucleotide sequence I comprises a nucleotide Z$_7$ at a corresponding site to Z$_5$, the nucleotide sequence II comprises a nucleotide Z$_8$ at a corresponding site to Z$_6$, and Z$_8$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 61, and/or the nucleotide sequence II has no more than one nucleotide difference from the nucleotide sequence shown in SEQ ID NO: 62.

In some embodiments, the nucleotide difference between the nucleotide sequence II and the nucleotide sequence shown in SEQ ID NO: 62 comprises a difference at the site of Z$_8$, and Z$_8$ is selected from U, C or G. In some embodiments, the nucleotide difference is a difference at the site of Z$_8$, and Z$_8$ is selected from U, C or G. In some embodiments, Z$_7$ is a nucleotide complementary to Z$_8$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 63, and the nucleotide sequence II is the nucleotide sequence shown in SEQ ID NO: 64:

(SEQ ID NO: 63)

5'-CAUAACUGGAAUUUGUAAZ$_7$-3';

(SEQ ID NO: 64)

5'-Z$_8$UUACAAAUUCCAGUUAUG-3', wherein, $Z_8$ is the first nucleotide from 5' terminal of the antisense strand; $Z_8$ is selected from A, U, G or C; and $Z_7$ is a nucleotide complementary to $Z_8$; and in some embodiments, $Z_7$ is U, and $Z_8$ is A.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 61 in the target mRNA and having the same length as the nucleotide sequence IV.

In some embodiments, the nucleotide sequence III and the nucleotide sequence IV both have a length of one nucleotide. The base of the nucleotide sequence III is A, and the base of the nucleotide sequence IV is U; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is AA, and the base composition of the nucleotide sequence IV is UU; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is UAA, and the base composition of the nucleotide sequence IV is UUA; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is GUAA, and the base composition of the nucleotide sequence IV is UUAC; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is AA, and the base composition of the nucleotide sequence IV is UU; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Third siRNA

According to the present disclosure, the siRNA may be the third siRNA.

The third siRNA comprises a sense strand and an antisense strand. Each nucleotide in the third siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 121; and the nucleotide sequence II has the same length and no more than three nucleotide differences from the nucleotide sequence shown in SEQ ID NO: 122:

(SEQ ID NO: 121)

5'-CAUUAUCACAAUUGAGGAZ$_9$-3';

(SEQ ID NO: 122)

5'-Z$_{10}$UCCUCAAUUGUGAUAAUG-3', wherein, $Z_9$ is U, $Z_{10}$ is A, the nucleotide sequence I comprises a nucleotide $Z_{11}$ at a corresponding site to $Z_9$, the nucleotide sequence II comprises a nucleotide $Z_{12}$ at a corresponding site to $Z_{10}$, and $Z_{12}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 121, and/or the nucleotide sequence II has no more than one nucleotide difference from the nucleotide sequence shown in SEQ ID NO: 122.

In some embodiments, the nucleotide difference between the nucleotide sequence II and the nucleotide sequence shown in SEQ ID NO: 122 comprises a difference at the site of $Z_{12}$, and $Z_{12}$ is selected from U, C or G. In some embodiments, the nucleotide difference is a difference at the site of $Z_{12}$, and $Z_{12}$ is selected from U, C or G. In some embodiments, $Z_{11}$ is a nucleotide complementary to $Z_{12}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 123, and the nucleotide sequence II is the nucleotide sequence shown in SEQ ID NO: 124:

(SEQ ID NO: 123)

5'-CAUUAUCACAAUUGAGGAZ$_{11}$-3';

(SEQ ID NO: 124)

5'-Z$_{12}$UCCUCAAUUGUGAUAAUG-3', wherein, $Z_{12}$ is the first nucleotide from 5' terminal of the antisense strand; $Z_{12}$ is selected from A, U, G or C; and $Z_{11}$ is a nucleotide complementary to $Z_{12}$; and in some embodiments, $Z_{11}$ is U, and $Z_{12}$ is A.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 121 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is C, and the base of the nucleotide sequence IV is G; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is GC, and the base composition of the nucleotide sequence IV is GC; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is AGC, and the base composition of the nucleotide sequence IV is GCU; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is CAGC, and the base composition of the nucleotide sequence IV is GCUG; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is GC, and the base composition of the nucleotide sequence IV is GC; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Fourth siRNA

According to the present disclosure, the siRNA may be the fourth siRNA.

The fourth siRNA comprises a sense strand and an antisense strand. Each nucleotide in the fourth siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 181; and the nucleotide sequence II has the same length and no more than three nucleotide differences from the nucleotide sequence shown in SEQ ID NO: 182:

$$\text{(SEQ ID NO: 181)}$$
$$\text{5'-GGAUCUCUCUCAGAGUAUZ}_{13}\text{-3';}$$

$$\text{(SEQ ID NO: 182)}$$
$$\text{5'-Z}_{14}\text{AUACUCUGAGAGAGAUCC-3',}$$

wherein, $Z_{13}$ is U, $Z_{14}$ is A, the nucleotide sequence I comprises a nucleotide $Z_{15}$ at a corresponding site to $Z_{13}$, the nucleotide sequence II comprises a nucleotide $Z_{16}$ at a corresponding site to $Z_{14}$, and $Z_{16}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 181, and/or the nucleotide sequence II has no more than one nucleotide difference from the nucleotide sequence shown in SEQ ID NO: 182.

In some embodiments, the nucleotide difference between the nucleotide sequence II and the nucleotide sequence shown in SEQ ID NO: 182 comprises a difference at the site of $Z_{16}$, and $Z_{16}$ is selected from U, C or G. In some embodiments, the nucleotide difference is a difference at the site of $Z_{16}$, and $Z_{16}$ is selected from U, C or G. In some embodiments, $Z_{15}$ is a nucleotide complementary to $Z_{16}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 183, and the nucleotide sequence II is the nucleotide sequence shown in SEQ ID NO: 184:

$$\text{(SEQ ID NO: 183)}$$
$$\text{5'-GGAUCUCUCUCAGAGUAUZ}_{15}\text{-3';}$$

$$\text{(SEQ ID NO: 184)}$$
$$\text{5'-Z}_{16}\text{AUACUCUGAGAGAGAUCC-3',}$$

wherein, $Z_{16}$ is the first nucleotide from 5' terminal of the antisense strand; $Z_{16}$ is selected from A, U, G or C; and $Z_{15}$ is a nucleotide complementary to $Z_{16}$; and in some embodiments, $Z_{15}$ is U, and $Z_{16}$ is A.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 181 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is A, and the base of the nucleotide sequence IV is U; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is CA, and the base composition of the nucleotide sequence IV is UG; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is CCA, and the base composition of the nucleotide sequence IV is UGG; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is CCCA, and the base composition of the nucleotide sequence IV is UGGG; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is CA, and the base composition of the nucleotide sequence IV is UG; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Fifth siRNA

According to the present disclosure, the siRNA may be the fifth siRNA.

The fifth siRNA comprises a sense strand and an antisense strand. Each nucleotide in the fifth siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 241; and the nucleotide sequence II has the same length and no more than three nucleotide differences from the nucleotide sequence shown in SEQ ID NO: 242:

$$\text{(SEQ ID NO: 241)}$$
$$\text{5'-ACAUGGACAACUGCUAUAZ}_{17}\text{-3';}$$

$$\text{(SEQ ID NO: 242)}$$
$$\text{5'-Z}_{18}\text{UAUAGCAGUUGUCCAUGU-3',}$$

wherein, $Z_{17}$ is A, $Z_{18}$ is U, the nucleotide sequence I comprises a nucleotide $Z_{10}$ at a corresponding site to $Z_{17}$, the nucleotide sequence II comprises a nucleotide $Z_{20}$ at a corresponding site to $Z_{18}$, and $Z_{20}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 241, and/or the nucleotide sequence II has no more than one nucleotide difference from the nucleotide sequence shown in SEQ ID NO: 242.

In some embodiments, the nucleotide difference between the nucleotide sequence II and the nucleotide sequence shown in SEQ ID NO: 242 comprises a difference at the site of $Z_{20}$, and $Z_{20}$ is selected from A, C or G. In some embodiments, the nucleotide difference is a difference at the site of $Z_{20}$, and $Z_{20}$ is selected from A, C or G. In some embodiments, $Z_{19}$ is a nucleotide complementary to $Z_{20}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 243, and the nucleotide sequence II is the nucleotide sequence shown in SEQ ID NO: 244:

$$\text{(SEQ ID NO: 243)}$$
$$\text{5'-ACAUGGACAACUGCUAUAZ}_{19}\text{-3';}$$

$$\text{(SEQ ID NO: 244)}$$
$$\text{5'-Z}_{20}\text{UAUAGCAGUUGUCCAUGU-3',}$$

wherein, $Z_{20}$ is the first nucleotide from 5' terminal of the antisense strand; $Z_{20}$ is selected from A, U, G or C; and $Z_{19}$ is a nucleotide complementary to $Z_{20}$; and in some embodiments, $Z_{19}$ is A, and $Z_{20}$ is U.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 241 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is C, and the base of the nucleotide sequence IV is G; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is CC, and the base composition of the nucleotide sequence IV is GG; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is UCC, and the base composition of the nucleotide sequence IV is GGA; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is UUCC, and the base composition of the nucleotide sequence IV is GGAA; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is CC, and the base composition of the nucleotide sequence IV is GG; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Sixth siRNA

According to the present disclosure, the siRNA may be the sixth siRNA.

The sixth siRNA comprises a sense strand and an antisense strand. Each nucleotide in the sixth siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 301; and the nucleotide sequence II has the same length and no more than three nucleotide differences from the nucleotide sequence shown in SEQ ID NO: 302:

$$5'\text{-UAGCAAGCUCUCAGUAUC}Z_{21}\text{-3';} \quad \text{(SEQ ID NO: 301)}$$

$$5'\text{-}Z_{22}\text{GAUACUGAGAGCUUGCUA-3',} \quad \text{(SEQ ID NO: 302)}$$

wherein, $Z_{21}$ is A, $Z_{22}$ is U, the nucleotide sequence I comprises a nucleotide $Z_{23}$ at a corresponding site to $Z_{21}$, the nucleotide sequence II comprises a nucleotide $Z_{24}$ at a corresponding site to $Z_{22}$, and $Z_{24}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 301, and/or the nucleotide sequence II has no more than one nucleotide difference from the nucleotide sequence shown in SEQ ID NO: 302.

In some embodiments, the nucleotide difference between the nucleotide sequence II and the nucleotide sequence shown in SEQ ID NO: 302 comprises a difference at the site of $Z_{24}$, and $Z_{24}$ is selected from A, C or G. In some embodiments, the nucleotide difference is a difference at the site of $Z_{24}$, and $Z_{24}$ is selected from A, C or G. In some embodiments, $Z_{23}$ is a nucleotide complementary to $Z_{24}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 303, and the nucleotide sequence II is the nucleotide sequence shown in SEQ ID NO: 304:

$$5'\text{-UAGCAAGCUCUCAGUAUC}Z_{23}\text{-3';} \quad \text{(SEQ ID NO: 303)}$$

$$5'\text{-}Z_{24}\text{GAUACUGAGAGCUUGCUA-3',} \quad \text{(SEQ ID NO: 304)}$$

wherein, $Z_{24}$ is the first nucleotide from 5' terminal of the antisense strand; $Z_{24}$ is selected from A, U, G or C; and $Z_{23}$ is a nucleotide complementary to $Z_{24}$; and in some embodiments, $Z_{23}$ is A, and $Z_{24}$ is U.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 301 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is C, and the base of the nucleotide sequence IV is G; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is CC, and the base composition of the nucleotide sequence IV is GG; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is GCC, and the base composition of the nucleotide sequence IV is GGC; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is UGCC, and the base composition of the nucleotide sequence IV is GGCA; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is CC, and the base composition of the nucleotide sequence IV is GG; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Seventh siRNA

According to the present disclosure, the siRNA may be the seventh siRNA.

The seventh siRNA comprises a sense strand an antisense strand. Each nucleotide in the seventh siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 361; and the nucleotide sequence II has the same length and no more than three nucleotide differences from the nucleotide sequence shown in SEQ ID NO: 362:

$$5'\text{-AUAAGGUUACUUGUGUUGZ}_{25}\text{-3'};$$
(SEQ ID NO: 361)

$$5'\text{-Z}_{26}\text{CAACACAAGUAACCUUAU-3'},$$
(SEQ ID NO: 362)

wherein, $Z_{25}$ is G, $Z_6$ is C, the nucleotide sequence I comprises a nucleotide $Z_{27}$ at a corresponding site to $Z_{25}$, the nucleotide sequence II comprises a nucleotide $Z_{28}$ at a corresponding site to $Z_{26}$, and $Z_{28}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 361, and/or the nucleotide sequence II has no more than one nucleotide difference from the nucleotide sequence shown in SEQ ID NO: 362.

In some embodiments, the nucleotide difference between the nucleotide sequence II and the nucleotide sequence shown in SEQ ID NO: 362 comprises a difference at the site of $Z_{28}$, and $Z_{28}$ is selected from A, U or G. In some embodiments, the nucleotide difference is a difference at the site of $Z_{28}$, and $Z_{28}$ is selected from A, U or G. In some embodiments, $Z_{27}$ is a nucleotide complementary to $Z_{28}$. The siRNAs having the above nucleotide difference has higher ability to inhibit the target mRNA, and these siRNAs comprising the nucleotide differences are also within the scope of the present disclosure.

In some embodiments, the sense strand exclusively comprises the nucleotide sequence I, and the antisense strand exclusively comprises the nucleotide sequence II.

In some embodiments, the nucleotide sequence I is the nucleotide sequence shown in SEQ ID NO: 363, and the nucleotide sequence II is the nucleotide sequence shown in SEQ ID NO: 364:

$$5'\text{-AUAAGGUUACUUGUGUUGZ}_{27}\text{-3'};$$
(SEQ ID NO: 363)

$$5'\text{-Z}_{28}\text{CAACACAAGUAACCUUAU-3'},$$
(SEQ ID NO: 364)

wherein, $Z_{28}$ is the first nucleotide from 5' terminal of the antisense strand; $Z_{28}$ is selected from A, U, G or C; and $Z_{27}$ is a nucleotide complementary to $Z_{28}$; and in some embodiments, $Z_{27}$ is and $Z_{28}$ is C.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. In some embodiments, the nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 362 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is and the base of the nucleotide sequence IV is C; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is GG, and the base composition of the nucleotide sequence IV is CC; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is AGG, and the base composition of the nucleotide sequence IV is CCU; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is AAGG, and the base composition of the nucleotide sequence IV is CCUU; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is GG, and the base composition of the nucleotide sequence IV is CC; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Eighth siRNA

According to the present disclosure, the siRNA may be the eighth siRNA.

The eighth siRNA comprises a sense strand an antisense strand. Each nucleotide in the eighth siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 421; and the nucleotide sequence II has the same length and no more than three nucleotide differences from the nucleotide sequence shown in SEQ ID NO: 422:

```
                                    (SEQ ID NO: 421)
      5'-GAAAAUCACCUAUGAAGAZ29-3';

(SEQ ID NO: 422)
      5'-Z30UCUUCAUAGGUGAUUUUC-3',
``` wherein, $Z_{29}$ is A, $Z_{30}$ is U, the nucleotide sequence I comprises a nucleotide $Z_{31}$ at a corresponding site to $Z_{29}$, the nucleotide sequence II comprises a nucleotide $Z_{32}$ at a corresponding site to $Z_{30}$, and $Z_{32}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 421, and/or the nucleotide sequence II has no more than one nucleotide difference from the nucleotide sequence shown in SEQ ID NO: 422.

In some embodiments, the nucleotide difference between the nucleotide sequence II and the nucleotide sequence shown in SEQ ID NO: 422 comprises a difference at the site of $Z_{32}$, and $Z_{32}$ is selected from A, C or G. In some embodiments, the nucleotide difference is a difference at the site of $Z_{32}$, and $Z_{32}$ is selected from A, C or G. In some embodiments, $Z_{31}$ is a nucleotide complementary to $Z_{32}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 423, and the nucleotide sequence II is the nucleotide sequence shown in SEQ ID NO: 424:

```
                                    (SEQ ID NO: 423)
      5'-GAAAAUCACCUAUGAAGAZ31-3';

(SEQ ID NO: 424)
      5'-Z32UCUUCAUAGGUGAUUUUC-3',
``` wherein, $Z_{32}$ is the first nucleotide from 5' terminal of the antisense strand; $Z_{32}$ is selected from A, U, G or C; and $Z_{31}$ is a nucleotide complementary to $Z_{32}$; and in some embodiments, $Z_{31}$ is A, and $Z_{32}$ is U.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. In some embodiments, the nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 421 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is U, and the base of the nucleotide sequence IV is A; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is GU, and the base composition of the nucleotide sequence IV is AC; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is GGU, and the base composition of the nucleotide sequence IV is ACC; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is GGGU, and the base composition of the nucleotide sequence IV is ACCC; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is GU, and the base composition of the nucleotide sequence IV is AC; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Ninth siRNA

According to the present disclosure, the siRNA may be the ninth siRNA.

The ninth siRNA comprises a sense strand an antisense strand. Each nucleotide in the ninth siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 481; and the nucleotide sequence II has the same length and no more than three nucleotide differences from the nucleotide sequence shown in SEQ ID NO: 482:

(SEQ ID NO: 481)
5'-GAUGCUAUAAAGAACAACZ$_{33}$-3';

(SEQ ID NO: 482)
5'-Z$_{34}$GUUGUUCUUUAUAGCAUC-3', wherein, Z$_{33}$ is U, Z$_{34}$ is A, the nucleotide sequence I comprises a nucleotide Z$_{35}$ at a corresponding site to Z$_{33}$, the nucleotide sequence II comprises a nucleotide Z$_{36}$ at a corresponding site to Z$_{34}$, and Z$_{36}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 481, and/or the nucleotide sequence II has no more than one nucleotide difference from the nucleotide sequence shown in SEQ ID NO: 482.

In some embodiments, the nucleotide difference between the nucleotide sequence II and the nucleotide sequence shown in SEQ ID NO: 482 comprises a difference at the site of Z$_{36}$, and Z$_{36}$ is selected from U, C or G. In some embodiments, the nucleotide difference is a difference at the site of Z$_{36}$, and Z$_{36}$ is selected from U, C or G. In some embodiments, Z$_{35}$ is a nucleotide complementary to Z$_{36}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 483, and the nucleotide sequence II is the nucleotide sequence shown in SEQ ID NO: 484:

(SEQ ID NO: 483)
5'-GAUGCUAUAAAGAACAACZ$_{35}$-3';

(SEQ ID NO: 484)
5'-Z$_{36}$GUUGUUCUUUAUAGCAUC-3', wherein, Z$_{36}$ is the first nucleotide from 5' terminal of the antisense strand; Z$_{36}$ is selected from A, U, G or C; and Z$_{35}$ is a nucleotide complementary to Z$_{36}$; and in some embodiments, Z$_{35}$ is U, and Z$_{36}$ is A.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 4821 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is G, and the base of the nucleotide sequence IV is C; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is AG, and the base composition of the nucleotide sequence IV is CU; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is GAG, and the base composition of the nucleotide sequence IV is CUC; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is UGAG, and the base composition of the nucleotide sequence IV is CUCA; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is AG, and the base composition of the nucleotide sequence IV is CU; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Tenth siRNA

According to the present disclosure, the siRNA may be the tenth siRNA.

The tenth siRNA comprises a sense strand an antisense strand. Each nucleotide in the tenth siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 541; and the nucleotide sequence II has the same length and no more than three nucleotide differences from the nucleotide sequence shown in SEQ ID NO: 542:

(SEQ ID NO: 541)
5'-GAACAACUCCUUUUAUGGZ$_{37}$-3';

(SEQ ID NO: 542)
5'-Z$_{38}$CCAUAAAAGGAGUUGUUC-3', wherein, Z$_{37}$ is A, Z$_{38}$ is U, the nucleotide sequence I comprises a nucleotide Z$_{39}$ at a corresponding site to Z$_{37}$, the nucleotide sequence II comprises a nucleotide Z$_{40}$ at a corresponding site to Z$_{38}$, and Z$_{40}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 541, and/or the nucleotide sequence II has no more than one nucleotide difference from the nucleotide sequence shown in SEQ ID NO: 542.

In some embodiments, the nucleotide difference between the nucleotide sequence II and the nucleotide sequence shown in SEQ ID NO: 542 comprises a difference at the site of Z$_{40}$, and Z$_{40}$ is selected from A, C or G. In some embodiments, the nucleotide difference is a difference at the site of Z$_{40}$, and Z$_{40}$ is selected from A, C or G. In some embodiments, Z$_{39}$ is a nucleotide complementary to Z$_{40}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 543, and the nucleotide sequence II is the nucleotide sequence shown in SEQ ID NO: 544:

(SEQ ID NO: 543)
5'-GAACAACUCCUUUUAUGGZ$_{39}$-3';

(SEQ ID NO: 544)
5'-Z$_{40}$CCAUAAAAGGAGUUGUUC-3', wherein, Z$_{40}$ is the first nucleotide from 5' terminal of the antisense strand; Z$_{40}$ is selected from A, U, G or C; and Z$_{39}$ is a nucleotide complementary to Z$_{40}$; and in some embodiments, Z$_{39}$ is A, and Z$_{40}$ is U.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 541 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is A, and the base of the nucleotide sequence IV is U; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is AA, and the base composition of the nucleotide sequence IV is UU; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is AAA, and the base composition of the nucleotide sequence IV is UUU; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is UAAA, and the base composition of the nucleotide sequence IV is UUUA; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is AA, and the base composition of the nucleotide sequence IV is UU; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Eleventh siRNA

According to the present disclosure, the siRNA may be the eleventh siRNA.

The eleventh siRNA comprises a sense strand an antisense strand. Each nucleotide in the eleventh siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 601; and the nucleotide sequence II has the same length and no more than three nucleotide differences from the nucleotide sequence shown in SEQ ID NO: 602:

(SEQ ID NO: 601)
5'-CUUGCUCUGAAGUAGAAAZ$_{41}$-3';

(SEQ ID NO: 602)
5'-Z$_{42}$AUUUCUACUUCAGAGCAAG-3', wherein, Z$_{41}$ is U, Z$_{42}$ is A, the nucleotide sequence I comprises a nucleotide Z$_{43}$ at a corresponding site to Z$_{41}$, the nucleotide sequence II comprises a nucleotide Z$_{44}$ at a corresponding site to Z$_{42}$, and Z$_{44}$ is the first nucleotide from the 5' terminal of the antisense strand.

In some embodiments, the sense strand exclusively comprises the nucleotide sequence I, and the antisense strand exclusively comprises the nucleotide sequence II.

In some embodiments, the nucleotide sequence I has no more than one nucleotide difference from the nucleotide sequence shown in SEQ ID NO: 601, and/or the nucleotide sequence II has no more than one nucleotide difference from the nucleotide sequence shown in SEQ ID NO: 602.

In some embodiments, the nucleotide difference between the nucleotide sequence II and the nucleotide sequence shown in SEQ ID NO: 602 comprises a difference at the site of $Z_{44}$, and $Z_{44}$ is selected from U, C or G. In some embodiments, the nucleotide difference is a difference at the site of $Z_{44}$, and $Z_{44}$ is selected from U, C or G. In some embodiments, $Z_{43}$ is a nucleotide complementary to $Z_{44}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 603, and the nucleotide sequence II is the nucleotide sequence shown in SEQ ID NO: 604:

(SEQ ID NO: 603)
5'-CUUGCUCUGAAGUAGAAAZ$_{43}$-3';

(SEQ ID NO: 604)
5'-Z$_{44}$UUUCUACUUCAGAGCAAG-3', wherein, $Z_{44}$ is the first nucleotide from 5' terminal of the antisense strand; $Z_{44}$ is selected from A, U, G or C; and $Z_{43}$ is a nucleotide complementary to $Z_{44}$; and in some embodiments, $Z_{43}$ is U, and $Z_{44}$ is A.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 601 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is and the base of the nucleotide sequence IV is C; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is GG, and the base composition of the nucleotide sequence IV is CC; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is UGG and the base composition of the nucleotide sequence IV is CCA; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is GUGG, and the base composition of the nucleotide sequence IV is CCAC; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is GG, and the base composition of the nucleotide sequence IV is CC; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The Twelfth siRNA

According to the present disclosure, the siRNA may be the twelfth siRNA.

The twelfth siRNA comprises a sense strand an antisense strand. Each nucleotide in the twelfth siRNA is independently a modified or unmodified nucleotide, wherein the sense strand comprises a segment of nucleotide sequence I, the antisense strand comprises a segment of nucleotide sequence II, and the nucleotide sequence I and the nucleotide sequence II are at least partly reverse complementary to form a double-stranded region, wherein the nucleotide sequence I has the same length and no more than three nucleotide differences from the nucleotide sequence shown in SEQ ID NO: 661; and the nucleotide sequence II has the same length and no more than three nucleotide differences from the nucleotide sequence shown in SEQ ID NO: 662:

(SEQ ID NO: 661)
5'-CUUCUUUGCCAUCAAAGAZ$_{45}$-3';

(SEQ ID NO: 662)
5'-Z$_{46}$UCUUUGAUGGCAAAGAAG-3', wherein, $Z_{45}$ is U, $Z_{46}$ is A, the nucleotide sequence I comprises a nucleotide $Z_{47}$ at a corresponding site to $Z_{45}$, the nucleotide sequence II comprises a nucleotide $Z_{48}$ at a corresponding site to $Z_{46}$, and $Z_{48}$ is the first nucleotide from the 5' terminal of the antisense strand.

In some embodiments, the nucleotide sequence I is basically reverse complementary, substantially reverse complementary, or completely reverse complementary to the nucleotide sequence II.

In some embodiments, the nucleotide sequence I has no more than one nucleotide difference from the nucleotide sequence shown in SEQ ID NO: 661, and/or the nucleotide sequence II has no more than one nucleotide difference from the nucleotide sequence shown in SEQ ID NO: 662.

In some embodiments, the nucleotide difference between the nucleotide sequence II and the nucleotide sequence shown in SEQ ID NO: 662 comprises a difference at the site of $Z_{48}$, and $Z_{48}$ is selected from U, C or G. In some embodiments, the nucleotide difference is a difference at the site of $Z_{48}$, and $Z_{48}$ is selected from U, C or G. In some embodiments, $Z_{47}$ is a nucleotide complementary to $Z_{48}$. The siRNAs having the above nucleotide difference has higher ability to inhibit the target mRNA, and these siRNAs comprising the nucleotide differences are also within the scope of the present disclosure.

In some embodiments, the nucleotide sequence I is basically reverse complementary, substantially reverse complementary, or completely reverse complementary to the nucleotide sequence II.

In some embodiments, the nucleotide sequence I is the nucleotide sequence shown in SEQ ID NO: 663, and the nucleotide sequence II is the nucleotide sequence shown in SEQ ID NO: 664:

(SEQ ID NO: 663)
5'-CUUCUUUGCCAUCAAAGAZ₄₇-3';

(SEQ ID NO: 664)
5'-Z₄₈UCUUUGAUGGCAAAGAAG-3', wherein, $Z_{48}$ is the first nucleotide from 5' terminal of the antisense strand; $Z_{48}$ is selected from A, U, G or C; and $Z_{47}$ is a nucleotide complementary to $Z_{48}$; and in some embodiments, $Z_{47}$ is U, and $Z_{48}$ is A.

Moreover, lengths of the sense strand and the antisense strand are the same or different, the length of the sense strand is 19-23 nucleotides, and the length of the antisense strand is 19-26 nucleotides.

In some embodiments, the sense strand further comprises a nucleotide sequence III, the antisense strand further comprises a nucleotide sequence IV, and the nucleotide sequence III and the nucleotide sequence IV each independently have a length of 1-4 nucleotides; the nucleotide sequence III has the same length and is substantially reverse complementary or completely reverse complementary to the nucleotide sequence IV; the nucleotide sequence III is linked to the 5' terminal of the nucleotide sequence I, and the nucleotide sequence IV is linked to the 3' terminal of the nucleotide sequence II. The nucleotide sequence IV is substantially reverse complementary or completely reverse complementary to the nucleotide sequence II, and the nucleotide sequence II refers to the nucleotide sequence adjacent to the 5' terminal of the nucleotide sequence represented by SEQ ID NO: 661 in the target mRNA and having the same length as the nucleotide sequence IV.

In some embodiments, in the direction from 5' to 3', the nucleotide sequence III and the nucleotide sequence IV both have a length of one nucleotide. The base of the nucleotide sequence III is U, and the base of the nucleotide sequence IV is A; in this case, the length ratio of the sense strand to the antisense strand is 20/20; or, the nucleotide sequences III and IV both have a length of two nucleotides, and in the direction from the 5' terminal to the 3' terminal, the base composition of the nucleotide sequence III is AU, and the base composition of the nucleotide sequence IV is AU; in this case, the length ratio of the sense strand to the antisense strand is 21/21; or, the nucleotide sequences III and IV both have a length of three nucleotides, and in the direction from the 5' terminal to the 3' terminal, the base composition of the nucleotide sequence III is UAU, and the base composition of the nucleotide sequence IV is AUA; in this case, the length ratio of the sense strand to the antisense strand is 22/22; or, the nucleotide sequences III and IV both have a length of four nucleotides, and in the direction from the 5' terminal to the 3' terminal, the base composition of the nucleotide sequence III is CUAU, and the base composition of the nucleotide sequence IV is AUAG; in this case, the length ratio of the sense strand to the antisense strand is 23/23. In some embodiments, the nucleotide sequence III and the nucleotide sequence IV have a length of two nucleotides, and in the direction from the 5' terminal to the 3' terminal, the base composition of the nucleotide sequence III is AU, and the base composition of the nucleotide sequence IV is AU; in this case, the length ratio of the sense strand to the antisense strand is 21/21.

In some embodiments, the nucleotide sequence III is completely reverse complementary to the nucleotide sequence IV. Thus, if the base of the nucleotide sequence III is provided, the base of the nucleotide sequence IV is also determined.

The following description of the nucleotide sequence V, the nucleic acid sequence, the nucleotide modification in the siRNA and the modified sequence is applicable to any one of the first siRNA to the twelfth siRNA. That is, unless otherwise specified, the following description of the siRNA should be regarded as describing the first siRNA, the second siRNA, the third siRNA, the fourth siRNA, the fifth siRNA, the sixth siRNA, the seventh siRNA, the eighth siRNA, the ninth siRNA, the tenth siRNA, the eleventh siRNA, and the twelfth siRNA one by one. For example, if no specific siRNA is specified, "the siRNA further comprises a nucleotide sequence V" means "the first siRNA, the second siRNA, the third siRNA, the fourth siRNA, the fifth siRNA, the sixth siRNA, the seventh siRNA, the eighth siRNA, the ninth siRNA, the tenth siRNA, the eleventh siRNA, or the twelfth siRNA further comprises a nucleotide sequence V".

In some embodiments, the sense strand and the antisense strand have different lengths. The nucleotide sequence II further comprises a nucleotide sequence V, which has a length of 1-3 nucleotides and is linked to 3' terminal of the antisense strand, thereby constituting a 3' overhang of the antisense strand. As such, the length ratio of the sense strand to the antisense strand in the siRNA of the present disclosure may be 19/20, 19/21, 19/22, 20/21, 20/22, 20/23, 21/22, 21/23, 21/24, 22/23, 22/24, 22/25, 23/24, 23/25, or 23/26. In some embodiments, the nucleotide sequence V has a length of 2 nucleotides. As such, the length ratio of the sense strand to the antisense strand in the siRNA of the present disclosure may be 19/21, 21/23 or 23/25.

Each nucleotide in the nucleotide sequence V may be any nucleotide. In order to facilitate synthesis and save synthesis cost, the nucleotide sequence V is 2 continuous thymidine deoxyribonucleotides (dTdT) or 2 continuous uracil ribonucleotides (UU); or, in order to improve the affinity of the antisense strand of the siRNA to the target mRNA, the nucleotide sequence V is complementary to the nucleotide (s0029 at the corresponding site of the target mRNA. Therefore, in some embodiments, the length ratio of the sense strand to the antisense strand of the siRNA of the present disclosure is 19/21 or 21/23. In this case, the siRNA of the present disclosure has better silencing activity against target mRNA.

The nucleotide at the corresponding site of the target mRNA refers to one segment of the nucleotide or nucleotide sequence adjacent to the nucleotide sequence I of the target mRNA at the 5' terminal. This segment of nucleotide sequence of the target mRNA is substantially reverse complementary or completely reverse complementary to the nucleotide sequence II, or, is a segment of nucleotide sequence which is substantially reverse complementary or completely reverse complementary to the nucleotide sequence formed by the nucleotide sequence II and the nucleotide sequence IV.

In some embodiments, for the first siRNA, the sense strand of the siRNA comprises the nucleotide sequence shown in SEQ ID NO: 5, and the antisense strand of the siRNA comprises the nucleotide sequence shown in SEQ ID NO: 6;

(SEQ ID NO: 5)
5'-GAGAUGAAGUUCAAGAAUZ$_3$-3';

(SEQ ID NO: 6)
5'-Z$_4$AUUCUUGAACUUCAUCUCAA-3';

or, the sense strand of the siRNA comprises the nucleotide sequence shown in SEQ ID NO: 7, and the antisense strand of the siRNA comprises the nucleotide sequence shown in SEQ ID NO: 8;

(SEQ ID NO: 7)
5'-UUGAGAUGAAGUUCAAGAAUZ$_3$-3';

(SEQ ID NO: 8)
5'-Z$_4$AUUCUUGAACUUCAUCUCAAUG-3';

wherein, $Z_4$ is the first nucleotide from 5' terminal of the antisense strand; $Z_4$ is selected from A, U, G or C; and $Z_3$ is a nucleotide complementary to $Z_4$.

In some embodiments, for the second siRNA, the sense strand of the siRNA comprises the nucleotide sequence shown in SEQ ID NO: 65, and the antisense strand of the siRNA comprises the nucleotide sequence shown in SEQ ID NO: 66:

(SEQ ID NO: 65)
5'-CAUAACUGGAAUUUGUAAZ$_7$-3';

(SEQ ID NO: 66)
5'-Z$_8$UUACAAAUUCCAGUUAUGUU-3', or, the sense strand of the siRNA comprises the nucleotide sequence shown in SEQ ID NO: 67, and the antisense strand of the siRNA comprises the nucleotide sequence shown in SEQ ID NO: 68:

(SEQ ID NO: 67)
5'-AACAUAACUGGAAUUUGUAAZ$_7$-3';

(SEQ ID NO: 68)
5'-Z$_8$UUACAAAUUCCAGUUAUGUUAC-3', wherein, $Z_8$ is the first nucleotide from 5' terminal of the antisense strand; $Z_8$ is selected from A, U, G or C; and $Z_7$ is a nucleotide complementary to $Z_8$.

In some embodiments, for the third siRNA, the sense strand of the siRNA comprises the nucleotide sequence shown in SEQ ID NO: 125, and the antisense strand of the siRNA comprises the nucleotide sequence shown in SEQ ID NO: 126:

(SEQ ID NO: 125)
5'-CAUUAUCACAAUUGAGGAZ$_{11}$-3';

(SEQ ID NO: 126)
5'-Z$_{12}$UCCUCAAUUGUGAUAAUGGC-3', or, the sense strand of the siRNA comprises the nucleotide sequence shown in SEQ ID NO: 127, and the antisense strand of the siRNA comprises the nucleotide sequence shown in SEQ ID NO: 128:

(SEQ ID NO: 127)
5'-GCCAUUAUCACAAUUGAGGAZ$_{11}$-3';

(SEQ ID NO: 128)
5'-Z$_{12}$UCCUCAAUUGUGAUAAUGGCUG-3', wherein, $Z_{12}$ is the first nucleotide from 5' terminal of the antisense strand; $Z_{12}$ is selected from A, U, G or C; and $Z_{11}$ is a nucleotide complementary to $Z_{12}$.

In some embodiments, for the fourth siRNA, the sense strand of the siRNA comprises the nucleotide sequence shown in SEQ ID NO: 185, and the antisense strand of the siRNA comprises the nucleotide sequence shown in SEQ ID NO: 186:

(SEQ ID NO: 185)
5'-GGAUCUCUCUCAGAGUAUZ15-3';

(SEQ ID NO: 186)
5'-Z$_{16}$AUACUCUGAGAGAGAUCCUG-3', or, the sense strand of the siRNA comprises the nucleotide sequence shown in SEQ ID NO: 187, and the antisense strand of the siRNA comprises the nucleotide sequence shown in SEQ ID NO: 188:

(SEQ ID NO: 187)
5'-CAGGAUCUCUCUCAGAGUAUZ$_{15}$-3';

(SEQ ID NO: 188)
5'-Z$_{16}$AUACUCUGAGAGAGAUCCUGGG-3', wherein, $Z_{16}$ is the first nucleotide from 5' terminal of the antisense strand; $Z_{16}$ is selected from A, U, G or C; and $Z_{15}$ is a nucleotide complementary to $Z_{16}$.

In some embodiments, for the fifth siRNA, the sense strand of the siRNA comprises the nucleotide sequence shown in SEQ ID NO: 245, and the antisense strand of the siRNA comprises the nucleotide sequence shown in SEQ ID NO: 246:

(SEQ ID NO: 245)
5'-ACAUGGACAACUGCUAUAZ$_{19}$-3';

(SEQ ID NO: 246)
5'-Z$_{20}$UAUAGCAGUUGUCCAUGUGG-3', or, the sense strand of the siRNA comprises the nucleotide sequence shown in SEQ ID NO: 247, and the antisense strand of the siRNA comprises the nucleotide sequence shown in SEQ ID NO: 248:

(SEQ ID NO: 247)
5'-CCACAUGGACAACUGCUAUAZ$_{19}$-3';

(SEQ ID NO: 248)
5'-Z20UAUAGCAGUUGUCCAUGUGGAA-3', wherein, $Z_{20}$ is the first nucleotide from 5' terminal of the antisense strand; $Z_{20}$ is selected from A, U, G or C; and $Z_{19}$ is a nucleotide complementary to $Z_{20}$.

In some embodiments, for the sixth siRNA, the sense strand of the siRNA comprises the nucleotide sequence shown in SEQ ID NO: 305, and the antisense strand of the siRNA comprises the nucleotide sequence shown in SEQ ID NO: 306:

(SEQ ID NO: 305)
5'-UAGCAAGCUCUCAGUAUCZ$_{23}$-3';

(SEQ ID NO: 306)
5'-Z$_{24}$GAUACUGAGAGCUUGCUAGG-3', or, the sense strand of the siRNA comprises the nucleotide sequence shown in SEQ ID NO: 307, and the antisense strand of the siRNA comprises the nucleotide sequence shown in SEQ ID NO: 308:

(SEQ ID NO: 307)
5'-CCUAGCAAGCUCUCAGUAUCZ$_{23}$-3';

(SEQ ID NO: 308)
5'-Z$_{24}$GAUACUGAGAGCUUGCUAGGCA-3', wherein, $Z_{24}$ is the first nucleotide from 5' terminal of the antisense strand; $Z_{24}$ is selected from A, U, G or C; and $Z_{23}$ is a nucleotide complementary to $Z_{24}$.

In some embodiments, for the seventh siRNA, the sense strand of the siRNA comprises the nucleotide sequence shown in SEQ ID NO: 365, and the antisense strand of the siRNA comprises the nucleotide sequence shown in SEQ ID NO: 366:

(SEQ ID NO: 365)
5'-AUAAGGUUACUUGUGUUGZ$_{27}$-3';

(SEQ ID NO: 366)
5'-Z$_{28}$CAACACAAGUAACCUUAUCC-3';

or, the sense strand of the siRNA comprises the nucleotide sequence shown in SEQ ID NO: 367, and the antisense strand comprises the nucleotide sequence shown in SEQ ID NO: 368;

(SEQ ID NO: 367)
5'-GGAUAAGGUUACUUGUGUUGZ$_{27}$-3';

(SEQ ID NO: 368)
5'-Z$_{28}$CAACACAAGUAACCUUAUCCUU-3', wherein, $Z_{28}$ is the first nucleotide from 5' terminal of the antisense strand; $Z_{28}$ is selected from A, U, G or C; and $Z_{27}$ is a nucleotide complementary to $Z_{28}$.

In some embodiments, for the eighth siRNA, the sense strand of the siRNA comprises the nucleotide sequence shown in SEQ ID NO: 425, and the antisense strand of the siRNA comprises the nucleotide sequence shown in SEQ ID NO: 426:

(SEQ ID NO: 425)
5'-GAAAAUCACCUAUGAAGAZ$_{31}$-3';

(SEQ ID NO: 426)
5'-Z$_{32}$UCUUCAUAGGUGAUUUUCAC-3', or, the sense strand of the siRNA comprises the nucleotide sequence shown in SEQ ID NO: 427, and the antisense strand of the siRNA comprises the nucleotide sequence shown in SEQ ID NO: 428:

(SEQ ID NO: 427)
5'-GUGAAAAUCACCUAUGAAGAZ$_{31}$-3';

(SEQ ID NO: 428)
5'-Z$_{32}$UCUUCAUAGGUGAUUUUCACCC-3', wherein, $Z_{32}$ is the first nucleotide from 5' terminal of the antisense strand; $Z_{32}$ is selected from A, U, G or C; and $Z_{31}$ is a nucleotide complementary to $Z_{32}$.

In some embodiments, for the ninth siRNA, the sense strand of the siRNA comprises the nucleotide sequence shown in SEQ ID NO: 485, and the antisense strand of the siRNA comprises the nucleotide sequence shown in SEQ ID NO: 486:

(SEQ ID NO: 485)
5'-GAUGCUAUAAAGAACAACZ$_{35}$-3';

(SEQ ID NO: 486)
5'-Z$_{36}$GUUGUUCUUUAUAGCAUCCU-3', or, the sense strand of the siRNA comprises the nucleotide sequence shown in SEQ ID NO: 487, and the antisense strand of the siRNA comprises the nucleotide sequence shown in SEQ ID NO: 488:

(SEQ ID NO: 487)
5'-AGGAUGCUAUAAAGAACAACZ$_{35}$-3';

(SEQ ID NO: 488)
5'-Z$_{36}$GUUGUUCUUUAUAGCAUCCUCA-3', wherein, $Z_{36}$ is the first nucleotide from 5' terminal of the antisense strand; $Z_{36}$ is selected from A, U, G or C; and $Z_{35}$ is a nucleotide complementary to $Z_{36}$.

In some embodiments, for the tenth siRNA, the sense strand of the siRNA comprises the nucleotide sequence shown in SEQ ID NO: 545, and the antisense strand of the siRNA comprises the nucleotide sequence shown in SEQ ID NO: 546:

(SEQ ID NO: 545)
5'-GAACAACUCCUUUUAUGGZ$_{39}$-3';

(SEQ ID NO: 546)
5'-Z$_{40}$CCAUAAAAGGAGUUGUUCUU-3', or, the sense strand of the siRNA comprises the nucleotide sequence shown in SEQ ID NO: 547, and the antisense strand of the siRNA comprises the nucleotide sequence shown in SEQ ID NO: 548:

(SEQ ID NO: 547)
5'-AAGAACAACUCCUUUUAUGGZ$_{39}$-3';

(SEQ ID NO: 548)
5'-Z$_{40}$CCAUAAAAGGAGUUGUUCUUUA-3', wherein, $Z_{40}$ is the first nucleotide from 5' terminal of the antisense strand; $Z_{40}$ is selected from A, U, G or C; and $Z_{39}$ is a nucleotide complementary to $Z_{40}$.

In some embodiments, for the eleventh siRNA, the sense strand of the siRNA comprises the nucleotide sequence shown in SEQ ID NO: 605, and the antisense strand of the siRNA comprises the nucleotide sequence shown in SEQ ID NO: 606:

(SEQ ID NO: 605)
5'-CUUGCUCUGAAGUAGAAAZ$_{43}$-3';

(SEQ ID NO: 606)
5'-Z$_{44}$UUUCUACUUCAGAGCAAGCC-3', or, the sense strand of the siRNA comprises the nucleotide sequence shown in SEQ ID NO: 607, and the antisense strand of the siRNA comprises the nucleotide sequence shown in SEQ ID NO: 608:

(SEQ ID NO: 607)
5'-GGCUUGCUCUGAAGUAGAAAZ$_{43}$-3';

(SEQ ID NO: 608)
5'-Z$_{44}$UUUCUACUUCAGAGCAAGCCAC-3', wherein, Z$_{44}$ is the first nucleotide from 5' terminal of the antisense strand; Z$_{44}$ is selected from A, U, G or C; and Z$_{43}$ is a nucleotide complementary to Z$_{44}$.

In some embodiments, for the twelfth siRNA, the sense strand of the siRNA comprises the nucleotide sequence shown in SEQ ID NO: 665, and the antisense strand of the siRNA comprises the nucleotide sequence shown in SEQ ID NO: 666:

(SEQ ID NO: 665)
5'-CUUCUUUGCCAUCAAAGAZ$_{47}$-3';

(SEQ ID NO: 666)
5'-Z$_{48}$UCUUUGAUGGCAAAGAAGAU-3', or, the sense strand of the siRNA comprises the nucleotide sequence shown in SEQ ID NO: 667, and the antisense strand of the siRNA comprises the nucleotide sequence shown in SEQ ID NO: 668:

(SEQ ID NO: 667)
5'-AUCUUCUUUGCCAUCAAAGAZ$_{47}$-3';

(SEQ ID NO: 668)
5'-Z$_{48}$UCUUUGAUGGCAAAGAAGAUAG-3', wherein, Z$_{48}$ is the first nucleotide from 5' terminal of the antisense strand; Z$_{48}$ is selected from A, U, G or C; and Z$_{47}$ is a nucleotide complementary to Z$_{48}$.

In some embodiments, the siRNA of the present disclosure is any one of siXOa1, siXOa2, siXOb1, siXOb2, siXOc1, siXOc2, siXOd1, siXOd2, siXOe1, siXOe2, siXOf1, siXOf2, siXOg1, siXOg2, siXOh1, siXOh2, siXOi1, siXOi2, siXOj1, siXOj2, siXOk1, siXOk2, siXOl1 and siXOl2 listed in Tables 1a-1l.

As described above, the nucleotides in the siRNA of the present disclosure are each independently modified or unmodified nucleotides. In some embodiments, each nucleotide in the siRNA of the present disclosure is an unmodified nucleotide. In some embodiments, some or all nucleotides in the siRNA of the present disclosure are modified nucleotides. Such modifications on the nucleotides would not cause significant decrease or loss of the function of the siRNA conjugate of the present disclosure to inhibit the expression of XO genes.

In some embodiments, the siRNA of the present disclosure comprises at least one modified nucleotide. In the context of the present disclosure, the term "modified nucleotide" employed herein refers to a nucleotide formed by substituting a 2'-hydroxy of a ribose group of a nucleotide with other groups, a nucleotide analogue, or a nucleotide with modified base. Such modified nucleotides would not cause significant decrease or loss of the function of the siRNA to inhibit the expression of genes. For example, the modified nucleotides disclosed in Chemically Modified siRNA: tools and applications. Drug Discov Today, 2008.13 (19-20): p. 842-55 written by J. K. Watts, G F. Deleavey and M. J. Damha may be selected.

In some embodiments, at least one nucleotide in the sense strand or the antisense strand of the siRNA provided by the present disclosure is a modified nucleotide, and/or at least one phosphate is a phosphate group with modified group. In other words, at least a portion of the phosphate group and/or ribose group in phosphate-ribose backbone of at least one single strand in the sense strand and the antisense strand are phosphate group with modified group and/or ribose group with modified group.

In some embodiments, all nucleotides in the sense strand and/or the antisense strand are modified nucleotides. In some embodiments, each nucleotide in the sense strand and the antisense strand of the siRNA provided by the present disclosure is independently a fluoro modified nucleotide or a non-fluoro modified nucleotide.

The inventors of the present disclosure have surprisingly found that the siRNA of the present disclosure has achieved a high degree of balance between the stability in serum and the gene silencing efficiency in animal experiments.

In some embodiments, the fluoro modified nucleotides are located in the nucleotide sequence I and the nucleotide sequence II; and in the direction from 5' terminal to 3' terminal, at least the nucleotides at positions 7, 8 and 9 of the nucleotide sequence I are fluoro modified nucleotides; and in the direction from 5' terminal to 3' terminal, at least the nucleotides at positions 2, 6, 14 and 16 of the nucleotide sequence ii are fluoro modified nucleotides.

In some embodiments, the fluoro modified nucleotides are located in the nucleotide sequence I and the nucleotide sequence II; no more than 5 fluoro modified nucleotides are present in the nucleotide sequence I, and in the direction from 5' terminal to 3' terminal, at least the nucleotides at positions 7, 8 and 9 in the nucleotide sequence I are fluoro modified nucleotides; no more than 7 fluoro modified nucleotides are present in the nucleotide sequence II, and at least the nucleotides at positions 2, 6, 14 and 16 in the nucleotide sequence II are fluoro modified nucleotides.

In some embodiments, in the direction from 5' terminal to 3' terminal, the nucleotides at positions 7, 8 and 9 or 5, 7, 8 and 9 of the nucleotide sequence I in the sense strand are fluoro modified nucleotides, and the nucleotides at the rest of positions in the sense strand are non-fluoro modified nucleotides; and in the direction from 5' terminal to 3' terminal, the nucleotides at positions 2, 6, 14 and 16 or 2, 6, 8, 9, 14 and 16 of the nucleotide sequence II in the antisense strand are fluoro modified nucleotides, and the nucleotides at the rest of positions in the antisense strand are non-fluoro modified nucleotides.

In the context of the present disclosure, a "fluoro modified nucleotide" refers to a nucleotide which is formed by substituting a 2'-hydroxy of a ribose group of a nucleotide with fluoro, which has a structure as shown by Formula (7). A "non-fluoro modified nucleotide", refers to a nucleotide which is formed by substituting a 2'-hydroxy of a ribose group of a nucleotide with a non-fluoro group, or a nucleotide analogue. In some embodiments, each non-fluoro modified nucleotide is independently selected from a nucleotide formed by substituting the 2'-hydroxy of the ribose group of the nucleotide with the non-fluoro group, or the nucleotide analogue.

These nucleotides formed by substituting the 2'-hydroxy of the ribose group with the non fluoro group are well-known to those skilled in the art, and these nucleotides may be selected from one of a 2' alkoxy modified nucleotide, a 2'-substituted alkoxy modified nucleotide, a 2'-alkyl modified nucleotide, a 2'-substituted alkyl modified nucleotide, a 2'-amino modified nucleotide, a 2' substituted amino modified nucleotide and a 2'-deoxy nucleotide.

In some embodiments, the 2'-alkoxy modified nucleotide is a methoxy modified nucleotide (2'-OMe), as shown by Formula (8). In some embodiments, the 2'-substituted alkoxy modified nucleotide is, for example, a 2'-O-methoxy-ethoxy modified nucleotide (2' MOE) as shown by Formula (9). In some embodiments, the 2'-amino modified nucleotide (2'-NH$_2$) is as shown by Formula (10). In some embodiments, the 2'-deoxy nucleotide (DNA) is as shown by Formula (11):

Formula (7)

Formula (8)

Formula (9)

Formula (10)

Formula (11)

The nucleotide analogue refers to a group that can replace a nucleotide in a nucleic acid, while structurally differs from an adenine ribonucleotide, a guanine ribonucleotide, a cyto-sine ribonucleotide, a uracil ribonucleotide or a thymidine deoxyribonucleotide. In some embodiments, the nucleotide analogue may be an isonucleotide, a bridged nucleic acid (referred to as BNA) or an acyclic nucleotide.

The BNA is a nucleotide that is constrained or is not accessible. The BNA may contain a 5-membered ring, 6-membered ring or 7-membered ring bridged structure with a "fixed" C3'-endo sugar puckering. The bridge is typically incorporated at the 2'- and 4'-position of the ribose to afford a 2',4'-BNA nucleotide. In some embodiments, the BNA may be an LNA, an ENA and a cET BNA, wherein the LNA is as shown by Formula (12), the ENA is as shown by Formula (13) and the cET BNA is as shown by Formula (14):

Formula (12)

Formula (13)

Formula (14)

An acyclic nucleotide is a nucleotide in which a ribose ring is opened. In some embodiments, the acyclic nucleotide may be an unlocked nucleic acid (UNA) or a glycerol nucleic acid (GNA), wherein the UNA is as shown by Formula (15), and the GNA is as shown by Formula (16):

Formula (15)

Base,

Formula (16)

Base.

O R

In the Formula (15) and the Formula (16), R is selected from H, OH or alkoxy (O-alkyl).

An isonucleotide is a compound which is formed by that a nucleotide in which a position of a base on a ribose ring alters. In some embodiments, the isonucleotide may be a compound in which the base is transposed from position-1' to position-2' or position-3' on the ribose ring, as shown by Formula (17) or (18).

Formula (17)

R

O

O Base, (Formula (18))

R

O

Base O.

In the compounds as shown by the Formula (17) and Formula (18) above, Base represents a nucleic acid base, such as A, U, G, C or T; and R is selected from H, OH, F or a non-fluoro group described above.

In some embodiments, the nucleotide analogue is selected from one of an isonucleotide, an LNA, an ENA, a cET, a UNA and a GNA. In some embodiments, each non-fluoro modified nucleotide is a methoxy modified nucleotide. In the context of the present disclosure, the methoxy modified nucleotide refers to a nucleotide formed by substituting the 2'-hydroxy of the ribose group with a methoxy group.

In the context of the present disclosure, a "fluoro modified nucleotide", a "2'-fluoro modified nucleotide", a "nucleotide in which 2'-hydroxy of the ribose group is substituted with fluoro" and a "2'-fluororibosyl" have the same meaning, referring to the compound formed by substituting the 2'-hydroxy of the ribose group of the nucleotide with fluoro, having a structure as shown by Formula (7). A "methoxy modified nucleotide", a "2'-methoxy modified nucleotide", a "nucleotide in which 2'-hydroxy of a ribose group is substituted with methoxy" and a "2'-methoxyribosyl" have the same meaning, referring to the compound formed by substituting the 2'-hydroxy of the ribose group of the nucleotide with methoxy, having a structure as shown by Formula (8).

In some embodiments, the siRNA of the present disclosure is an siRNA with the following modifications: in the direction from 5' terminal to 3' terminal, the nucleotides at positions 7, 8 and 9 or 5, 7, 8 and 9 of the nucleotide sequence I in the sense strand are fluoro modified nucleotides, and the nucleotides at the rest of positions in the sense strand are methoxy modified nucleotides; and the nucleotides at positions 2, 6, 14 and 16 or 2, 6, 8, 9, 14 and 16 of the nucleotide sequence II in the antisense strand are fluoro modified nucleotides, and the nucleotides at the rest of positions in the antisense strand are methoxy modified nucleotides.

In some embodiments, the siRNA of the present disclosure is an siRNA with the following modifications: in the direction from 5' terminal to 3' terminal, the nucleotides at positions 5, 7, 8 and 9 of the nucleotide sequence I in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 8, 9, 14 and 16 of the nucleotide sequence II in the antisense strand of the siRNA are fluoro modified nucleotides, and the nucleotides at the rest of positions in the antisense strand of the siRNA are methoxy modified nucleotides;

or, in the direction from 5' terminal to 3' terminal, the nucleotides at positions 5, 7, 8 and 9 of the nucleotide sequence I in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 14 and 16 of the nucleotide sequence II in the antisense strand of the siRNA are fluoro modified nucleotides, and the nucleotides at the rest of positions in the antisense strand of the siRNA are methoxy modified nucleotides;

or, in the direction from 5' terminal to 3' terminal, the nucleotides at positions 7, 8 and 9 of the nucleotide sequence I in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 14 and 16 of the nucleotide sequence II in the antisense strand of the siRNA are fluoro modified nucleotides, and the nucleotides at the rest of positions in the antisense strand of the siRNA are methoxy modified nucleotides.

In some embodiments, the siRNA provided by the present disclosure is any one of siXOa1-M1, siXOa1-M2, siXOa1-M3, siXOa2-M1, siXOa2-M2, siXOa2-M3, siXOb1-M1, siXOb1-M2, siXOb1-M3, siXOb2-M1, siXOb2-M2, siXOb2-M3, siXOc1-M1, siXOc1-M2, siXOc1-M3, siXOc2-M1, siXOc2-M2, siXOc2-M3, siXOd1-M1, siXOd1-M2, siXOd1-M3, siXOd2-M1, siXOd2-M2, siXOd2-M3, siXOe1-M1, siXOe1-M2, siXOe1-M3, siXOe2-M1, siXOe2-M2, siXOe2-M3, siXOf1-M1, siXOf1-M2, siXOf1-M3, siXOf2-M1, siXOf2-M2, siXOf2-M3, siXOg1-M1, siXOg1-M2, siXOg1-M3, siXOg2-M1, siXOg2-M2, siXOg2-M3, siXOh1-M1, siXOh1-M2, siXOh1-M3, siXOh2-M1, siXOh2-M2, siXOh2-M3, siXOi1-M1, siXOi1-M2, siXOi1-M3, siXOi2-M1, siXOi2-M2, siXOi2-M3, siXOj1-M1, siXOj1-M2, siXOj1-M3, siXOj2-M1, siXOj2-M2, siXOj2-M3, siXOk1-M1, siXOk1-M2, siXOk1-M3, siXOk2-M1, siXOk2-M2, siXOk2-M3, siXOl1-M1, siXOl1-M2, siXOl1-M3, siXOl2-M1, siXOl2-M2 and siXOl2-M3 listed in Tables 1a-1l.

The siRNAs with the above modifications can not only be afforded at lower costs, but also allow the ribonucleases in the blood to be less liable to cleaving the nucleic acid so as to increase the stability of the nucleic acid and enable the nucleic acid to have stronger resistance against nuclease hydrolysis. Meanwhile, the modified siRNA above has higher activity of inhibiting the target mRNA.

In some embodiments, at least a portion of the phosphate group in phosphate-ribose backbone of at least one single strand in the sense strand and the antisense strand of the siRNA provided by the present disclosure is a phosphate group with modified group. In some embodiments, the phosphate group with modified group is a phosphorothioate group formed by substituting at least one oxygen atom in a phosphodiester bond in the phosphate group with a sulfur atom; and in some embodiments, the phosphate group with modified group is a phosphorothioate group having a structure as shown by Formula (1):

Formula (1)

This modification can stabilize the double-stranded structure of the siRNA, thereby maintaining high specificity and high affinity for base pairing.

In some embodiments, in the siRNA provided by the present disclosure, a phosphorothioate linkage exists in at least one of the following positions: the position between the first nucleotide and second nucleotides at either terminal of the sense strand or antisense strand; the position between the second and third nucleotides at either terminal of the sense strand or antisense strand; or any combination thereof. In some embodiments, a phosphorothioate linkage exists at all the above positions except for 5' terminal of the sense strand. In some embodiments, a phosphorothioate linkage exists at all the above positions except for 3' terminal of the sense strand. In some embodiments, a phosphorothioate linkage exists in at least one of the following positions:

the position between the first nucleotide and the second nucleotide at 5' terminal of the sense strand;

the position between the second nucleotide and the third nucleotide at 5' terminal of the sense strand;

the position between the first nucleotide and the second nucleotide at 3' terminal of the sense strand;

the position between the second nucleotide and the third nucleotide at 3' terminal of the sense strand;

the position between the first nucleotide and the second nucleotide at 5' terminal of the antisense strand;

the position between the second nucleotide and the third nucleotide at 5' terminal of the antisense strand;

the position between the first nucleotide and the second nucleotide at 3' terminal of the antisense strand; and the position between the second nucleotide and the third nucleotide at 3' terminal of the antisense strand.

In some embodiments, the siRNA provided by the present disclosure is any one of siXOa1-M1S, siXOa1-M2S, siXOa1-M3S, siXOa2-M1S, siXOa2-M2S, siXOa2-M3S, siXOb1-M1S, siXOb1-M2S, siXOb1-M3S, siXOb2-M1S, siXOb2-M2S, siXOb2-M3S, siXOc1-M1S, siXOc1-M2S, siXOc1-M3S, siXOc2-M1S, siXOc2-M2S, siXOc2-M3S, siXOd1-M1S, siXOd1-M2S, siXOd1-M3S, siXOd2-M1S, siXOd2-M2S, siXOd2-M3S, siXOe1-M1S, siXOe1-M2S, siXOe1-M3S, siXOe2-M1S, siXOe2-M2S, siXOe2-M3S, siXOf1-M1S, siXOf1-M2S, siXOf1-M3S, siXOf2-M1S, siXOf2-M2S, siXOf2-M3S, siXOg1-M1S, siXOg1-M2S, siXOg1-M3S, siXOg2-M1S, siXOg2-M2S, siXOg2-M3S, siXOh1-M1S, siXOh1-M2S, siXOh1-M3S, siXOh2-M1S, siXOh2-M2S, siXOh2-M3S, XOi1-M1S, siXOi1-M2S, siXOi1-M3S, siXOi2-M1S, siXOi2-M2S, siXOi2-M3S, siXOj1-M1S, siXOj1-M2S, siXOj1-M3S, siXOj2-M1S, siXOj2-M2S, siXOj2-M3S, siXOk1-M1S, siXOk1-M2S, siXOk1-M3S, siXOk2-M1S, siXOk2-M2S, siXOk2-M3S, siXOl1-M1S, siXOl1-M2S, siXOl1-M3S, siXOl2-M1S, siXOl2-M2 and siXOl2-M3S listed in Tables 1a-1l.

In some embodiments, the 5'-terminal nucleotide in the antisense strand of the siRNA is a 5'-phosphate nucleotide or a 5'-phosphate analogue modified nucleotide.

Common types of the 5'-phosphate nucleotides or 5'-phosphate analogue modified nucleotides are well known to those skilled in the art; for example, the 5'-phosphate nucleotides may have the following structure:

Formula (2)

Base;

For another example, The chemical evolution of oligo-nucleotide therapies of clinical utility. Nature Biotechnology, 2017, 35(3): 238-48 written by Anastasia Khvorova and Jonathan K. Watts, disclose the following four 5'-phosphate analogue modified nucleotides:

Formula (3)

Base

-continued

Formula (4)

Formula (5)

Formula (6)

wherein, R is selected from H, OH, methoxy or F; and Base represents a nucleic acid base selected from A, U, C, or T.

In some embodiments, the 5'-phosphate nucleotide is a nucleotide with 5'-phosphate modification as shown by Formula (2); the 5'-phosphate analogue modified nucleotide is a nucleotide with 5'-(E)-vinylphosphonate (E-VP) modification as shown by Formula (3) or a phosphorothioate modified nucleotide as shown by Formula (5).

In some embodiments, the siRNA provided by the present disclosure is any one of siXOa1-M1P1, siXOa1-M2P1, siXOa1-M3P1, siXOa2-M1P1, siXOa2-M2P1, siXOa2-M3P1, siXOa1-M1SP1, siXOa1-M2SP1, siXOa1-M3SP1, siXOa2-M1SP1, siXOa2-M2SP1, siXOa2-M3SP1, siXOb1-M1P1, siXOb1-M2P1, siXOb1-M3P1, siXOb2-M1P1, siXOb2-M2P1, siXOb2-M3P1, siXOb1-M1SP1, siXOb1-M2SP1, siXOb1-M3SP1, siXOb2-M1SP1, siXOb2-M2SP1, siXOb2-M3SP1, siXOc1-M1P1, siXOc1-M2P1, siXOc1-M3P1, siXOc2-M1P1, siXOc2-M2P1, siXOc2-M3P1, siXOc1-M1SP1, siXOc1-M2SP1, siXOc1-M3SP1, siXOc2-M1SP1, siXOc2-M2SP1, siXOc2-M3SP1, siXOd1-M1P1, siXOd1-M2P1, siXOd1-M3P1, siXOd2-M1P1, siXOd2-M2P1, siXOd2-M3P1, siXOd1-M1SP1, siXOd1-M2SP1, siXOd1-M3SP1, siXOd2-M1SP1, siXOd2-M2SP1, siXOd2-M3SP1, siXOe1-M1P1, siXOe1-M2P1, siXOe1-M3P1, siXOe2-M1P1, siXOe2-M2P1, siXOe2-M3P1, siXOe1-M1SP1, siXOe1-M2SP1, siXOe1-M3SP1, siXOe2-M1SP1, siXOe2-M2SP1, siXOe2-M3SP1, siXOf1-M1P1, siXOf1-M2P1, siXOf1-M3P1, siXOf2-M1P1, siXOf2-M2P1, siXOf2-M3P1, siXOf1-M1SP1, siXOf1-M2SP1, siXOf1-M3SP1, siXOf2-M1SP1, siXOf2-M2SP1, siXOf2-M3SP1, siXOg1-M1P1, siXOg1-M2P1, siXOg1-M3P1, siXOg2-M1P1, siXOg2-M2P1, siXOg2-M3P1, siXOg1-

M1SP1, siXOg1-M2SP1, siXOg1-M3SP1, siXOg2-M1SP1, siXOg2-M2SP1, siXOg2-M3SP1, siXOh1-M1P1, siXOh1-M2P1, siXOh1-M3P1, siXOh2-M1P1, siXOh2-M2P1, siXOh2-M3P1, siXOh1-M1SP1, siXOh1-M2SP1, siXOh1-M3SP1, siXOh2-M1SP1, siXOh2-M2SP1, siXOh2-M3SP1, XOi1-M1P1, siXOi1-M2P1, siXOi1-M3P1, siXOi2-M1P1, siXOi2-M2P1, siXOi2-M3P1, siXOi1-M1SP1, siXOi1-M2SP1, siXOi1-M3SP1, siXOi2-M1SP1, siXOi2-M2SP1, siXOi2-M3SP1, siXOj1-M1P1, siXOj1-M2P1, siXOj1-M3P1, siXOj2-M1P1, siXOj2-M2P1, siXOj2-M3P1, siXOk1-M1P1, siXOk1-M2P1, siXOk1-M3P1, siXOk2-M1P1, siXOk2-M2P1, siXOk2-M3P1, siXOl1-M1P1, siXOl1-M2P1, siXOl1-M3P1, siXOl2-M1P1, siXOl2-M2P1, siXOl2-M3P1, siXOj1-M1SP1, siXOj1-M2SP1, siXOj1-M3SP1, siXOj2-M1SP1, siXOj2-M2SP1, siXOj2-M3SP1, siXOk1-M1SP1, siXOk1-M2SP1, siXOk1-M3SP1, siXOk2-M1SP1, siXOk2-M2SP1, siXOk2-M3SP1, siXOl1-M1SP1, siXOl1-M2SP1, siXOl1-M3SP1, siXOl2-M1SP1, siXOl2-M2SP1 and siXOl2-M3SP1 listed in Tables 1a-1l.

The inventors of the present disclosure have surprisingly found that the siRNA provided by the present disclosure has significantly enhanced plasma and lysosomal stability, and has higher inhibitory activity of target mRNA.

The siRNA provided by the present disclosure can be obtained by conventional methods for preparing siRNAs in the art (e.g., solid phase synthesis and liquid phase synthesis methods).

Commercial customization services have already been available for solid phase synthesis. Modified nucleotides can be introduced into the siRNAs of the present disclosure by using a nucleotide monomer having a corresponding modification, wherein the methods for preparing a nucleotide monomer having a corresponding modification and the methods for introducing a modified nucleotide into an siRNA are also well-known to those skilled in the art. Modified nucleotide groups may be introduced into the siRNA of the present disclosure by using a nucleotide monomer having a corresponding modification, wherein the methods for preparing the nucleotide monomer having the corresponding modification and the methods for introducing the modified nucleotide group into the siRNA are also well-known to those skilled in the art.

Pharmaceutical Composition

The present disclosure provides a pharmaceutical composition, wherein the pharmaceutical composition comprises the siRNA described above as an active ingredient, and a pharmaceutically acceptable carrier.

The pharmaceutically acceptable carrier may be a carrier conventionally used in the field of siRNA administration, for example, but not limited to, one or more of magnetic nanoparticles (such as $Fe_3O_4$ or $Fe_2O_3$-based nanoparticle), carbon nanotubes, mesoporous silicon, calcium phosphate nanoparticles, polyethylenimine (PEI), polyamidoamine (PAMAM) dendrimer, poly(L-lysine) (PLL), chitosan, 1,2-dioleoyl-3-trimethylammonium-propane (DOTAP), poly (D&L-lactic/glycolic acid) copolymer (PLGA), poly(2-aminoethyl ethylene phosphate) (PPEEA), poly(2-dimethylaminoethyl methacrylate) (PDMAEMA), and derivatives thereof.

In the pharmaceutical composition, there are no special requirements for the contents of the siRNA and the pharmaceutically acceptable carrier, which may be the conventional content of each component. In some embodiments, the weight ratio of the siRNA to the pharmaceutically acceptable carrier is 1:(1-500), and in some embodiments, the weight ratio above is 1:(1-50).

In some embodiments, the pharmaceutical composition may also comprise other pharmaceutically acceptable excipients, which may be one or more of various conventional formulations or compounds in the art. For example, the other pharmaceutically acceptable excipients may comprise at least one of a pH buffer solution, a protective agent and an osmotic pressure regulator.

The pH buffer solution may be a tris(hydroxymethyl) aminomethane hydrochloride buffer solution with a pH of 7.5-8.5, and/or a phosphate buffer solution with a pH of 5.5-8.5, preferably a phosphate buffer solution with a pH of 5.5-8.5.

The protective agent may be at least one of inositol, sorbitol, sucrose, trehalose, mannose, maltose, lactose, and glucose. The content of the protective agent may be from 0.01 wt % to 30 wt % on the basis of the total weight of the pharmaceutical composition.

The osmotic pressure regulator may be sodium chloride and/or potassium chloride. The content of the osmotic pressure regulator allows an osmotic pressure of the pharmaceutical composition to be 200-700 milliosmol/kg (mOsm/kg). Depending on the desired osmotic pressure, those skilled in the art can readily determine the content of the osmotic pressure regulator.

In some embodiments, the pharmaceutical composition may be a liquid formulation, for example, an injection solution; or a lyophilized powder for injection, which is mixed with a liquid excipient to form a liquid formulation upon administration. The liquid formulation may be administered by, but not limited to, subcutaneous, intramuscular or intravenous injection routes, and also may be administered to, but not limited to, lung by spray, or other organs (such as liver) via lung by spray. In some embodiments, the pharmaceutical composition is administered by intravenous injection.

In some embodiments, the pharmaceutical composition may be in the form of a liposome formulation. In some embodiments, the pharmaceutically acceptable carrier used in the liposome formulation comprises an amine-containing transfection compound (hereinafter also referred to as an organic amine), a helper lipid and/or a pegylated lipid. The organic amine, the helper lipid and the pegylated lipid may be respectively selected from one or more of the amine-containing transfection compounds or the pharmaceutically acceptable salts or derivatives thereof, the helper lipids and the pegylated lipids as described in CN103380113A (which is incorporated herein by reference in its entirety).

In some embodiments, the organic amine may be a compound as shown by Formula (201) as described in CN103380113A or a pharmaceutically acceptable salt thereof:

Formula (201)

wherein:
each of $X_{101}$ or $X_{102}$ is independently O, S, N-A or C-A, wherein A is hydrogen or a C1-C20 hydrocarbon chain;

each of $Y_{101}$ or $Z_{101}$ is independently C=O, C=S, S=O, CH—OH or $SO_2$;

each of $R_{101}$, $R_{102}$, $R_{103}$, $R_{104}$, $R_{105}$, $R_{106}$ or $R_{107}$ is independently hydrogen; a cyclic or aliphatic, substituted or unsubstituted, branched or linear aliphatic group; a cyclic or aliphatic, substituted or unsubstituted, branched or linear heteroaliphatic group; a substituted or unsubstituted, branched or linear acyl group; a substituted or unsubstituted, branched or linear aryl, or a substituted or unsubstituted, branched or linear heteroaryl;

x is an integer of 1-10;

n is an integer of 1-3, m is an integer of 0-20, and p is 0 or 1, wherein if m=p=0, then $R_{102}$ is hydrogen, and if at least one of n or m is 2, then $R_{103}$ and the nitrogen in Formula (201) form a structure as shown by Formula (202) or (203):

Formula (202)

Formula (203)

wherein g, e and f are each independently an integer of 1-6, "HCC" represents a hydrocarbon chain, and each *N represents a nitrogen atom shown in Formula (201).

In some embodiments, $R_{103}$ is a polyamine. In other embodiments, $R_{103}$ is a ketal. In some embodiments, each of $R_{101}$ and $R_{102}$ in the Formula (201) is independently any substituted or unsubstituted, branched or linear alkyl or alkenyl, wherein the alkyl or alkenyl has 3 to about 20 carbon atoms (such as 8 to about 18 carbon atoms) and 0 to 4 double bonds (such as 0 to 2 double bonds).

In some embodiments, if each of n and m is independently 1-3, $R_{103}$ may be any in the following Formulae (204)-(213):

Formula (204)

Formula (205)

Formula (206)

-continued

Formula (207)

Formula (208)

Formula (209)

Formula (210)

Formula (211)

-continued

Formula (212)

and

Formula (213)

wherein, in Formula (204) to Formula (213), each of g, e and f is independently an integer of 1-6; each "HCC" represents a hydrocarbon chain, and each * represents a potential attachment point of $R_{103}$ to the nitrogen atom in Formula (201), wherein each H at any * position may be replaced to realize the attachment to the nitrogen atom in Formula (201).

The compound as shown by (201) may be prepared as described in CN103380113A.

In some embodiments, the organic amine may be an organic amine as shown by Formula (214) and/or an organic amine as shown by Formula (215):

Formula (214)

-continued

Formula (215)

the helper lipid is a cholesterol, a cholesterol analogue and/or a cholesterol derivative;

the pegylated lipid is 1,2-dipalmitoyl-sn-glycero-3-phosphatidylethanolamine-N-[methoxy(polyethylene glycol)]-2000.

In some embodiments, the molar ratio among the organic amine, the helper lipid, and the pegylated lipid in the pharmaceutical composition is (19.7-80):(19.7-80):(0.3-50); for example, the molar ratio may be (50-70):(20-40):(3-20).

In some embodiments, the pharmaceutical compositions formed by the siRNA of the present disclosure and the above amine-containing transfection agent have an average diameter from about 30 nm to about 200 nm, typically from about 40 nm to about 135 nm, and more typically, the average diameter of the liposome particles is from about 50 nm to about 120 nm, from about 50 nm to about 100 nm, from about 60 nm to about 90 nm, or from about 70 nm to about 90 nm, for example, the average diameter of the liposome particles is about 30, 40, 50, 60, 70, 75, 80, 85, 90, 100, 110, 120, 130, 140, 150 or 160 nm.

In some embodiments, in the pharmaceutical composition formed by the siRNA of the present disclosure and the above amine-containing transfection agent, the weight ratio (weight/weight ratio) of the siRNA to total lipids (e.g., the organic amine, the helper lipid and/or the pegylated lipid), ranges from about 1:1 to about 1:50, from about 1:1 to about 1:30, from about 1:3 to about 1:20, from about 1:4 to about 1:18, from about 1:5 to about 1:17, from about 1:5 to about 1:15, from about 1:5 to about 1:12, from about 1:6 to about 1:12, or from about 1:6 to about 1:10. For example, the ratio of the siRNA of the present disclosure to the total lipids is about 1:5, 1:6, 1:7, 1:8, 1:9, 1:10, 1:11, 1:12, 1:13, 1:14, 1:15, 1:16, 1:17 or 1:18 by weight.

In some embodiments, the pharmaceutical composition may be marketed with each component being separate, and used in the form of a liquid formulation. In some embodiments, the pharmaceutical composition formed by the siRNA of the present disclosure and the above pharmaceutically acceptable carrier may be prepared by various known processes, except replacing the existing siRNA with the siRNA of the present disclosure. In some embodiments, the pharmaceutical composition may be prepared according to the following process.

The organic amines, helper lipids and pegylated lipids are suspended in alcohol at a molar ratio as described above and mixed homogeneously to yield a lipid solution; and the alcohol is used in an amount such that the resultant lipid solution is present at a total mass concentration of 2 to 25 mg/mL, e.g., 8 to 18 mg/mL. The alcohol is a pharmaceutically acceptable alcohol, such as an alcohol that is in liquid form at about room temperature, for example, one or more of ethanol, propylene glycol, benzyl alcohol, glycerol, PEG 200, PEG 300, PEG 400, and for example, ethanol.

The siRNA provided by the present disclosure is dissolved in a buffered salt solution to produce an aqueous solution of the siRNA. The buffered salt solution has a concentration of 0.05-0.5 M, such as 0.1-0.2 M. The pH of the buffered salt solution is adjusted to 4.0-5.5, such as 5.0-5.2. The buffered salt solution is used in an amount such that the siRNA is present at a concentration of less than 0.6 mg/ml, such as 0.2-0.4 mg/mL. The buffered salt may be one or more selected from the group consisting of soluble acetate and soluble citrate, such as sodium acetate and/or potassium acetate.

The lipid solution and the aqueous solution of the siRNA are mixed. The product obtained after mixing is incubated at a temperature of 40-60° C. for at least 2 minutes (e.g., 5-30 minutes) to produce an incubated lipid formulation. The volume ratio of the lipid solution to the aqueous solution of the siRNA is 1:(2-5), for example, may be 1:4.

The incubated liposome formulation is concentrated or diluted, purified to remove impurities, and then sterilized to obtain the pharmaceutical composition provided by the present disclosure, which has physicochemical parameters as follows: a pH of 6.5-8, an encapsulation percentage of more than 80%, a particle size of 40-200 nm, a polydispersity index of less than 0.30, and an osmotic pressure of 250-400 mOsm/kg; for example, the physicochemical parameters may be as follows: a pH of 7.2-7.6, an encapsulation percentage of more than 90%, a particle size of 60-100 nm, a polydispersity index of less than 0.20, and an osmotic pressure of 300-400 mOsm/kg.

The concentration or dilution step may be performed before, after or simultaneously with the step of impurity removal. The method for removing impurities may be any of various existing methods, for example, ultrafiltration using 100 KDa hollow fiber column and a phosphate buffer solution (PBS) at pH 7.4 as an ultrafiltration exchange solution and a tangential flow system. The method for sterilization may be any of various existing methods, such as filtration sterilization on a 0.22 μm filter.

siRNA Conjugate

The present disclosure provides an siRNA conjugate, wherein the siRNA conjugate comprises the siRNA above and a conjugating group conjugatively linked to the siRNA.

The conjugating group typically comprises at least one pharmaceutically acceptable targeting group and an optional linker. Moreover, the siRNA, the linker and the targeting group are linked in succession. In some embodiments, there are 1-6 targeting groups. In some embodiments, there are 2-4 targeting groups. The siRNA molecule may be non-covalently or covalently conjugated to the conjugating group, for example, the siRNA molecule may be covalently conjugated to the conjugating group. The conjugating site between siRNA and the conjugating group may be at 3'-terminal or 5'-terminal of the sense strand of the siRNA, or at 5'-terminal of the antisense strand, or within the internal sequence of the siRNA. In some embodiments, the conjugating site between the siRNA and the conjugating group is at 3' terminal of the sense strand of the siRNA.

In some embodiments, the conjugation group is linked to a phosphate group, a 2'-hydroxy or a base of a nucleotide. In some embodiments, the conjugation group may be linked to a 3'-hydroxy when the nucleotides are linked via a 2'-5'-phosphodiester bond. When the conjugating group is linked to a terminal of the siRNA, the conjugating group is typically linked to a phosphate group of a nucleotide; when the conjugating group is linked to an internal sequence of the siRNA, the conjugating group is typically linked to a ribose ring or a base. For specific linking modes, reference may be made to: siRNA conjugates carrying sequentially assembled trivalent N-acetylgalactosamine linked through nucleosides elicit robust gene silencing in vivo in hepatocytes. ACS Chemical biology, 2015, 10(5):1181-7, written by Muthiah Manoharan et. al.

In some embodiments, the siRNA and the conjugating group may be linked by an acid labile or reducible chemical bond, and these chemical bonds may be degraded under the acidic environment of cell endosomes, thereby rendering the siRNA to be in free state. For non degradable conjugating modes, the conjugating group may be linked to the sense strand of the siRNA, thereby minimizing the effect of conjugating on the activity of the siRNA.

In some embodiments, the pharmaceutically acceptable targeting group may be a conventionally used ligand in the field of siRNA administration, for example, the various ligands as described in WO2009082607A2, which is incorporated herein by reference in its entirety.

In some embodiments, the pharmaceutically acceptable targeting group may be selected from one or more of the ligands formed by the following targeting molecules or derivatives thereof: lipophilic molecules, such as cholesterol, bile acids, vitamins (such as vitamin E), lipid molecules of different chain lengths; polymers, such as polyethylene glycol; polypeptides, such as cell-penetrating peptide; aptamers; antibodies; quantum dots; saccharides, such as lactose, polylactose, mannose, galactose, and N-acetylgalactosamine (GalNAc); folate; and receptor ligands expressed in hepatic parenchymal cells, such as asialoglycoprotein, asialo-sugar residue, lipoproteins (such as high density lipoprotein, low density lipoprotein), glucagon, neurotransmitters (such as adrenaline), growth factors, transferrin and the like.

In some embodiments, each ligand is independently a ligand capable of binding to a cell surface receptor. In some embodiments, at least one ligand is a ligand capable of binding to a hepatocyte surface receptor. In some embodiments, at least one ligand is a ligand capable of binding to a mammalian cell surface receptor. In some embodiments, at least one ligand is a ligand capable of binding to a human cell surface receptor. In some embodiments, at least one ligand is a ligand capable of binding to a hepatic surface asialoglycoprotein receptor (ASGP-R). The types of these ligands are well-known to those skilled in the art and they typically serve the function of binding to specific receptors on the surface of the target cell, thereby mediating delivery of the siRNA linked to the ligand into the target cell.

In some embodiments, the pharmaceutically acceptable targeting group may be any ligand that binds to asialoglycoprotein receptors (ASGP-R) on the surface of mammalian hepatocytes. In one embodiment, each ligand is independently an asialoglycoprotein, such as asialoorosomucoid (ASOR) or asialofetuin (ASF). In some embodiments, the ligand is a saccharide or a saccharide derivative.

In some embodiments, at least one ligand is a saccharide. In some embodiments, each ligand is a saccharide. In some embodiments, at least one ligand is a monosaccharide, polysaccharide, modified monosaccharide, modified polysaccharide, or saccharide derivative. In some embodiments, at least one ligand may be a monosaccharide, disaccharide or trisaccharide. In some embodiments, at least one ligand is a modified saccharide. In some embodiments, each ligand is a modified saccharide. In some embodiments, each ligand is independently selected from the group consisting of polysaccharides, modified polysaccharides, monosaccharides, modified monosaccharides, polysaccharide derivatives or monosaccharide derivatives. In some embodiments, each ligand or at least one ligand is selected from the group consisting of the following saccharides: glucose and derivative thereof, mannose and derivative thereof, galactose and derivative thereof, xylose and derivative thereof, ribose and derivative thereof, fucose and derivative thereof, lactose and derivative thereof, maltose and derivative thereof, arabinose and derivative thereof, fructose and derivative thereof, and sialic acid.

In some embodiments, each ligand may be independently selected from one of D-mannopyranose, L-mannopyranose, D-arabinose, D-xylofuranose, L-xylofuranose, D-glucose, L-glucose, D-galactose, L-galactose, α-D-mannofuranose, β-D-mannofuranose, α-D-mannopyranose, β-D-mannopyranose, α-D-glucopyranose, β-D-glucopyranose, α-D-glucofuranose, β-D-glucofuranose, α-D-fructofuranose, α-D-fructopyranose, α-D-galactopyranose, β-D-galactopyranose, α-D-galactofuranose, β-D-galactofuranose, glucosamine, sialic acid, galactosamine, N-acetylgalactosamine, N-trifluoroacetylgalactosamine, N-propionylgalactosamine, N-n-butyrylgalactosamine, N-isobutyrylgalactosamine, 2-amino-3-O—[(R)-1-carboxyethyl]-2-deoxy-β-D-glucopyranose, 2-deoxy-2-methylamino-L-glucopyranose, 4,6-dideoxy-4-formamido-2,3-di-O-methyl-D-mannopyranose, 2-deoxy-2-sulfoamino-D-glucopyranose, N-glycolyl-α-neuraminic acid, 5-thio-β-D-glucofuranose, methyl 2,3,4-tris-O-acetyl-1-thio-6-O-trityl-α-D-glucofuranose, 4-thio-β-D-galactopyranose, ethyl 3,4, 6,7-tetra-O-acetyl-2-deoxy-1,5-dithio-α-D-glucoheptopyranoside, 2,5-anhydro-D-allononitrile, ribose, D-ribose, D-4-thioribose, L-ribose, or L-4-thioribose. Other ligand selections may be found, for example, in the disclosure of CN105378082A, which is incorporated herein by reference in its entirety.

In some embodiments, the pharmaceutically acceptable targeting group in the siRNA conjugate may be galactose or N-acetylgalactosamine, wherein the galactose or N-acetylgalactosamine molecules may be monovalent, bivalent, trivalent and tetravalent. It should be understood that the terms monovalent, bivalent, trivalent and tetravalent described herein respectively mean that the molar ratio of the siRNA molecule to the galactose or N-acetylgalactosamine molecule in the siRNA conjugate is 1:1, 1:2, 1:3 or 1:4, wherein the siRNA conjugate is formed from the siRNA molecule and the conjugating group containing galactose or N-acetylgalactosamine as the targeting group. In some embodiments, the pharmaceutically acceptable targeting group is N-acetylgalactosamine. In some embodiments, when the siRNA of the present disclosure is conjugated to a conjugation group comprising N-acetylgalactosamine, the N-acetylgalactosamine molecule is trivalent or tetravalent. In some embodiments, when the siRNA of the present disclosure is conjugated to a conjugating group containing N-acetylgalactosamine, the N-acetylgalactosamine molecule is trivalent.

The targeting group may be linked to the siRNA molecule via an appropriate linker, and the appropriate linker may be selected by those skilled in the art according to the specific type of the targeting group. The types of these linkers and targeting groups and the linking modes with the siRNA may be found in the disclosure of W2015006740A2, which is incorporated herein by reference in its entirety.

In some embodiments, when the targeting group is N-acetylgalactosamine, an appropriate linker may be a structure as shown by Formula (301):

$$\left[ \begin{matrix} L^C-L^B \text{\textbackslash} \\ / \\ L^A \end{matrix} \right]_k$$

Formula (301)

wherein, k is an integer of 1-3; and $L^A$ is an amide bond-comprising chain moiety that has a structure as shown by Formula (302), each $L^A$ being respectively linked to the targeting group and the $L^C$ moiety through an ether bond at two terminals thereof:

Formula (302)

$L^B$ is an N-acylpyrrolidine-comprising chain moiety that has a structure as shown by Formula (303), the chain moiety having a carbonyl at one terminal thereof and being linked to the $L^C$ moiety through an amide bond, and having an oxy-group at the other terminal thereof and being linked to the siRNA via a phosphoester bond:

Formula (303)

$L^C$ is a bivalent to tetravalent linking group based on hydroxymethyl aminomethane, dihydroxymethyl aminomethane or trihydroxymethyl aminomethane, the $L^C$ being linked to each of the $L^A$ moieties through an ether bond via an oxygen atom, and being linked to the $L^B$ moiety through an amide bond via a nitrogen atom.

In some embodiments, when n=3 and $L^C$ is a tetravalent linking group based on trihydroxymethyl aminomethane, the siRNA conjugate formed by linking an N-acetylgalactosamine molecule with an siRNA molecule via -$(L^A)_3$-trihydroxymethyl aminomethane-$L^B$- as a linker has a structure as shown by Formula (304):

Formula (304)

wherein the double helix structure represents an siRNA.

Likewise, the conjugating site between the siRNA and the conjugating group nay be at the 3'-terminal or 5'-terminal of the sense strand of the siRNA, or at the 5'-terminal of the antisense strand, or within the internal sequence of the siRNA.

In some embodiments, the 3'-terminal of the sense strand of the siRNA of the present disclosure is covalently conjugated to three N-acetylgalactosamine (GalNAc) molecules via a linker -$(L^A)_3$-trihydroxymethyl aminomethane-$L^B$- to obtain an siRNA conjugate in which the molar ratio of the siRNA molecule to the GalNAc molecule is 1:3, which may also be hereinafter referred to as (GalNAc)$_3$-siRNA), and the siRNA conjugate has a structure as shown by Formula (305):

Formula (305)

wherein the double helix structure represents an siRNA; and the linker is linked to the 3' terminal of the sense strand of the siRNA.

In some embodiments, when the targeting group is N-acetylgalactosamine, an appropriate linker may be a structure as shown by Formula (306):

Formula (306)

wherein, l is an integer of 0-3;

# represents a site linked to the targeting group via an ether bond on the linker; and # represents a site linked to the siRNA via a phosphoester bond on the linker.

In some embodiments, when l=2, the siRNA conjugate has a structure as shown by Formula (307):

Formula (307)

wherein the double helix structure represents an siRNA; and the linker is linked to the 3' terminal of the sense strand of the siRNA.

The above conjugates may be synthesized according to the methods described in detail in the prior art. For example, WO2015006740A2 describes the method of preparing various conjugates in detail. The siRNA conjugate of the present disclosure may be obtained by methods well known to those skilled in the art. As another example, WO2014025805A1 describes the preparation method of the conjugate having a structure as shown by Formula (305). Rajeev et al., describes the preparation method of the conjugate having a structure as shown by Formula (307) in Chem Bio Chem 2015, 16, 903-908.

In some embodiments, the siRNA conjugate has a structure as shown by Formula (308):

Formula (308)

wherein:

n1 is an integer of 1-3, and n3 is an integer of 0-4;

m1, m2, and m3 is independently an integer of 2-10;

$R_{10}$, $R_{11}$, $R_{12}$, $R_{13}$, $R_{14}$ or $R_{15}$ is independently H or selected from the group consisting of $C_1$-$C_{10}$ alkyl, $C_1$-$C_{10}$ haloalkyl and $C_1$-$C_{10}$ alkoxy; and $R_3$ is a group having a structure as shown by Formula A59:

(A59)

wherein, $E_1$ is OH, SH or $BH_2$, and Nu is the siRNA of the present disclosure;

$R_2$ is a linear alkylene of 1-20 carbon atoms in length, wherein one or more carbon atoms are optionally replaced with any one or more of the group consisting of: C(O), NH, O, S, CH=N, S(O)$_2$, $C_2$-$C_{10}$ alkeylene, $C_2$-$C_{10}$ alkynylene, $C_6$-$C_{10}$ arylene, $C_3$-$C_{18}$ heterocyclylene, and $C_5$-$C_{10}$ heteroarylene; and wherein $R_2$ is optionally substituted by any one or more of the group consisting of: $C_1$-$C_{10}$ alkyl, $C_6$-$C_{10}$ aryl, $C_5$-$C_{10}$ heteroaryl, $C_1$-$C_{10}$ haloalkyl, —O$C_1$-$C_{10}$ alkyl, —O$C_1$-$C_{10}$ alkylphenyl, —$C_1$-$C_{10}$ alkyl-OH, —O$C_1$-$C_{10}$ haloalkyl, —S$C_1$-$C_{10}$ alkyl, —S$C_1$-$C_{10}$ alkylphenyl, —$C_1$-$C_{10}$ alkyl-SH, —S$C_1$-$C_{10}$ haloalkyl, halo substituent, —OH, —SH, —NH$_2$, —$C_1$-$C_{10}$ alkyl-NH$_2$, —N($C_1$-$C_{10}$ alkyl)($C_1$-$C_{10}$ alkyl), —NH($C_1$-$C_{10}$ alkyl), —N($C_1$-$C_{10}$ alkyl)($C_1$-$C_{10}$ alkylphenyl), —NH($C_1$-$C_{10}$ alkylphenyl), cyano, nitro, —CO$_2$H, —C(O)O($C_1$-$C_{10}$ alkyl), —CON($C_1$-$C_{10}$ alkyl)($C_1$-$C_{10}$ alkyl), —CONH ($C_1$-$C_{10}$ alkyl), —CONH$_2$, —NHC(O)($C_1$-$C_{10}$ alkyl), —NHC(O)(phenyl), —N($C_1$-$C_{10}$ alkyl)C(O)($C_1$-$C_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O)C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH(phenyl), —NHSO$_2$(C$_1$-C$_{10}$ alkyl), —NHSO$_2$(phenyl), and —NHSO$_2$(C$_1$-C$_{10}$ haloalkyl); and each L$_1$ is a linear alkylene of 1-70 carbon atoms in length, wherein one or more carbon atoms are optionally replaced with any one or more of the group consisting of: C(O), NH, O, S, CH=N, S(O)$_2$, C$_2$-C$_{10}$ alkeylene, C$_2$-C$_{10}$ alkynylene, C$_6$-C$_{10}$ arylene, C$_3$-C$_{18}$ heterocyclylene, and C$_5$-C$_{10}$ heteroarylene; and wherein L$_1$ is optionally substituted by any one or more of the group consisting of: C$_1$-C$_{10}$ alkyl, C$_6$-C$_{10}$ aryl, C$_5$-C$_{10}$ heteroaryl, haloalkyl, —OC$_1$-C$_{10}$ alkyl, —OC$_1$-C$_{10}$ alkylphenyl, —C$_1$-C$_{10}$ alkyl-OH, —OC$_1$-C$_{10}$ haloalkyl, —SC$_1$-C$_{10}$ alkyl, —SC$_1$-C$_{10}$ alkylphenyl, —C$_1$-C$_{10}$alkyl-SH, —SC$_1$-C$_{10}$ haloalkyl, halo substituent, —OH, —SH, —NH$_2$, —C$_1$-C$_{10}$ alkyl-NH$_2$, —N(C$_1$-C$_{10}$ alkyl)(C$_1$-C$_{10}$ alkyl), —NH(C$_1$-C$_{10}$ alkyl), —N(C$_1$-C$_{10}$ alkyl)(C$_1$-C$_{10}$ alkylphenyl), —NH(C$_1$-C$_{10}$ alkylphenyl), cyano, nitro, —CO$_2$H, —C(O)O(C$_1$-C$_{10}$ alkyl), —CON(C$_1$-C$_{10}$ alkyl)(C$_1$-C$_{10}$ alkyl), —CONH (C$_1$-C$_{10}$ alkyl), —CONH$_2$, —NHC(O)(C$_1$-C$_{10}$ alkyl), —NHC(O)(phenyl), —N(C$_1$-C$_{10}$ alkyl)C(O)(C$_1$-C$_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O)C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH(phenyl), —NHSO$_2$(C$_1$-C$_{10}$ alkyl), —NHSO$_2$(phenyl), and —NHSO$_2$(C$_1$-C$_{10}$ haloalkyl).

In some embodiments, L$_1$ may be selected from the group consisting of groups A1-A26 and any combination thereof, wherein the structures and definitions of A1-A26 are as follows:

(A1)

(A2)

(A3)

(A4)

(A5)

(A6)

-continued (A7)

(A8)

(A9)

(A10)

(A11)

(A12)

(A13)

(A14)

(A15)

(A16)

(A17)

(A18)

(A19)

-continued

-continued (A20)

(A21)

(A22)

(A23)

(A24)

(A25)

(A26)

wherein, j1 is an integer of 1-20; and j2 is an integer of 1-20;

R' is a $C_1$-$C_{10}$ alkyl; and

Ra is selected from the group consisting of groups A27-A45 and any combinations thereof:

(A27)

(A28)

(A29)

(A30)

(A31)

(A32)

(A33)

(A34)

(A35)

(A36)

(A37)

(A38)

(A39)

-continued (A40)

(A41)

(A42)

(A43)

(A44)

or (A45)

Rb is a $C_1$-$C_{10}$ alkyl; and ⁓⁓⁓ represents a site where the group is covalently linked.

Those skilled in the art would understand that, though $L_1$ is defined as a linear alkylene for convenience, but it may not be a linear group or be named differently, such as an amine or alkenyl produced by the above replacement and/or substitution. For the purpose of the present disclosure, the length of $L_1$ is the number of the atoms in the chain connecting the two attaching points. For this purpose, a ring obtained by replacement of a carbon atom of the linear alkylene, such as a heterocyclylene or heteroarylene, is counted as one atom.

$M_1$ represents a targeting group, of which the definitions and options are the same as those described above. In some embodiments, each $M_1$ is independently selected from one of the ligands that have affinity to the asialoglycoprotein receptor on the surface of mammalian hepatocytes.

When $M_1$ is a ligand that has affinity to the asialoglyco-protein receptor on the surface of mammalian hepatocytes, in some embodiments, n1 may be an integer of 1-3, and n3 may be an integer of 0-4 to ensure that the number of the $M_1$ targeting group in the siRNA conjugate may be at least 2. In some embodiments, n1+n3≥2, such that the number of the $M_1$ targeting group in the conjugate may be at least 3, thereby allowing the $M_1$ targeting group to more conveniently bind to the asialoglycoprotein receptor on the surface of hepatocytes, which may facilitate the endocytosis of the siRNA conjugate into cells. Experiments have shown that when the number of the $M_1$ targeting group is greater than 3, the ease of binding the $M_1$ targeting group to the asialo-glycoprotein receptor on the surface of hepatocytes is not significantly increased. Therefore, in view of various aspects such as synthesis convenience, structure/process costs and delivery efficiency, in some embodiments, n1 is an integer of 1-2, n3 is an integer of 0-1, and n+n3=2-3.

In some embodiments, when m1, m2, or m3 is independently selected from selected from an integer of 2-10, the steric mutual positions among a plurality of $M_1$ targeting groups may be fit for binding the $M_1$ targeting groups to the asialoglycoprotein receptor on the surface of hepatocytes. In order to make the siRNA conjugate provided by the present disclosure have simpler structure, easier synthesis and/or reduced cost, in some embodiments, m1, m2 and m3 are independently an integer of 2-5, and in some embodiments, m1=m2=m3.

Those skilled in the art would understand that when $R_{10}$, $R_{11}$, $R_{12}$, $R_{13}$, $R_{14}$, or $R_{15}$ is each independently selected from one of H, $C_1$-$C_{10}$ alkyl, $C_1$-$C_{10}$ haloalkyl, and $C_1$-$C_{10}$ alkoxy, they would not change the properties of the siRNA conjugate of the present disclosure and could all achieve the purpose of the present disclosure. In some embodiments, $R_{10}$, $R_{11}$, $R_{12}$, $R_{13}$, $R_{14}$, or $R_{15}$ is each independently selected from selected from H, methyl or ethyl. In some embodiments, $R_{10}$, $R_{11}$, $R_{12}$, $R_{13}$, $R_{14}$, and $R_{15}$ are all H.

$R_3$ is a group having the structure as shown by Formula A59, wherein $E_1$ is OH, SH or $BH_2$, and considering the availability of starting materials, in some embodiments, $E_1$ is OH or SH.

$R_2$ is selected to achieve the linkage between the group as shown by Formula A59 and the N atom on a nitrogenous backbone. In the context of the present disclosure, the "nitrogenous backbone" refers to a chain structure in which the carbon atoms attached to $R_{10}$, $R_{11}$, $R_{12}$, $R_{13}$, $R_{14}$, and $R_{15}$ and the N atoms are linked to each other. Therefore, $R_2$ may be any linking group capable of attaching the group as shown by Formula A59 to the N atom on a nitrogenous backbone by suitable means. In some embodiments, in the case where the siRNA conjugate as shown by Formula (308) of the present disclosure is prepared by a solid phase synthesis process, $R_2$ group needs to have both a site linking to the N atom on the nitrogenous backbone and a site linking to the P atom in $R_3$. In some embodiments, in $R_2$, the site linking to the N atom on the nitrogenous backbone forms an amide bond with the N atom, and the site linking to the P atom in $R_3$ forms a phosphoester bond with the P atom. In some embodiments, $R_2$ may be B5, B6, B5' or B6':

(B5)

(B6)

(B5')

(B6')

wherein, ⌇⌇⌇ represents a site where the group is covalently linked.

A value range of $q_2$ may be an integer of 1-10; and in some embodiments, $q_2$ is an integer of 1-5.

$L_1$ is used to link the $M_1$ targeting group to the N atom on the nitrogenous backbone, thereby providing liver targeting function for the siRNA conjugate as shown by Formula (308). In some embodiments, $L_1$ is selected from the connection combinations of one or more of groups as shown by Formulae A1-A26. In some embodiments, $L_1$ is selected from the connection combinations of one or more of A1, A4, A5, A6, A8, A10, A11, and A13. In some embodiments, $L_1$ is selected from the connection combinations of at least two of A1, A4, A8, A10, and A11. In some embodiments, $L_1$ is selected from the connection combinations of at least two of A1, A8, and A10.

In some embodiments, the length of $L_1$ may be 3-25 atoms, 3-20 atoms, 4-15 atoms or 5-12 atoms. In some embodiments, the length of $L_1$ is 3, 4, 5, 6, 7, 8, 9, 10, 11, 12, 13, 14, 15, 16, 17, 18, 19, 20, 21, 22, 23, 24, 25, 30, 35, 40, 45, 50, 55, 60 atoms.

In some embodiments, j1 is an integer of 2-10, and in some embodiments, j1 is an integer of 3-5. In some embodiments, j2 is an integer of 2-10, and in some embodiments, j2 is an integer of 3-5. R' is a $C_1$-$C_4$ alkyl, and in some embodiments, R' is one of methyl, ethyl, and isopropyl. Ra is one of A27, A28, A29, A30, and A31, and in some embodiments, Ra is A27 or A28. Rb is a C1-C5 alkyl, and in some embodiments, Rb is one of methyl, ethyl, isopropyl, and butyl. In some embodiments, j1, j2, R', Ra, and Rb of Formulae A1-A26 are respectively selected to achieve the linkage between the $M_1$ targeting group and the N atom on the nitrogenous backbone, and to make the steric mutual position among the $M_1$ targeting group more suitable for binding the $M_1$ targeting group to the asialoglycoprotein receptor on the surface of hepatocytes.

In some embodiments, the siRNA conjugate has a structure as shown by Formula (403), (404), (405), (406), (407), (408), (409), (410), (411), (412), (413), (414), (415), (416), (417), (418), (419), (420), (421) or (422):

Formula (403)

-continued

Formula (404)

Formula (405)

77

78

-continued

Formula (406)

Formula (407)

Formula (408)

Formula (409)

Formula (410)

-continued

Formula (411)

Formula (412)

81

82

-continued

Formula (413)

Formula (414)

Formula (415)

83                                                                 84

Formula (416)                                                      Formula (417)

Formula (418)                                                      Formula (419)

-continued

Formula (420)

Formula (421)

Formula (422)

In some embodiments, the P atom in Formula A59 may be linked to any possible position in the siRNA sequence, for example, the P atom in Formula A59 may be linked to any nucleotide in the sense strand or the antisense strand of the siRNA. In some embodiments, the P atom in Formula A59 is linked to any nucleotide in the sense strand of the siRNA. In some embodiments, the P atom in Formula A59 is linked to a terminal of the sense strand or the antisense strand of the siRNA. In some embodiments, the P atom in Formula A59 is linked to a terminal of the sense strand of the siRNA. The terminal refers to the first 4 nucleotides counted from one terminal of the sense strand or antisense strand. In some embodiments, the P atom in Formula A59 is linked to the terminal of the sense strand or the antisense strand of the siRNA. In some embodiments, the P atom in Formula A59 is linked to 3' terminal of the sense strand of the siRNA. In the case where the P atom in Formula A59 is linked to the above position in the sense strand of the siRNA, after entering into cells, the siRNA conjugate as shown by Formula (308) can release a separate antisense strand of the siRNA during unwinding, thereby blocking the translation of the XO mRNA into protein and inhibiting the expression of XO gene.

In some embodiments, the P atom in Formula A59 may be linked to any possible position of a nucleotide in the siRNA, for example, to position 5', 2' or 3', or to the base of the nucleotide. In some embodiments, the P atom in Formula A59 may be linked to position 2', 3', or 5' of a nucleotide in the siRNA by forming a phosphodiester bond. In some embodiments, the P atom in Formula A59 is linked to an oxygen atom formed by deprotonation of 3' hydroxy of the nucleotide at 3'terminal of the sense strand of the siRNA (in this time, the P atom in Formula A59 may also be regarded as a P atom in a phosphate group contained in the siRNA), or the P atom in Formula A59 is linked to a nucleotide by substituting a hydrogen atom in 2'-hydroxy of a nucleotide of the sense strand of the siRNA, or the P atom in Formula A59 is linked to a nucleotide by substituting hydrogen in 5'-hydroxy of the nucleotide at 5' terminal of the sense strand of the siRNA.

The inventors of the present disclosure have surprisingly found that the siRNA conjugate of the present disclosure has significantly improved stability in plasma and low off-target effect, and also shows higher silencing activity against XO mRNA. In some embodiments, the siRNA of the present disclosure may be one of the siRNAs shown in Tables 1a-1l. The siRNA conjugates containing these siRNA show higher silencing activity against XO mRNA.

TABLE 1a

| siRNA No. | SEQ ID NO: | The first siRNA sequence of the present disclosure |
|---|---|---|
| | | Sequence direction 5'-3' |
| siXOa1 | 9 | GAGAUGAAGUUCAAGAAUA |
| | 10 | UAUUCUUGAACUUCAUCUCAA |
| siXOa2 | 11 | UUGAGAUGAAGUUCAAGAAUA |
| | 12 | UAUUCUUGAACUUCAUCUCAAUG |
| siXOa1-M1 | 13 | GmAmGmAmUmGmAfAfGfUmUmCmAmAmGmAmAmUmAm |
| | 14 | UmAfUmUmCmUfUmGmAmAmCmUmUmCfAmUfCmUmCmAmAm |
| siXOa1-M2 | 15 | GmAmGmAmUfGmAfAfGfUmUmCmAmAmGmAmAmUmAm |
| | 16 | UmAfUmUmCmUfUmGfAfAmCmUmUmCfAmUfCmUmCmAmAm |
| siXOa1-M3 | 17 | GmAmGmAmUfGmAfAfGfUmUmCmAmAmGmAmAmUmAm |
| | 18 | UmAfUmUmCmUfUmGmAmAmCmUmUmCfAmUfCmUmCmAmAm |
| siXOa2-M1 | 19 | UmUmGmAmGmAmUmGmAfAfGfUmUmCmAmAmGmAmAmUmAm |
| | 20 | UmAfUmUmCmUfUmGmAmAmCmUmUmCfAmUfCmUmCmAmAmUmGm |
| siXOa2-M2 | 21 | UmUmGmAmGmAmUfGmAfAfGfUmUmCmAmAmGmAmAmUmAm |
| | 22 | UmAfUmUmCmUfUmGfAfAmCmUmUmCfAmUfCmUmCmAmAmUmGm |
| siXOa2-M3 | 23 | UmUmGmAmGmAmUfGmAfAfGfUmUmCmAmAmGmAmAmUmAm |
| | 24 | UmAfUmUmCmUfUmGmAmAmCmUmUmCfAmUfCmUmCmAmAmUmGm |
| siXOa1-M1S | 25 | GmsAmsGmAmUmGmAfAfGfUmUmCmAmAmGmAmAmUmAm |
| | 26 | UmsAfsUmUmCmUfUmGmAmAmCmUmUmCfAmUfCmUmCmsAmsAm |
| siXOa1-M2S | 27 | GmsAmsGmAmUfGmAfAfGfUmUmCmAmAmGmAmAmUmAm |
| | 28 | UmsAfsUmUmCmUfUmGfAfAmCmUmUmCfAmUfCmUmCmsAmsAm |
| siXOa1-M3S | 29 | GmsAmsGmAmUfGmAfAfGfUmUmCmAmAmGmAmAmUmAm |
| | 30 | UmsAfsUmUmCmUfUmGmAmAmCmUmUmCfAmUfCmUmCmsAmsAm |
| siXOa2-M1S | 31 | UmsUmsGmAmGmAmUmGmAfAfGfUmUmCmAmAmGmAmAmUmAm |
| | 32 | UmsAfsUmUmCmUfUmGmAmAmCmUmUmCfAmUfCmUmCmAmAmsUmsGm |
| siXOa2-M2S | 33 | UmsUmsGmAmGmAmUfGmAfAfGfUmUmCmAmAmGmAmAmUmAm |
| | 34 | UmsAfsUmUmCmUfUmGfAfAmCmUmUmCfAmUfCmUmCmAmAmsUmsGm |
| siXOa2-M3S | 35 | UmsUmsGmAmGmAmUfGmAfAfGfUmUmCmAmAmGmAmAmUmAm |
| | 36 | UmsAfsUmUmCmUfUmGmAmAmCmUmUmCfAmUfCmUmCmAmAmsUmsGm |
| siXOa1-M1P1 | 37 | GmAmGmAmUmGmAfAfGfUmUmCmAmAmGmAmAmUmAm |
| | 38 | P1UmAfUmUmCmUfUmGmAmAmCmUmUmCfAmUfCmUmCmAmAm |
| siXOa1-M2P1 | 39 | GmAmGmAmUfGmAfAfGfUmUmCmAmAmGmAmAmUmAm |
| | 40 | P1UmAfUmUmCmUfUmGfAfAmCmUmUmCfAmUfCmUmCmAmAm |

TABLE 1a-continued

| The first siRNA sequence of the present disclosure | | |
|---|---|---|
| siRNA No. | SEQ ID NO: | Sequence direction 5'-3' |
| siXOa1-M3P1 | 41 | GmAmGmAmUfGmAfAfGfUmUmCmAmAmGmAmAmUmAm |
| | 42 | P1UmAfUmUmCmUfUmGmAmAmCmUmUmCfAmUfCmUmCmAmAm |
| siXOa2-M1P1 | 43 | UmUmGmAmGmAmUmGmAfAfGfUmUmCmAmAmGmAmAmUmAm |
| | 44 | P1UmAfUmUmCmUfUmGmAmAmCmUmUmCfAmUfCmUmCmAmAmUmGm |
| siXOa2-M2P1 | 45 | UmUmGmAmGmAmUfGmAfAfGfUmUmCmAmAmGmAmAmUmAm |
| | 46 | P1UmAfUmUmCmUfUmGfAfAmCmUmUmCfAmUfCmUmCmAmAmUmGm |
| siXOa2-M3P1 | 47 | UmUmGmAmGmAmUfGmAfAfGfUmUmCmAmAmGmAmAmUmAm |
| | 48 | P1UmAfUmUmCmUfUmGmAmAmCmUmUmCfAmUfCmUmCmAmAmUmGm |
| siXOa1-M1SP1 | 49 | GmsAmsGmAmUmGmAfAfGfUmUmCmAmAmGmAmAmUmAm |
| | 50 | P1UmsAfsUmUmCmUfUmGmAmAmCmUmUmCfAmUfCmUmCmsAmsAm |
| siXOa1-M2SP1 | 51 | GmsAmsGmAmUfGmAfAfGfUmUmCmAmAmGmAmAmUmAm |
| | 52 | P1UmsAfsUmUmCmUfUmGfAfAmCmUmUmCfAmUfCmUmCmsAmsAm |
| siXOa1-M3SP1 | 53 | GmsAmsGmAmUfGmAfAfGfUmUmCmAmAmGmAmAmUmAm |
| | 54 | P1UmsAfsUmUmCmUfUmGmAmAmCmUmUmCfAmUfCmUmCmsAmsAm |
| siXOa2-M1SP1 | 55 | UmsUmsGmAmGmAmUmGmAfAfGfUmUmCmAmAm GmAmAmUmAm |
| | 56 | P1UmsAfsUmUmCmUfUmGmAmAmCmUmUmCfAmUfCmUmCmAmAmsUmsGm |
| siXOa2-M2SP1 | 57 | UmsUmsGmAmGmAmUfGmAfAfGfUmUmCmAmAmGmAmAmUmAm |
| | 58 | P1UmsAfsUmUmCmUfUmGfAfAmCmUmUmCfAmUfCmUmCmAmAmsUmsGm |
| siXOa2-M3SP1 | 59 | UmsUmsGmAmGmAmUfGmAfAfGfUmUmCmAmAmGmAmAmUmAm |
| | 60 | P1UmsAfsUmUmCmUfUmGmAmAmCmUmUmCfAmUfCmUmCmAmAmsUmsGm |

TABLE 1b

| The second siRNA sequence of the present disclosure | | |
|---|---|---|
| siRNA No. | SEQ ID NO: | Sequence direction 5'-3' |
| siXOb1 | 69 | CAUAACUGGAAUUUGUAAU |
| | 70 | AUUACAAAUUCCAGUUAUGUU |
| siXOb2 | 71 | AACAUAACUGGAAUUUGUAAU |
| | 72 | AUUACAAAUUCCAGUUAUGUUAC |
| siXOb1-M1 | 73 | CmAmUmAmAmCmUfGfGfAmAmUmUmUmGmUmAmAmUm |
| | 74 | AmUfUmAmCmAfAmAmUmUmCmCmAmGfUmUfAmUmGmUmUm |
| siXOb1-M2 | 75 | CmAmUmAmAfCmUfGfGfAmAmUmUmUmGmUmAmAmUm |
| | 76 | AmUfUmAmCmAfAmAfUfUmCmCmAmGfUmUfAmUmGmUmUm |
| siXOb1-M3 | 77 | CmAmUmAmAfCmUfGfGfAmAmUmUmUmGmUmAmAmUm |
| | 78 | AmUfUmAmCmAfAmAmUmUmCmCmAmGfUmUfAmUmGmUmUm |
| siXOb2-M1 | 79 | AmAmCmAmUmAmAmCmUfGfGfAmAmUmUmUmGmUmAmAmUm |
| | 80 | AmUfUmAmCmAfAmAmUmUmCmCmAmGfUmUfAmUmGmUmUmAmCm |

TABLE 1b-continued

| The second siRNA sequence of the present disclosure | | |
|---|---|---|
| siRNA No. | SEQ ID NO: | Sequence direction 5'-3' |
| siXOb2 M2 | 81 82 | AmAmCmAmUmAmAfCmUfGfGfAmAmUmUmUmGmUmAmAmUm AmUfUmAmCmAfAmAfUfUmCmCmAmGfUmUfAmUmGmUmUmA mCm |
| siXOb2- M3 | 83 84 | AmAmCmAmUmAmAfCmUfGfGfAmAmUmUmUmGmUmAmAmUm AmUfUmAmCmAfAmAmUmUmCmCmAmGfUmUfAmUmGmUmUm AmCm |
| siXOb1- M1S | 85 86 | CmsAmsUmAmAmCmUfGfGfAmAmUmUmUmGmUmAmAmUm AmsUfsUmAmCmAfAmAmUmUmCmCmAmGfUmUfAmUmGmsUms Um |
| siXOb1- M2S | 87 88 | CmsAmsUmAmAfCmUfGfGfAmAmUmUmUmGmUmAmAmUm AmsUfsUmAmCmAfAmAfUfUmCmCmAmGfUmUfAmUmGmsUmsU m |
| siXOb1- M3S | 89 90 | CmsAmsUmAmAfCmUfGfGfAmAmUmUmUmGmUmAmAmUm AmsUfsUmAmCmAfAmAmUmUmCmCmAmGfUmUfAmUmGmsUms Um |
| siXOb2- M1S | 91 92 | AmsAmsCmAmUmAmAmCmUfGfGfAmAmUmUmUmGmUmAmAm Um AmsUfsUmAmCmAfAmAmUmUmCmCmAmGfUmUfAmUmGmUmU msAmsCm |
| siXOb2- M2S | 93 94 | AmsAmsCmAmUmAmAfCmUfGfGfAmAmUmUmUmGmUmAmAmU m AmsUfsUmAmCmAfAmAfUfUmCmCmAmGfUmUfAmUmGmUmUm sAmsCm |
| siXOb2- M3S | 95 96 | AmsAmsCmAmUmAmAfCmUfGfGfAmAmUmUmUmGmUmAmAmU m AmsUfsUmAmCmAfAmAmUmUmCmCmAmGfUmUfAmUmGmUmU msAmsCm |
| siXOb1- M1P1 | 97 98 | CmAmUmAmAmCmUfGfGfAmAmUmUmUmGmUmAmAmUm P1AmUfUmAmCmAfAmAmUmUmCmCmAmGfUmUfAmUmGmUm Um |
| siXOb1- M2P1 | 99 100 | CmAmUmAmAfCmUfGfGfAmAmUmUmUmGmUmAmAmUm P1AmUfUmAmCmAfAmAfUfUmCmCmAmGfUmUfAmUmGmUmUm |
| siXOb1- M3P1 | 101 102 | CmAmUmAmAfCmUfGfGfAmAmUmUmUmGmUmAmAmUm P1AmUfUmAmCmAfAmAmUmUmCmCmAmGfUmUfAmUmGmUm Um |
| siXOb2- M1P1 | 103 104 | AmAmCmAmUmAmAmCmUfGfGfAmAmUmUmUmGmUmAmAmU m P1AmUfUmAmCmAfAmAmUmUmCmCmAmGfUmUfAmUmGmUm UmAmCm |
| siXOb2- M2P1 | 105 106 | AmAmCmAmUmAmAfCmUfGfGfAmAmUmUmUmGmUmAmAmUm P1AmUfUmAmCmAfAmAfUfUmCmCmAmGfUmUfAmUmGmUmUm AmCm |
| siXOb2- M3P1 | 107 108 | AmAmCmAmUmAmAfCmUfGfGfAmAmUmUmUmGmUmAmAmUm P1AmUfUmAmCmAfAmAmUmUmCmCmAmGfUmUfAmUmGmUm UmAmCm |
| siXOb1- M1SP1 | 109 110 | CmsAmsUmAmAmCmUfGfGfAmAmUmUmUmGmUmAmAmUm P1AmsUfsUmAmCmAfAmAmUmUmCmCmAmGfUmUfAmUmGmsU msUm |
| siXOb1- M2SP1 | 111 112 | CmsAmsUmAmAfCmUfGfGfAmAmUmUmUmGmUmAmAmUm P1AmsUfsUmAmCmAfAmAfUfUmCmCmAmGfUmUfAmUmGmsUms Um |
| siXOb1- M3SP1 | 113 114 | CmsAmsUmAmAfCmUfGfGfAmAmUmUmUmGmUmAmAmUm P1AmsUfsUmAmCmAfAmAmUmUmCmCmAmGfUmUfAmUmGmsU msUm |
| siXOb2- M1SP1 | 115 116 | AmsAmsCmAmUmAmAmCmUfGfGfAmAmUmUmUmGmUmAmAm Um P1AmsUfsUmAmCmAfAmAmUmUmCmCmAmGfUmUfAmUmGmU mUmsAmsCm |

TABLE 1b-continued

| The second siRNA sequence of the present disclosure | | |
|---|---|---|
| siRNA No. | SEQ ID NO: | Sequence direction 5'-3' |
| siXOb2-M2SP1 | 117 | AmsAmsCmAmUmAmAfCmUfGfGfAmAmUmUmUmGmUmAmAmUm |
| | 118 | P1AmsUfsUmAmCmAfAmAfUfUmCmCmAmGfUmUfAmUmGmUmUmsAmsCm |
| siXOb2-M3SP1 | 119 | AmsAmsCmAmUmAmAfCmUfGfGfAmAmUmUmUmGmUmAmAmUm |
| | 120 | P1AmsUfsUmAmCmAfAmAmUmUmCmCmAmGfUmUfAmUmGmUmUmUmsAmsCm |

TABLE 1c

| The third siRNA sequence of the present disclosure | | |
|---|---|---|
| siRNA No. | SEQ ID NO: | Sequence direction 5'-3' |
| siXOc1 | 129 | CAUUAUCACAAUUGAGGAU |
| | 130 | AUCCUCAAUUGUGAUAAUGGC |
| siXOc2 | 131 | GCCAUUAUCACAAUUGAGGAU |
| | 132 | AUCCUCAAUUGUGAUAAUGGCUG |
| siXOc1-M1 | 133 | CmAmUmUmAmUmCfAfCfAmAmUmUmGmAmGmGmAmUm |
| | 134 | AmUfCmCmUmCfAmAmUmUmGmUmGmAfUmAfAmUmGmGmCm |
| siXOc1-M2 | 135 | CmAmUmUmAfUmCfAfCfAmAmUmUmGmAmGmGmAmUm |
| | 136 | AmUfCmCmUmCfAmAfUfUmGmUmGmAfUmAfAmUmGmGmCm |
| siXOc1-M3 | 137 | CmAmUmUmAfUmCfAfCfAmAmUmUmGmAmGmGmAmUm |
| | 138 | AmUfCmCmUmCfAmAmUmUmGmUmGmAfUmAfAmUmGmGmCm |
| siXOc2-M1 | 139 | GmCmCmAmUmUmAmUmCfAfCfAmAmUmUmGmAmGmGmAmUm |
| | 140 | AmUfCmCmUmCfAmAmUmUmGmUmGmAfUmAfAmUmGmGmCmUmGm |
| siXOc2-M2 | 141 | GmCmCmAmUmUmAfUmCfAfCfAmAmUmUmGmAmGmGmAmUm |
| | 142 | AmUfCmCmUmCfAmAfUfUmGmUmGmAfUmAfAmUmGmGmCmUmGm |
| siXOc2-M3 | 143 | GmCmCmAmUmUmAfUmCfAfCfAmAmUmUmGmAmGmGmAmUm |
| | 144 | AmUfCmCmUmCfAmAmUmUmGmUmGmAfUmAfAmUmGmGmCmUmGm |
| siXOc1-M1S | 145 | CmsAmsUmUmAmUmCfAfCfAmAmUmUmGmAmGmGmAmUm |
| | 146 | AmsUfsCmCmUmCfAmAmUmUmGmUmGmAfUmAfAmUmGmsGmsCm |
| siXOc1-M2S | 147 | CmsAmsUmUmAfUmCfAfCfAmAmUmUmGmAmGmGmAmUm |
| | 148 | AmsUfsCmCmUmCfAmAfUfUmGmUmGmAfUmAfAmUmGmsGmsCm |
| siXOc1-M3S | 149 | CmsAmsUmUmAfUmCfAfCfAmAmUmUmGmAmGmGmAmUm |
| | 150 | AmsUfsCmCmUmCfAmAmUmUmGmUmGmAfUmAfAmUmGmsGmsCm |
| siXOc2-M1S | 151 | GmsCmsCmAmUmUmAmUmCfAfCfAmAmUmUmGmAmGmGmAmUm |
| | 152 | AmsUfsCmCmUmCfAmAmUmUmGmUmGmAfUmAfAmUmGmGmCmsUmsGm |
| siXOc2-M2S | 153 | GmsCmsCmAmUmUmAfUmCfAfCfAmAmUmUmGmAmGmGmAmUm |
| | 154 | AmsUfsCmCmUmCfAmAfUfUmGmUmGmAfUmAfAmUmGmGmCmsUmsGm |
| siXOc2-M3S | 155 | GmsCmsCmAmUmUmAfUmCfAfCfAmAmUmUmGmAmGmGmAmUm |
| | 156 | AmsUfsCmCmUmCfAmAmUmUmGmUmGmAfUmAfAmUmGmGmCmsUmsGm |

TABLE 1c-continued

| | | The third siRNA sequence of the present disclosure |
|---|---|---|
| siRNA No. | SEQ ID NO: | Sequence direction 5'-3' |
| siXOc1-M1P1 | 157 | CmAmUmUmAmUmCfAfCfAmAmUmUmGmAmGmGmAmUm |
| | 158 | P1AmUfCmCmUmCfAmAmUmUmGmUmGmAfUmAfAmUmGmGmCm |
| siXOc1-M2P1 | 159 | CmAmUmUmAfUmCfAfCfAmAmUmUmGmAmGmGmAmUm |
| | 160 | P1AmUfCmCmUmCfAmAfUfUmGmUmGmAfUmAfAmUmGmGmCm |
| siXOc1-M3P1 | 161 | CmAmUmUmAfUmCfAfCfAmAmUmUmGmAmGmGmAmUm |
| | 162 | P1AmUfCmCmUmCfAmAmUmUmGmUmGmAfUmAfAmUmGmGmCm |
| siXOc2-M1P1 | 163 | GmCmCmAmUmUmAmUmCfAfCfAmAmUmUmGmAmGmGmAmUm |
| | 164 | P1AmUfCmCmUmCfAmAmUmUmGmUmGmAfUmAfAmUmGmGmCmUmGm |
| siXOc2-M2P1 | 165 | GmCmCmAmUmUmAfUmCfAfCfAmAmUmUmGmAmGmGmAmUm |
| | 166 | P1AmUfCmCmUmCfAmAfUfUmGmUmGmAfUmAfAmUmGmGmCmUmGm |
| siXOc2-M3P1 | 167 | GmCmCmAmUmUmAfUmCfAfCfAmAmUmUmGmAmGmGmAmUm |
| | 168 | P1AmUfCmCmUmCfAmAmUmUmGmUmGmAfUmAfAmUmGmGmCmUmGm |
| siXOc1-M1SP1 | 169 | CmsAmsUmUmAmUmCfAfCfAmAmUmUmGmAmGmGmAmUm |
| | 170 | P1AmsUfsCmCmUmCfAmAmUmUmGmUmGmUmGmAfUmAfAmUmGmsGmsCm |
| siXOc1-M2SP1 | 171 | CmsAmsUmUmAfUmCfAfCfAmAmUmUmGmAmGmGmAmUm |
| | 172 | P1AmsUfsCmCmUmCfAmAfUfUmGmUmGmAfUmAfAmUmGmsGmsCm |
| siXOc1-M3SP1 | 173 | CmsAmsUmUmAfUmCfAfCfAmAmUmUmGmAmGmGmAmUm |
| | 174 | P1AmsUfsCmCmUmCfAmAmUmUmGmUmGmAfUmAfAmUmGmsGmsCm |
| siXOc2-M1SP1 | 175 | GmsCmsCmAmUmUmAmUmCfAfCfAmAmUmUmGmAmGmGmAmUm |
| | 176 | P1AmsUfsCmCmUmCfAmAmUmUmGmUmGmAfUmAfAmUmGmGmCmsUmsGm |
| siXOc2-M2SP1 | 177 | GmsCmsCmAmUmUmAfUmCfAfCfAmAmUmUmGmAmGmGmAmUm |
| | 178 | P1AmsUfsCmCmUmCfAmAfUfUmGmUmGmAfUmAfAmUmGmGmCmsUmsGm |
| siXOc2-M3SP1 | 179 | GmsCmsCmAmUmUmAfUmCfAfCfAmAmUmUmGmAmGmGmAmUm |
| | 180 | P1AmsUfsCmCmUmCfAmAmUmUmGmUmGmAfUmAfAmUmGmGmCmsUmsGm |

TABLE 1d

| | | The fourth siRNA sequence of the present disclosure |
|---|---|---|
| siRNA No. | SEQ ID NO: | Sequence direction 5'-3' |
| siXOd1 | 189 | GGAUCUCUCUCAGAGUAUU |
| | 190 | AAUACUCUGAGAGAGAUCCUG |
| siXOd2 | 191 | CAGGAUCUCUCUCAGAGUAUU |
| | 192 | AAUACUCUGAGAGAGAUCCUGGG |
| siXOd1-M1 | 193 | GmGmAmUmCmUmCfUfCfUmCmAmGmAmGmUmAmUmUm |
| | 194 | AmAfUmAmCmUfCmUmGmAmGmAmGmAmGmAfGmAfUmCmCmUmGm |
| siXOd1-M2 | 195 | GmGmAmUmCfUmCfUfCfUmCmAmGmAmGmUmAmUmUm |
| | 196 | AmAfUmAmCmUfCmUfGfAmGmAmGmAmGmAfGmAfUmCmCmUmGm |

TABLE 1d-continued

| The fourth siRNA sequence of the present disclosure | | |
| --- | --- | --- |
| siRNA No. | SEQ ID NO: | Sequence direction 5'-3' |
| siXOd1-M3 | 197 | GmGmAmUmCfUmCfUfCfUmCmAmGmAmGmUmAmUmUm |
| | 198 | AmAfUmAmCmUfCmUmGmAmGmAmGmAfGmAfUmCmCmUmGm |
| siXOd2-M1 | 199 | CmAmGmGmAmUmCmUmCfUfCfUmCmAmGmAmGmUmAmUmUm |
| | 200 | AmAfUmAmCmUfCmUmGmAmGmAmGmAfGmAfUmCmCmUmGmGmGm |
| siXOd2-M2 | 201 | CmAmGmGmAmUmCfUmCfUfCfUmCmAmGmAmGmUmAmUmUm |
| | 202 | AmAfUmAmCmUfCmUfGfAmGmAmGmAfGmAfUmCmCmUmGmGmGm |
| siXOd2-M3 | 203 | CmAmGmGmAmUmCfUmCfUfCfUmCmAmGmAmGmUmAmUmUm |
| | 204 | AmAfUmAmCmUfCmUmGmAmGmAmGmAfGmAfUmCmCmUmGmGmGm |
| siXOd1-M1S | 205 | GmsGmsAmUmCmUmCfUfCfUmCmAmGmAmGmUmAmUmUm |
| | 206 | AmsAfsUmAmCmUfCmUmGmAmGmAmGmAfGmAfUmCmCmsUmsGm |
| siXOd1-M2S | 207 | GmsGmsAmUmCfUmCfUfCfUmCmAmGmAmGmUmAmUmUm |
| | 208 | AmsAfsUmAmCmUfCmUfGfAmGmAmGmAfGmAfUmCmCmsUmsGm |
| siXOd1-M3S | 209 | GmsGmsAmUmCfUmCfUfCfUmCmAmGmAmGmUmAmUmUm |
| | 210 | AmsAfsUmAmCmUfCmUmGmAmGmAmGmAfGmAfUmCmCmsUmsGm |
| siXOd2-M1S | 211 | CmsAmsGmGmAmUmCmUmCfUfCfUmCmAmGmAmGmUmAmUmUm |
| | 212 | AmsAfsUmAmCmUfCmUmGmAmGmAmGmAfGmAfUmCmCmUmGmsGmsGm |
| siXOd2-M2S | 213 | CmsAmsGmGmAmUmCfUmCfUfCfUmCmAmGmAmGmUmAmUmUm |
| | 214 | AmsAfsUmAmCmUfCmUfGfAmGmAmGmAfGmAfUmCmCmUmGmsGmsGm |
| siXOd2-M3S | 215 | CmsAmsGmGmAmUmCfUmCfUfCfUmCmAmGmAmGmUmAmUmUm |
| | 216 | AmsAfsUmAmCmUfCmUmGmAmGmAmGmAfGmAfUmCmCmUmGmsGmsGm |
| siXOd1-M1P1 | 217 | GmGmAmUmCmUmCfUfCfUmCmAmGmAmGmUmAmUmUm |
| | 218 | P1AmAfUmAmCmUfCmUmGmAmGmAmGmAfGmAfUmCmCmUmGm |
| siXOd1-M2P1 | 219 | GmGmAmUmCfUmCfUfCfUmCmAmGmAmGmUmAmUmUm |
| | 220 | P1AmAfUmAmCmUfCmUfGfAmGmAmGmAfGmAfUmCmCmUmGm |
| siXOd1-M3P1 | 221 | GmGmAmUmCfUmCfUfCfUmCmAmGmAmGmUmAmUmUm |
| | 222 | P1AmAfUmAmCmUfCmUmGmAmGmAmGmAfGmAfUmCmCmUmGm |
| siXOd2-M1P1 | 223 | CmAmGmGmAmUmCmUmCfUfCfUmCmAmGmAmGmUmAmUmUm |
| | 224 | P1AmAfUmAmCmUfCmUmGmAmGmAmGmAfGmAfUmCmCmUmGmGmGm |
| siXOd2-M2P1 | 225 | CmAmGmGmAmUmCfUmCfUfCfUmCmAmGmAmGmUmAmUmUm |
| | 226 | P1AmAfUmAmCmUfCmUfGfAmGmAmGmAfGmAfUmCmCmUmGmGmGm |
| siXOd2-M3P1 | 227 | CmAmGmGmAmUmCfUmCfUfCfUmCmAmGmAmGmUmAmUmUm |
| | 228 | P1AmAfUmAmCmUfCmUmGmAmGmAmGmAfGmAfUmCmCmUmGmGmGm |
| siXOd1-M1SP1 | 229 | GmsGmsAmUmCmUmCfUfCfUmCmAmGmAmGmUmAmUmUm |
| | 230 | P1AmsAfsUmAmCmUfCmUmGmAmGmAmGmAfGmAfUmCmCmsUmsGm |
| siXOd1-M2SP1 | 231 | GmsGmsAmUmCfUmCfUfCfUmCmAmGmAmGmUmAmUmUm |
| | 232 | P1AmsAfsUmAmCmUfCmUfGfAmGmAmGmAfGmAfUmCmCmsUmsGm |

TABLE 1d-continued

| The fourth siRNA sequence of the present disclosure | | |
|---|---|---|
| siRNA No. | SEQ ID NO: | Sequence direction 5'-3' |
| siXOd1-M3SP1 | 233 | GmsGmsAmUmCfUmCfUfCfUmCmAmGmAmGmUmAmUmUm |
| | 234 | P1AmsAfsUmAmCmUfCmUmGmAmGmAmGmAfGmAfUmCmCmsUmsGm |
| siXOd2-M1SP1 | 235 | CmsAmsGmGmAmUmCmUmCfUfCfUmCmAmGmAmGmUmAmUmUm |
| | 236 | P1AmsAfsUmAmCmUfCmUmGmAmGmAmGmAmGmAfGmAfUmCmCmUmGmsGmsGm |
| siXOd2-M2SP1 | 237 | CmsAmsGmGmAmUmCfUmCfUfCfUmCmAmGmAmGmUmAmUmUm |
| | 238 | P1AmsAfsUmAmCmUfCmUfGfAmGmAmGmAfGmAfUmCmCmUmGmsGmsGm |
| siXOd2-M3SP1 | 239 | CmsAmsGmGmAmUmCfUmCfUfCfUmCmAmGmAmGmUmAmUmUm |
| | 240 | P1AmsAfsUmAmCmUfCmUmGmAmGmAmGmAmGmAfGmAfUmCmCmUmGmsGmsGm |

TABLE 1e

| The fifth siRNA sequence of the present disclosure | | |
|---|---|---|
| siRNA No. | SEQ ID NO: | Sequence direction 5'-3' |
| siXOe1 | 249 | ACAUGGACAACUGCUAUAA |
| | 250 | UUAUAGCAGUUGUCCAUGUGG |
| siXOe2 | 251 | CCACAUGGACAACUGCUAUAA |
| | 252 | UUAUAGCAGUUGUCCAUGUGGAA |
| siXOe1-M1 | 253 | AmCmAmUmGmGmAfCfAfAmCmUmGmCmUmAmUmAmAm |
| | 254 | UmUfAmUmAmGfCmAmGmUmUmGmUmCfCmAfUmGmUmGmGm |
| siXOe1-M2 | 255 | AmCmAmUmGfGmAfCfAfAmCmUmGmCmUmAmUmAmAm |
| | 256 | UmUfAmUmAmGfCmAfGfUmUmGmUmCfCmAfUmGmUmGmGm |
| siXOe1-M3 | 257 | AmCmAmUmGfGmAfCfAfAmCmUmGmCmUmAmUmAmAm |
| | 258 | UmUfAmUmAmGfCmAmGmUmUmGmUmCfCmAfUmGmUmGmGm |
| siXOe2-M1 | 259 | CmCmAmCmAmUmGmGmAfCfAfAmCmUmGmCmUmAmUmAmAm |
| | 260 | UmUfAmUmAmGfCmAmGmUmUmGmUmCfCmAfUmGmUmGmGmAmAm |
| siXOe2-M2 | 261 | CmCmAmCmAmUmGfGmAfCfAfAmCmUmGmCmUmAmUmAmAm |
| | 262 | UmUfAmUmAmGfCmAfGfUmUmGmUmCfCmAfUmGmUmGmGmAmAm |
| siXOe2-M3 | 263 | CmCmAmCmAmUmGfGmAfCfAfAmCmUmGmCmUmAmUmAmAm |
| | 264 | UmUfAmUmAmGfCmAmGmUmUmGmUmCfCmAfUmGmUmGmGmAmAm |
| siXOe1-M1S | 265 | AmsCmsAmUmGmGmAfCfAfAmCmUmGmCmUmAmUmAmAm |
| | 266 | UmsUfsAmUmAmGfCmAmGmUmUmGmUmCfCmAfUmGmUmsGmsGm |
| siXOe1-M2S | 267 | AmsCmsAmUmGfGmAfCfAfAmCmUmGmCmUmAmUmAmAm |
| | 268 | UmsUfsAmUmAmGfCmAfGfUmUmGmUmCfCmAfUmGmUmsGmsGm |
| siXOe1-M3S | 269 | AmsCmsAmUmGfGmAfCfAfAmCmUmGmCmUmAmUmAmAm |
| | 270 | UmsUfsAmUmAmGfCmAmGmUmUmGmUmCfCmAfUmGmUmsGmsGm |
| siXOe2-M1S | 271 | CmsCmsAmCmAmUmGmGmAfCfAfAmCmUmGmCmUmAmUmAmAm |
| | 272 | UmsUfsAmUmAmGfCmAmGmUmUmGmUmCfCmAfUmGmUmGmGmsAmsAm |

TABLE 1e-continued

| The fifth siRNA sequence of the present disclosure | | |
|---|---|---|
| siRNA No. | SEQ ID NO: | Sequence direction 5'-3' |
| siXOe2-M2S | 273 | CmsCmsAmCmAmUmGfGmAfCfAfAmCmUmGmCmUmAmUmAmAm |
| | 274 | UmsUfsAmUmAmGfCmAfGfUmUmGmUmCfCmAfUmGmUmGmGmsAmsAm |
| siXOe2-M3S | 275 | CmsCmsAmCmAmUmGfGmAfCfAfAmCmUmGmCmUmAmUmAmAm |
| | 276 | UmsUfsAmUmAmGfCmAmGmUmUmGmUmCfCmAfUmGmUmGmGmsAmsAm |
| siXOe1-M1P1 | 277 | AmCmAmUmGmGmAfCfAfAmCmUmGmCmUmAmUmAmAm |
| | 278 | P1UmUfAmUmAmGfCmAmGmUmUmGmUmCfCmAfUmGmUmGmGm |
| siXOe1-M2P1 | 279 | AmCmAmUmGfGmAfCfAfAmCmUmGmCmUmAmUmAmAm |
| | 280 | P1UmUfAmUmAmGfCmAfGfUmUmGmUmCfCmAfUmGmUmGmGmGm |
| siXOe1-M3P1 | 281 | AmCmAmUmGfGmAfCfAfAmCmUmGmCmUmAmUmAmAm |
| | 282 | P1UmUfAmUmAmGfCmAmGmUmUmGmUmCfCmAfUmGmUmGmGm |
| siXOe2-M1P1 | 283 | CmCmAmCmAmUmGmGmAfCfAfAmCmUmGmCmUmAmUmAmAm |
| | 284 | P1UmUfAmUmAmGfCmAmGmUmUmGmUmCfCmAfUmGmUmGmGmGmAmAm |
| siXOe2-M2P1 | 285 | CmCmAmCmAmUmGfGmAfCfAfAmCmUmGmCmUmAmUmAmAm |
| | 286 | P1UmUfAmUmAmGfCmAfGfUmUmGmUmCfCmAfUmGmUmGmGmAmAm |
| siXOe2-M3P1 | 287 | CmCmAmCmAmUmGfGmAfCfAfAmCmUmGmCmUmAmUmAmAm |
| | 288 | P1UmUfAmUmAmGfCmAmGmUmUmGmUmCfCmAfUmGmUmGmGmAmAm |
| siXOe1-M1SP1 | 289 | AmsCmsAmUmGmGmAfCfAfAmCmUmGmCmUmAmUmAmAm |
| | 290 | P1UmsUfsAmUmAmGfCmAmGmUmUmGmUmCfCmAfUmGmUmsGmsGm |
| siXOe1-M2SP1 | 291 | AmsCmsAmUmGfGmAfCfAfAmCmUmGmCmUmAmUmAmAm |
| | 292 | P1UmsUfsAmUmAmGfCmAfGfUmUmGmUmCfCmAfUmGmUmsGmsGm |
| siXOe1-M3SP1 | 293 | AmsCmsAmUmGfGmAfCfAfAmCmUmGmCmUmAmUmAmAm |
| | 294 | P1UmsUfsAmUmAmGfCmAmGmUmUmGmUmCfCmAfUmGmUmsGmsGm |
| siXOe2-M1SP1 | 295 | CmsCmsAmCmAmUmGmGmAfCfAfAmCmUmGmCmUmAmUmAmAm |
| | 296 | P1UmsUfsAmUmAmGfCmAmGmUmUmGmUmCfCmAfUmGmUmGmGmsAmsAm |
| siXOe2-M2SP1 | 297 | CmsCmsAmCmAmUmGfGmAfCfAfAmCmUmGmCmUmAmUmAmAm |
| | 298 | P1UmsUfsAmUmAmGfCmAfGfUmUmGmUmCfCmAfUmGmUmGmGmGmsAmsAm |
| siXOe2-M3SP1 | 299 | CmsCmsAmCmAmUmGfGmAfCfAfAmCmUmGmCmUmAmUmAmAm |
| | 300 | P1UmsUfsAmUmAmGfCmAmGmUmUmGmUmCfCmAfUmGmUmGmGmsAmsAm |

TABLE 1f

| The sixth siRNA sequence of the present disclosure | | |
|---|---|---|
| siRNA No. | SEQ ID NO: | Sequence direction 5'-3' |
| siXOf1 | 309 | UAGCAAGCUCUCAGUAUCA |
| | 310 | UGAUACUGAGAGCUUGCUAGG |

TABLE 1f-continued

| The sixth siRNA sequence of the present disclosure | | |
| --- | --- | --- |
| siRNA No. | SEQ ID NO: | Sequence direction 5'-3' |
| siXOf2 | 311 | CCUAGCAAGCUCUCAGUAUCA |
| | 312 | UGAUACUGAGAGCUUGCUAGGCA |
| siXOf1-M1 | 313 | UmAmGmCmAmAmGfCfUfCmUmCmAmGmUmAmUmCmAm |
| | 314 | UmGfAmUmAmCfUmGmAmGmAmGmCmUfUmGfCmUmAmGmGm |
| siXOf1-M2 | 315 | UmAmGmCmAfAmGfCfUfCmUmCmAmGmUmAmUmCmAm |
| | 316 | UmGfAmUmAmCfUmGfAfGmAmGmCmUfUmGfCmUmAmGmGm |
| siXOf1-M3 | 317 | UmAmGmCmAfAmGfCfUfCmUmCmAmGmUmAmUmCmAm |
| | 318 | UmGfAmUmAmCfUmGmAmGmAmGmCmUfUmGfCmUmAmGmGm |
| siXOf2-M1 | 319 | CmCmUmAmGmCmAmAmGfCfUfCmUmCmAmGmUmAmUmCmAm |
| | 320 | UmGfAmUmAmCfUmGmAmGmAmGmCmUfUmGfCmUmAmGmGmCmAm |
| siXOf2-M2 | 321 | CmCmUmAmGmCmAfAmGfCfUfCmUmCmAmGmUmAmUmCmAm |
| | 322 | UmGfAmUmAmCfUmGfAfGmAmGmCmUfUmGfCmUmAmGmGmCmAm |
| siXOf2-M3 | 323 | CmCmUmAmGmCmAfAmGfCfUfCmUmCmAmGmUmAmUmCmAm |
| | 324 | UmGfAmUmAmCfUmGmAmGmAmGmCmUfUmGfCmUmAmGmGmCmAm |
| siXOf1-M1S | 325 | UmsAmsGmCmAmAmGfCfUfCmUmCmAmGmUmAmUmCmAm |
| | 326 | UmsGfsAmUmAmCfUmGmAmGmAmGmCmUfUmGfCmUmAmsGmsGm |
| siXOf1-M2S | 327 | UmsAmsGmCmAfAmGfCfUfCmUmCmAmGmUmAmUmCmAm |
| | 328 | UmsGfsAmUmAmCfUmGfAfGmAmGmCmUfUmGfCmUmAmsGmsGm |
| siXOf1-M3S | 329 | UmsAmsGmCmAfAmGfCfUfCmUmCmAmGmUmAmUmCmAm |
| | 330 | UmsGfsAmUmAmCfUmGmAmGmAmGmCmUfUmGfCmUmAmsGmsGm |
| siXOf2-M1S | 331 | CmsCmsUmAmGmCmAmAmGfCfUfCmUmCmAmGmUmAmUmCmAm |
| | 332 | UmsGfsAmUmAmCfUmGmAmGmAmGmCmUfUmGfCmUmAmGmGmsCmsAm |
| siXOf2-M2S | 333 | CmsCmsUmAmGmCmAfAmGfCfUfCmUmCmAmGmUmAmUmCmAm |
| | 334 | UmsGfsAmUmAmCfUmGfAfGmAmGmCmUfUmGfCmUmAmGmGmsCmsAm |
| siXOf2-M3S | 335 | CmsCmsUmAmGmCmAfAmGfCfUfCmUmCmAmGmUmAmUmCmAm |
| | 336 | UmsGfsAmUmAmCfUmGmAmGmAmGmCmUfUmGfCmUmAmGmGmsCmsAm |
| siXOf1-M1P1 | 337 | UmAmGmCmAmAmGfCfUfCmUmCmAmGmUmAmUmCmAm |
| | 338 | P1UmGfAmUmAmCfUmGmAmGmAmGmCmUfUmGfCmUmAmGmGm |
| siXOf1-M2P1 | 339 | UmAmGmCmAfAmGfCfUfCmUmCmAmGmUmAmUmCmAm |
| | 340 | P1UmGfAmUmAmCfUmGfAfGmAmGmCmUfUmGfCmUmAmGmGm |
| siXOf1-M3P1 | 341 | UmAmGmCmAfAmGfCfUfCmUmCmAmGmUmAmUmCmAm |
| | 342 | P1UmGfAmUmAmCfUmGmAmGmAmGmCmUfUmGfCmUmAmGmGm |
| siXOf2-M1P1 | 343 | CmCmUmAmGmCmAmAmGfCfUfCmUmCmAmGmUmAmUmCmAm |
| | 344 | P1UmGfAmUmAmCfUmGmAmGmAmGmCmUfUmGfCmUmAmGmGmCmAm |
| siXOf2-M2P1 | 345 | CmCmUmAmGmCmAfAmGfCfUfCmUmCmAmGmUmAmUmCmAm |
| | 346 | P1UmGfAmUmAmCfUmGfAfGmAmGmCmUfUmGfCmUmAmGmGmCmAm |
| siXOf2-M3P1 | 347 | CmCmUmAmGmCmAfAmGfCfUfCmUmCmAmGmUmAmUmCmAm |
| | 348 | P1UmGfAmUmAmCfUmGmAmGmAmGmCmUfUmGfCmUmAmGmGmCmAm |

TABLE 1f-continued

The sixth siRNA sequence of the present disclosure

| siRNA No. | SEQ ID NO: | Sequence direction 5'-3' |
|---|---|---|
| siXOf1-M1SP1 | 349 | UmsAmsGmCmAmAmGfCfUfCmUmCmAmGmUmAmUmCmAm |
| | 350 | P1UmsGfsAmUmAmCfUmGmAmGmAmGmCmUfUmGfCmUmAmsGmsGm |
| siXOf1-M2SP1 | 351 | UmsAmsGmCmAfAmGfCfUfCmUmCmAmGmUmAmUmCmAm |
| | 352 | P1UmsGfsAmUmAmCfUmGfAfGmAmGmCmUfUmGfCmUmAmsGmsGm |
| siXOf1-M3SP1 | 353 | UmsAmsGmCmAfAmGfCfUfCmUmCmAmGmUmAmUmCmAm |
| | 354 | P1UmsGfsAmUmAmCfUmGmAmGmAmGmCmUfUmGfCmUmAmsGmsGm |
| siXOf2-M1SP1 | 355 | CmsCmsUmAmGmCmAmAmGfCfUfCmUmCmAmGmUmAmUmCmAm |
| | 356 | P1UmsGfsAmUmAmCfUmGmAmGmAmGmCmUfUmGfCmUmAmGmGmsCmsAm |
| siXOf2-M2SP1 | 357 | CmsCmsUmAmGmCmAfAmGfCfUfCmUmCmAmGmUmAmUmCmAm |
| | 358 | P1UmsGfsAmUmAmCfUmGfAfGmAmGmCmUfUmGfCmUmAmGmGmsCmsAm |
| siXOf2-M3SP1 | 359 | CmsCmsUmAmGmCmAfAmGfCfUfCmUmCmAmGmUmAmUmCmAm |
| | 360 | P1UmsGfsAmUmAmCfUmGmAmGmAmGmCmUfUmGfCmUmAmGmGmsCmsAm |

TABLE 1g

The seventh siRNA sequence of the present disclosure

| siRNA No. | SEQ ID NO: | Sequence direction 5'-3' |
|---|---|---|
| siXOg1 | 369 | AUAAGGUUACUUGUGUUGG |
| | 370 | CCAACACAAGUAACCUUAUCC |
| siXOg2 | 371 | GGAUAAGGUUACUUGUGUUGG |
| | 372 | CCAACACAAGUAACCUUAUCCUU |
| siXOg1-M1 | 373 | AmUmAmAmGmGmUfUfAfCmUmUmGmUmGmUmUmGmGm |
| | 374 | CmCfAmAmCmAfCmAmAmGmUmAmAmCfCmUfUmAmUmCmCm |
| siXOg1-M2 | 375 | AmUmAmAmGfGmUfUfAfCmUmUmGmUmGmUmUmGmGm |
| | 376 | CmCfAmAmCmAfCmAfAfGmUmAmAmCfCmUfUmAmUmCmCm |
| siXOg1-M3 | 377 | AmUmAmAmGfGmUfUfAfCmUmUmGmUmGmUmUmGmGm |
| | 378 | CmCfAmAmCmAfCmAmAmGmUmAmAmCfCmUfUmAmUmUmCmCm |
| siXOg2-M1 | 379 | GmGmAmUmAmAmGmGmUfUfAfCmUmUmGmUmGmUmUmGmGm |
| | 380 | CmCfAmAmCmAfCmAmAmGmUmAmAmCfCmUfUmAmUmCmCmUmUm |
| siXOg2-M2 | 381 | GmGmAmUmAmAmGfGmUfUfAfCmUmUmGmUmGmUmUmGmGm |
| | 382 | CmCfAmAmCmAfCmAfAfGmUmAmAmCfCmUfUmAmUmUmCmCmUmUm |
| siXOg2-M3 | 383 | GmGmAmUmAmAmGfGmUfUfAfCmUmUmGmUmGmUmUmGmGm |
| | 384 | CmCfAmAmCmAfCmAmAmGmUmAmAmCfCmUfUmAmUmUmCmCmUmUm |
| siXOg1-M1S | 385 | AmsUmsAmAmGmGmUfUfAfCmUmUmGmUmGmUmUmGmGm |
| | 386 | CmsCfsAmAmCmAfCmAmAmGmUmAmAmCfCmUfUmAmUmsCmsCm |
| siXOg1-M2S | 387 | AmsUmsAmAmGfGmUfUfAfCmUmUmGmUmGmUmUmGmGm |
| | 388 | CmsCfsAmAmCmAfCmAfAfGmUmAmAmCfCmUfUmAmUmsCmsCm |

TABLE 1g-continued

| The seventh siRNA sequence of the present disclosure | | |
|---|---|---|
| siRNA No. | SEQ ID NO: | Sequence direction 5'-3' |
| siXOg1-M3S | 389 | AmsUmsAmAmGfGmUfUfAfCmUmUmGmUmGmUmUmGmGm |
| | 390 | CmsCfsAmAmCmAfCmAmAmGmUmAmAmCfCmUfUmAmUmsCms Cm |
| siXOg2-M1S | 391 | GmsGmsAmUmAmAmGmGmUfUfAfCmUmUmGmUmGmUmUmGm Gm |
| | 392 | CmsCfsAmAmCmAfCmAmAmGmGmUmAmAmCfCmUfUmAmUmCmC msUmsUm |
| siXOg2-M2S | 393 | GmsGmsAmUmAmAmGfGmUfUfAfCmUmUmGmUmGmUmUmGmG m |
| | 394 | CmsCfsAmAmCmAfCmAfAfGmUmAmAmCfCmUfUmAmUmCmCms UmsUm |
| siXOg2-M3S | 395 | GmsGmsAmUmAmAmGfGmUfUfAfCmUmUmGmUmGmUmUmGmG m |
| | 396 | CmsCfsAmAmCmAfCmAmAmGmUmAmAmCfCmUfUmAmUmCmC msUmsUm |
| siXOg1-M1P1 | 397 | AmUmAmAmGmGmUfUfAfCmUmUmGmUmGmUmUmGmGm |
| | 398 | P1CmCfAmAmCmAfCmAmAmGmUmAmAmCfCmUfUmAmUmCmC m |
| siXOg1-M2P1 | 399 | AmUmAmAmGfGmUfUfAfCmUmUmGmUmGmUmUmGmGm |
| | 400 | P1CmCfAmAmCmAfCmAfAfGmUmAmAmCfCmUfUmAmUmCmCm |
| siXOg1-M3P1 | 401 | AmUmAmAmGfGmUfUfAfCmUmUmGmUmGmUmUmGmGm |
| | 402 | P1CmCfAmAmCmAfCmAmAmGmUmAmAmCfCmUfUmAmUmCmC m |
| siXOg2-M1P1 | 403 | GmGmAmUmAmAmGmGmUfUfAfCmUmUmGmUmGmUmUmGmG m |
| | 404 | P1CmCfAmAmCmAfCmAmAmGmUmAmAmCfCmUfUmAmUmCmC mUmUm |
| siXOg2-M2P1 | 405 | GmGmAmUmAmAmGfGmUfUfAfCmUmUmGmUmGmUmUmGmGm |
| | 406 | P1CmCfAmAmCmAfCmAfAfGmUmAmAmCfCmUfUmAmUmCmCm UmUm |
| siXOg2-M3P1 | 407 | GmGmAmUmAmAmGfGmUfUfAfCmUmUmGmUmGmUmUmGmGm |
| | 408 | P1CmCfAmAmCmAfCmAmAmGmUmAmAmCfCmUfUmAmUmCmC mUmUm |
| siXOg1-M1SP1 | 409 | AmsUmsAmAmGmGmUfUfAfCmUmUmGmUmGmUmUmGmGm |
| | 410 | P1CmsCfsAmAmCmAfCmAmAmGmUmAmAmCfCmUfUmAmUmsC msCm |
| siXOg1-M2SP1 | 411 | AmsUmsAmAmGfGmUfUfAfCmUmUmGmUmGmUmUmGmGm |
| | 412 | P1CmsCfsAmAmCmAfCmAfAfGmUmAmAmCfCmUfUmAmUmsCms Cm |
| siXOg1-M3SP1 | 413 | AmsUmsAmAmGfGmUfUfAfCmUmUmGmUmGmUmUmGmGm |
| | 414 | P1CmsCfsAmAmCmAfCmAmAmGmUmAmAmCfCmUfUmAmUmsC msCm |
| siXOg2-M1SP1 | 415 | GmsGmsAmUmAmAmGmGmUfUfAfCmUmUmGmUmGmUmUmGm Gm |
| | 416 | P1CmsCfsAmAmCmAfCmAmAmGmUmAmAmCfCmUfUmAmUmCm CmsUmsUm |
| siXOg2-M2SP1 | 417 | GmsGmsAmUmAmAmGfGmUfUfAfCmUmUmGmUmGmUmUmGmG m |
| | 418 | P1CmsCfsAmAmCmAfCmAfAfGmUmAmAmCfCmUfUmAmUmCmC msUmsUm |
| siXOg2-M3SP1 | 419 | GmsGmsAmUmAmAmGfGmUfUfAfCmUmUmGmUmGmUmUmGmG m |
| | 420 | P1CmsCfsAmAmCmAfCmAmAmGmUmAmAmCfCmUfUmAmUmCm CmsUmsUm |

TABLE 1h

| | | |
|---|---|---|
| | | The eighth siRNA sequence of the present disclosure |
| siRNA No. | SEQ ID NO: | Sequence direction 5'-3' |
| siXOh1 | 429 | GAAAAUCACCUAUGAAGAA |
| | 430 | UUCUUCAUAGGUGAUUUUCAC |
| siXOh2 | 431 | GUGAAAAUCACCUAUGAAGAA |
| | 432 | UUCUUCAUAGGUGAUUUUCACCC |
| siXOh1-M1 | 433 | GmAmAmAmUmCfAfCfCmUmAmUmGmAmAmGmAmAm |
| | 434 | UmUfCmUmUmCfAmUmAmGmGmUmGmAfUmUfUmUmCmAmCm |
| siXOh1-M2 | 435 | GmAmAmAfUmCfAfCfCmUmAmUmGmAmAmGmAmAm |
| | 436 | UmUfCmUmUmCfAmUfAfGmGmUmGmAfUmUfUmUmCmAmCm |
| siXOh1-M3 | 437 | GmAmAmAfUmCfAfCfCmUmAmUmGmAmAmGmAmAm |
| | 438 | UmUfCmUmUmCfAmUmAmGmGmUmGmAfUmUfUmUmCmAmCm |
| siXOh2-M1 | 439 | GmUmGmAmAmAmUmCfAfCfCmUmAmUmGmAmAmGmAmAm |
| | 440 | UmUfCmUmUmCfAmUmAmGmGmUmGmAfUmUfUmUmCmAmCmCmCm |
| siXOh2-M2 | 441 | GmUmGmAmAmAfUmCfAfCfCmUmAmUmGmAmAmGmAmAm |
| | 442 | UmUfCmUmUmCfAmUfAfGmGmUmGmAfUmUfUmUmCmAmCmCmCm |
| siXOh2-M3 | 443 | GmUmGmAmAmAfUmCfAfCfCmUmAmUmGmAmAmGmAmAm |
| | 444 | UmUfCmUmUmCfAmUmAmGmGmUmGmAfUmUfUmUmCmAmCmCmCm |
| siXOh1-M1S | 445 | GmsAmsAmAmUmCfAfCfCmUmAmUmGmAmAmGmAmAm |
| | 446 | UmsUfsCmUmUmCfAmUmAmGmGmUmGmAfUmUfUmUmCmsAmsCm |
| siXOh1-M2S | 447 | GmsAmsAmAfUmCfAfCfCmUmAmUmGmAmAmGmAmAm |
| | 448 | UmsUfsCmUmUmCfAmUfAfGmGmUmGmAfUmUfUmUmCmsAmsCm |
| siXOh1-M3S | 449 | GmsAmsAmAfUmCfAfCfCmUmAmUmGmAmAmGmAmAm |
| | 450 | UmsUfsCmUmUmCfAmUmAmGmGmUmGmAfUmUfUmUmCmsAmsCm |
| siXOh2-M1S | 451 | GmsUmsGmAmAmAmUmCfAfCfCmUmAmUmGmAmAmGmAmAm |
| | 452 | UmsUfsCmUmUmCfAmUmAmGmGmUmGmAfUmUfUmUmCmAmCmsCmsCm |
| siXOh2-M2S | 453 | GmsUmsGmAmAmAfUmCfAfCfCmUmAmUmGmAmAmGmAmAm |
| | 454 | UmsUfsCmUmUmCfAmUfAfGmGmUmGmAfUmUfUmUmCmAmCmsCmsCm |
| siXOh2-M3S | 455 | GmsUmsGmAmAmAfUmCfAfCfCmUmAmUmGmAmAmGmAmAm |
| | 456 | UmsUfsCmUmUmCfAmUmAmGmGmUmGmAfUmUfUmUmCmAmCmsCmsCm |
| siXOh1-M1P1 | 457 | GmAmAmAmUmCfAfCfCmUmAmUmGmAmAmGmAmAm |
| | 458 | P1UmUfCmUmUmCfAmUmAmGmGmUmGmAfUmUfUmUmCmAmCm |
| siXOh1-M2P1 | 459 | GmAmAmAfUmCfAfCfCmUmAmUmGmAmAmGmAmAm |
| | 460 | P1UmUfCmUmUmCfAmUfAfGmGmUmGmAfUmUfUmUmCmAmCm |
| siXOh1-M3P1 | 461 | GmAmAmAfUmCfAfCfCmUmAmUmGmAmAmGmAmAm |
| | 462 | P1UmUfCmUmUmCfAmUmAmGmGmUmGmAfUmUfUmUmCmAmCm |
| siXOh2-M1P1 | 463 | GmUmGmAmAmAmUmCfAfCfCmUmAmUmGmAmAmGmAmAm |
| | 464 | P1UmUfCmUmUmCfAmUmAmGmGmUmGmAfUmUfUmUmCmAmCmCmCm |
| siXOh2-M2P1 | 465 | GmUmGmAmAmAfUmCfAfCfCmUmAmUmGmAmAmGmAmAm |
| | 466 | P1UmUfCmUmUmCfAmUfAfGmGmUmGmAfUmUfUmUmCmAmCmCmCm |

TABLE 1h-continued

| | | The eighth siRNA sequence of the present disclosure |
|---|---|---|
| siRNA No. | SEQ ID NO: | Sequence direction 5'-3' |
| siXOh2-M3P1 | 467 | GmUmGmAmAmAmAfUmCfAfCfCmUmAmUmGmAmAmGmAmAm |
| | 468 | P1UmUfCmUmUmCfAmUmAmGmGmUmGmAfUmUfUmUmCmAmCmCmCm |
| siXOh1-M1SP1 | 469 | GmsAmsAmAmAmUmCfAfCfCmUmAmUmGmAmAmGmAmAm |
| | 470 | P1UmsUfsCmUmUmCfAmUmAmGmGmUmGmAfUmUfUmUmCmsAmsCm |
| siXOh1-M2SP1 | 471 | GmsAmsAmAmAfUmCfAfCfCmUmAmUmGmAmAmGmAmAm |
| | 472 | P1UmsUfsCmUmUmCfAmUfAfGmGmUmGmAfUmUfUmUmCmsAmsCm |
| siXOh1-M3SP1 | 473 | GmsAmsAmAmAfUmCfAfCfCmUmAmUmGmAmAmGmAmAm |
| | 474 | P1UmsUfsCmUmUmCfAmUmAmGmGmUmGmAfUmUfUmUmCmsAmsCm |
| siXOh2-M1SP1 | 475 | GmsUmsGmAmAmAmAmUmCfAfCfCmUmAmUmGmAmAmGmAmAm |
| | 476 | P1UmsUfsCmUmUmCfAmUmAmGmGmUmGmAfUmUfUmUmCmAmCmsCmsCm |
| siXOh2-M2SP1 | 477 | GmsUmsGmAmAmAmAfUmCfAfCfCmUmAmUmGmAmAmGmAmAm |
| | 478 | P1UmsUfsCmUmUmCfAmUfAfGmGmUmGmAfUmUfUmUmCmAmCmsCmsCm |
| siXOh2-M3SP1 | 479 | GmsUmsGmAmAmAmAfUmCfAfCfCmUmAmUmGmAmAmGmAmAm |
| | 480 | P1UmsUfsCmUmUmCfAmUmAmGmGmUmGmAfUmUfUmUmCmAmCmsCmsCm |

TABLE 1i

| | | The ninth siRNA sequence of the present disclosure |
|---|---|---|
| siRNA No. | SEQ ID NO: | Sequence direction 5'-3' |
| siXOi1 | 489 | GAUGCUAUAAAGAACAACU |
| | 490 | AGUUGUUCUUUAUAGCAUCCU |
| siXOi2 | 491 | AGGAUGCUAUAAAGAACAACU |
| | 492 | AGUUGUUCUUUAUAGCAUCCUCA |
| siXOi1-M1 | 493 | GmAmUmGmCmUmAfUfAfAmAmGmAmAmCmAmAmCmUm |
| | 494 | AmGfUmUmGmUfUmCmUmUmUmAmUmAfGmCfAmUmCmCmUm |
| siXOi1-M2 | 495 | GmAmUmGmCfUmAfUfAfAmAmGmAmAmCmAmAmCmUm |
| | 496 | AmGfUmUmGmUfUmCfUfUmUmAmUmAfGmCfAmUmCmCmUm |
| siXOi1-M3 | 497 | GmAmUmGmCfUmAfUfAfAmAmGmAmAmCmAmAmCmUm |
| | 498 | AmGfUmUmGmUfUmCmUmUmUmAmUmAfGmCfAmUmCmCmUm |
| siXOi2-M1 | 499 | AmGmGmAmUmGmCmUmAfUfAfAmAmGmAmAmCmAmAmCmUm |
| | 500 | AmGfUmUmGmUfUmCmUmUmUmAmUmAfGmCfAmUmCmCmUmCmAm |
| siXOi2-M2 | 501 | AmGmGmAmUmGmCfUmAfUfAfAmAmGmAmAmCmAmAmCmUm |
| | 502 | AmGfUmUmGmUfUmCfUfUmUmAmUmAfGmCfAmUmCmCmCmUmCmAm |
| siXOi2-M3 | 503 | AmGmGmAmUmGmCfUmAfUfAfAmAmGmAmAmCmAmAmCmUm |
| | 504 | AmGfUmUmGmUfUmCmUmUmUmAmUmAfGmCfAmUmCmCmUmCmAm |
| siXOi1-M1S | 505 | GmsAmsUmGmCmUmAfUfAfAmAmGmAmAmCmAmAmCmUm |
| | 506 | AmsGfsUmUmGmUfUmCmUmUmUmAmUmAfGmCfAmUmCmsCmsUm |

TABLE 1i-continued

| The ninth siRNA sequence of the present disclosure | | |
|---|---|---|
| siRNA No. | SEQ ID NO: | Sequence direction 5'-3' |
| siXOi1- M2S | 507 508 | GmsAmsUmGmCfUmAfUfAfAmAmGmAmAmCmAmAmCmUm AmsGfsUmUmGmUfUmCfUfUmUmAmUmAfGmCfAmUmCmsCmsU m |
| siXOi1- M3S | 509 510 | GmsAmsUmGmCfUmAfUfAfAmAmGmAmAmCmAmAmCmUm AmsGfsUmUmGmUfUmCmUmUmUmAmUmAfGmCfAmUmCmsCms Um |
| siXOi2- M1S | 511 512 | AmsGmsGmAmUmGmCmUmAfUfAfAmAmGmAmAmCmAmAmCm Um AmsGfsUmUmGmUfUmCmUmUmUmAmUmAfGmCfAmUmCmCmU msCmsAm |
| siXOi2- M2S | 513 514 | AmsGmsGmAmUmGmCfUmAfUfAfAmAmGmAmAmCmAmAmCmU m AmsGfsUmUmGmUfUmCfUfUmUmAmUmAfGmCfAmUmCmCmUms CmsAm |
| siXOi2- M3S | 515 516 | AmsGmsGmAmUmGmCfUmAfUfAfAmAmGmAmAmCmAmAmCmU m AmsGfsUmUmGmUfUmCmUmUmUmAmUmAfGmCfAmUmCmCmU msCmsAm |
| siXOi1- M1P1 | 517 518 | GmAmUmGmCmUmAfUfAfAmAmGmAmAmCmAmAmCmUm P1AmGfUmUmGmUfUmCmUmUmUmAmUmAfGmCfAmUmCmCmU m |
| siXOi1- M2P1 | 519 520 | GmAmUmGmCfUmAfUfAfAmAmGmAmAmCmAmAmCmUm P1AmGfUmUmGmUfUmCfUfUmUmAmUmAfGmCfAmUmCmCmUm |
| siXOi1- M3P1 | 521 522 | GmAmUmGmCfUmAfUfAfAmAmGmAmAmCmAmAmCmUm P1AmGfUmUmGmUfUmCmUmUmUmAmUmAfGmCfAmUmCmCmU m |
| siXOi2- M1P1 | 523 524 | AmGmGmAmUmGmCmUmAfUfAfAmAmGmAmAmCmAmAmCmU m P1AmGfUmUmGmUfUmCmUmUmUmAmUmAfGmCfAmUmCmCmU mCmAm |
| siXOi2- M2P1 | 525 526 | AmGmGmAmUmGmCfUmAfUfAfAmAmGmAmAmCmAmAmCmUm P1AmGfUmUmGmUfUmCfUfUmUmAmUmAfGmCfAmUmCmCmUm CmAm |
| siXOi2- M3P1 | 527 528 | AmGmGmAmUmGmCfUmAfUfAfAmAmGmAmAmCmAmAmCmUm P1AmGfUmUmGmUfUmCmUmUmUmAmUmAfGmCfAmUmCmCmU mCmAm |
| siXOi1- M1SP1 | 529 530 | GmsAmsUmGmCmUmAfUfAfAmAmGmAmAmCmAmAmCmUm P1AmsGfsUmUmGmUfUmCmUmUmUmAmUmAfGmCfAmUmCmsC msUm |
| siXOi1- M2SP1 | 531 532 | GmsAmsUmGmCfUmAfUfAfAmAmGmAmAmCmAmAmCmUm P1AmsGfsUmUmGmUfUmCfUfUmUmAmUmAfGmCfAmUmCmsCms Um |
| siXOi1- M3SP1 | 533 534 | GmsAmsUmGmCfUmAfUfAfAmAmGmAmAmCmAmAmCmUm P1AmsGfsUmUmGmUfUmCmUmUmUmAmUmAfGmCfAmUmCmsC msUm |
| siXOi2- M1SP1 | 535 536 | AmsGmsGmAmUmGmCmUmAfUfAfAmAmGmAmAmCmAmAmCm Um P1AmsGfsUmUmGmUfUmCmUmUmUmAmUmAfGmCfAmUmCmC mUmsCmsAm |
| siXOi2- M2SP1 | 537 538 | AmsGmsGmAmUmGmCfUmAfUfAfAmAmGmAmAmCmAmAmCmU m P1AmsGfsUmUmGmUfUmCfUfUmUmAmUmAfGmCfAmUmCmCmU msCmsAm |
| siXOi2- M3SP1 | 539 540 | AmsGmsGmAmUmGmCfUmAfUfAfAmAmGmAmAmCmAmAmCmU m P1AmsGfsUmUmGmUfUmCmUmUmUmAmUmAfGmCfAmUmCmC mUmsCmsAm |

TABLE 1j

| | | |
|---|---|---|
| | | The tenth siRNA sequence of the present disclosure |
| siRNA No. | SEQ ID NO: | Sequence direction 5'-3' |
| siXOj1 | 549 | GAACAACUCCUUUUAUGGA |
| | 550 | UCCAUAAAAGGAGUUGUUCUU |
| siXOj2 | 551 | AAGAACAACUCCUUUUAUGGA |
| | 552 | UCCAUAAAAGGAGUUGUUCUUUA |
| siXOj1-M 1 | 553 | GmAmAmCmAmAmCfUfCfCmUmUmUmAmUmGmGmAm |
| | 554 | UmCfCmAmUmAfAmAmAmGmAmGmUfUmGfUmUmCmUmUm |
| siXOj1-M 2 | 555 | GmAmAmCmAfAmCfUfCfCmUmUmUmAmUmGmGmAm |
| | 556 | UmCfCmAmUmAfAmAfAfGmAmGmUfUmGfUmUmCmUmUm |
| siXOj1-M 3 | 557 | GmAmAmCmAfAmCfUfCfCmUmUmUmAmUmGmGmAm |
| | 558 | UmCfCmAmUmAfAmAmAmGmAmGmUfUmGfUmUmCmUmUm |
| siXOj2-M 1 | 559 | AmAmGmAmAmCmAmAmCfUfCfCmUmUmUmAmUmGmGmAm |
| | 560 | UmCfCmAmUmAfAmAmAmGmAmGmUfUmGfUmUmCmUmUmUmAm |
| siXOj2-M 2 | 561 | AmAmGmAmAmCmAfAmCfUfCfCmUmUmUmAmUmGmGmAm |
| | 562 | UmCfCmAmUmAfAmAfAfGmAmGmUfUmGfUmUmCmUmUmUmAm |
| siXOj2-M 3 | 563 | AmAmGmAmAmCmAfAmCfUfCfCmUmUmUmAmUmGmGmAm |
| | 564 | UmCfCmAmUmAfAmAmAmGmAmGmUfUmGfUmUmCmUmUmUmAm |
| siXOj1-M 1S | 565 | GmsAmsAmCmAmAmCfUfCfCmUmUmUmAmUmGmGmAm |
| | 566 | UmsCfsCmAmUmAfAmAmAmGmAmGmUfUmGfUmUmCmsUmsUm |
| siXOj1-M 2S | 567 | GmsAmsAmCmAfAmCfUfCfCmUmUmUmAmUmGmGmAm |
| | 568 | UmsCfsCmAmUmAfAmAfAfGmAmGmUfUmGfUmUmCmsUmsUm |
| siXOj1-M 3S | 569 | GmsAmsAmCmAfAmCfUfCfCmUmUmUmAmUmGmGmAm |
| | 570 | UmsCfsCmAmUmAfAmAmAmGmAmGmUfUmGfUmUmCmsUmsUm |
| siXOj2-M 1S | 571 | AmsAmsGmAmAmCmAmAmCfUfCfCmUmUmUmAmUmGmGmAm |
| | 572 | UmsCfsCmAmUmAfAmAmAmGmAmGmUfUmGfUmUmCmUmUmsUmsAm |
| siXOj2-M 2S | 573 | AmsAmsGmAmAmCmAfAmCfUfCfCmUmUmUmAmUmGmGmAm |
| | 574 | UmsCfsCmAmUmAfAmAfAfGmAmGmUfUmGfUmUmCmUmUmsUmsAm |
| siXOj2-M 3S | 575 | AmsAmsGmAmAmCmAfAmCfUfCfCmUmUmUmAmUmGmGmAm |
| | 576 | UmsCfsCmAmUmAfAmAmAmGmAmGmUfUmGfUmUmCmUmUmsUmsAm |
| siXOj1-M1P1 | 577 | GmAmAmCmAmAmCfUfCfCmUmUmUmAmUmGmGmAm |
| | 578 | P1UmCfCmAmUmAfAmAmAmGmAmGmUfUmGfUmUmCmUmUm |
| siXOj1-M2P1 | 579 | GmAmAmCmAfAmCfUfCfCmUmUmUmAmUmGmGmAm |
| | 580 | P1UmCfCmAmUmAfAmAfAfGmAmGmUfUmGfUmUmCmUmUm |
| siXOj1-M3P1 | 581 | GmAmAmCmAfAmCfUfCfCmUmUmUmAmUmGmGmAm |
| | 582 | P1UmCfCmAmUmAfAmAmAmGmAmGmUfUmGfUmUmCmUmUm |
| siXOj2-M1P1 | 583 | AmAmGmAmAmCmAmAmCfUfCfCmUmUmUmAmUmGmGmAm |
| | 584 | P1UmCfCmAmUmAfAmAmAmGmAmGmUfUmGfUmUmCmUmUmUmAm |
| siXOj2-M2P1 | 585 | AmAmGmAmAmCmAfAmCfUfCfCmUmUmUmAmUmGmGmAm |
| | 586 | P1UmCfCmAmUmAfAmAfAfGmAmGmUfUmGfUmUmCmUmUmUmAm |

TABLE 1j-continued

| The tenth siRNA sequence of the present disclosure | | |
|---|---|---|
| siRNA No. | SEQ ID NO: | Sequence direction 5'-3' |
| siXOj2-M3P1 | 587 | AmAmGmAmAmCmAfAmCfUfCfCmUmUmUmAmUmGmGmAm |
| | 588 | P1UmCfCmAmUmAfAmAmAmGmGmAmGmUfUmGfUmUmCmUm UmUmAm |
| siXOj1-M1SP1 | 589 | GmsAmsAmCmAmAmCfUfCfCmUmUmUmAmUmGmGmAm |
| | 590 | P1UmsCfsCmAmUmAfAmAmAmGmGmAmGmUfUmGfUmUmCmsU msUm |
| siXOj1-M2SP1 | 591 | GmsAmsAmCmAfAmCfUfCfCmUmUmUmAmUmGmGmAm |
| | 592 | P1UmsCfsCmAmUmAfAmAfAfGmGmAmGmUfUmGfUmUmCmsUms Um |
| siXOj1-M3SP1 | 593 | GmsAmsAmCmAfAmCfUfCfCmUmUmUmAmUmGmGmAm |
| | 594 | P1UmsCfsCmAmUmAfAmAmAmGmGmAmGmUfUmGfUmUmCmsU msUm |
| siXOj2-M1SP1 | 595 | AmsAmsGmAmAmCmAmAmCfUfCfCmUmUmUmAmUmGmGm Am |
| | 596 | P1UmsCfsCmAmUmAfAmAmAmGmGmAmGmUfUmGfUmUmCmU mUmsUmsAm |
| siXOj2-M2SP1 | 597 | AmsAmsGmAmAmCmAfAmCfUfCfCmUmUmUmAmUmGmGmA m |
| | 598 | P1UmsCfsCmAmUmAfAmAfAfGmGmAmGmUfUmGfUmUmCmUmU msUmsAm |
| siXOj2-M3SP1 | 599 | AmsAmsGmAmAmCmAfAmCfUfCmUmUmUmAmUmGmGmA m |
| | 600 | P1UmsCfsCmAmUmAfAmAmAmGmGmAmGmUfUmGfUmUmCmU mUmsUmsAm |

TABLE 1k

| The eleventh siRNA sequence of the present disclosure | | |
|---|---|---|
| siRNA No. | SEQ ID NO: | Sequence direction 5'-3' |
| siXOk1 | 609 | CUUGCUCUGAAGUAGAAAU |
| | 610 | AUUUCUACUUCAGAGCAAGCC |
| siXOk2 | 611 | GGCUUGCUCUGAAGUAGAAAU |
| | 612 | AUUUCUACUUCAGAGCAAGCCAC |
| siXOk1-M1 | 613 | CmUmUmGmCmUmCfUfGfAmAmGmUmAmGmAmAmAmUm |
| | 614 | AmUfUmUmCmUfAmCmUmUmCmAmGmAfGmCfAmAmGmCmCm |
| siXOk1-M2 | 615 | CmUmUmGmCfUmCfUfGfAmAmGmUmAmGmAmAmAmUm |
| | 616 | AmUfUmUmCmUfAmCfUfUmCmAmGmAfGmCfAmAmGmCmCm |
| siXOk1-M3 | 617 | CmUmUmGmCfUmCfUfGfAmAmGmUmAmGmAmAmAmUm |
| | 618 | AmUfUmUmCmUfAmCmUmUmCmAmGmAfGmCfAmAmGmCmCm |
| siXOk2-M1 | 619 | GmGmCmUmUmGmCmUmCfUfGfAmAmGmUmAmGmAmAmAmU m |
| | 620 | AmUfUmUmCmUfAmCmUmUmCmAmGmAfGmCfAmAmGmCmCm AmCm |
| siXOk2-M2 | 621 | GmGmCmUmUmGmCfUmCfUfGfAmAmGmUmAmGmAmAmAmUm |
| | 622 | AmUfUmUmCmUfAmCfUfUmCmAmGmAfGmCfAmAmGmCmCmA mCm |
| siXOk2-M3 | 623 | GmGmCmUmUmGmCfUmCfUfGfAmAmGmUmAmGmAmAmAmUm |
| | 624 | AmUfUmUmCmUfAmCmUmUmCmAmGmAfGmCfAmAmGmCmCm AmCm |
| siXOk1-M1S | 625 | CmsUmsUmGmCmUmCfUfGfAmAmGmUmAmGmAmAmAmUm |
| | 626 | AmsUfsUmUmCmUfAmCmUmUmCmAmGmAfGmCfAmAmGmsCms Cm |

TABLE 1k-continued

| The eleventh siRNA sequence of the present disclosure | | |
|---|---|---|
| siRNA No. | SEQ ID NO: | Sequence direction 5'-3' |
| siXOk1-M2S | 627 | CmsUmsUmGmCfUmCfUfGfAmAmGmUmAmGmAmAmAmUm |
| | 628 | AmsUfsUmUmCmUfAmCfUfUmCmAmGmAfGmCfAmAmGmsCmsCm |
| siXOk1-M3S | 629 | CmsUmsUmGmCfUmCfUfGfAmAmGmUmAmGmAmAmAmUm |
| | 630 | AmsUfsUmUmCmUfAmCmUmUmCmAmGmAfGmCfAmAmGmsCmsCm |
| siXOk2-M1S | 631 | GmsGmsCmUmUmGmCmUfCfUfGfAmAmGmUmAmGmAmAmAmUm |
| | 632 | AmsUfsUmUmCmUfAmCmUmUmCmAmGmAfGmCfAmAmGmCmCmsAmsCm |
| siXOk2-M2S | 633 | GmsGmsCmUmUmGmCfUmCfUfGfAmAmGmUmAmGmAmAmAmUm |
| | 634 | AmsUfsUmUmCmUfAmCfUfUmCmAmGmAfGmCfAmAmGmCmCmsAmsCm |
| siXOk2-M3S | 635 | GmsGmsCmUmUmGmCfUmCfUfGfAmAmGmUmAmGmAmAmAmUm |
| | 636 | AmsUfsUmUmCmUfAmCmUmUmCmAmGmAfGmCfAmAmGmCmCmsAmsCm |
| siXOk1-M1P1 | 637 | CmUmUmGmCmUmCfUfGfAmAmGmUmAmGmAmAmAmUm |
| | 638 | P1AmUfUmUmCmUfAmCmUmUmCmAmGmAfGmCfAmAmGmCmCm |
| siXOk1-M2P1 | 639 | CmUmUmGmCfUmCfUfGfAmAmGmUmAmGmAmAmAmUm |
| | 640 | P1AmUfUmUmCmUfAmCfUfUmCmAmGmAfGmCfAmAmGmCmCm |
| siXOk1-M3P1 | 641 | CmUmUmGmCfUmCfUfGfAmAmGmUmAmGmAmAmAmUm |
| | 642 | P1AmUfUmUmCmUfAmCmUmUmCmAmGmAfGmCfAmAmGmCmCm |
| siXOk2-M1P1 | 643 | GmGmCmUmUmGmCmUmCfUfGfAmAmGmUmAmGmAmAmAmUm |
| | 644 | P1AmUfUmUmCmUfAmCmUmUmCmAmGmAfGmCfAmAmGmCmCmAmCm |
| siXOk2-M2P1 | 645 | GmGmCmUmUmGmCfUmCfUfGfAmAmGmUmAmGmAmAmAmUm |
| | 646 | P1AmUfUmUmCmUfAmCfUfUmCmAmGmAfGmCfAmAmGmCmCmAmCm |
| siXOk2-M3P1 | 647 | GmGmCmUmUmGmCfUmCfUfGfAmAmGmUmAmGmAmAmAmUm |
| | 648 | P1AmUfUmUmCmUfAmCmUmUmCmAmGmAfGmCfAmAmGmCmCmAmCm |
| siXOk1-M1SP1 | 649 | CmsUmsUmGmCmUmCfUfGfAmAmGmUmAmGmAmAmAmUm |
| | 650 | P1AmsUfsUmUmCmUfAmCmUmUmCmAmGmAfGmCfAmAmGmsCmsCm |
| siXOk1-M2SP1 | 651 | CmsUmsUmGmCfUmCfUfGfAmAmGmUmAmGmAmAmAmUm |
| | 652 | P1AmsUfsUmUmCmUfAmCfUfUmCmAmGmAfGmCfAmAmGmsCmsCm |
| siXOk1 M3SP1 | 653 | CmsUmsUmGmCfUmCfUfGfAmAmGmUmAmGmAmAmAmUm |
| | 654 | P1AmsUfsUmUmCmUfAmCmUmUmCmAmGmAfGmCfAmAmGmsCmsCm |
| siXOk2-M1SP1 | 655 | GmsGmsCmUmUmGmCmUmCfUfGfAmAmGmUmAmGmAmAmAmUm |
| | 656 | P1AmsUfsUmUmCmUfAmCmUmUmCmAmGmAfGmCfAmAmGmCmCmsAmsCm |
| siXOk2-M2SP1 | 657 | GmsGmsCmUmUmGmCfUmCfUfGfAmAmGmUmAmGmAmAmAmUm |
| | 658 | P1AmsUfsUmUmCmUfAmCfUfUmCmAmGmAfGmCfAmAmGmCmCmsAmsCm |
| siXOk2-M3SP1 | 659 | GmsGmsCmUmUmGmCfUmCfUfGfAmAmGmUmAmGmAmAmAmUm |
| | 660 | P1AmsUfsUmUmCmUfAmCmUmUmCmAmGmAfGmCfAmAmGmCmCmsAmsCm |

TABLE 11

| siRNA No. | SEQ ID NO: | Sequence direction 5'-3' |
|---|---|---|
| siXO11 | 669 | CUUCUUUGCCAUCAAAGAU |
| | 670 | AUCUUUGAUGGCAAAGAAGAU |
| siXO12 | 671 | AUCUUCUUUGCCAUCAAAGAU |
| | 672 | AUCUUUGAUGGCAAAGAAGAUAG |
| siXO11-M1 | 673 | CmUmUmCmUmUmUfGfCfCmAmUmCmAmAmAmGmAmUm |
| | 674 | AmUfCmUmUmUfGmAmUmGmGmCmAmAfAmGfAmAmGmAmUm |
| siXO11-M2 | 675 | CmUmUmCmUfUmUfGfCfCmAmUmCmAmAmAmGmAmUm |
| | 676 | AmUfCmUmUmUfGmAfUfGmGmCmAmAfAmGfAmAmGmAmUm |
| siXO11-M3 | 677 | CmUmUmCmUfUmUfGfCfCmAmUmCmAmAmAmGmAmUm |
| | 678 | AmUfCmUmUmUfGmAmUmGmGmCmAmAfAmGfAmAmGmAmUm |
| siXO12-M1 | 679 | AmUmCmUmUmCmUmUmUfGfCfCmAmUmCmAmAmAmGmAmUm |
| | 680 | AmUfCmUmUmUfGmAmUmGmGmCmAmAfAmGfAmAmGmAmUmAmGm |
| siXO12-M2 | 681 | AmUmCmUmUmCmUfUmUfGfCfCmAmUmCmAmAmAmGmAmUm |
| | 682 | AmUfCmUmUmUfGmAfUfGmGmCmAmAfAmGfAmAmGmAmUmAmGm |
| siXO12-M3 | 683 | AmUmCmUmUmCmUfUmUfGfCfCmAmUmCmAmAmAmGmAmUm |
| | 684 | AmUfCmUmUmUfGmAmUmGmGmCmAmAfAmGfAmAmGmAmUmAmGm |
| siXO11-M1S | 685 | CmsUmsUmCmUmUmUfGfCfCmAmUmCmAmAmAmGmAmUm |
| | 686 | AmsUfsCmUmUmUfGmAmUmGmGmCmAmAfAmGfAmAmGmsAmsUm |
| siXO11-M2S | 687 | CmsUmsUmCmUfUmUfGfCfCmAmUmCmAmAmAmGmAmUm |
| | 688 | AmsUfsCmUmUmUfGmAfUfGmGmCmAmAfAmGfAmAmGmsAmsUm |
| siXO11-M3S | 689 | CmsUmsUmCmUfUmUfGfCfCmAmUmCmAmAmAmGmAmUm |
| | 690 | AmsUfsCmUmUmUfGmAmUmGmGmCmAmAfAmGfAmAmGmsAmsUm |
| siXO12-M1S | 691 | AmsUmsCmUmUmCmUmUmUfGfCfCmAmUmCmAmAmAmGmAmUm |
| | 692 | AmsUfsCmUmUmUfGmAmUmGmGmCmAmAfAmGfAmAmGmAmUmsAmsGm |
| siXO12-M2S | 693 | AmsUmsCmUmUmCmUfUmUfGfCfCmAmUmCmAmAmAmGmAmUm |
| | 694 | AmsUfsCmUmUmUfGmAfUfGmGmCmAmAfAmGfAmAmGmAmUmsAmsGm |
| siXO12-M3S | 695 | AmsUmsCmUmUmCmUfUmUfGfCfCmAmUmCmAmAmAmGmAmUm |
| | 696 | AmsUfsCmUmUmUfGmAmUmGmGmCmAmAfAmGfAmAmGmAmUmsAmsGm |
| siXO11-M1P1 | 697 | CmUmUmCmUmUmUfGfCfCmAmUmCmAmAmAmGmAmUm |
| | 698 | P1AmUfCmUmUmUfGmAmUmGmGmCmAmAfAmGfAmAmGmAmUm |
| siXO11-M2P1 | 699 | CmUmUmCmUfUmUfGfCfCmAmUmCmAmAmAmGmAmUm |
| | 700 | P1AmUfCmUmUmUfGmAfUfGmGmCmAmAfAmGfAmAmGmAmUm |
| siXO11-M3P1 | 701 | CmUmUmCmUfUmUfGfCfCmAmUmCmAmAmAmGmAmUm |
| | 702 | P1AmUfCmUmUmUfGmAmUmGmGmCmAmAfAmGfAmAmGmAmUm |
| siXO12-M1P1 | 703 | AmUmCmUmUmCmUmUmUfGfCfCmAmUmCmAmAmAmGmAmUm |
| | 704 | P1AmUfCmUmUmUfGmAmUmGmGmCmAmAfAmGfAmAmGmAmUmAmGm |
| siXO12-M2P1 | 705 | AmUmCmUmUmCmUfUmUfGfCfCmAmUmCmAmAmAmGmAmUm |
| | 706 | P1AmUfCmUmUmUfGmAfUfGmGmCmAmAfAmGfAmAmGmAmUmAmGm |

TABLE 11-continued

| | | The twelveth siRNA sequence of the present disclosure |
|---|---|---|
| siRNA No. | SEQ ID NO: | Sequence direction 5'-3' |
| siXO12-M3P1 | 707 | AmUmCmUmUmCmUfUmUfGfCfCmAmUmCmAmAmAmGmAmUm |
| | 708 | P1AmUfCmUmUmUfGmAmUmGmGmCmAmAfAmGfAmAmGmAm UmAmGm |
| siXO11-M1SP1 | 709 | CmsUmsUmCmUmUmUfGfCfCmAmUmCmAmAmAmGmAmUm |
| | 710 | P1AmsUfsCmUmUmUfGmAmUmGmGmCmAmAfAmGfAmAmGmsA msUm |
| siXO11-M2SP1 | 711 | CmsUmsUmCmUfUmUfGfCfCmAmUmCmAmAmAmGmAmUm |
| | 712 | P1AmsUfsCmUmUmUfGmAfUfGmGmCmAmAfAmGfAmAmGmsAm sUm |
| siXO11-M3SP1 | 713 | CmsUmsUmCmUfUmUfGfCfCmAmUmCmAmAmAmGmAmUm |
| | 714 | P1AmsUfsCmUmUmUfGmAmUmGmGmCmAmAfAmGfAmAmGmsA msUm |
| siXO12-M1SP1 | 715 | AmsUmsCmUmUmCmUmUmUfGfCfCmAmUmCmAmAmAmGmAm Um |
| | 716 | P1AmsUfsCmUmUmUfGmAmUmGmGmCmAmAfAmGfAmAmGmA mUmsAmsGm |
| siXO12-M2SP1 | 717 | AmsUmsCmUmUmCmUfUmUfGfCfCmAmUmCmAmAmAmGmAmU m |
| | 718 | P1AmsUfsCmUmUmUfGmAfUfGmGmCmAmAfAmGfAmAmGmAmU msAmsGm |
| siXO12-M3SP1 | 719 | AmsUmsCmUmUmCmUfUmUfGfCfCmAmUmCmAmAmAmGmAmU m |
| | 720 | P1AmsUfsCmUmUmUfGmAmUmGmGmCmAmAfAmGfAmAmGmA mUmsAmsGm | wherein, capital letters C, G, U, and A indicate the base composition of the nucleotides; the lowercase m indicates that the nucleotide adjacent to the left side of the letter m is a methoxy modified nucleotide; the lowercase f indicates that the nucleotide adjacent to the left side of the letter f is a fluoro modified nucleotide; the lowercase letter s indicates that the two nucleotides adjacent to the left and right of the letter s are linked by phosphorothioate; and P1 represents that the nucleotide adjacent to the right side of P1 is a 5'-phosphate nucleotide or a 5'-phosphate analogue modified nucleotide. In some embodiments, P1 represents specifically modified VP, Ps or P, wherein the letter combination VP represents that the nucleotide adjacent to the right side of the letter combination VP is a 5'-(E)-vinylphosphonate (E-VP) modified nucleotide, the letter combination Ps represents that the nucleotide adjacent to the right side of the letter combination Ps is a phosphorothioate modified nucleotide, and the capital letter P represents that the nucleotide adjacent to the right side of the letter P is a 5'-phosphate nucleotide.

In the siRNA or the siRNA conjugate of the present disclosure, each pair of adjacent nucleotides is linked via a phosphodiester bond or phosphorothioate diester bond. The non-bridging oxygen atom or sulfur atom in the phosphodiester bond or phosphorothioate diester bond is negatively charged, and may be present in the form of hydroxy or sulfhydryl. Moreover, the hydrogen ion in the hydroxy or sulfhydryl may be partially or completely substituted with a cation. The cation may be any cation, such as a metal cation, an ammonium ion NH4$^+$ or an organic ammonium cation. In order to increase solubility, in some embodiments, the cation is selected from one or more of an alkali metal ion, an ammonium cation formed by a tertiary amine and a quaternary ammonium cation. The alkali metal ion may be K$^+$ and/or Na$^+$, and the cation formed by the tertiary amine may be an ammonium ion formed by triethylamine and/or an ammonium ion formed by N,N-diisopropylethylamine. Thus, the siRNA or siRNA conjugate of the present disclosure may be at least partially present in the form of salt. In one embodiment, the non-bridging oxygen atom or sulfur atom in the phosphodiester bond or phosphorothioate diester bond at least partly binds to a sodium ion, and thus the siRNA or the siRNA conjugate of the present disclosure is present or partially present in the form of sodium salt.

Those skilled in the art clearly know that a modified nucleotide group may be introduced into the siRNA of the present disclosure by a nucleoside monomer having a corresponding modification. The methods for preparing the nucleoside monomer having the corresponding modification and the methods for introducing the modified nucleotide group into the siRNA are also well-known to those skilled in the art. All the modified nucleoside monomers may be either commercially available or prepared by known methods.

Preparation of the siRNA Conjugate as Shown by Formula (308)

The siRNA conjugate as shown by Formula (308) may be prepared by any appropriate synthetic routes.

In some embodiments, the siRNA conjugate as shown by Formula (308) may be prepared by the following method. The method comprises: successively linking nucleoside monomers in the direction from 3' to 5' according to the nucleotide types and sequences in the sense strand and antisense strand respectively under the condition of solid phase phosphoramidite synthesis, wherein the step of linking each nucleoside monomer comprises a four-step reaction of deprotection, coupling, capping, and oxidation or sulfurization; isolating the sense strand and the antisense strand of the siRNA; and annealing; wherein the siRNA is the siRNA of the present disclosure mentioned above.

Moreover, the method further comprises: contacting the compound as shown by Formula (321) with a nucleoside monomer or a nucleotide sequence linked to a solid phase support under coupling reaction condition and in the presence of a coupling agent, thereby linking the compound as shown by Formula (321) to the nucleotide sequence through a coupling reaction. Hereinafter, the compound as shown by Formula (321) is also called a conjugating molecule.

Formula (321)

$$\text{H} - [\text{N} - (\text{C})_{m1}]_{n1} - \text{N} - (\text{C})_{m2} - [\text{N} - (\text{C})_{m3}]_{n3} - \text{NH,}$$

with substituents $S_1$, $L_1$, $R_{10}$, $R_4$, $R_{11}$, $S_1$, $L_1$, $R_{12}$, $S_1$, $L_1$, $R_{13}$, $R_{14}$, $R_{15}$ wherein:

$R_4$ is a group capable of binding to the siRNA represented by Nu in the compound as shown by Formula (308). In some embodiments, $R_4$ is a group capable of binding to the siRNA represented by Nu via a covalent bond. In some embodiments, $R_4$ is a group capable of being conjugated to any functional group of the siRNA represented by Nu via a phosphodiester bond by reaction;

Each $S_1$ is independently an $M_1$, which is a group formed by substituting all active hydroxy with a YCOO— group, wherein each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is a methyl.

Definitions and options of n1, n3, m1, m2, m3, $R_{10}$, $R_{11}$, $R_{12}$, $R_{13}$, $R_{14}$, $R_{15}$, $L_1$, and $M_1$ are respectively as described above.

$R_4$ is selected to achieve the linkage to the N atom on a nitrogenous backbone and to provide a suitable reaction site for synthesizing the siRNA conjugate as shown by Formula (308). In some embodiments, $R_4$ comprises a $R_2$ linking group or a protected $R_2$ linking group, and can form a functional group as shown by Formula (A59) with an siRNA via reaction.

In some embodiments, R4 comprises a first functional group that can react with a group on an siRNA or a nucleoside monomer represented by Nu to form a phosphite ester, and a second functional group that can form a covalent bond with a hydroxy or an amino, or comprises a solid phase support linked via the covalent bond. In some embodiments, the first functional group is a phosphoramidite, a hydroxy or a protected hydroxy. In some embodiments, the second functional group is a phosphoramidite, a carboxyl or a carboxylate. In some embodiments, the second functional group is a solid phase support linked to the rest of the molecule via a covalent bond which is formed by a hydroxy or an amino. In some embodiments, the solid phase support is linked via a phosphoester bond, a carboxyl ester bond, or an amide bond. In some embodiments, the solid phase support is a resin.

In some embodiments, the first functional group comprises a hydroxy, —$OR_k$ or a group as shown by Formula (C3); and the second functional group comprises a group as shown by Formula (C1), (C2), (C3), (C1'), or (C3'):

(C1)

(C2)

(C3)

(C1')

(C3')

wherein $q_1$ is an integer of 1-4, X is O or NH, $M^+$ is a cation, $R_k$ is a hydroxy protecting group, SPS represents a solid phase support, and 〜〜〜 represents the site where a group is covalently linked.

In some embodiments, the first functional group comprises a phosphoramidite group as shown by Formula (C3). The phosphoramidite group can form a phosphite ester with a hydroxy at any position on a nucleotide such as a 2' or 3' hydroxy by a coupling reaction, and the phosphite ester can form a phosphodiester bond or phosphorothioate ester bond as shown by Formula (A59) via oxidation or sulfurization, so as to conjugate the conjugating molecule to the siRNA. In this case, even if the second functional group does not exist, the compound as shown by Formula (321) will still be able to be conjugated to the nucleotide, without affecting the acquisition of the siRNA conjugate as shown by Formula (308). Under such circumstances, after obtaining a sense strand or an antisense strand of the siRNA by a method such as solid phase phosphoramidite synthesis, the compound as shown by Formula (321) is reacted with a hydroxy on the terminal nucleotide of the nucleotide sequence, and phosphodiester bonding or phosphorothioate bonding is formed by a subsequent oxidation or sulfurization process, thereby conjugating the compound as shown by Formula (321) to the siRNA.

In some embodiments, the first functional group comprises a protected hydroxy. In some embodiments, the second functional group comprises a group that can react with a solid phase support to provide a conjugating molecule comprising the solid phase support. In some embodiments, the second functional group comprises a carboxyl, a carboxylate or a phosphoramidite as shown by Formula (C1), (C2) or (C3). When the second functional group comprises a carboxyl or a carboxylate, the compound as shown by Formula (321) reacts with a hydroxy or an amino on a solid phase support such as a resin via an esterification or an amidation reaction, to form a conjugating molecule comprising the solid phase support linked via a carboxyl ester bond. When the second functional group comprises a phosphoramidite functional group, the compound as shown by Formula (321) may be coupled with a hydroxy on a universal solid phase support, such as a resin, and form, by oxidation, a conjugating molecule comprising the solid phase support linked via a phosphodiester bond. Subsequently, starting from the above product linked to the solid phase support, the nucleoside monomers are linked sequentially by a solid phase phosphoramidite synthesis method, thereby obtaining a sense or strand or an antisense strand of the siRNA linked to the conjugation group. During the solid phase phosphoramidite synthesis, the first functional group is deprotected, and then coupled with a phosphoramidite group on a nucleoside monomer under coupling reaction condition.

In some embodiments, the first functional group comprises a hydroxy or a protected hydroxy; and the second functional group comprises a solid phase support linked via a carboxyl ester bond, a solid phase support linked via an amide bond or a solid phase support linked via a phosphoester bond, as shown by Formula (C1') or (C3'). In this case, starting from the compound as shown by Formula (321) in place of the solid phase support, the nucleoside monomers are linked sequentially by a solid phase phosphoramidite synthesis, thereby obtaining a sense strand or an antisense strand of the siRNA linked to a conjugating group.

In some embodiments, the carboxylate may be expressed as $-COO-M^+$, wherein $M^+$ is a cation such as one of a metal cation, an ammonium cation $NH4^+$ and an organic ammonium cation. In one embodiment, the metal ion may be an alkali metal ion, such as $K^+$ or $Na^+$. In order to increase solubility and facilitate the reaction, in some embodiments, the organic ammonium ion is an ammonium cation formed by a tertiary amine, or a quaternary ammonium cation, such as an ammonium ion formed by triethylamine or an ammonium ion formed by N,N-diisopropylethylamine. In some embodiments, the carboxylate is a triethylamine carboxylate or an N,N-diisopropylethylamine carboxylate.

In some embodiments, $R_4$ comprises a structure as shown by Formula (B9), (B10), (B9'), (B10'), (B11), (B12), (B11') or (B12'):

(B9)

-continued (B10)

(B9')

(B10')

(B11)

(B12)

(B11')

-continued (B12′)

wherein $q_1$ is an integer of 1-4, $q_2$ is an integer of 1-10, X is O or NH, $M^+$ is a cation, $R_k$ is a hydroxy protecting group, SPS represents a solid phase support, and ∿∿∿ represents a site where a group is covalently linked. In some embodiments, $q_1$ is 1 or 2. In some embodiments, q2 is an integer of 1-5. In some embodiments, $R_4$ comprises a structure as shown by Formula (B9) or (B10). In some embodiments, $R_4$ comprises a structure as shown by Formula (B11) or (B12).

In some embodiments, $R_k$ is one or more of Tr(trityl), MMTr(4-methoxytrityl), DMTr(4,4′-dimethoxytrityl), and TMTr(4,4′,4″-trimethoxytrityl). In some embodiments, $R_k$ may be DMTr, i.e., 4,4′-dimethoxytrityl.

The definition of $L_1$ is as described above.

In some embodiments, $L_1$ is used to link the $M_1$ targeting group to the N atom on the nitrogenous backbone, thereby providing liver targeting function for the siRNA conjugate as shown by Formula (308). In some embodiments, $L_1$ comprises any one of A1-A26, or the combination thereof.

According to the description above, those skilled in the art would easily understand that as compared with the well-known solid phase phosphoramidite synthesis methods in the art, an siRNA conjugate in which a conjugating molecule is linked to any possible position of the nucleotide sequence can be obtained through the above first functional group and an optional second functional group. For example, the conjugating molecule is linked to a terminal of the nucleotide sequence or to either terminal of the nucleotide sequence. Correspondingly, unless otherwise specified, in the following description regarding siRNA conjugate and/or conjugating molecule preparation, when referring to the reactions such as "deprotection", "coupling", "capping", "oxidation", "sulfurization", it will be understood that the reaction conditions and agents involved in the well-known phosphoramidite nucleic acid solid phase synthesis methods in the art would also apply to these reactions. Exemplary reaction conditions and agents will be described in detail hereinafter.

In some embodiments, each $S_1$ is independently an $M_1$. In some embodiments, each $S_1$ is independently a group formed by protecting at least one active hydroxy in $M_1$ with a hydroxy protecting group. In some embodiments, each $S_1$ is independently a group formed by protecting all active hydroxys in $M_1$ with hydroxy protecting groups. In some embodiments, any hydroxy protecting group known to those skilled in the art may be used to protect the active hydroxy in $M_1$. In some embodiments, the protected hydroxy is expressed as the formula YCOO—, wherein each Y is independently selected from the group consisting of $C_1$-$C_{10}$ alkyl and $C_6$-$C_{10}$ aryl, wherein the $C_1$-$C_{10}$ alkyl and $C_6$-$C_{10}$ aryl are optionally substituted with one or more substituents selected from the group consisting of halo and $C_1$-$C_6$ alkyl. In some embodiments, each Y is independently selected from the group consisting of methyl, trifluoromethyl, difluoromethyl, monofluoromethyl, trichloromethyl, dichloromethyl, monochloromethyl, ethyl, n-propyl, isopropyl, phenyl, halophenyl, and $C_1$-$C_6$ alkylphenyl.

In some embodiments, each $S_1$ is independently selected from the group consisting of Formulae A46-A54:

(A46)

(A47)

(A48)

(A49)

(A50)

-continued (A51)

(A52)

(A53)

(A54)

In some embodiments, $S_1$ is Formula A49 or A50.

In some embodiments, each Y is independently selected from one of methyl, trifluoromethyl, difluoromethyl, monofluoromethyl, trichloromethyl, dichloromethyl, monochloromethyl, ethyl, n-propyl, isopropyl, phenyl, halophenyl, and alkylphenyl. In some embodiments, Y is a methyl.

As mentioned previously, the method for preparing the siRNA conjugate as shown by Formula (308) further comprises the following steps of: synthesizing the other strand of the siRNA (for example, when the sense strand of the siRNA linked to the conjugating molecule is synthesized in the above step, the method further comprises synthesizing the antisense strand of the siRNA by the solid phase synthesis method, and vice versa); isolating the sense strand and the antisense strand; and annealing. In particular, in the isolating step, the solid phase support linked to the nucleotide sequence and/or the conjugating molecule is cleaved and at the same time the necessary protecting group is removed (in this case, each $S_1$ group in the compound as shown by Formula (321) is converted to a corresponding $M_1$ targeting group), thereby providing the sense strand (or antisense strand) of the siRNA linked to the conjugating molecule and the corresponding antisense strand (or sense strand). The sense strand and the antisense strand are annealed to form a double-stranded RNA structure, thereby obtaining the siRNA conjugate as shown by Formula (308).

In some embodiments, the method for preparing the siRNA conjugate as shown by Formula (308) further comprises the following steps of: contacting the compound as shown by Formula (321) with the first nucleoside monomer at 3'terminal of the sense strand or antisense strand under coupling reaction condition in the presence of a coupling agent, thereby linking the compound as shown by Formula (321) to the first nucleotide in the sequence; successively linking nucleoside monomers in the direction from 3' to 5' to synthesize the sense strand or the antisense strand of the siRNA according to the desired nucleotide type and sequence of the sense strand or antisense strand, under the condition of solid phase phosphoramidite synthesis; wherein the compound as shown by Formula (321) is a compound in which R4 comprises a first functional group and a second functional group, the first functional group comprises a protected hydroxy and the second functional group comprises a group as shown by Formula (C1') or (C3'), and the compound as shown by Formula (321) is deprotected before linked to the first nucleoside monomer; and the linking of each nucleoside monomer comprises a four-step reaction of deprotection, coupling, capping, and oxidation or sulfurization, thus obtaining a sense strand or an antisense strand of a nucleic acid linked to the conjugating molecule; successively linking the nucleoside monomers in the direction from 3' to 5' to synthesize the sense strand or antisense strand of the nucleic acid according to the nucleotide type and sequence of the sense strand or the antisense strand, under the condition of solid phase phosphoramidite synthesis; wherein the linking of each nucleoside monomer comprises a four-step reaction of deprotection, coupling, capping, and oxidation or sulfurization; removing the protecting groups and cleaving the solid phase support; isolating and purifying to obtain the sense strand and the antisense strand; and annealing.

In some embodiments, the method for preparing the siRNA conjugate as shown by Formula (308) further comprises the following steps of: successively linking nucleoside monomers in the direction from 3' to 5' to synthesize the sense strand or the antisense strand according to the nucleotide type and sequence of the sense strand or antisense strand in the double-stranded siRNA; wherein the linking of each nucleoside monomer comprises a four-step reaction of deprotection, coupling, capping, and oxidation or sulfurization, thus obtaining a sense strand linked to the solid phase support and an antisense strand linked to the solid phase support; contacting the compound as shown by Formula (321) with the sense strand linked to the solid phase support or the antisense strand linked to the solid phase support under coupling reaction condition in the presence of a coupling agent, thereby linking the compound as shown by Formula (321) to the sense strand or the antisense strand; wherein the compound as shown by Formula (321) is a compound in which R4 comprises a phosphoramidite group as the first functional group; removing the protecting groups and cleaving the solid phase support; respectively isolating and purifying to obtain the sense strand or the antisense strand of the siRNA; and annealing; wherein the sense strand or the antisense strand of the siRNA is linked to a conjugating molecule.

In some embodiments, the P atom in Formula A59 is linked to the 3' terminal of the sense strand of the siRNA, and the method for preparing the siRNA conjugate as shown by Formula (308) comprises:

(1) removing the hydroxy protecting group $R_k$ in the compound as shown by Formula (321) (wherein the compound as shown by Formula (321) is a compound in which $R_4$ comprises a first functional group and a second function group, the first functional group comprises a protected hydroxy $OR_k$, and the second function group has a structure as shown by Formula (C1') or (C3')); and contacting the deprotected product with a nucleoside monomer to obtain a nucleoside monomer linked to a solid phase support via the conjugating molecule under a coupling reaction condition in the presence of a coupling agent;

(2) starting from the nucleoside monomer linked to the solid phase support via the conjugating molecule, synthesizing the sense strand of the siRNA in the direction from 3' to 5' by a solid phase phosphoramidite synthesis;

(3) synthesizing the antisense strand of the siRNA by a solid phase phosphoramidite synthesis method; and (4) isolating the sense strand and the antisense strand of the siRNA, and annealing the same to obtain the siRNA conjugate as shown by Formula (308).

In step (1), the method for removing the protecting group $R_k$ in the compound as shown by Formula (321) comprises contacting the compound as shown by Formula (321) with a deprotection agent under a deprotection condition. The deprotection condition comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, the deprotection agent is dichloroacetic acid. The molar ratio of the deprotection agent to the compound as shown by Formula (321) may be 10:1 to 1000:1, and in some embodiments, 50:1 to 500:1.

The coupling reaction condition and the coupling agent may be any conditions and agents suitable for the above coupling reaction. In some embodiments, the same condition and agent as those of the coupling reaction in the solid phase synthesis method may be used.

In some embodiments, the coupling reaction condition comprises a reaction temperature of 0-50° C., and in some embodiments, 15-35° C. The molar ratio of the compound as shown by Formula (321) to the nucleoside monomer may be 1:1 to 1:50, and in some embodiments, 1:2 to 1:5. The molar ratio of the compound as shown by Formula (321) to the coupling agent may be 1:1 to 1:50, and in some embodiments, 1:3 to 1:10. The reaction time may be 200-3000 seconds, and in some embodiments, 500-1500 seconds. The coupling agent may be selected from one or more of 1H-tetrazole, 5-ethylthio-1H-tetrazole and 5-benzylthio-1H-tetrazole, and in some embodiments, is 5-ethylthio-1H-tetrazole. The organic solvent may be selected from one or more of anhydrous acetonitrile, anhydrous DMF and anhydrous dichloromethane, and in some embodiments, is anhydrous acetonitrile. The amount of the organic solvent may be 3-50 L/mol, and in some embodiments, 5-20 L/mol, with respect to the compound as shown by Formula (321).

In step (2), a sense strand SS of the second siRNA conjugate is synthesized in the direction from 3' to 5' by the phosphoramidite nucleic acid solid phase synthesis method, starting from the nucleoside monomer linked to the solid phase support via the conjugating molecule prepared in the above steps. In this case, the conjugating molecule is linked to 3'terminal of the resultant sense strand. In this case, the conjugating molecule is linked to 3'terminal of the resultant sense strand.

Other conditions for the solid phase synthesis in steps (2) and (3), comprising the deprotection condition for the nucleoside monomer, the type and amount of the deprotection agent, the coupling reaction condition, the type and amount of the coupling agent, the capping reaction condition, the type and amount of the capping agent, the oxidation reaction condition, the type and amount of the oxidation agent, the sulfurization reaction condition, and the type and amount of the sulfurization agent, adopt various conventional agents, amounts, and conditions in the art.

For instance, in some embodiments, the solid phase synthesis in steps (2) and (3) may use the following conditions:

The deprotection condition for the nucleoside monomer comprises a temperature of 0-50° C., and in some embodiments, 15-35° C., and a reaction time of 30-300 seconds, and in some embodiments, 50-150 seconds. The deprotection agent may be selected from one or more of trifluoroacetic acid, trichloroacetic acid, dichloroacetic acid, and monochloroacetic acid, and in some embodiments, the deprotection agent is dichloroacetic acid. The molar ratio of the deprotection agent to the protecting group 4,4'-dimethoxytrityl on the solid phase support is 2:1 to 100:1, and in some embodiments, is 3:1 to 50:1.

The coupling reaction condition comprises a reaction temperature of 0-50° C., and in some embodiments, 15-35° C. The molar ratio of the nucleic acid sequence linked to the solid phase support to the nucleoside monomer is 1:1 to 1:50, and in some embodiments, is 1:5 to 1:15. The molar ratio of the nucleic acid sequence linked to the solid phase support to the coupling agent is 1:1 to 1:100, and in some embodiments, is 1:50 to 1:80. The selection of the reaction time and the coupling agent can be same as above.

The capping reaction condition comprises a reaction temperature of 0-50° C., and in some embodiments, 15-35° C., and a reaction time of 5-500 seconds, and in some embodiments, 10-100 seconds. The selection of the capping agent can be same as above. The molar ratio of the total amount of the capping agent to the nucleic acid sequence linked to the solid phase support may be 1:100 to 100:1, and in some embodiments, is 1:10 to 10:1. In the case where the capping agent uses equimolar acetic anhydride and N-methylimidazole, the molar ratio of the acetic anhydride to the N-methylimidazole and the nucleic acid sequence linked to the solid phase support may be 1:1:10 to 10:10:1, and in some embodiments, is 1:1:2 to 2:2:1.

The oxidation reaction condition comprises a reaction temperature of 0-50° C., and in some embodiments, 15-35° C., and a reaction time of 1-100 seconds, and in some embodiments, 5-50 seconds. In some embodiments, the oxidation agent is iodine (in some embodiments, provided as iodine water). The molar ratio of the oxidation agent to the nucleic acid sequence linked to the solid phase support in the coupling step may be 1:1 to 100:1, and in some embodiments, is 5:1 to 50:1. In some embodiments, the oxidation reaction is performed in a mixed solvent in which the ratio of tetrahydrofuran:water:pyridine is 3:1:1 to 1:1:3. The sulfurization reaction condition comprises a reaction temperature of 0-50° C., and in some embodiments, 15-35° C., and a reaction time of 50-2000 seconds, and in some embodiments, 100-1000 seconds. In some embodiments, the sulfurization agent is xanthane hydride. The molar ratio of the sulfurization agent to the nucleic acid sequence linked to the solid phase support in the coupling step is 10:1 to 1000:1, and in some embodiments, is 10:1 to 500:1. In some embodiments, the sulfurization reaction is performed in a mixed solvent in which the ratio of acetonitrile:pyridine is 1:3 to 3:1.

The method further comprises isolating the sense strand and the antisense strand of the siRNA after linking all nucleoside monomers and before the annealing. Methods for isolation are well-known to those skilled in the art and generally comprise cleaving the synthesized nucleotide sequence from the solid phase support, removing protecting groups on the bases, phosphate groups and ligands, purifying and desalting.

The conventional cleavage and deprotection methods in the synthesis of siRNAs can be used to cleave the synthesized nucleotide sequence from the solid phase support, and remove the protecting groups on the bases, phosphate groups and ligands. For example, contacting the resultant nucleotide sequence linked to the solid phase support with strong aqua; during deprotection, the protecting group YCOO— in groups A46-A54 is converted to a hydroxy, and thus the $S_1$ groups is converted to a corresponding $M_1$ group, providing the siRNA conjugate as shown by Formula (308); wherein the strong aqua may be aqueous ammonia of a concentration of 25-30% by weight. The amount of the strong aqua may be 0.2 ml/μmol-0.8 ml/μmol with respect to the target siRNA.

When there is at least one 2'-TBDMS protection on the synthesized nucleotide sequence, the method further comprises contacting the nucleotide sequence removed from the solid phase support with triethylamine trihydrofluoride to remove the 2'-TBDMS protection. In this case, the resultant target siRNA sequence comprises the corresponding nucleoside having free 2'-hydroxy. The amount of pure triethylamine trihydrofluoride is 0.4 ml/μmol-1.0 ml/μmol with respect to the target siRNA sequence. As such, the siRNA conjugate as shown by Formula (308) may be obtained.

Methods for purification and desalination are well-known to those skilled in the art. For example, nucleic acid purification may be performed using a preparative ion chromatography purification column with a gradient elution of NaBr or NaCl; after collection and combination of the product, the desalination may be performed using a reverse phase chromatography purification column.

The non-bridging oxygen atom or sulfur atom in the phosphodiester bond or phosphorothioate diester bond between the nucleotides in the resultant siRNA conjugate as shown by Formula (308) substantially binds to a sodium ion, and the siRNA conjugate as shown by Formula (308) is substantially present in the form of a sodium salt. The well-known ion-exchange methods may be used, in which the sodium ion may be replaced with hydrogen ion and/or other cations, thereby providing other forms of siRNA conjugates as shown by Formula (308). The cations are as described above.

During synthesis, the purity and molecular weight of the nucleic acid sequence may be determined at any time. In order to better control the synthesis quality, such detection methods are well-known to those skilled in the art. For example, the purity of the nucleic acid may be detected by ion exchange chromatography, and the molecular weight may be determined by liquid chromatography-mass spectrometry (LC-MS).

Methods for annealing are also well-known to those skilled in the art. For example, the synthesized sense strand (S strand) and antisense strand (AS strand) may be simply mixed in water for injection at an equimolar ratio, heated to 70-95° C., and then cooled at room temperature to form a double-stranded structure via hydrogen bond. As such, the siRNA conjugate as shown by Formula (308) may be obtained.

After obtaining the siRNA conjugate, in some embodiments, the siRNA conjugate as shown by Formula (308) thus synthesized can also be characterized by the means such as molecular weight detection using the methods such as liquid chromatography-mass spectrometry, to confirm that the synthesized siRNA conjugate is the designed siRNA conjugate as shown by Formula (308) of interest, and the sequence of the synthesized siRNA is the sequence of the siRNA sequence desired to be synthesized, for example, is one of the sequences listed in Tables 1.

The compound as shown by Formula (321) may be prepared by the following method comprising: contacting a compound as shown by Formula (313) with a cyclic anhydride in an organic solvent under esterification reaction condition in the presence of a base and an esterification catalyst; and isolating the compound as shown by Formula (321) by ion exchange:

Formula (313)

wherein the definitions and options of n1, n3, m1, m2, m3, $R_{10}$, $R_{11}$, $R_{12}$, $R_{13}$, $R_{14}$, $R_{15}$, $L_1$, and $S_1$ are respectively as described above;

$R_6$ is a group for providing $R_4$ of Formula (321). In some embodiments, $R_6$ comprises a structure as shown by Formula (A61):

(A61)

wherein, $R_i$ is any group capable of linking to the N atom on the nitrogenous backbone, linking to $R_kO$ and linking to a free hydroxy; and $R_k$ is a hydroxy protecting group. In this case, the compound as shown by Formula (321) is obtained, wherein $R_4$ comprises a first functional group as a hydroxy protecting group and a second functional group comprising a group as shown by Formula (C1) or (C2).

The esterification reaction condition comprises a reaction temperature of 0-100° C. and a reaction time of 8-48 hours. In some embodiments, the esterification reaction condition comprises a reaction temperature of 10-40° C. and a reaction time of 20-30 hours.

In some embodiments, the organic solvent comprises one or more of an epoxy solvent, an ether solvent, a haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tertbutyl ether, and the haloalkane solvent is one or more of dichloromethane, trichloromethane and 1,2-dichloroethane. In some embodiments, the organic solvent is dichloromethane. The amount of the organic solvent is 3-50 L/mol, and in some embodiments, 5-20 L/mol, with respect to the compound as shown by Formula (313).

In some embodiments, the cyclic anhydride is one of succinic anhydride, glutaric anhydride, adipic anhydride or pimelic anhydride, and in some embodiments, the cyclic anhydride is succinic anhydride. The molar ratio of the cyclic anhydride to the compound as shown by Formula (313) is 1:1 to 10:1, and in some embodiments, 2:1 to 5:1.

The esterification catalyst may be any catalyst capable of catalyzing esterification, for example, the catalyst may be 4-dimethylaminopyridine. The molar ratio of the catalyst to the compound as shown by Formula (313) is 1:1 to 10:1, and in some embodiments, 2:1 to 5:1.

In some embodiments, the base may be any inorganic base, organic base or a combination thereof. Considering solubility and product stability, the base may be, for example, tertiary amine. In some embodiments, the tertiary amine is triethylamine or N,N-diisopropylethylamine. The molar ratio of the tertiary amine to the compound as shown by Formula (313) is 1:1 to 20:1, and in some embodiments, is 3:1 to 10:1.

The ion exchange serves the function of converting the compound as shown by Formula (321) into a desired form of carboxylic acid or carboxylic salt and the methods of ion exchange are well-known to those skilled in the art. The above conjugating molecule in which the cation is $M^+$ may be obtained by using suitable ion exchange solution and ion exchange condition, which is not described here in detail. In some embodiments, a triethylamine phosphate solution is used in the ion exchange reaction, and the concentration of the triethylamine phosphate solution is 0.2-0.8 M. In some embodiments, the concentration of the triethylamine phosphate solution is 0.4-0.6 M. In some embodiments, the amount of the triethylamine phosphate solution is 3-6 L/mol, and in further embodiment, 4-5 L/mol, with respect to the compound as shown by Formula (313).

The compound as shown by Formula (321) may be isolated from the reaction mixture using any suitable isolation methods. In some embodiments, the compound as shown by Formula (321) may be isolated by removal of solvent via evaporation followed by chromatography, for example, using the following two chromatographic conditions for the isolation: (1) normal phase purification of 200-300 mesh silica gel filler, and gradient elution of 1 wt % triethylamine in dichloromethane:methanol=100:18 to 100:20; or (2) reverse phase purification of C18 and C8 reverse phase filler, and gradient elution of methanol:acetonitrile=0.1:1 to 1:0.1. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the product obtained from the above ion exchanging reaction with a solid phase support containing amino or hydroxy in an organic solvent under condensation reaction condition in the presence of a condensing agent, a condensing catalyst and tertiary amine. In this case, the compound as shown by Formula (321) is obtained, wherein $R_4$ comprises a first functional group comprising a hydroxy protecting group and a second functional group having a structure as shown by Formula (C1').

The solid phase support is one of the carriers used in solid phase synthesis of siRNA, some of which are well-known to those skilled in the art. For example, the solid phase support may be selected from the solid phase supports containing an active hydroxy or amino functional group. In some embodiments, the solid phase support is an amino resin or hydroxy resin. In some embodiments, the amino or hydroxy resin has the following parameters: particle size of 100-400 mesh, and surface amino or hydroxy loading of 0.2-0.5 mmol/g. The ratio of the compound as shown by Formula (321) to the solid phase support is 10-400 µmol compound per gram of solid phase support (µmol/g). In some embodiments, the ratio of the compound of Formula (321) to the solid phase support is 50-200 µmol/g.

The organic solvent may be any suitable solvent or mixed solvents known to those skilled in the art. In some embodiments, the organic solvent comprises one or more of acetonitrile, an epoxy solvent, an ether solvent, a haloalkane solvent, dimethyl sulfoxide, N,N-dimethylformamide, and N,N-diisopropylethylamine. In some embodiments, the epoxy solvent is dioxane and/or tetrahydrofuran, the ether solvent is diethyl ether and/or methyl tertbutyl ether, and the haloalkane solvent is one or more of dichloromethane, trichloromethane and 1,2-dichloroethane. In some embodiments, the organic solvent is acetonitrile. The amount of the organic solvent may be 20-200 L/mol, and in some embodiments, 50-100 L/mol, with respect to the compound as shown by Formula (321).

In some embodiments, the condensing agent may be benzotriazol-1-yl-oxytripyrrolidino phosphonium hexafluorophosphate (PyBop), 3-(Diethoxyphosphoryloxy)-1,2,3-benzotriazin-4(3H)-one (DEPBT) and/or O-benzotriazol-1-yl-tetramethyluronium hexafluorophosphate. In some embodiments, the condensing agent is O-benzotriazol-1-yl-tetramethyluronium hexafluorophosphate. The molar ratio of the condensing agent to the compound as shown by Formula (321) is 1:1 to 20:1, and in some embodiments, 1:1 to 5:1.

In some embodiments, the tertiary amine is triethylamine and/or N,N-diisopropylethylamine, and in some embodiments, N,N-diisopropylethylamine. The molar ratio of the tertiary amine to the compound as shown by Formula (321) is 1:1 to 20:1, and in some embodiments, 1:1 to 5:1.

In some embodiments, the method for preparing the compound as shown by Formula (321) further comprises: contacting the resultant condensation product with a capping agent and an acylation catalyst in an organic solvent under capping reaction condition, and isolating the compound as shown by Formula (321). The capping reaction is used to remove any active functional group that does not completely react, so as to avoid producing unnecessary by products in subsequent reactions. The capping reaction condition comprises a reaction temperature of 0-50° C., and in some embodiments, 15-35° C., and a reaction time of 1-10 hours, and in some embodiments, 3-6 hours. The capping agent may be a capping agent used in solid phase synthesis of siRNA, and the capping agent used in solid phase synthesis of siRNA is well known to those skilled in the art.

In some embodiments, the capping agent is composed of a capping agent 1 (cap1) and a capping agent 2 (cap2). The cap1 is N-methylimidazole, and in some embodiments, provided as a mixed solution of N-methylimidazole in pyridine/acetonitrile, wherein the volume ratio of the pyridine to the acetonitrile is 1:10 to 1:1, and in some embodiments, 1:3 to 1:1. In some embodiments, the ratio of the total volume of the pyridine and acetonitrile to the volume of the N-methylimidazole is 1:1 to 10:1, and in some embodiments, 3:1 to 7:1. The capping agent 2 is acetic anhydride. In some embodiments, the capping agent 2 is provided as a solution of acetic anhydride in acetonitrile, wherein the volume ratio of the acetic anhydride to the acetonitrile is 1:1 to 1:10, and in some embodiments, 1:2 to 1:6.

In some embodiments, the ratio of the volume of the mixed solution of N-methylimidazole in pyridine/acetonitrile to the mass of the compound as shown by Formula (321) is 5 ml/g to 50 ml/g, and in some embodiments, 15 ml/g to 30 ml/g. The ratio of the volume of the solution of acetic anhydride in acetonitrile to the mass of the compound as shown by Formula (321) is 0.5 ml/g to 10 ml/g, and in some embodiments, 1 ml/g to 5 ml/g.

In some embodiments, the capping agent comprises equimolar acetic anhydride and N-methylimidazole. In some embodiments, the organic solvent comprises one or more of acetonitrile, an epoxy solvent, an ether solvent, a haloalkane solvent, dimethyl sulfoxide, N,N-dimethylformamide, and N,N-diisopropylethylamine. In some embodiments, the organic solvent is acetonitrile. The amount of the organic solvent may be 10-50 L/mol, and in some embodiments, 5-30 L/mol, with respect to the compound as shown by Formula (321).

In some embodiments, the acylation catalyst may be selected from any catalyst that may be used for esterification condensation or amidation condensation, such as alkaline heterocyclic compounds. In some embodiments, the acylation catalyst is 4-dimethylaminopyridine. The mass ratio of the catalyst to the compound as shown by Formula (321) may be 0.001:1 to 1:1, and in some embodiments, 0.01:1 to 0.1:1.

In some embodiments, the compound as shown by Formula (321) may be isolated from the reaction mixture using any suitable isolation methods. In some embodiments, the compound as shown by Formula (321) may be obtained by thoroughly washing with an organic solvent and filtering to remove unreacted reactants, excess capping agent and other impurities, wherein the organic solvent is selected from acetonitrile, dichloromethane, or methanol. In some embodiments, the organic solvent is acetonitrile.

In some embodiments, the preparation of the conjugating molecule as shown by Formula (321) comprises contacting a compound as shown by Formula (313) with a phosphorodiamidite in an organic solvent under coupling reaction condition in the presence of a coupling agent, and isolating the compound as shown by Formula (321). In this case, the compound as shown by Formula (321) is obtained, where $R_4$ comprises a first functional group comprising a hydroxy protecting group and a second functional group having a structure as shown by Formula (C3).

In some embodiments, the coupling reaction condition comprises a reaction temperature of 0-50° C., such as 15-35° C. The molar ratio of the compound as shown by Formula (313) to the phosphorodiamidite may be 1:1 to 1:50, such as 1:5 to 1:15. The molar ratio of the compound as shown by Formula (313) to the coupling agent may be 1:1 to 1:100, such as 1:50 to 80. The reaction time may be 200-3000 seconds, such as 500-1500 seconds. The phosphorodiamidite may be, for example, bis(diisopropylamino)(2-cyanoethoxy)phosphine, which may be commercially available or synthesized according to well-known methods in the art. The coupling agent is selected from one or more of 1H-tetrazole, 5-ethylthio-1H-tetrazole and 5-benzylthio-1H tetrazole, such as 5-ethylthio-1H-tetrazole. The coupling reaction may be performed in an organic solvent, and the organic solvent is selected from one or more of anhydrous acetonitrile, anhydrous DMF and anhydrous dichloromethane, such as anhydrous acetonitrile. The amount of the organic solvent may be 3-50 L/mol, such as 5-20 L/mol, with respect to the compound as shown by Formula (313). By performing the coupling reaction, the hydroxy in the compound as shown by Formula (313) reacts with the phosphorodiamidite to form a phosphoramidite group. In some embodiments, the solvent may be directly removed to obtain a crude product of the compound as shown by Formula (321), which may be directly used in subsequent reactions.

In some embodiments, the method for preparing the compound as shown by Formula (321) further comprises: contacting the isolated product with a solid phase support containing hydroxy in an organic solvent under coupling reaction condition in the presence of a coupling agent, followed by capping, oxidation, and isolation, to obtain the compound as shown by Formula (321). In this case, the compound as shown by Formula (321) is obtained, where $R_4$ comprises a first functional group comprising a hydroxy protecting group and a second functional group having a structure as shown by Formula (C3').

In some embodiments, the solid phase support is a well-known solid phase support in the art for solid phase synthesis of a nucleic acid, such as a deprotected commercially available universal solid phase support (NittoPhase®HL UnyLinker™ 300 Oligonucleotide Synthesis Support, Kinovate Life Sciences, as shown by Formula B80):

(B80)

A deprotection reaction is well-known in the art. In some embodiments, the deprotection condition comprises a temperature of 0-50° C., such as 15-35° C.; and a reaction time of 30-300 seconds, such as 50-150 seconds. The deprotection agent may be selected from one or more of trifluoroacetic acid, trichloroacetic acid, dichloroacetic acid, and monochloroacetic acid. In some embodiments, the deprotection agent is dichloroacetic acid. The molar ratio of the deprotection agent to the protecting group -DMTr(4,4'-dimethoxytrityl) on the solid phase may be 2:1 to 100:1, such as 3:1 to 50:1. By such deprotection, hydroxys with reactivity are obtained on the surface of the solid phase support, for facilitating the subsequent coupling reaction.

The coupling reaction condition and the coupling agent may be selected as above. By performing coupling reaction, the free hydroxys formed in the deprotection reaction reacts with the phosphoramidite groups, so as to form a phosphite ester linkage.

In some embodiments, the capping reaction condition comprises a reaction temperature of 0-50° C., such as 15-35° C., and a reaction time of 5-500 seconds, such as 10-100 seconds. The capping reaction is performed in the presence of a capping agent. The selection and amount of the capping agent are as above.

The oxidation reaction condition may comprise a temperature of 0-50° C., such as 15 35° C., and a reaction time of 1-100 seconds, such as 5-50 seconds. The oxidation agent may be, for example, iodine (in some embodiments, provided as iodine water). In some embodiments, the molar ratio of the oxidation agent to the nucleic acid sequence linked to the solid phase support is 1:1 to 100:1, such as 5:1 to 50:1. In some embodiments, the oxidation reaction is performed in a mixed solvent in which the ratio of tetrahydrofuran:water:pyridine is 3:1:1 to 1:1:3.

In some embodiments, $R_6$ is a group as shown by Formula B7 or B8:

(B7)

(B8)

wherein the definition of $q_2$ is as described above.

In this case, the compound as shown by Formula (313) may be prepared by the following method: contacting a compound as shown by Formula (314) with a compound as shown by Formula (A-1) or a compound as shown by Formula (A-2) in an organic solvent under amidation reaction condition in the presence of an agent for amidation condensation and tertiary amine, and isolating:

Formula (314)

(A-1)

(A-2)

wherein the definitions and options of n1, n3, m1, m2, m3, $R_{10}$, $R_{11}$, $R_{12}$, $R_{13}$, $R_{14}$, $R_{15}$, $L_1$, $S_1$, $q_2$ and $R_k$ are respectively as described above.

The amidation reaction condition may comprise a reaction temperature of 0-100° C. and a reaction time of 1-48 hours.

In some embodiments, the amidation reaction condition comprises a reaction temperature of 10-40° C. and a reaction time of 2-16 hours.

In some embodiments, the organic solvent is one or more of an alcohol solvent, an epoxy solvent, an ether solvent, a haloalkane solvent, dimethyl sulfoxide, N,N-dimethylformamide, and N,N-diisopropylethylamine. In some embodiments, the alcohol solvent is one or more of methanol, ethanol and propanol, and in some embodiments, ethanol. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is dichloromethane. The amount of the organic solvent is 3-50 L/mol, and in further embodiments, 3-20 L/mol, with respect to the compound as shown by Formula (314).

In some embodiments, the agent for amidation condensation is benzotriazol-1-yl-oxytripyrrolidinophosphonium hexafluorophosphate, 3-(Diethoxyphosphoryloxy)-1,2,3-benzotriazin-4(3H)-one, 4-(4,6-dimethoxytriazin-2-yl)-4-methylmorpholine hydrochloride, 2 ethoxy-1-ethoxycarbonyl-1,2-dihydroquinoline (EEDQ) or O-benzotriazol-1-yl-tetramethyluronium hexafluorophosphate, and in further embodiments, 3-(Diethoxyphosphoryloxy)-1,2,3-benzotriazin-4(3H)-one. The molar ratio of the agent for amidation condensation to the compound as shown by Formula (314) may be 1:1 to 10:1, and in some embodiments, 2.5:1 to 5:1.

In some embodiments, the tertiary amine is triethylamine and/or N,N-diisopropylethylamine, and in further embodiments, N,N-diisopropylethylamine. The molar ratio of the tertiary to the compound as shown by Formula (314) is 3:1 to 20:1, and in some embodiments, is 5:1 to 10:1.

The compounds as shown by Formula (A-1) and Formula (A-2) may be prepared by any suitable methods. For example, when $R_k$ is a DMTr group, the compound as shown by Formula (A-1) may be prepared by reacting calcium glycerate with DMTrCl. Similarly, the compound as shown by Formula (A-2) may be prepared by contacting 3-amino-1,2-propanediol with a cyclic anhydride and then reacting with DMTrCl, wherein the cyclic anhydride may have 4-13 carbon atoms, and in some embodiments, 4-8 carbon atoms. Those skilled in the art would readily understand that the selections of the cyclic anhydride correspond to different values for $q_2$ in the compound as shown by Formula (A-2). For example, when the cyclic anhydride is succinic anhydride, $q_2=1$; when the cyclic anhydride is glutaric anhydride, $q_2=2$, and so on.

In some variants, the compound as shown by Formula (313) can also be prepared by successively reacting the compound as shown by Formula (314) with the cyclic anhydride, 3-amino-1,2 propanediol, and DMTrCl. Those skilled in the art would readily understand that these variants would not affect the structure and function of the compound as shown by Formula (313), and these variants can be readily achieved by those skilled in the art on the basis of the above methods.

Similarly, the compound as shown by Formula (313) may be isolated from the reaction mixture by any suitable isolation methods. In some embodiments, the compound as shown by Formula (313) may be isolated by removal of solvent via evaporation followed by chromatography, for example, using the following two chromatographic conditions for isolation: (1) normal phase purification of 200-300 mesh silica gel filler, and gradient elution of petroleum ether:ethyl acetate:dichloromethane:N,N-dimethylformamide=1:1:1:0.5 1:1:1:0.6; and (2) reverse phase purification of C18 and C8 reverse phase fillers, and gradient elution of methanol:acetonitrile=0.1:1 to 1:0.1. In some embodiments, the solvent may be directly removed to obtain a crude product of the compound as shown by Formula (313), which may be directly used in subsequent reactions.

In some embodiments, the compound as shown by Formula (314) may be prepared by the following method comprising: contacting a compound as shown by Formula (320) with a compound as shown by Formula (316) in an organic solvent under under condensation reaction condition in the presence of an agent for amidation condensation and tertiary amine, and isolating:

$$S_1 \!-\! L_1 \!-\! OH \qquad \text{Formula (316)}$$

Formula (320)

$$H \!-\! [N \!-\! (C)_{m1}]_{n1} \!-\! N \!-\! (C)_{m2} \!-\! [N \!-\! (C)_{m3}]_{n3} \!-\! NH_2$$

wherein the definitions and options of n1, n3, m1, m2, m3, $R_{10}, R_{11}, R_{12}, R_{13}, R_{14}$, and $R_{15}$ are respectively as described above.

The compound as shown by Formula (316) can be, such as, those disclosed in J. Am. Chem. Soc. 2014, 136, 16958-16961, or, the compounds as shown by Formula (316) may be prepared by those skilled in the art via various methods. For example, some compound as shown by Formula (316) may be prepared according to the methods as disclosed in Example 1 of U.S. Pat. No. 8,106,022 B2, which is incorporated herein by reference in its entirety.

In some embodiments, the condensation reaction condition comprises a reaction temperature of 0-100° C. and a reaction time of 0.1-24 hours. In some embodiments, the condensation reaction condition comprises a reaction temperature is 10-40° C. and a reaction time is 0.5-16 hours.

Considering the structure of the desired compound as shown by Formula (314), the molar ratio of the compound as shown by Formula (316) to the compound as shown by Formula (320) should be determined based on the sum of n1 and n3 in Formula (320). In some embodiments, for example, when n1+n3=3, in order to ensure that the reaction is complete and not excessive, the molar ratio of the compound as shown by Formula (316) to the compound as shown by Formula (320) may be 3:1 to 3.5:1, and in some embodiments, is 3.01:1 to 3.15:1.

In some embodiments, the organic solvent is one or more of acetonitrile, an epoxy solvent, an ether solvent, a haloalkane solvent, dimethyl sulfoxide, N,N-dimethylformamide, and N,N-diisopropylethylamine. In some embodiments, the epoxy solvent is dioxane and/or tetrahydrofuran. In some embodiments, the ether solvent is diethyl ether and/or methyl tertbutyl ether. In some embodiments, the haloalkane solvent is one or more of dichloromethane, trichloromethane and 1,2-dichloroethane. In some embodiments, the organic solvent is acetonitrile. The amount of the organic solvent is 3-50 L/mol, and in some embodiments, 5-20 L/mol, with respect to the compound as shown by Formula (320).

In some embodiments, the agent for amidation condensation is benzotriazol-1-yl-oxytripyrrolidinophosphonium hexafluorophosphate, 3-(Diethoxyphosphoryloxy)-1,2,3-benzotriazin-4(3H)-one (DEPBT), O-benzotriazol-1-yl-te-tramethyluronium hexafluorophosphate, 4-(4,6-dimethoxytriazin-2-yl)-4-methylmorpholine hydrochloride or 1-hydroxybenzotriazole, and in further embodiments, is a mixture of the benzotriazol-1-yl-oxytripyrrolidinophosphonium hexafluorophosphate and the 1-hydroxybenzotriazole, wherein the benzotriazol-1-yl-oxytripyrrolidino phosphonium hexafluorophosphate (PyBop) and the 1-hydroxybenzotriazole are equimolar. The molar ratio of the total agent for amidation condensation to the compound as shown by Formula (316) may be 1:1 to 3:1, and in some embodiments, is 1.05:1 to 1.5:1.

The tertiary amine may be N-methylmorpholine, triethylamine or N,N-diisopropylethylamine, and in some embodiments, N-methylmorpholine. The molar ratio of the tertiary amine to the compound as shown by Formula (316) may be 2:1 to 10:1, and in some embodiments, is 2:1 to 5:1.

Similarly, the compound as shown by Formula (314) may be isolated from the reaction mixture by any suitable isolation methods. In some embodiments, the compound as shown by Formula (314) is isolated by removal of solvent via evaporation followed by chromatography, for example, using the following two chromatographic conditions for isolation: (1) normal phase purification of 200-300 mesh silica gel filler, and gradient elution of dichloromethane:methanol=100:5 to 100:7; and (2) reverse phase purification of C18 and C8 reverse phase fillers, and gradient elution of methanol:acetonitrile=0.1:1 to 1:0.1. In some embodiments, the solvent is directly removed to obtain a crude product of the compound as shown by Formula (314), and the crude product can be directly used in subsequent reactions.

The compound as shown by Formula (320) may be commercially available, or obtained by those skilled in the art via the known methods. For example, in the case that m1=m2=m3=3, n1=1, n3=2, and $R_{10}$, $R_{11}$, $R_{12}$, $R_{13}$, $R_{14}$, and $R_{15}$ are all H, the compound as shown by Formula (320) is commercially available from Alfa Aesar Inc.

The siRNA conjugate of the present disclosure may also be used in combination with other pharmaceutically acceptable excipients, which may be one or more of the various conventional formulations or compounds in the art. For details, please refer to the above description of the pharmaceutical compositions of the present disclosure.

Use of the siRNA, the Pharmaceutical Composition and the siRNA Conjugate of the Present Disclosure In some embodiments, the present disclosure provides use of the siRNA and/or the pharmaceutical composition and/or the siRNA conjugate according to the present disclosure in the manufacture of a medicament for treating and/or preventing abnormal uric acid metabolism or a disease or a physiological condition caused by abnormal uric acid metabolism. In some embodiments, the disease or physiological condition caused by abnormal uric acid metabolism is hyperuricemia or gout.

In some embodiments, the present disclosure provides a method for preventing and/or treating abnormal uric acid metabolism or a disease or a physiological condition caused by abnormal uric acid metabolism, wherein the method comprises administering an effective amount of the siRNA and/or the pharmaceutical composition and/or the siRNA conjugate of the present disclosure to a subject in need. In some embodiments, the disease or physiological condition caused by abnormal uric acid metabolism is hyperuricemia or gout.

It is possible to achieve the purpose of preventing and/or treating abnormal uric acid metabolism or the disease or physiological condition caused by abnormal uric acid metabolism based on a mechanism of RNA interference by administering the active ingredients of the siRNA of the present disclosure to the subject in need. Thus, the siRNA and/or the pharmaceutical composition and/or the siRNA conjugate of the present disclosure may be used for preventing and/or treating abnormal uric acid metabolism or the disease or physiological condition caused by abnormal uric acid metabolism, or for the manufacture of a medicament for preventing and/or treating abnormal uric acid metabolism or the disease or physiological condition caused by abnormal uric acid metabolism. In some embodiments, the abnormal uric acid metabolism, or the disease or physiological condition caused by abnormal uric acid metabolism is hyperuricemia or gout.

As used herein, the term "administration/administer" refers to the delivery of the siRNA, the pharmaceutical composition, and/or the siRNA conjugate of the present disclosure into a body of a subject by a method or a route that at least partly locates the siRNA, the pharmaceutical composition, and/or the siRNA conjugate of the present disclosure at a desired site to produce a desired effect. Suitable administration routes for the methods of the present disclosure comprise topical administration and systemic administration. In general, the topical administration results in the delivery of more siRNA conjugate to a particular site compared with the systemic circulation of the subject; whereas the systemic administration results in the delivery of the siRNA, the pharmaceutical composition, and/or the siRNA conjugate of the present disclosure to the substantial systemic circulation of the subject. Considering that the present disclosure can provide a means for preventing and/or treating the abnormal uric acid metabolism, or the disease or physiological condition caused by abnormal uric acid metabolism, in some embodiments, an administration mode capable of delivering drugs to liver is used.

The administration to a subject may be achieved by any suitable routes known in the art, including but not limited to, oral or parenteral route, such as intravenous administration, intramuscular administration, subcutaneous administration, transdermal administration, intratracheal administration (aerosol), pulmonary administration, nasal administration, rectal administration and topical administration (including buccal administration and sublingual administration). The administration frequency may be once or more times daily, weekly, biweekly, triweekly, monthly or annually.

The dose of the siRNA, the pharmaceutical composition, or the second siRNA conjugate of the present disclosure may be a conventional dose in the art, and the dose may be determined according to various parameters, especially age, weight and gender of a subject. Toxicity and efficacy may be measured in cell cultures or experimental animals by standard pharmaceutical procedures, for example, by determining $LD_{50}$ (the lethal dose that causes 50% population death), and $ED_{50}$ (the dose that can cause 50% of the maximum response intensity in a quantitative response, and that causes 50% of the experimental subjects to have a positive response in a qualitative response). The dose range for human may be derived based on the data obtained from cell culture analysis and animal studies.

When administrating the siRNA, the pharmaceutical composition or the siRNA conjugate of the present disclosure, for example, to male or female C57BL/6J mice of 6-12 weeks old and 18-25 g body weight or ob/ob mice of 30-45 g, and calculating based on the amount of the siRNA: (i) for the siRNA conjugate, the dosage of the siRNA thereof may be 0.001-100 mg/kg body weight, and in further embodiments, is 0.01-50 mg/kg body weight, and in some embodiments, is 0.05-20 mg/kg body weight, in some another embodiments is 0.1-15 mg/kg body weight, and in some another embodiments, is 0.1-10 mg/kg body weight; and (ii) for a pharmaceutical composition formed by an siRNA and a pharmaceutically acceptable carrier, the dosage of the siRNA thereof may be 0.001-50 mg/kg body weight, in some embodiments, is 0.01-10 mg/kg body weight, in some embodiments, is 0.05-5 mg/kg body weight, and in some embodiments, is 0.1-3 mg/kg body weight.

In some embodiments, the present disclosure provides a method for inhibiting expression of a XO gene in a cell. The method comprises contacting an effective amount of the siRNA and/or the pharmaceutical composition and/or the siRNA conjugate of the present disclosure with the cell, introducing the siRNA and/or the pharmaceutical composition and/or the siRNA conjugate of the present disclosure into the cell, and achieving the purpose of inhibiting the expression of the XO gene in the cell through a mechanism of RNA interference. The cell may be selected from SMIVIC-7721, CAL-27, Huh7 and other cancer cell lines or isolated primary hepatocytes. In some embodiments, the cells are CAL-27 cells.

In the case where the expression of the XO in the cell is inhibited by using the method provided by the present disclosure, the amount of the siRNA in the modified siRNA, the pharmaceutical composition, and/or the siRNA conjugate provided is typically: an amount sufficient to reduce the expression of the target gene and result in an extracellular concentration of 1 µM to 1 µM, or 0.01 nM to 100 nM, or 0.05 nM to 50 nM or 0.05 nM to about 5 nM on the surface of the target cell.

The amount required to achieve this local concentration will vary with various factors, including the delivery method, the delivery site, the number of cell layers between the delivery site and the target cells or tissues, the delivery route (topical or systemic), etc. The concentration at the delivery site may be significantly higher than that on the surface of the target cells or tissues.

Kit

The present disclosure provides a kit, wherein the kit comprises an effective amount of at least one of the modified siRNA, the pharmaceutical composition, and the siRNA conjugate of the present disclosure.

In some embodiments, the kit disclosed herein may provide a modified siRNA in one container. In some embodiments, the kit of the present disclosure may comprise a container providing pharmaceutically acceptable excipients. In some embodiments, the kit may further comprise additional ingredients, such as stabilizers or preservatives. In some embodiments, the kit herein may comprise at least one additional therapeutic agent in other container than the container providing the modified siRNA herein. In some embodiments, the kit may comprise an instruction for mixing the modified siRNA with the pharmaceutically acceptable carrier and/or adjuvants or other ingredients (if any).

In the kit of the present disclosure, the modified siRNA and the pharmaceutically acceptable carrier and/or the adjuvants as well as the modified siRNA, the pharmaceutical composition, and/or the siRNA conjugate and/or the pharmaceutically acceptable adjuvants may be provided in any form, e.g., in a liquid form, a dry form, or a lyophilized form. In some embodiments, the modified siRNA and the pharmaceutically acceptable carrier and/or the adjuvants as well as the pharmaceutical composition and/or the siRNA conjugate and optional pharmaceutically acceptable adjuvants are substantially pure and/or sterile. In some embodiments, sterile water may be provided in the kit of the present disclosure.

Hereinafter, the present disclosure will be further described by examples, but is not limited thereto in any respect.

EXAMPLES

Unless otherwise specified, the agents and culture media used in following examples are all commercially available, and the procedures used such as nucleic acid electrophoresis and real-time PCR are all performed according to methods described in Molecular Cloning (Cold Spring Harbor Laboratory Press (1989)).

C57BL/6N mice: 6-8 weeks old, purchased from Beijing Charles River Laboratory Animal Technology Co., Ltd., hereinafter referred to as C57 mice.

Unless otherwise specified, ratios of reagents provided below are all calculated by volume ratio (v/v).

Unless otherwise specified, the following experimental data of the in vivo/in vitro are all expressed as X±SEM, and the data analysis is carried out by using Graphpad prism5.0 statistical analysis software.

Preparation Example 1

Preparation of siRNA Conjugate L10-siXOi1M1S

In this preparation example, the siRNA conjugate L10-siXOi1M1S was synthesized. The siRNA conjugate is an siRNA conjugate formed after a L L-9 conjugating molecule is conjugated with an siRNA with a number of siXOi1M1S. See Table 3 for the sequence of the conjugated siRNA in the siRNA conjugate.

(1-1) Synthesis of Compound L-10

The compound L-10 was synthesized according to the following method:

-continued

L-7

L-9

-continued

L-10

(1-1-1) Synthesis of GAL-5 (A Terminal Segment of the Conjugating Molecule)

GAL-1
Molecular Weight: 215.6

GAL-2
Molecular Weight: 389.3

GAL-3
Molecular Weight: 329:3

GAL-4
Molecular Weight: 429.5

GAL-5
Molecular Weight: 447.4

(1-1-1a) Synthesis of GAL-2

100.0 g of GAL-1 (N-acetyl-D-galactosamine hydrochloride, CAS No.: 1772-03-8, purchased from Ningbo Hongxiang Bio-Chem Co., Ltd., 463.8 mmol) was dissolved in 1000 ml of anhydrous pyridine, to which 540 ml of acetic anhydride (purchased from Enox Inc., 5565.6 mmol) was added in an ice water bath to react under stirring at room temperature for 1.5 hours. The resultant reaction solution was poured into 10 L of ice water and subjected to suction filtration under reduced pressure. The residue was washed with 2 L of ice water, and then added with a mixed solvent of acetonitrile/toluene (v/v ratio=1:1) until completely dissolved. The solvent was removed by evaporation to give 130.0 g of product GAL-2 as a white solid.

(1-1-1b) Synthesis of GAL-3

GAL-2 (35.1 g, 90.0 mmol) obtained in step (1-1-1a) was dissolved in 213 ml of anhydrous 1,2-dichloroethane, to which 24.0 g of TMSOTf (CAS No.: 27607-77-8, purchased from Macklin Inc., 108.0 mmol) was added under an ice water bath and nitrogen protection to react at room temperature overnight.

400 ml of dichloromethane was added to the reaction solution for dilution, filtered with diatomite, and then added with 1 L of saturated aqueous sodium bicarbonate solution and stirred evenly. An organic phase was isolated. An aqueous phase remained was extracted twice, each with 300 ml of dichloroethane, and all organic phases were combined and washed with 300 ml of saturated aqueous sodium bicarbonate solution and 300 ml of saturated brine, respectively. The organic phase resulted from washing was isolated and dried with anhydrous sodium sulfate. The solvent was removed by evaporation under reduced pressure to give 26.9 g of product GAL-3 as a light yellow viscous syrup.

(1-1-1c) Synthesis of GAL-4

GAL-3 (26.9 g, 81.7 mmol) obtained in step (1-1-1b) was dissolved in 136 ml of anhydrous 1,2-dichloroethane, added with 30 g of dry 4 Å molecular sieve powder followed by 9.0 g of 5-hexen-1-ol (CAS No.: 821-41-0, purchased from Adamas-beta Inc., 89.9 mmol), and stirred at room temperature for 30 minutes. 9.08 ml of TMSOTf (40.9 mmol) was added in an ice bath and nitrogen protection to react under stirring at room temperature overnight. The 4 Å molecular sieve powder was removed by filtration. The filtrate was added with 300 ml of dichloroethane for dilution, filtered with diatomite, and then added with 500 ml of saturated aqueous sodium bicarbonate solution and stirred for 10 minutes for washing. An organic phase was isolated. An aqueous phase was extracted once with 300 ml of dichloroethane. All organic phases were combined and washed with 300 ml of saturated aqueous sodium bicarbonate solution and 300 ml of saturated brine respectively. The organic phase resulted from the washing was isolated and dried with anhydrous sodium sulfate. The solvent was removed by evaporation under reduced pressure to give 41.3 g of product GAL-4 as a yellow syrup, which was directly used in the next oxidation reaction without purification.

(1-1-1d) Synthesis of GAL-5

GAL-4 (14.9 g, 34.7 mmol) obtained according to the method described in step (1-1-1c) was dissolved in a mixed solvent of 77 ml of dichloromethane and 77 ml of acetonitrile, added with 103 ml of deionized water and 29.7 g of sodium periodate (CAS No.: 7790-28-5, purchased from Aladdin Inc., 138.8 mmol) respectively, and stirred in an ice bath for 10 minutes. Ruthenium trichloride (CAS No.: 14898-67-0, purchased from Energy Chemical, 238 mg, 1.145 mmol) was added to react at room temperature overnight. The resultant reaction solution was diluted by adding 300 ml of water under stirring, and adjusted to a pH of about 7.5 by adding saturated sodium bicarbonate. An organic phase was isolated and discarded. An aqueous phase was extracted three times, each with 200 ml of dichloromethane, and the organic phase resulted from the extraction was discarded. The aqueous phase resulted from the extraction was adjusted to a pH of about 3 with citric acid solids and extracted three times, each with 200 ml of dichloromethane, and the resultant organic phases were combined and dried with anhydrous sodium sulfate. The solvent is removed by evaporation under reduced pressure to give 6.85 g of product GAL-5 as a white foamy solid. $^1$H NMR (400 MHz, DMSO) δ 12.01 (br, 1H), 7.83 (d, J=9.2 Hz, 1H), 5.21 (d, J=3.2 Hz, 1H), 4.96 (dd, J=11.2, 3.2 Hz, 1H), 4.49 (d, J=8.4 Hz, 1H), 4.07-3.95 (m, 3H), 3.92-3.85 (m, 1H), 3.74-3.67 (m, 1H), 3.48-3.39 (m, 1H), 2.20 (t, J=6.8 Hz, 2H), 2.11 (s, 3H), 2.00 (s, 3H), 1.90 (s, 3H), 1.77 (s, 3H), 1.55-1.45 (m, 4H).

(1-1-2) Synthesis of L-8

J-0 (9.886 g, 52.5 mmol, purchased from AlfaAesar) and GAL-5 (72.819 g, 162.75 mmol, obtained by combining the products of multiple batches) obtained in step (1-1-1d) were dissolved in 525 ml of dichloromethane, added with diisopropylethylamine (DIEA, 44.782 g, 346.50 mmol), benzotriazol-1-yl-oxytripyrrolidino phosphonium hexafluorophosphate (PyBop, 90.158 g, 173.25 mmol) and hydroxybenzotriazole (HOBt, 23.410 g, 173.25 mmol) to react at room temperature for 4 hours, and then added with 20 ml of saturated sodium bicarbonate and 200 ml of saturated brine for washing. An aqueous phase was extracted twice, each with 100 ml of dichloromethane, and the resultant organic phases were combined and dried with anhydrous sodium sulfate. The solvent was removed by evaporation under reduced pressure to give a crude product. The crude product was purified by using a normal phase silica gel column (200-300 mesh). The column was added with 10 wt % triethylamine for neutralizing the acidity of silica gel and equilibrated with 1 wt % triethylamine, and eluted with a gradient elution of dichloromethane:methanol=100:30 to 100:40. The eluate was collected, and the solvent was removed by evaporation under reduced pressure to give 38.8 g of pure product L-8. $^1$H NMR (400 MHz, DMSO) δ 7.84 (d, J=9.0 Hz, 3H), 7.27-7.23 (m, 1H), 7.13-7.18 (m, 1H), 5.22 (d, J=3.1 Hz, 3H), 4.97 (dd, J=11.3, 3.1 Hz, 3H), 4.48 (d, J=8.4 Hz, 3H), 4.09-3.98 (m, 9H), 3.88 (dd, J=19.3, 9.3 Hz, 3H), 3.75-3.66 (m, 3H), 3.44-3.38 (m, 3H), 3.17-3.30 (m, 4H), 3.10-2.97 (m, 4H), 2.35-2.20 (m, 6H), 2.15-2.08 (m, 9H), 2.07-1.98 (m, 13H), 1.94-1.87 (m, 9H), 1.81-1.74 (m, 9H), 1.65-1.42 (m, 18H). MS m/z: $C_{85}H_{119}N_7O_{30}$, [M+H]$^+$, called: 1477.59, measured: 1477.23.

(1-1-3a) Synthesis of A-1

Molecular Weight: 286.25

A-1
Molecular Weight: 509.64

DMTrCl (4,4'-dimethoxytrityl chloride, 101.65 g, 300 mmol) was dissolved in 1000 ml of anhydrous pyridine, and added with calcium DL-glycerate hydrate (28.63 g, 100 mmol) to react at 45° C. for 20 hours. The reaction solution was filtered. The residue was rinsed with 200 ml of DCM, and the filtrate was concentrated to dryness under reduced pressure. The residue was redissolved in 500 ml of dichloromethane and washed twice, each with 200 ml of 0.5 M triethylamine phosphate (pH=7-8). An aqueous phase isolated was extracted twice, each with 200 ml of dichloromethane. All organic phases were combined, dried with anhydrous sodium sulfate, and filtered. The solvent was removed by evaporation under reduced pressure, and the residue was purified by using a normal phase silica gel column (200-300 mesh) which was eluted with a gradient elution of petroleum ether:ethyl acetate:dichloromethane:methanol=1:1:1:0.35 to 1:1:1:0.55. The eluate was collected, and the solvent was removed by evaporation under reduced pressure. The residue was redissolved in 600 ml of dichloromethane, and washed once with 200 ml of 0.5 M triethylamine phosphate. The aqueous phase isolated was extracted once with 200 ml of dichloromethane. All organic phases were combined, dried with anhydrous sodium sulfate, and filtered. The solvent was removed by evaporation under reduced pressure and overnight under reduced pressure in a vacuum oil pump to give 50.7 g of product A-1 as a white solid. $^1$H NMR (400 MHz, DMSO-d6) δ 7.46 (ddd, J=6.5, 2.3, 1.1 Hz, 1H), 7.40-7.28 (m, 7H), 6.89-6.81 (m, 4H), 4.84 (d, J=5.0 Hz, 1H), 4.36-4.24 (m, 1H), 4.29 (s, 6H), 3.92 (dd, J=12.4, 7.0 Hz, 1H), 3.67 (dd, J=12.3, 7.0 Hz, 1H), 2.52 (q, J=6.3 Hz, 6H), 1.03 (t, J=6.3 Hz, 9H). MS m/z: $C_{24}H_{23}O_6$, [M–H]$^-$, called: 407.15, measured: 406.92.

(1-1-3b) Synthesis of L-7

L-8

L-7

L-8 (40 g, 27.09 mmol, obtained by combining the products of multiple batches) obtained in step (1-1-2) and A-1 (41.418 g, 81.27 mmol) obtained in step (1-1-3a) were mixed and dissolved in 271 ml of dichloromethane, added with 3-(Diethoxyphosphoryloxy)-1,2,3-benzotriazin-4(3H)-one (DEPBT, 24.318 g, 81.37 mmol), and further added with diisopropylethylamine (21.007 g, 162.54 mmol) to react under stirring at 25° C. for 1.5 hours. An organic phase was washed with 800 ml of saturated sodium bicarbonate. An aqueous phase isolated was extracted three times, each with 50 ml of dichloromethane. The organic phase was washed with 150 ml of saturated brine, and the aqueous phase was extracted once with 50 ml of dichloromethane. The resultant organic phases were combined and dried with anhydrous sodium sulfate. The solvent was removed by evaporation under reduced pressure and the residue was foam-dried in a vacuum oil pump overnight to give a crude product. The crude product was subjected to a column purification. The column was filled with 2 kg of normal phase silica gel (200-300 mesh), added with 200 ml of triethylamine for neutralizing the acidity of the silica gel, equilibrated with petroleum ether containing 1 wt % triethylamine, and eluted with a gradient elution of petroleum ether:ethyl acetate:

dichloromethane:N,N-dimethylformamide=1:1:1:0.5 to 1:1: 1:0.6. The eluate was collected, and the solvent was removed by evaporation under reduced pressure to give 40.4 g of pure product L-7. $^1$H NMR (400 MHz, DMSO) δ 7.90-7.78 (m, 4H), 7.75-7.64 (m, 1H), 7.38-7.18 (m, 9H), 6.91-6.83 (m, 4H), 5.25-5.10 (m, 4H), 4.97 (dd, J=11.2, 3.2 Hz, 3H), 4.48-4.30 (m, 4H), 4.02 (s, 9H), 3.93-3.84 (m, 3H), 3.76-3.66 (m, 9H), 3.45-3.35 (m, 3H), 3.24-2.98 (m, 10H), 2.30-2.20 (m, 2H), 2.11-1.88 (m, 31H), 1.80-1.40 (m, 28H). MS m/z: $C_{90}H_{128}N_7O_{35}$, [M-DMTr]$^+$, called: 1564.65, measured: 1564.88.

(1-1-4) Synthesis of L-9 added with diisopropylethylamine (DIPEA, 13.845 g, 107.1235 mmol), and stirred at 25° C. for 24 hours. The reaction solution was washed with 800 ml of 0.5 M triethylamine phosphate. An aqueous phase was extracted three times, each with 5 ml of dichloromethane. All organic phases were combined, and the solvent was evaporated under reduced pressure to give a crude product. The crude product was subjected to a column purification. The column was filled with 1 kg normal phase silica gel (200-300 mesh), added with 1 wt % triethylamine for neutralizing the acidity of the silica gel, equilibrated with dichloromethane and eluted with a gradient elution of 1 wt % triethylamine- L-7 (40 g, 21.4247 mmol) obtained in step (1-1-3b), succinic anhydride (4.288 g, 42.8494 mmol) and 4-dimethylaminopyridine (DMAP, 5.235 g, 42.8494 mmol) were mixed and dissolved in 215 ml of dichloromethane, further containing dichloromethane:methanol=100:18 to 100:20. The eluate was collected, and the solvent was evaporated under reduced pressure to give 31.0 g of pure product of L-9 conjugating molecule. $^1$H NMR (400 MHz, DMSO) δ 8.58

(d, J=4.2 Hz, 1H), 7.94-7.82 (m, 3H), 7.41-7.29 (m, 5H), 7.22 (d, J=8.1 Hz, 5H), 6.89 (d, J=8.3 Hz, 4H), 5.49-5.37 (m, 1H), 5.21 (d, J=3.0 Hz, 3H), 4.97 (d, J=11.1 Hz, 3H), 4.49 (d, J=8.2 Hz, 3H), 4.02 (s, 9H), 3.88 (dd, J=19.4, 9.4 Hz, 3H), 3.77-3.65 (m, 9H), 3.50-3.39 (m, 6H), 3.11-2.90 (m, 5H), 2.61-2.54 (m, 4H), 2.47-2.41 (m, 2H), 2.26-2.17 (m, 2H), 2.15-1.95 (m, 22H), 1.92-1.84 (m, 9H), 1.80-1.70 (m, 10H), 1.65-1.35 (m, 17H), 1.31-1.19 (m, 4H), 0.96 (t, J=7.1 Hz, 9H). MS m/z: $C_{94}H_{132}N_7O_{38}$, [M-DMTr]$^+$, called: 1664.72, measured: 1665.03.

(1-1-5) Synthesis of Compound L-10 and diisopropylethylamine (DIEA, 2.843 g, 22 mmol) were mixed and dissolved in 900 ml of acetonitrile, and stirred at room temperature for 5 minutes. Aminomethyl resin (88 g, 100-200 mesh, amino loading: 400 μmol/g, purchased from Tianjin Nankai HECHENG S&T Co., Ltd.) was added into the reaction liquid. A reaction was performed on a shaker at 25° C. and 150 rpm/min for 18 hours, followed by filtration. The residue was rinsed twice, each with 300 ml of DCM, and rinsed three times, each with 300 ml of acetonitrile, and dried for 18 hours with a vacuum oil pump. Then a capping reaction was performed by adding starting materials (CapA,

L-9

L-10

In this step, the compound L-10 was prepared by linking the L-9 conjugating molecule to a solid phase support.

The L-9 conjugating molecule (22.751 g, 0.1126 mmol) obtained in step (1-1-4), O-benzotriazol-1-yl-tetramethyl-uronium hexafluorophosphate (HBTU, 6.257 g, 16.5 mmol)

CapB, 4-dimethylaminopyridine (DMAP) and acetonitrile) according to the charge ratio shown in Table 2. A reaction was performed on a shaker at 25° C. and 150 rpm/min for 5 hours. The reaction liquid was filtrated. The residue was rinsed three times, each with 300 ml of acetonitrile, the solvent was evaporated to dryness, and the mixture was dried overnight under a reduced pressure with a vacuum oil pump to give 102 g of compound L-10 (i.e., the L-9 conjugating molecule linked to the solid phase support), with a loading of 90.8 μmol/g.

linked to the solid phase support in the coupling step was 30:1. The reaction was carried out in a mixed solvent in which the ratio of tetrahydrofuran:water:pyridine was 3:1:1.

The condition for sulfurization reaction in each step was identical, comprising a temperature of 25° C., a reaction

TABLE 2

| The charge ratio of capping reaction | | | | |
| --- | --- | --- | --- | --- |
| Starting materials | Amount | Grade | Lot No. | Manufacturer |
| CapA | 1980 ml | — | — | — |
| CapB | 220 ml | — | — | — |
| DMAP | 1.100 g | Analytical pure | I1422139 | Aladdin |
| Acetonitrile | 220 ml | Spectroscopic pure | O15161001 | CINC (Shanghai) Co., Ltd |

In the above table, CapA and CapB are solutions of capping agents. CapA is a solution of 20% by volume of N-methylimidazole in a mixture of pyridine/acetonitrile, wherein the volume ratio of the pyridine to the acetonitrile is 3: 5. CapB is a solution of 20% by volume of acetic anhydride in acetonitrile.

(1-2) Synthesis of Sense Strand of siRNA Conjugate L10-siXOi1M1S

Nucleoside monomers were linked one by one in the direction from 3' to 5' according to the arrangement sequence of nucleotides in the sense strand by the solid phase phosphoramidite method, starting the cycles from the Compound L-10 prepared in the above step. The linking of each nucleoside monomer comprised a four-step reaction of deprotection, coupling, capping, and oxidation or sulfuriza-tion. When two nucleotides are linked via a phosphoester, a four-step reaction of deprotection, coupling, capping, and oxidation was comprised during linking of the later nucleo-side monomer. When two nucleotides are linked via a phosphorothioate, a four-step reaction of deprotection, cou-pling, capping, and sulfurization was comprised during linking of the later nucleoside monomer. The synthesis condition was given as follows.

The nucleoside monomers were provided in a 0.1 M acetonitrile solution. The condition for deprotection reaction in each step was identical, i.e., a temperature of 25° C., a reaction time of 70 seconds, a solution of dichloroacetic acid in dichloromethane (3% v/v) as a deprotection agent, and a molar ratio of the dichloroacetic acid to the protecting group 4,4'-dimethoxytrityl on the solid phase support of 5:1.

The condition for coupling reaction in each step was identical, comprising a temperature of 25° C., a molar ratio of the nucleic acid sequence linked to the solid phase support to the nucleoside monomers of 1:10, a molar ratio of the nucleic acid sequence linked to the solid phase support to a coupling agent of 1:65, a reaction time of 600 seconds, and 0.5 M acetonitrile solution of 5-ethylthio-1H-tetrazole (ETT) as a coupling agent.

The condition for capping reaction in each step was identical, comprising a temperature of 25° C. and a reaction time of 15 seconds. A capping agent was a mixed solution of Cap A and Cap B in a molar ratio of 1:1, and a molar ratio of the capping agent to the nucleic acid sequence linked to the solid phase support was 1:1:1 (anhydride:N-methylimi-dazole:the nucleic acid sequence linked to the solid phase support).

The condition for oxidation reaction in each step was identical, comprising a temperature of 25° C., a reaction time of 15 seconds, and 0.05 M iodine water as an oxidation agent. A molar ratio of iodine to the nucleic acid sequence time of 300 seconds, and xanthane hydride as a sulfurization agent. A molar ratio of the sulfurization agent to the nucleic acid sequence linked to the solid phase support in the coupling step was 120:1. The reaction was carried out in a mixed solvent in which the ratio of acetonitrile:pyridine was 1:1.

After the last nucleoside monomer was linked, the nucleic acid sequence linked to the solid phase support was cleaved, deprotected, purified and desalted in turn, and then freeze-dried to obtain the sense strand, wherein, The conditions for cleavage and deprotection were as follows: adding the synthesized nucleotide sequence linked to the support into 25 wt % aqueous ammonia to react for 16 hours at 55° C., wherein the aqueous ammonia was in an amount of 0.5 ml/μmol; filtering to remove the support, and concentrating the supernatant in vacuum to dryness.

The conditions for purification and desalination were as follows: purifying the nucleic acid by using a preparative ion chromatography column (Source 15Q) with a gradient elu-tion of NaCl. Specifically, eluent A: 20 mM sodium phos-phate (pH 8.1), solvent: water/acetonitrile=9:1 (v/v); eluent B: 1.5 M sodium chloride, 20 mM sodium phosphate (pH 8.1), solvent: water/acetonitrile=9:1 (v/v); elution gradient: eluent A:eluent B=100:0 to 50:50. The eluate was collected, combined and desalted by using a reverse phase chroma-tography purification column. The specific conditions com-prised using a Sephadex column (filler: Sephadex-G25) for desalination and deionized water for eluting.

The detection method was as follows: determining the purity of the sense strand above by ion exchange chroma-tography (IEX-HPLC); and analyzing the molecular weight by Liquid Chromatography-Mass Spectrometry (LC-MS). The called value was 7584.5, and the measured value was 7584.0. The measured value was in conformity with the called value, indicating that a sense strand SS conjugated with L-9 conjugating molecule at 3' terminal was synthe-sized.

(1-3) Synthesis of Antisense Strand of siRNA Conjugate L10-siXOi1M1S

The antisense strand of the siRNA conjugate L10-siXOf1M1S was synthesized by starting the cycles using a universal solid phase support (UnyLinker™ loaded NittoPhase®HL Solid Supports, Kinovate Life Sciences Inc.) according to the solid phase phosphoramidite method. The deprotection, coupling, capping, oxidation or sulfuriza-tion reaction conditions, cleavage and deprotection, purifi-cation and desalting conditions in the solid phase synthesis method were conducted under the same conditions as those in the synthesis of the sense strand. The residue was freeze-dried to obtain the antisense strand AS.

The purity of the antisense strand was detected by ion exchange chromatography (IEX-HPLC), and the molecular weight was analyzed by liquid chromatography-mass spectrometry (LC-MS). The measured value was in conformity with the called value, indicating that an antisense strand AS having a target sequence was synthesized.

(1-4) Synthesis of siRNA Conjugate L10-siXOi1M1S

For the siRNA conjugate L10-siXOi1M1S, the sense strand and the antisense strand were respectively dissolved in water for injection to give a solution of 40 mg/mL, mixed at an equimolar ratio, heated at 50° C. for 15 minutes, and then cooled at room temperature, such that an annealed product was obtained and then freeze-dried to obtain lyophilized powder. The siRNA conjugate was diluted to a concentration of 0.2 mg/mL with ultra-pure water (prepared by Milli-Q ultra-pure water instrument, with resistivity of 18.2 MΩ*cm (25° C.)). The molecular weight was measured by Liquid Chromatography-Mass Spectrometry (LC-MS, purchased from Waters Corp., model: LCT Premier). Since the measured value was in conformity with the called value, it was confirmed that the synthesized siRNA conjugate was the designed double stranded nucleic acid sequence of interest with the L-9 conjugating molecule. The structure thereof was as shown by Formula (403). The siRNA was the sequence shown in Table 3 corresponding to the siRNA conjugate L10-siXOi1M1S.

siRNA conjugate NC were further synthesized. The siRNAs contained in these siRNA conjugates had the sense strands and antisense strands corresponding to L10-siXOk1M1S and NC in Table 3. The only difference between the preparation methods was that the sequences of the sense strands and the antisense strands of the siRNA conjugate L10-siXOi1M1S were replaced by the sense strands and the antisense strands corresponding to L10-siXOk1M1S and NC in Table 3.

After preparation, the molecular weights of the prepared siRNA conjugate L10-siXOk1M1S and NC were detected according to the method of the Preparation Example 1, and the measured values were consistent with the called values, indicating that the synthesized siRNA conjugate was a target designed double-stranded nucleic acid sequence with the L-9 conjugating molecule. The structure thereof was as shown by Formula (403). The siRNAs contained in these siRNA conjugates were respectively the sequences corresponding to the siRNA conjugate L10-siXOk1M1S and NC in Table 3.

Preparation Examples 4-18 and Comparison Preparation Example 19

Synthesis of the siRNA Provided by the Present Disclosure

The sense strands or the antisense strands of the siRNA sequences listed in Table 4 were respectively synthesized by

TABLE 3 siRNA conjugates

| Preparation Example No. | siRNA conjugate | | Sequence direction 5'-3' | SEQ ID NO |
|---|---|---|---|---|
| Preparation Example 1 | L10-siXOi1 M1S | Sense strand | GmsAmsUmGmCmUmAfUfAfAmAmGmA mAmCmAmAmCmUm | 505 |
| | | Antisense strand | AmsGfsUmUmGmUfUmCmUmUmUmAm UmAfGmCfAmUmCmsCmsUm | 506 |
| Preparation Example 2 | L10-siXOk 1M1S | Sense strand | CmsUmsUmGmCmUmCfUfGfAmAmGmU mAmGmAmAmAmUm | 625 |
| | | Antisense strand | AmsUfsUmUmCmUfAmCmUmUmCmAm GmAfGmCfAmAmGmsCmsCm | 626 |
| Comparison Preparation Example 3 | NC | Sense strand | UmsUmsCmUmCmCmGfAfAfCmGmUmGm UmCmAmCmGmUm | 721 |
| | | Antisense strand | AmsCfsGmUmGmAfCmAmCmGmUmUmC mGfGmAfGmAmAmsCmsUm | 722 | wherein, capital letters C, U, and A indicated the base composition of the nucleotides; the lowercase m indicated that the nucleotide adjacent to the left side of the letter m was a methoxy modified nucleotide; the lowercase f indicated that the nucleotide adjacent to the left side of the letter f was a fluoro modified nucleotide; and the lowercase letter s indicated that the two nucleotides adjacent to the left and right of the letter s were linked by phosphorothioate.

Preparation Example 2 and Comparison Preparation Example 3

According to the method of Preparation Example 1, the siRNA conjugate L10-siXOk1M1S and the comparison a solid phase synthesis method, and DEPC water was used to dissolve the mutually complementary sense strands and antisense strands in equimolar in Table 4, and then followed by annealing to obtain the following siRNAs provided by the present disclosure comprising siXOa1M1S, siXOb1M1S, siXOc1M1S, siXOd1M1S, siXOe1M1S, siXOf1M1S, siXOg1M1S, siXOh1M1S, siXOi1M1S, siXOj1M1S, siXOk1M1S, siXOl1M1S, siXOa0, siXOe0 and siXOf0, as well as the comparison siRNA CON-siXOf. The sequences of the above siRNAs were shown in Table 4.

TABLE 4

| | | | | SEQ |
|---|---|---|---|---|
| Preparation Example No. | No. | | Sequence direction 5'-3' | SEQ ID NO |
| Preparation Example 4 | siXOa1 M1S | Sense strand | GmsAmsGmAmUmGmAfAfGfUmUmCmA mAmGmAmAmUmAm | 25 |
| | | Antisense strand | UmsAfsUmUmCmUfUmGmAmAmCmUmU mCfAmUfCmUmCmsAmsAm | 26 |
| Preparation Example 5 | siXOb1 M1S | Sense strand | CmsAmsUmAmAmCmUfGfGfAmAmUmU mUmGmUmAmAmUm | 85 |
| | | Anti sense strand | AmsUfsUmAmCmAfAmAmUmUmCmCmA mGfUmUfAmUmGmsUmsUm | 86 |
| Preparation Example 6 | siXOc1 M1S | Sense strand | CmsAmsUmUmAmUmCfAfCfAmAmUmU mGmAmGmGmAmUm | 145 |
| | | Antisense strand | AmsUfsCmCmUmCfAmAmUmUmGmUmG mAfUmAfAmUmGmsGmsCm | 146 |
| Preparation Example 7 | siXOd1 M1S | Sense strand | GmsGmsAmUmCmUmCfUfCfUmCmAmG mAmGmUmAmUmUm | 205 |
| | | Antisense strand | AmsAfsUmAmCmUfCmUmGmAmGmAmG mAfGmAfUmCmCmsUmsGm | 206 |
| Preparation Example 8 | siXOe1 M1S | Sense strand | AmsCmsAmUmGmGmAfCfAfAmCmUmG mCmUmAmUmAmAm | 265 |
| | | Antisense strand | UmsUfsAmUmAmGfCmAmGmUmUmGmU mCfCmAfUmGmUmsGmsGm | 266 |
| Preparation Example 9 | siXOf1 M1S | Sense strand | UmsAmsGmCmAmAmGfCfUfCmUmCmA mGmUmAmUmCmAm | 325 |
| | | Antisense strand | UmsGfsAmUmAmCfUmGmAmGmAmGmC mUfUmGfCmUmAmsGmsGm | 326 |
| Preparation Example 10 | siXOg1 M1S | Sense strand | AmsUmsAmAmGmGmUfUfAfCmUmUmG mUmGmUmUmGmGm | 385 |
| | | Antisense strand | CmsCfsAmAmCmAfCmAmAmGmUmAmA mCfCmUfUmAmUmsCmsCm | 386 |
| Preparation Example 11 | siXOh1 M1S | Sense strand | GmsAmsAmAmUmCfAfCfCmUmAmU mGmAmAmGmAmAm | 445 |
| | | Antisense strand | UmsUfsCmUmUmCfAmUmAmGmGmUmG mAfUmUfUmUmCmsAmsCm | 446 |
| Preparation Example 12 | siXOi1 M1S | Sense strand | GmsAmsUmGmCmUmAfUfAfAmAmGmA mAmCmAmAmCmUm | 505 |
| | | Antisense strand | AmsGfsUmUmGmUfUmCmUmUmUmAmU mAfGmCfAmUmCmsCmsUm | 506 |
| Preparation Example 13 | siXOj1 M1S | Sense strand | GmsAmsAmCmAmAmCfUfCfCmUmUmU mUmAmUmUmGmGmAm | 565 |
| | | Antisense strand | UmsCfsCmAmUmAfAmAmAmGmGmAmG mUfUmGfUmUmCmsUmsUm | 566 |
| Preparation Example 14 | siXOk1 M1S | Sense strand | CmsUmsUmGmCmUmCfUfGfAmAmGmU mAmGmAmAmAmUm | 625 |
| | | Antisense strand | AmsUfsUmUmCmUfAmCmUmUmCmAmG mAfGmCfAmAmGmsCmsCm | 626 |
| Preparation Example 15 | siXOl1 M1S | Sense strand | CmsUmsUmCmUmUmUfGfCfCmAmUmC mAmAmAmGmAmUm | 685 |
| | | Antisense strand | AmsUfsCmUmUmUfGmAmUmGmGmCmA mAfAmGfAmAmGmsAmsUm | 686 |
| Preparation Example 16 | siXOa0 | Sense strand | GAGAUGAAGUUCAAGAAUA | 723 |
| | | Antisense strand | UAUUCUUGAACUUCAUCUC | 724 |
| Preparation Example 17 | siXOe0 | Sense strand | ACAUGGACAACUGCUAUAA | 725 |
| | | Antisense strand | UUAUAGCAGUUGUCCAUGU | 726 |
| Preparation Example 18 | siXOf0 | Sense strand | UAGCAAGCUCUCAGUAUCA | 727 |
| | | Antisense strand | UGAUACUGAGAGCUUGCUA | 728 |

TABLE 4-continued

| siRNA sequences | | | | |
| --- | --- | --- | --- | --- |
| Preparation Example No. | No. | | Sequence direction 5'-3' | SEQ ID NO |
| Comparison Preparation Example 19 | CON-siXOf | Sense strand | CUAGCAAGCUCUCAGUAUC | 729 |
| | | Antisense strand | GATACTGAGAGCTTGCTAG | 730 | wherein, capital letters C, U, and A indicated the base composition of the nucleotides; the lowercase m indicated that the nucleotide adjacent to the left side of the letter m was a methoxy modified nucleotide; the lowercase f indicated that the nucleotide adjacent to the left side of the letter f was a fluoro modified nucleotide; and the lowercase letter s indicated that the two nucleotides adjacent to the left and right of the letter s were linked by phosphorothioate.

In the preparation process of the sequences above, when the target sequence contained an unmodified nucleotide, under the conditions of cleavage and deprotection, after aqueous ammonia treatment, 0.4 ml/μmol N-methyl pyrrolidone was used to dissolve the product, and then 0.3 ml/μmol triethylamine and 0.6 ml/μmol triethylamine trihydrofluoride were added to remove 2'-TBDMS protection on ribose, with respect to the amount of the single-stranded nucleic acid.

After the siRNA or siRNA conjugate above was prepared, the siRNA or siRNA conjugate was freeze-dried into solid powder for later use. When in use, for example, water for injection, normal saline (NS), phosphate buffer (PB) or phosphate buffer solution (PBS) could be used to redissolve the siRNA or siRNA conjugate into a solution with the required concentration for use.

Experimental Example 1

In Vitro Inhibitory Activity of the siRNA of the Present Disclosure

HEK293A cells (purchased from Nanjing COBIOER Biotechnology Co., Ltd.) were cultured in H-DMEM complete media (HyClone company) containing 10% fetal bovine serum (FBS, Hyclone company) and 0.2 v % Penicillin-Streptomycin (Gibco, Invitrogen company) at 37° C. in an incubator containing 5% $CO_2$/95% air.

According to the methods disclosed in Functional dissection of siRNA sequence by systematic DNA substitution: modified siRNA with a DNA seed arm is a powerful tool for mammalian gene silencing with significantly reduced off-target effect. Nucleic Acids Research, 2008.36(7), 2136-2151 written by Kumico Ui-Tei et. al., detection plasmids were constructed, and the to-be-evaluated siRNAs (siXOa0, siXOe0, siXOf0 and CON-siXOf) were transfected into HEK293A cells, and the inhibitory activity of siRNA was reflected by the expression level of double luciferase reporter gene. The specific steps were as follows:
[1] Construction of Detection Plasmids Detection plasmids were constructed using psi-CHECK™-2(Promega™) plasmid. The plasmid comprised one target sequence, i.e., the target sequence of the siRNA. For the to-be-evaluated siRNAs, the target sequences were respectively as shown below:

The target sequence of the siXOa0 was:

(SEQ ID NO: 731)
GAGATGAAGTTCAAGAATA

The target sequence of the siXOe0 was:

(SEQ ID NO: 732)
ACATGGACAACTGCTATAA

The target sequence of the siXOf0 was:

(SEQ ID NO: 733)
TAGCAAGCTCTCAGTATCA

The target sequence of the CON-siXOf was:

(SEQ ID NO: 734)
CTAGCAAGCTCTCAGTATC

The target sequence was cloned into the Xho I/Not I site of the psiCHECK™-2 plasmid.
[2] Transfection HEK293A cells were seeded in a 96-well plate with $8\times10^3$ cells/well. After 16 hours, when the growth density of the cells reached 70-80%, the H-DMEM complete media in the culture wells were sucked up, and 80 μl of Opti-MEM media (GIBCO company) was added to each well to continue the culture for 1.5 hours.

For each siRNA, the corresponding detection plasmid was diluted into 200 ng/μl detection plasmid working solution with DEPC water. For each siRNA, siRNA and DEPC water were used to prepare siRNA working solutions with concentrations (calculated by siRNA) of 10 nM, 3 nM and 1 nM respectively.

For each siRNA, a 1A1 solution was prepared, and each part of the 1A1 solution contained 1 μl of siRNA working solution with a concentration of 10 nM, 0.05 μl of detection plasmid working solution (containing 10 ng of detection plasmids) and 10 μl of Opti-MEM media.

For each siRNA, a 1A2 solution was prepared, and each part of the 1A2 solution contained 1 μl of siRNA working solution with a concentration of 3 nM, 0.05 μl of detection plasmid working solution (containing 10 ng of detection plasmids) and 10 μl of Opti-MEM media.

For each siRNA, a 1A3 solution was prepared, and each part of the 1A3 solution contained 1 μl of siRNA working solution with a concentration of 1 nM, 0.05 μl of detection plasmid working solution (containing 10 ng of detection plasmids) and 10 μl of Opti-MEM media.

A 1B solution was prepared, and each part of the 1B solution contained 0.2 μl of Lipofectamine™ 2000 and 10 μl of Opti-MEM media.

A 1C solution was prepared, and each part of the 1C solution contained 0.05 μl of detection plasmid working solution (containing 10 ng of detection plasmids) and 10 μl of Opti-MEM media.

For each siRNA, one part of the 1B solution was mixed with one part of the 1A1 solution, one part of the 1A2 solution and one part of the 1A3 solution, and incubated for 20 minutes at room temperature to obtain transfection complexes 1X1, 1X2 and 1X3 respectively. One part of the 1B solution was mixed with one part of the 1C solution and incubated for 20 minutes at room temperature to obtain a transfection complex 1X4.

For each siRNA, the transfection complex 1X1 was respectively added into three culture wells, and evenly (Ren) was read with a microplate reader according to the arrangement of reading the Fir.

The luminous ratio (Ratio=Ren/Fir) of each well was calculated, and the luminous Ratio (test) or Ratio (control) of each test group or control group was the average value of the Ratio of three culture wells; on the basis of the luminous ratio of the control group, the luminous ratio of each test group was normalized to obtain the ratio R of the Ratio (test)/Ratio (control), which was used to express the expression level of *Renilla* reporter gene, i.e., the residual activity. Inhibition percentage to the target sequence=(1−R)×100%.

The inhibitory activities of to-be-evaluated siRNA with different concentrations on the target sequence were shown in Table 5.

TABLE 5

| Inhibition percentage on target sequence | | | | |
| --- | --- | --- | --- | --- |
| | | Inhibition percentage to target sequence (%) | | |
| Preparation Example No. | No. | 0.1 nM | 0.03 nM | 0.01 nM |
| Preparation Example 16 | siXOa0 | 61.39 | 43.69 | 22.74 |
| Preparation Example 17 | siXOe0 | 68.41 | 46.94 | 17.04 |
| Preparation Example 18 | siXOf0 | 85.43 | 68.79 | 38.69 |
| Comparison Preparation Example 19 | CON-siXOf | 48.24 | 24.86 | 13.61 | mixed, with an addition amount of 20 μl/well, to obtain a co-transfection mixture containing the siRNA with the final concentration of the siRNA about 0.1 nM, which was designated as test group 1.

For each siRNA, the transfection complex 1X2 was respectively added into another three culture wells, and evenly mixed, with an addition amount of 20 μl/well, to obtain a co-transfection mixture containing the siRNA with the final concentration of the siRNA about 0.03 nM, which was designated as test group 2.

For each siRNA, the transfection complex 1X3 was respectively added into another three culture wells, and evenly mixed, with an addition amount of 20 μl/well, to obtain a co-transfection mixture containing the siRNA with the final concentration of the siRNA about 0.01 nM, which was designated as test group 3.

The transfection complex 1X4 was respectively added into another three culture wells, and evenly mixed, with an addition amount of 20 μl/well, to obtain a co-transfection mixture not containing the siRNA, which was designated as a control group.

The co-transfection mixture containing the siRNA and the transfection mixture not containing the siRNA were co-transfected in culture wells for 4 hours, and then 100 μl of H-DMEM complete media containing 20% FBS was added to each well. The 96-well plate was placed in a $CO_2$ incubator to continuously culture for 24 hours.

[3] Detection

The media in the culture wells were sucked off, and 150 μl of a mixed solution of Dual-Gb® Luciferase and H-DMEM complete media (volume ratio 1:1) was added to each well, thoroughly mixed, and incubated at room temperature for 10 minutes, then 120 μl of the mixed solution was transferred to a 96-well enzyme-labeled plate, and a Firefly chemiluminescence value (Fir) was read by using Synergy II multifunctional microplate reader (BioTek company); then, 60 μl of Dual-Glo® Stop & Gb® was added to each well, thoroughly mixed, incubated at room temperature for 10 minutes, then a *Renilla* chemiluminescence value The results show that the siRNA disclosed in the present disclosure has good inhibitory activity on the target sequences in vitro at all concentrations, and show a concentration dependence. Especially, the inhibition percentage to the target sequence is at least 61.39% when the concentration of the siRNA is 0.1 nM. Particularly, the siXOf shows 68.79% inhibition percentage to the target sequence at the concentration of 0.03 nM, and the inhibition percentage to the target sequence at the concentration of 0.1 nM is as high as 85.43%. In sharp contrast, although the sequence is very similar to the siXOf, in comparison to that the siRNA CON-siXOf only shows a inhibition percentage to the target sequence of 48.24% at the concentration of 0.1 nM, it is indicated that the siRNA of the present disclosure unexpectedly shows a good effect of inhibiting the expression of XO genes.

Experimental Example 2

$IC_{50}$ Detection of XO mRNA by siRNA in CAL-27 Cells

CAL-27 cells (purchased from Nanjing COBIOER Biotechnology Co., Ltd.) were cultured in H-DMEM complete media (HyClone company) containing 10% fetal bovine serum (FBS, Hyclone company) and 0.2 v % Penicillin-Streptomycin (Gibco, Invitrogen company) at 37° C. in an incubator containing 5% $CO_2$/95% air.

CAL-27 cells were seeded in a 24-well plate with $7.5×10^4$ cells/well. After 16 hours, when the growth density of the cells reached 70-80%, the H-DMEM complete media in the culture wells were sucked up, and 500 μl of Opti-MEM medium (GIBCO company) was added to each well to continue the culture for 1.5 hours. After washing with an HBSS solution, the cells were mixed evenly, and then seeded in a 96-well plate with $6×10^5$ cells/well and an inoculation solution volume of 45 μl/well.

DEPC water was used to prepare each of the following siRNAs into eight siRNA working solutions with different concentrations comprising 20 μM, 4 μM, 0.8 μM, 0.16 μM, 0.032 μM, 0.0064 μM, 1.44 nM and 0.72 nM (calculated by siRNA). The used siRNAS were siXOa1M1S, siXOb1M1S, siXOc1M1S, siXOd1M1S, siXOe1M1S, and siXOf1M1S respectively.

The eight siRNA working solutions with different concentrations above were added into the above different culture wells seeded with CAL-27 cells at a volume of 15 µL/well. In this way, for each siRNA mentioned above, the final concentration of the siRNA in each culture well was 5 µM, 1 µM, 0.2 µM, 0.04 µM, 0.008 µM, 0.0016 µM, 0.32 nM, and 0.064 nM in turn, which were uniformly mixed and recorded as test groups. The culture wells seeded only with CAL-27 cells and not added with the siRNA working solution were taken as the control group.

An electrotransfer instrument (produced by EBXP-H1, Etta Cell Electrotransfer Instrument) was used for performing electrotransfection on the test groups and the control group. The transfection parameters were as follows: Voltage of 210 V; Pulse Duration of 100 µs; Pulse Number of 6 times; and Pulse Interval of 1000 ms.

Co., Ltd., article No. E096-01B), wherein the PCR primer sequences for amplifying the target gene XO and internal reference gene GAPDH were shown in Table 7, and the final concentration of each primer was 0.25 µM. Each qPCR reaction system was placed on ABI StepOnePlus Real-Time PCR instrument, and amplified by three-step method. The amplification procedure was pre-denatured at 95° C. for 10 minutes, then denatured at 95° C. for 30 seconds, annealed at 60° C. for 30 seconds, and extended at 72° C. for 30 seconds. After repeating the above denaturation, annealing and extension processes for 40 times, the product W containing amplified target gene XO and internal reference gene GAPDH was obtained. The product W was incubated at 95° C. for 1 minute, 55° C. for 30 seconds and 95° C. for 30 seconds in turn. The dissolution curves of the target gene XO and the internal reference gene GAPDH in the product W were collected by real-time fluorescence quantitative PCR, and the Ct values of the target gene XO and the internal reference gene GAPDH were obtained.

TABLE 6

Sequences of Detection Primers

| Gene | Upstream primer (5'-3' direction) | Downstream primer (5'-3' direction) |
|---|---|---|
| Human XO | GACCCGACGGTATCTCCTTT (SEQ ID NO: 735) | ACGCCACAGACTTGACTTGC (SEQ ID NO: 736) |
| Human GAPDH | GGTCGGAGTCAACGGATTT (SEQ ID NO: 737) | CCAGCATCGCCCCACTTGA (SEQ ID NO: 738) |

240 µl of H-DMEM complete media containing 20% FBS was added to each culture well of the transfected test group and control group samples to obtain transfected cell culture solution. For each culture well, the transfected cell culture solution was transferred to two culture wells of a 24-well plate with 140 µl of cell culture solution per well, and then 855 µl of H-DMEM complete media containing 20% FBS was added to each culture well of the 24-well plate, and the culture was continued for 24 hours to obtain a to-be-tested cell culture solution. Then, RNAVzol (purchased from Vigorous Biotechnology Beijing Co., Ltd., article number N002) was used to respectively extract the total RNA from each well of the to-be-tested cell culture solution according to the steps described in the instructions.

For the cells in each well of the 24-well plate, 1 µg of the total RNA was taken, and the reagent provided by the reverse transcription kit Goldenstar™ RT6 cDNA Synthesis Kit (purchased from Beijing Tsingke Biotechnology Co., Ltd., article number TSK301M) was used, wherein Goldenstar™ Oligo (dT)$_{17}$ was selected as the primer, and 20 µl of reverse transcription reaction system was configured according to the reverse transcription operation steps in the kit manual to reverse the total RNA of the cells. The conditions for reverse transcription were as follows: the reverse transcription reaction system was incubated at 50° C. for 50 minutes, then incubated at 85° C. for 5 minutes, and finally incubated at 4° C. for 30 seconds. After the reaction, 80 µl of DEPC water was added to the reverse transcription reaction system to obtain a solution containing cDNA.

For each reverse transcription reaction system, 5 µl of the solution containing cDNA was taken as the template, and 20 µl of qPCR reaction system was prepared by using the reagent provided by NovoStart® SYBR qPCR SuperMix Plus (purchased from Novoprotein Science and Technology Comparative Ct(ΔΔCt) method was used to calculate relative quantitative expression of the target gene XO in each test group and the control group. The calculation method was as follows:

ΔCt(test group)=Ct(target gene of test group)−Ct (internal reference gene of test group)

ΔCt(control group)=Ct(target gene of control group)−Ct(internal reference gene of control group)

ΔΔCt(test group)=ΔCt(test group)−ΔCt(mean value of control group)

ΔΔCt(control group)=ΔCt(control group)−ΔCt(mean value of control group)

wherein, ΔCt(mean value of control group) was the arithmetic mean value of ΔCt(control group) of each of the two ulture wells of the control group. Therefore, each culture well of the test group and the control group corresponded to one ΔΔCt value.

On the basis of the control group, the expression level of XO mRNA in the test group was normalized, and the expression level of XO mRNA in the control group was defined as 100%.

The relative expression level of XO mRNA in the test group=$2^{-\Delta\Delta Ct(test\ group)}$×100%.

For the siRNAs of the same test group, the mean value of the relative expression level of the XO mRNA of the test group at each concentration was the arithmetic mean value of the relative expression level of two culture wells at the concentration.

The log(inhibitor) vs. response—Variable slope of Graphpad 6.0 software was used to fit the dose-effect curve, and the IC50 value of each siRNA to XO mRNA was calculated according to the dose-effect curve. Specifically, the dose-response curve obtained by fitting conformed to the following calculation formula:

$$Y = Bot + \frac{Top - Bot}{1 + 10^{(X' - X) \times HillSlope}}$$

wherein:

Y is the relative expression level of mRNA of each test group,

X is the logarithmic value of the concentration of the siRNA used corresponding to the test group, Bot is the Y value at the bottom of the steady stage, Top is the Y value at the top of the steady stage, and X' is the X value at which Y is median value between the bottom and the top of the asymptote, and HillSlope is the slope of the curve obtained by fitting at X'.

FIGS. 1A-1F are fitted dose-effect curve of the relative expression levels of XO mRNA in CAL-27 cells in vitro after transfection of siXOa1M1S, siXOb1M1S, siXOc1M1S, siXOd1M1S, siXOe1M1S and siXOf1M1S. According to the dose-effect curve and the corresponding calculation formula, the corresponding $X_{50}$ value when Y=50% was determined, and the $IC_{50}$ value of each siRNA was calculated to be $10^{\wedge}X50$ (nM).

The $IC_{50}$ value to XO mRNA of each siRNA is summarized in Table 7.

TABLE 7

| $IC_{50}$ of siRNA against XO mRNA | | |
| --- | --- | --- |
| Preparation Example No. | siRNA | $IC_{50}$ |
| Preparation Example 4 | siXOa1M1S | 0.1115 μM |
| Preparation Example 5 | siXOb1M1S | 0.8012 μM |
| Preparation Example 6 | siXOc1M1S | 0.3277 μM |
| Preparation Example 7 | siXOd1M1S | 0.0805 μM |
| Preparation Example 8 | siXOe1M1S | 0.0370 μM |
| Preparation Example 9 | siXOf1M1S | 0.0375 μM |

It can be seen from Table 7 that the siRNA provided by the present disclosure exhibits higher inhibitory activity against XO mRNA in CAL-27 cells in vitro, and the $IC_{50}$ is between 0.037 μM and 0.3277 μM.

Experimental Example 3

Determination of Inhibition Percentage of siRNA to XO mRNA in Primary Hepatocytes of Mice Primary hepatocytes of mice were extracted from fresh liver tissues of normal C57BL/6N mice, seeded into tissue culture dishes coated with type I collagen, and cultured in RPMI 1460 media containing 1×double-antibody and 10% FBS at 37° C., and cultured in an incubator containing 5% $CO_2$/95% air for 30 minutes.

The culture media were discarded, and the density of the primary hepatocytes of mice was adjusted to $1 \times 10^6$ cells/mL by opti-MEM, to obtain the suspension of the primary hepatocytes of mice. Then, the suspension of the primary hepatocytes of mice obtained was added into different culture wells of a 24-well plate, and the primary hepatocytes of mice were seeded into the culture wells. The volume of the added suspension of the primary hepatocytes of mice was 0.5 mL/well, and the number of the primary hepatocytes of mice was $5 \times 10^4$ cells/well.

DEPC water was used to prepare each siRNA in the following siRNAs into 20 μM siRNA working solution, and the siRNA used was respectively siXOg1M1S, siXOh1M1S, siXOi1M1S, siXOj1M1S, siXOk1M1S or siXOl1M1S.

A 1A solution was prepared. For each siRNA, the 1A solution was prepared respectively, and each part of the 1A solution contained 0.6 μl of the siRNA working solution above and 50 μl of Opti-MEM media in turn.

A 1B solution was prepared, and each part of the 1B solution contained 1 μl of Lipofectamine™ 2000 and 50 μl of Opti-MEM media.

One part of the 1B solution was respectively mixed with one part of the 1A solution of each siRNA obtained, and incubated at room temperature for 20 minutes to obtain a transfection complex 1X of each siRNA.

One part of the 1B solution was mixed with 50 μl of Opti-MEM media and incubated at room temperature for 20 minutes to obtain a transfection complex 1X'.

The transfection complex 1X of each siRNA was respectively added in the culture well, and evenly mixed, with an addition amount of 100 μl/well, to obtain a transfection complex containing the siRNA with the final concentration of the siRNA about 20 nM. The transfection complex 1X of each siRNA was respectively transfected with three culture wells to obtain a transfection mixture containing the siRNA, which was designated as the test group.

The transfection complex 1X' was respectively added into another three culture wells with an addition amount of 100 μl/well, to obtain a transfection mixture not containing the siRNA, which was designated as a blank control group.

Each transfection mixture containing the siRNA and the transfection mixture not containing the siRNA were respectively transfected in different culture wells for 4 hours, and then 1 ml of H-DMEM complete media containing 20% FBS was added to each well. The 24-well plate was placed in a $CO_2$ incubator to continuously culture at 37° C. for 24 hours.

Then, RNAVzol (purchased from Vigorous Biotechnology Beijing Co., Ltd., article number N002) was used to respectively extract the total RNA from the cells in each well according to the methods described in the instructions.

For the cells in each well, 1 μg of the total RNA was taken, and a reagent provided by a reverse transcription kit Goldenstar™ RT6 cDNA Synthesis Kit (purchased from Beijing Tsingke Biotechnology Co., Ltd., article number TSK301M) was used, wherein Goldenstar™ Oligo (dT)$_{17}$ was selected as the primer, and 20 μl of reverse transcription reaction system was configured according to the reverse transcription operation steps in the kit manual to reverse the total RNA of the cells in each well. The conditions for reverse transcription were as follows: for each reverse transcription reaction system, the reverse transcription reaction system was incubated at 50° C. for 50 minutes, then incubated at 85° C. for 5 minutes, and finally incubated at 4° C. for 30 seconds. After the reaction, 80 μl of DEPC water was added to the reverse transcription reaction system to obtain a solution containing cDNA.

For each reverse transcription reaction system, 5 μl of the solution containing cDNA was taken as the template, and 20 μl of qPCR reaction system was prepared by using the reagent provided by NovoStart® SYBR qPCR SuperMix Plus (purchased from Novoprotein Science and Technology Co., Ltd., article No. E096-01B), wherein the PCR primer sequences for amplifying the target gene XO and internal reference gene GAPDH were shown in Table 7, and the final concentration of each primer was 0.25 μM. Each qPCR reaction system was placed on ABI StepOnePlus Real-Time PCR instrument, and amplified by three-step method. The amplification procedure was pre-denatured at 95° C. for 10 minutes, then denatured at 95° C. for 30 seconds, annealed at 60° C. for 30 seconds, and extended at 72° C. for 30 seconds. After repeating the above denaturation, annealing and extension processes for 40 times, the product W containing amplified target gene XO and internal reference gene GAPDH was obtained. The product W was incubated at 95° C. for 15 seconds, 60° C. for 1 minute and 95° C. for 15 seconds in turn. The dissolution curves of the target gene XO and the internal reference gene GAPDH in the product W were collected by real-time fluorescence quantitative PCR, and the Ct values of the target gene XO and the internal reference gene GAPDH were obtained.

TABLE 8

| Primer information | | | |
|---|---|---|---|
| Name of gene | Type of primer | Nucleotide sequence (5'-3') | SEQ ID NO |
| Mouse XO | Upstream primer | AACAGAATTGTAGTCCGAGTGAA | 739 |
| | Downstream primer | GTCTGCCACCAGTTATGAGC | 740 |
| Mouse GAPDH | Upstream primer | TGCACCACCAACTGCTTAG | 741 |
| | Downstream primer | GGATGCAGGGATGATGTTC | 742 |

Comparative Ct(ΔΔCt) method was used to calculate relative quantitative expression of the target gene XO in each test group. The calculation method was as follows:

ΔCt(test group)=Ct(target gene of test group)−Ct (internal reference gene of test group)

ΔCt(control group)=Ct(target gene of control group)−Ct(internal reference gene of control group)

ΔΔCt(test group)=ΔCt(test group)−ΔCt(mean value of control group)

ΔΔCt(control group)=ΔCt(control group)−ΔCt(mean value of control group)

wherein, ΔCt(mean value of control group) was the arithmetic mean value of ΔCt(control group) of each of the three ulture wells of the control group. Therefore, each culture well of the test group and the control group corresponded to one ΔΔCt value.

On the basis of the control group, the expression level of XO mRNA in the test group was normalized, and the expression level of XO mRNA in the blank control group was defined as 100%.

The relative expression level of XO mRNA in the test group=$2^{-\Delta\Delta Ct(test\ group)}\times 100\%$ The inhibition percentage to XO mRNA of the test group=(1−the relative expression level of XO mRNA of the test group)×100%

Figure 2:
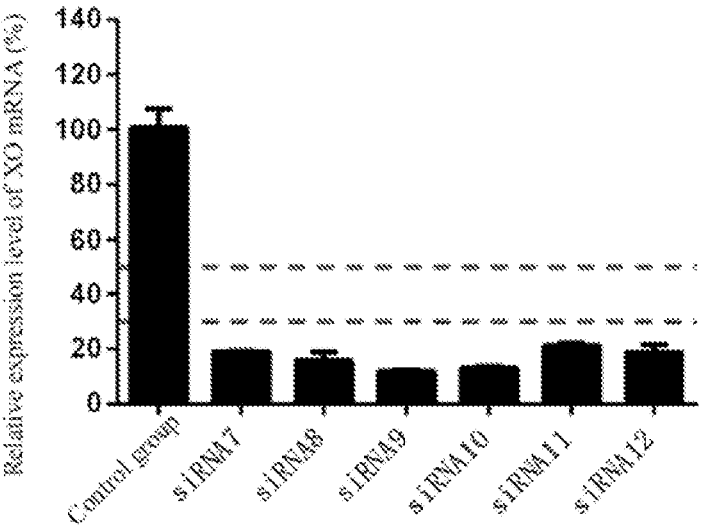
FIG. 2 is a histogram showing the relative expression level of XO mRNA in primary hepatocytes of mice after transfection of different siRNAs.

FIG. 2 is a histogram showing the relative expression level of XO mRNA in primary hepatocytes of mice after transfection of the siXOg1M1S, the siXOh1M1S, the siXOi1M1S, the siXOj1M1S, the siXOk1M1S and the siXOl1M1S of the present disclosure. Further, the inhibition percentage to XO mRNA of each siRNA is summarized in Table 9. For the siRNAs of the same test group, the inhibition percentage to the XO mRNA was the arithmetic mean value of the inhibition percentage of the test group to XO mRNA determined through the three culture wells. In FIG. 2, the siRNA7-12 was corresponding to siXOg1M1S, siXOh1M1S, siXOi1M1S, siXOj1M1S, siXOk1M1S and siXOl1M1S in sequence.

TABLE 9

| Inhibition to XO mRNA in primary hepatocytes of mice | | |
|---|---|---|
| Preparation Example | No. | Inhibition percentage to XO mRNA % |
| Preparation Example 10 | siXOg1M1S | 80.90 |
| Preparation Example 11 | siXOh1M1S | 84.19 |
| Preparation Example 12 | siXOi1M1S | 88.07 |
| Preparation Example 13 | siXOj1M1S | 86.92 |

TABLE 9-continued

| Inhibition to XO mRNA in primary hepatocytes of mice | | |
|---|---|---|
| Preparation Example | No. | Inhibition percentage to XO mRNA % |
| Preparation Example 14 | siXOk1M1S | 78.95 |
| Preparation Example 15 | siXOl1M1S | 81.25 |

It can be seen from the results in Table 9 that the siRNA provided by the present disclosure shows high inhibitory activity to XO mRNA in primary hepatocytes of mice, and the inhibition percentage to XO mRNA is at least 78.95%, even as high as 88.07% under the siRNA concentration of 20 nM.

Experimental Example 4

Expression Inhibition of XO mRNA by siRNA Conjugate in Mice

C57BL/6N mice were randomly divided into groups (all females) with five mice in each group and respectively numbered. In the way of subcutaneous injection, siRNA conjugates L10-siXOi1M1S and L10-siXOk1M1S and comparison siRNA conjugate NC were given to each group of mice at a dose of 3 mg/kg (calculated by siRNA). The siRNA conjugates were provided in the form of 0.9% sodium chloride aqueous solution containing 0.6 mg/ml siRNA conjugate (calculated by siRNA), and the administration volume was 5 ml/kg.

One group of mice was given 1×PBS with an administration volume of 5 ml/kg, and served as the blank control group.

The animals were sacrificed on the 7$^{th}$ day after administration, and liver tissues of each mouse were collected and stored with RNA later (Sigma Aldrich company). The liver tissues were homogenized with a tissue homogenizer, and then extracted with Trizol (Thermo Fisher company) according to the operation steps described in the manual to obtain the total RNA.

Figure 3:
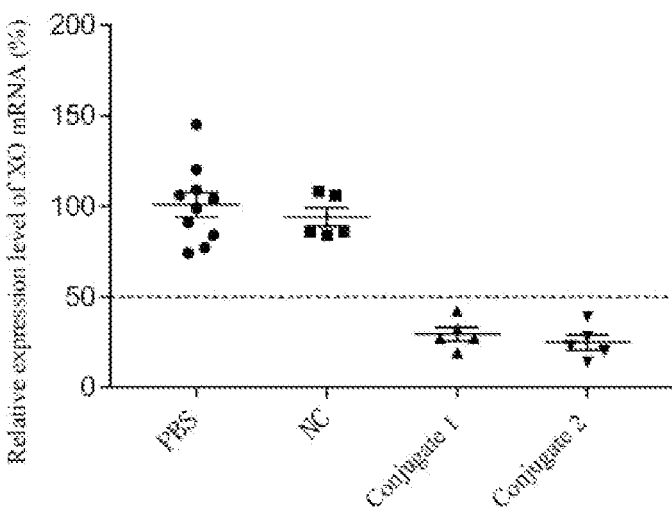
FIG. 3 is a scatter diagram of the relative expression level of XO mRNA in mice after administration of 3 mg/kg of different siRNA conjugates.

According to the method of the Experimental Example 3, the expression level and inhibition percentage to XO mRNA were detected by fluorescence quantitative PCR. The only difference was that the extracted total RNA was reversely transcribed into cDNA by using ImProm-II™ reverse transcription kit (Promega company) according to the instructions thereof to obtain a solution containing cDNA, and then the expression level of XO mRNA in the liver tissues was detected by fluorescence quantitative PCR kit (Beijing CoWin Biosciences). In this fluorescence quantitative PCR method, mouse GAPDH(mGAPDH) genes were used as internal reference genes, and XO and mouse GAPDH were detected by using primers for XO and mouse GAPDH respectively. The sequences of the detection primers were shown in Table 8. The expression level of XO mRNA in the blank control group was recorded as 100%, and accordingly, the inhibition percentage to XO mRNA expression level was recorded as 0%. The test results of the test group of the siRNA conjugate were normalized by the expression level of XO mRNA in the control group, and the results were shown in FIG. 3 and Table 10. In FIG. 3, conjugate 1 refers to L10-siXOi1M1S, and conjugate 2 refers to L10-siXOk1M1S.

TABLE 10

Inhibition percentages to XO mRNA by
siRNA conjugates of different concentrations

| Preparation Example No. | siRNA conjugate | Inhibition percentage to XO mRNA (%) |
|---|---|---|
| Preparation Example 1 | L10-siXOi1M1S | 70.9 |
| Preparation Example 2 | L10-siXOk1M1S | 76.2 |

TABLE 10-continued

Inhibition percentages to XO mRNA by
siRNA conjugates of different concentrations

| Preparation Example No. | siRNA conjugate | Inhibition percentage to XO mRNA (%) |
|---|---|---|
| Comparison Preparation Example 3 | NC | 10.0 |

It can be seen from the results in Table 10 that the siRNA conjugate provided by the present disclosure shows an inhibition rate of at least 70.9% and even as high as 76.2% to XO mRNA under the siRNA concentration of 3 mg/kg, and shows an excellent inhibition effect to XO mRNA.

Some embodiments of the present disclosure are described in detail above, but the present disclosure is not limited to the specific details of the above-described embodiments. Various simple variations of the technical solution of the present disclosure can be made within the scope of the technical concept of the present disclosure, and these simple variations are within the scope of the present disclosure.

In addition, it is to be noted that each of the specific technical features described in the above embodiments can be combined in any suitable manner as long as no contradiction is caused. In order to avoid unnecessary repetition, the various possible combination manners are no longer described in the present disclosure.

In addition, the various different embodiments of the present disclosure may also be carried out in any combination as long as it does not contravene the idea of the present disclosure, which should also be regarded as the disclosure of the present disclosure.

The invention claimed is:

1. An siRNA conjugate, wherein the siRNA conjugate has a structure as shown by Formula (308):

Formula (308)

wherein:

n1 is an integer of 1-3, and n3 is an integer of 0-4;

each of m1, m2, and m3 is independently an integer of 2-10;

each of $R_{10}$, $R_{11}$, $R_{12}$, $R_{13}$, $R_{14}$ or $R_{15}$ is independently H or selected from the group consisting of $C_1$-$C_{10}$ alkyl, $C_1$-$C_{10}$ haloalkyl and $C_1$-$C_{10}$ alkoxy; and $R_3$ is a group having a structure as shown by Formula A59:

(A59)

wherein, $E_1$ is OH, SH or $BH_2$, and Nu is an siRNA, wherein the siRNA comprises a sense strand and an antisense strand, and each nucleotide in the siRNA is independently a modified or unmodified nucleotide, wherein the sense strand ix) the nucleotide sequence I has the same length and no more than three nucleotides differences from the nucleotide sequence shown in SEQ ID NO: 481; and the nucleotide sequence II has the same length and no more than three nucleotides differences from the nucleotide sequence shown in SEQ ID NO: 482:

```
                                      (SEQ ID NO: 481)
5'-GAUGCUAUAAAGAACAACZ33-3';

(SEQ ID NO: 482)
5'-Z34GUUGUUCUUUAUAGCAUC-3',
``` wherein, $Z_{33}$ is U, $Z_{34}$ is A, the nucleotide sequence I comprises a nucleotide $Z_{35}$ at a corresponding site to $Z_{33}$, the nucleotide sequence II comprises a nucleotide $Z_{36}$ at a corresponding site to $Z_{34}$, and $Z_{36}$ is the first nucleotide from the 5' terminal of the antisense strand;

x) the nucleotide sequence I has the same length and no more than three nucleotides differences from the nucleotide sequence shown in SEQ ID NO: 541; and the nucleotide sequence II has the same length and no more than three nucleotides differences from the nucleotide sequence shown in SEQ ID NO: 542:

(SEQ ID NO: 541)
5'-GAACAACUCCUUUUAUGGZ$_{37}$-3';

(SEQ ID NO: 542)
5'-Z$_{38}$CCAUAAAAGGAGUUGUUC-3', wherein, $Z_{37}$ is A, $Z_{38}$ is U, the nucleotide sequence I comprises a nucleotide $Z_{39}$ at a corresponding site to $Z_{37}$, the nucleotide sequence II comprises a nucleotide $Z_{40}$ at a corresponding site to $Z_{38}$, and $Z_{40}$ is the first nucleotide from the 5' terminal of the antisense strand;

xi) the nucleotide sequence I has the same length and no more than three nucleotides differences from the nucleotide sequence shown in SEQ ID NO: 601; and the nucleotide sequence II has the same length and no more than three nucleotides differences from the nucleotide sequence shown in SEQ ID NO: 602:

(SEQ ID NO: 601)
5'-CUUGCUCUGAAGUAGAAAZ$_{41}$-3';

(SEQ ID NO: 602)
5'-Z$_{42}$AUUUCUACUUCAGAGCAAG-3', wherein, $Z_{41}$ is U, $Z_{42}$ is A, the nucleotide sequence I comprises a nucleotide $Z_{43}$ at a corresponding site to $Z_{41}$, the nucleotide sequence II comprises a nucleotide $Z_{44}$ at a corresponding site to $Z_{42}$, and $Z_{44}$ is the first nucleotide from the 5' terminal of the antisense strand; and xii) the nucleotide sequence I has the same length and no more than three nucleotides differences from the nucleotide sequence shown in SEQ ID NO: 661; and the nucleotide sequence II has the same length and no more than three nucleotides differences from the nucleotide sequence shown in SEQ ID NO: 662:

(SEQ ID NO: 661)
5'-CUUCUUUGCCAUCAAAGAZ$_{45}$-3';

(SEQ ID NO: 662)
5'-Z$_{46}$UCUUUGAUGGCAAAGAAG-3', wherein, $Z_{45}$ is U, $Z_{46}$ is A, the nucleotide sequence I comprises a nucleotide $Z_{47}$ at a corresponding site to $Z_{45}$, the nucleotide sequence II comprises a nucleotide $Z_{48}$ at a corresponding site to $Z_{46}$, and $Z_{48}$ is the first nucleotide from the 5' terminal of the antisense strand;

wherein the corresponding site means being at the same site in the nucleotide sequence by counting from the same terminal of the nucleotide sequence;

$R_2$ is a linear alkylene of 1-20 carbon atoms in length, wherein one or more carbon atoms are optionally replaced with any one or more of the group consisting of: C(O), NH, O, S, CH=N, S(O)$_2$, C$_2$-C$_{10}$ alkenylene, C$_2$-C$_{10}$ alkynylene, C$_6$-C$_{10}$ arylene, C$_3$-C$_{18}$ heterocyclylene, and C$_5$-C$_{10}$ heteroarylene; and wherein R$_2$ is optionally substituted by any one or more of the group consisting of: C$_1$-C$_{10}$ alkyl, C$_6$-C$_{10}$ aryl, C$_5$-C$_{10}$ heteroaryl, C$_1$-C$_{10}$ haloalkyl, —OC$_1$-C$_{10}$ alkyl, —OC$_1$-C$_{10}$ alkylphenyl, —C$_1$-C$_{10}$ alkyl-OH, —OC$_1$-C$_{10}$ haloalkyl, —SC$_1$-C$_{10}$ alkyl, —SC$_1$-C$_{10}$ alkylphenyl, —C$_1$-C$_{10}$ alkyl-SH, —SC$_1$-C$_{10}$ haloalkyl, halo substituent, —OH, —SH, —NH$_2$, —C$_1$-C$_{10}$ alkyl-NH$_2$, —N(C$_1$-C$_{10}$ alkyl)(C$_1$-C$_{10}$ alkyl), —NH(C$_1$-C$_{10}$ alkyl), —N(C$_1$-C$_{10}$ alkyl)(C$_1$-C$_{10}$ alkylphenyl), —NH(C$_1$-C$_{10}$ alkylphenyl), cyano, nitro, —CO$_2$H, —C(O)O(C$_1$-C$_{10}$ alkyl), —CON(C$_1$-C$_{10}$ alkyl)(C$_1$-C$_{10}$ alkyl), —CONH (C$_1$-C$_{10}$ alkyl), —CONH$_2$, —NHC(O)(C$_1$-C$_{10}$ alkyl), —NHC(O)(phenyl), —N(C$_1$-C$_{10}$ alkyl)C(O)(C$_1$-C$_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O)C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH(phenyl), —NHSO$_2$(C$_1$-C$_{10}$ alkyl), —NHSO$_2$(phenyl), and —NHSO$_2$(C$_1$-C$_{10}$ haloalkyl);

each L$_1$ is a linear alkylene of 1-70 carbon atoms in length, wherein one or more carbon atoms are optionally replaced with any one or more of the group consisting of: C(O), NH, O, S, CH=N, S(O)$_2$, C$_2$-C$_{10}$ alkenylene, C$_2$-C$_{10}$ alkynylene, C$_6$-C$_{10}$ arylene, C$_3$-C$_{18}$ heterocyclylene, and C$_5$-C$_{10}$ heteroarylene; and wherein L$_1$ is optionally substituted by any one or more of the group consisting of: C$_1$-C$_{10}$ alkyl, C$_6$-C$_{10}$ aryl, C$_5$-C$_{10}$ heteroaryl, C$_1$-C$_{10}$ haloalkyl, —OC$_1$-C$_{10}$ alkyl, —OC$_1$-C$_{10}$ alkylphenyl, —C$_1$-C$_{10}$ alkyl-OH, —OC$_1$-C$_{10}$ haloalkyl, —SC$_1$-C$_{10}$ alkyl, —SC$_1$-C$_{10}$ alkylphenyl, —C$_1$-C$_{10}$ alkyl-SH, —SC$_1$-C$_{10}$ haloalkyl, halo substituent, —OH, —SH, —NH$_2$, —C$_1$-C$_{10}$ alkyl-NH$_2$, —N(C$_1$-C$_{10}$ alkyl)(C$_1$-C$_{10}$ alkyl), —NH(C$_1$-C$_{10}$ alkyl), —N(C$_1$-C$_{10}$ alkyl)(C$_1$-C$_{10}$ alkylphenyl), —NH (C$_1$-C$_{10}$ alkylphenyl), cyano, nitro, —CO$_2$H, —C(O) O(C$_1$-C$_{10}$ alkyl), —CON(C$_1$-C$_{10}$ alkyl)(C$_1$-C$_{10}$ alkyl), —CONH(C$_1$-C$_{10}$ alkyl), —CONH$_2$, —NHC(O)(C$_1$-C$_{10}$ alkyl), —NHC(O)(phenyl), —N(C$_1$-C$_{10}$ alkyl)C (O)(C$_1$-C$_{10}$ alkyl), —N(C$_1$-C$_{10}$ alkyl)C(O)(phenyl), —C(O)C$_1$-C$_{10}$ alkyl, —C(O)C$_1$-C$_{10}$ alkylphenyl, —C(O)C$_1$-C$_{10}$ haloalkyl, —OC(O)C$_1$-C$_{10}$ alkyl, —SO$_2$(C$_1$-C$_{10}$ alkyl), —SO$_2$(phenyl), —SO$_2$(C$_1$-C$_{10}$ haloalkyl), —SO$_2$NH$_2$, —SO$_2$NH(C$_1$-C$_{10}$ alkyl), —SO$_2$NH(phenyl), —NHSO$_2$(C$_1$-C$_{10}$ alkyl), —NHSO$_2$(phenyl), and —NHSO$_2$(C$_1$-C$_{10}$ haloalkyl);

〜〜 represents the site where a group is covalently linked; and

M$_1$ represents a targeting group.

2. The siRNA conjugate according to claim 1, wherein lengths of the sense strand and the antisense strand are the same or different, the length of the sense strand is 19 to 23 nucleotides, and the length of the antisense strand is 19 to 26 nucleotides; and, the nucleotide sequence I is the nucleotide sequence shown in SEQ ID NO: 3, and the nucleotide sequence II is the nucleotide sequence shown in SEQ ID NO: 4:

(SEQ ID NO: 3)
5'-GAGAUGAAGUUCAAGAAUZ$_3$-3';

(SEQ ID NO: 4)
5'-Z$_4$AUUCUUGAACUUCAUCUC-3', wherein, $Z_4$ is selected from A, U, G or C; and $Z_3$ is a nucleotide complementary to $Z_4$;

or, the nucleotide sequence I is the nucleotide sequence shown in SEQ ID NO: 63, and the nucleotide sequence II is the nucleotide sequence shown in SEQ ID NO: 64:

(SEQ ID NO: 63)
5'-CAUAACUGGAAUUUGUAAZ$_7$-3';

(SEQ ID NO: 64)
5'-Z$_8$UUACAAAUUCCAGUUAUG-3', wherein, $Z_8$ is selected from A, U, G or C; and $Z_7$ is a nucleotide complementary to $Z_8$;

or, the nucleotide sequence I is the nucleotide sequence shown in SEQ ID NO: 123, and the nucleotide sequence II is the nucleotide sequence shown in SEQ ID NO: 124:

(SEQ ID NO: 123)
5'-CAUUAUCACAAUUGAGGAZ$_{11}$-3';

(SEQ ID NO: 124)
5'-Z$_{12}$UCCUCAAUUGUGAUAAUG-3', wherein, $Z_{12}$ is selected from A, U, G or C; and $Z_{11}$ is a nucleotide complementary to $Z_{12}$;

or, the nucleotide sequence I is the nucleotide sequence shown in SEQ ID NO: 183, and the nucleotide sequence II is the nucleotide sequence shown in SEQ ID NO: 184:

(SEQ ID NO: 183)
5'-GGAUCUCUCUCAGAGUAUZ$_{15}$-3';

(SEQ ID NO: 184)
5'-Z$_{16}$AUACUCUGAGAGAGAUCC-3', wherein, $Z_{16}$ is selected from A, U, G or C; and $Z_{15}$ is a nucleotide complementary to $Z_{16}$;

or, the nucleotide sequence I is the nucleotide sequence shown in SEQ ID NO: 243, and the nucleotide sequence II is the nucleotide sequence shown in SEQ ID NO: 244:

(SEQ ID NO: 243)
5'-ACAUGGACAACUGCUAUAZ$_{19}$-3';

(SEQ ID NO: 244)
5'-Z$_{20}$UAUAGCAGUUGUCCAUGU-3', wherein, $Z_{20}$ is selected from A, U, G or C; and $Z_{19}$ is a nucleotide complementary to $Z_{20}$;

or, the nucleotide sequence I is the nucleotide sequence shown in SEQ ID NO: 303, and the nucleotide sequence II is the nucleotide sequence shown in SEQ ID NO: 304:

(SEQ ID NO: 303)
5'-UAGCAAGCUCUCAGUAUCZ$_{23}$-3';

(SEQ ID NO: 304)
5'-Z$_{24}$GAUACUGAGAGCUUGCUA-3', wherein, $Z_{24}$ is selected from A, U, G or C; and $Z_{23}$ is a nucleotide complementary to $Z_{24}$;

or, the nucleotide sequence I is the nucleotide sequence shown in SEQ ID NO: 363, and the nucleotide sequence II is the nucleotide sequence shown in SEQ ID NO: 364:

(SEQ ID NO: 363)
5'-AUAAGGUUACUUGUGUUGZ$_{27}$-3';

-continued (SEQ ID NO: 364)
5'-Z$_{28}$CAACACAAGUAACCUUAU-3', wherein, $Z_{28}$ is selected from A, U, G or C; and $Z_{27}$ is a nucleotide complementary to $Z_{28}$;

or, the nucleotide sequence I is the nucleotide sequence shown in SEQ ID NO: 423, and the nucleotide sequence II is the nucleotide sequence shown in SEQ ID NO: 424:

(SEQ ID NO: 423)
5'-GAAAAUCACCUAUGAAGAZ$_{31}$-3';

(SEQ ID NO: 424)
5'-Z$_{32}$UCUUCAUAGGUGAUUUUC-3', wherein, $Z_{32}$ is selected from A, U, G or C; and $Z_{31}$ is a nucleotide complementary to $Z_{32}$;

or, the nucleotide sequence I is the nucleotide sequence shown in SEQ ID NO: 483, and the nucleotide sequence II is the nucleotide sequence shown in SEQ ID NO: 484:

(SEQ ID NO: 483)
5'-GAUGCUAUAAAGAACAACZ$_{35}$-3';

(SEQ ID NO: 484)
5'-Z$_{36}$GUUGUUCUUUAUAGCAUC-3', wherein, $Z_{36}$ is selected from A, U, G or C; and $Z_{35}$ is a nucleotide complementary to $Z_{36}$;

or, the nucleotide sequence I is the nucleotide sequence shown in SEQ ID NO: 543, and the nucleotide sequence II is the nucleotide sequence shown in SEQ ID NO: 544:

(SEQ ID NO: 543)
5'-GAACAACUCCUUUUAUGGZ$_{39}$-3';

(SEQ ID NO: 544)
5'-Z$_{40}$CCAUAAAAGGAGUUGUUC-3', wherein, $Z_{40}$ is selected from A, U, G or C; and $Z_{39}$ is a nucleotide complementary to $Z_{40}$;

or, the nucleotide sequence I is the nucleotide sequence shown in SEQ ID NO: 603, and the nucleotide sequence II is the nucleotide sequence shown in SEQ ID NO: 604:

(SEQ ID NO: 603)
5'-CUUGCUCUGAAGUAGAAAZ$_{43}$-3';

(SEQ ID NO: 604)
5'-Z$_{44}$UUUCUACUUCAGAGCAAG-3', wherein, $Z_{44}$ is selected from A, U, G or C; and $Z_{43}$ is a nucleotide complementary to $Z_{44}$;

or, the nucleotide sequence I is the nucleotide sequence shown in SEQ ID NO: 663, and the nucleotide sequence II is the nucleotide sequence shown in SEQ ID NO: 664:

(SEQ ID NO: 663)
5'-CUUCUUUGCCAUCAAAGAZ$_{47}$-3';

-continued (SEQ ID NO: 664)
5'-Z<sub>48</sub>UCUUUGAUGGCAAAGAAG-3', wherein, $Z_{48}$ is selected from A, U, G or C; and $Z_{47}$ is a nucleotide complementary to $Z_{48}$.

3. The siRNA conjugate according to claim 1, wherein the sense strand further comprises nucleotide sequence III, the antisense strand further comprises a nucleotide sequence IV, the nucleotide sequence III and the nucleotide sequence IV each independently have a length of 1 to 4 nucleotides, the nucleotide sequence III is linked to the 5' terminal of the nucleotide sequence I, the nucleotide sequence IV is linked to the 3' terminal of the nucleotide sequence II, and the nucleotide sequence III has the same length and is substantially reverse complementary or completely reverse complementary to the nucleotide sequence IV; the substantially reverse complementary refers to no more than one base mispairing between two nucleotide sequences; and the completely reverse complementary refers to no mispairing between two nucleotide sequences.

4. The siRNA conjugate according to claim 3, wherein the nucleotide sequence I has the same length and no more than three nucleotides differences from the nucleotide sequence shown in SEQ ID NO: 1; and, the nucleotide sequences III and IV both have a length of one nucleotide, and a base of the nucleotide sequence III is U; or, the nucleotide sequences III and IV both have a length of two nucleotides, and in the direction from the 5' terminal to the 3' terminal, the base composition of the nucleotide sequence III is UU; or, the nucleotide sequences III and IV both have a length of three nucleotides, and in the direction from the 5' terminal to the 3' terminal, the base composition of the nucleotide sequence III is AUU; or, the nucleotide sequences III and IV both have a length of four nucleotides, and in the direction from the 5' terminal to the 3' terminal, the base composition of the nucleotide sequence III is CAUU;

or, the nucleotide sequence I has the same length and no more than three nucleotides differences from the nucleotide sequence shown in SEQ ID NO: 61; and, the nucleotide sequences III and IV both have a length of one nucleotide, and the base of the nucleotide sequence III is A; or, the nucleotide sequences III and IV both have a length of two nucleotides, and in the direction from the 5' terminal to the 3' terminal, the base composition of the nucleotide sequence III is AA; or, the nucleotide sequences III and IV both have a length of three nucleotides, and in the direction from the 5' terminal to the 3' terminal, the base composition of the nucleotide sequence III is UAA; or, the nucleotide sequences III and IV both have a length of four nucleotides, and in the direction from the 5' terminal to the 3' terminal, the base composition of the nucleotide sequence III is GUAA;

or, the nucleotide sequence I has the same length and no more than three nucleotides differences from the nucleotide sequence shown in SEQ ID NO: 121; and, the nucleotide sequences III and IV both have a length of one nucleotide, and the base of the nucleotide sequence III is C; or, the nucleotide sequences III and IV both have a length of two nucleotides, and in the direction from the 5' terminal to the 3' terminal, the base composition of the nucleotide sequence III is GC; or, the nucleotide sequences III and IV both have a length of three nucleotides, and in the direction from the 5' terminal to the 3' terminal, the base composition of the nucleotide sequence III is AGC; or, the nucleotide sequences III and IV both have a length of four nucleotides, and in the direction from the 5' terminal to the 3' terminal, the base composition of the nucleotide sequence III is CAGC;

or, the nucleotide sequence I has the same length and no more than three nucleotides differences from the nucleotide sequence shown in SEQ ID NO: 181; and, the nucleotide sequences III and IV both have a length of one nucleotide, and the base of the nucleotide sequence III is A; or, the nucleotide sequences III and IV both have a length of two nucleotides, and in the direction from the 5' terminal to the 3' terminal, the base composition of the nucleotide sequence III is CA; or, the nucleotide sequences III and IV both have a length of three nucleotides, and in the direction from the 5' terminal to the 3' terminal, the base composition of the nucleotide sequence III is CCA; or, the nucleotide sequences III and IV both have a length of four nucleotides, and in the direction from the 5' terminal to the 3' terminal, the base composition of the nucleotide sequence III is CCCA;

or, the nucleotide sequence I has the same length and no more than three nucleotides differences from the nucleotide sequence shown in SEQ ID NO: 241; and, the nucleotide sequences III and IV both have a length of one nucleotide, and the base of the nucleotide sequence III is C; or, the nucleotide sequences III and IV both have a length of two nucleotides, and in the direction from the 5' terminal to the 3' terminal, the base composition of the nucleotide sequence III is CC; or, the nucleotide sequences III and IV both have a length of three nucleotides, and in the direction from the 5' terminal to the 3' terminal, the base composition of the nucleotide sequence III is UCC; or, the nucleotide sequences III and IV both have a length of four nucleotides, and in the direction from the 5' terminal to the 3' terminal, the base composition of the nucleotide sequence III is UUCC;

or, the nucleotide sequence I has the same length and no more than three nucleotides differences from the nucleotide sequence shown in SEQ ID NO: 301; and, the nucleotide sequences III and IV both have a length of one nucleotide, and the base of the nucleotide sequence III is C; or, the nucleotide sequences III and IV both have a length of two nucleotides, and in the direction from the 5' terminal to the 3' terminal, the base composition of the nucleotide sequence III is CC; or, the nucleotide sequences III and IV both have a length of three nucleotides, and in the direction from the 5' terminal to the 3' terminal, the base composition of the nucleotide sequence III is GCC; or, the nucleotide sequences III and IV both have a length of four nucleotides, and in the direction from the 5' terminal to the 3' terminal, the base composition of the nucleotide sequence III is UGCC;

or, the nucleotide sequence I has the same length and no more than three nucleotides differences from the nucleotide sequence shown in SEQ ID NO: 361; and, the nucleotide sequences III and IV both have a length of one nucleotide, and the base of the nucleotide sequence III is G; or, the nucleotide sequences III and IV both have a length of two nucleotides, and in the direction from the 5' terminal to the 3' terminal, the base composition of the nucleotide sequence III is GG; or, the nucleotide sequences III and IV both have a length of three nucleotides, and in the direction from the 5' terminal to the 3' terminal, the base composition of the nucleotide sequence III is AGG; or, the nucleotide sequences III and IV both have a length of four nucleotides, and in the direction from the 5' terminal to the 3' terminal, the base composition of the nucleotide sequence III is AAGG;

or, the nucleotide sequence I has the same length and no more than three nucleotides differences from the nucleotide sequence shown in SEQ ID NO: 421; and, the nucleotide sequences III and IV both have a length of one nucleotide, and the base of the nucleotide sequence III is U; or, the nucleotide sequences III and IV both have a length of two nucleotides, and in the direction from the 5' terminal to the 3' terminal, the base composition of the nucleotide sequence III is GU; or, the nucleotide sequences III and IV both have a length of three nucleotides, and in the direction from the 5' terminal to the 3' terminal, the base composition of the nucleotide sequence III is GGU; or, the nucleotide sequences III and IV both have a length of four nucleotides, and in the direction from the 5' terminal to the 3' terminal, the base composition of the nucleotide sequence III is GGGU;

or, the nucleotide sequence I has the same length and no more than three nucleotides differences from the nucleotide sequence shown in SEQ ID NO: 481; and, the nucleotide sequences III and IV both have a length of one nucleotide, and the base of the nucleotide sequence III is G; or, the nucleotide sequences III and IV both have a length of two nucleotides, and in the direction from the 5' terminal to the 3' terminal, the base composition of the nucleotide sequence III is AG; or, the nucleotide sequences III and IV both have a length of three nucleotides, and in the direction from the 5' terminal to the 3' terminal, the base composition of the nucleotide sequence III is GAG; or, the nucleotide sequences III and IV both have a length of four nucleotides, and in the direction from the 5' terminal to the 3' terminal, the base composition of the nucleotide sequence III is UGAG;

or, the nucleotide sequence I has the same length and no more than three nucleotides differences from the nucleotide sequence shown in SEQ ID NO: 541; and, the nucleotide sequences III and IV both have a length of one nucleotide, and the base of the nucleotide sequence III is A; or, the nucleotide sequences III and IV both have a length of two nucleotides, and in the direction from the 5' terminal to the 3' terminal, the base composition of the nucleotide sequence III is AA; or, the nucleotide sequences III and IV both have a length of three nucleotides, and in the direction from the 5' terminal to the 3' terminal, the base composition of the nucleotide sequence III is AAA; or, the nucleotide sequences III and IV both have a length of four nucleotides, and in the direction from the 5' terminal to the 3' terminal, the base composition of the nucleotide sequence III is UAAA;

or, the nucleotide sequence I has the same length and no more than three nucleotides differences from the nucleotide sequence shown in SEQ ID NO: 601; and, the nucleotide sequences III and IV both have a length of one nucleotide, and the base of the nucleotide sequence III is G; or, the nucleotide sequences III and IV both have a length of two nucleotides, and in the direction from the 5' terminal to the 3' terminal, the base composition of the nucleotide sequence III is GG; or, the nucleotide sequences III and IV both have a length of three nucleotides, and in the direction from the 5' terminal to the 3' terminal, the base composition of the nucleotide sequence III is UGG; or, the nucleotide sequences III and IV both have a length of four nucleotides, and in the direction from the 5' terminal to the 3' terminal, the base composition of the nucleotide sequence III is GUGG;

or, the nucleotide sequence I has the same length and no more than three nucleotides differences from the nucleotide sequence shown in SEQ ID NO: 661; and, the nucleotide sequences III and IV both have a length of one nucleotide, and the base of the nucleotide sequence III is U; or, the nucleotide sequences III and IV both have a length of two nucleotides, and in the direction from the 5' terminal to the 3' terminal, the base composition of the nucleotide sequence III is AU; or, the nucleotide sequences III and IV both have a length of three nucleotides, and in the direction from the 5' terminal to the 3' terminal, the base composition of the nucleotide sequence III is UAU; or, the nucleotide sequences III and IV both have a length of four nucleotides, and in the direction from the 5' terminal to the 3' terminal, the base composition of the nucleotide sequence III is CUAU.

5. The siRNA conjugate according to claim 1, wherein the antisense strand further comprises a nucleotide sequence V, which has a length of 1 to 3 nucleotides and is linked to 3' terminal of the antisense strand, thereby constituting a 3' overhang of the antisense strand.

6. The siRNA conjugate according to claim 1, wherein the sense strand of the siRNA comprises the nucleotide sequence shown in SEQ ID NO: 5, and the antisense strand comprises the nucleotide sequence shown in SEQ ID NO: 6:

$$\text{(SEQ ID NO: 5)}$$
$$5'\text{-GAGAUGAAGUUCAAGAAUZ}_3\text{-3';}$$

$$\text{(SEQ ID NO: 6)}$$
$$5'\text{-Z}_4\text{AUUCUUGAACUUCAUCUCAA-3';}$$

or, the sense strand of the siRNA comprises the nucleotide sequence shown in SEQ ID NO: 7, and the antisense strand of the siRNA comprises the nucleotide sequence shown in SEQ ID NO: 8;

$$\text{(SEQ ID NO: 7)}$$
$$5'\text{-UUGAGAUGAAGUUCAAGAAUZ}_3\text{-3';}$$

$$\text{(SEQ ID NO: 8)}$$
$$5'\text{-Z}_4\text{AUUCUUGAACUUCAUCUCAAUG-3';}$$

wherein, $Z_4$ is the first nucleotide from 5' terminal of the antisense strand; $Z_4$ is selected from A, U, G or C; and $Z_3$ is a nucleotide complementary to $Z_4$;

or, the sense strand of the siRNA comprises the nucleotide sequence shown in SEQ ID NO: 65, and the antisense strand of the siRNA comprises the nucleotide sequence shown in SEQ ID NO: 66:

$$\text{(SEQ ID NO: 65)}$$
$$5'\text{-CAUAACUGGAAUUUGUAAZ}_7\text{-3';}$$

$$\text{(SEQ ID NO: 66)}$$
$$5'\text{-Z}_8\text{UUACAAAUUCCAGUUAUGUU-3',}$$

or, the sense strand of the siRNA comprises the nucleotide sequence shown in SEQ ID NO: 67, and the antisense strand of the siRNA comprises the nucleotide sequence shown in SEQ ID NO:

```
                                  (SEQ ID NO: 67)
    5'-AACAUAACUGGAAUUUGUAAZ₇-3';
```

```
                                  (SEQ ID NO: 68)
    5'-Z₈UUACAAAUUCCAGUUAUGUUAC-3',
``` wherein, $Z_8$ is the first nucleotide from 5' terminal of the antisense strand; $Z_8$ is selected from A, U, G or C; and $Z_7$ is a nucleotide complementary to $Z_8$;

or, the sense strand of the siRNA comprises the nucleotide sequence shown in SEQ ID NO: 125, and the antisense strand of the siRNA comprises the nucleotide sequence shown in SEQ ID NO: 126:

```
                                  (SEQ ID NO: 125)
    5'-CAUUAUCACAAUUGAGGAZ₁₁-3';
```

```
                                  (SEQ ID NO: 126)
    5'-Z₁₂UCCUCAAUUGUGAUAAUGGC-3',
``` or, the sense strand of the siRNA comprises the nucleotide sequence shown in SEQ ID NO: 127, and the antisense strand of the siRNA comprises the nucleotide sequence shown in SEQ ID NO: 128:

```
                                  (SEQ ID NO: 127)
    5'-GCCAUUAUCACAAUUGAGGAZ₁₁-3';
```

```
                                  (SEQ ID NO: 128)
    5'-Z₁₂UCCUCAAUUGUGAUAAUGGCUG-3',
``` wherein, $Z_{12}$ is the first nucleotide from 5' terminal of the antisense strand; $Z_{12}$ is selected from A, U, G or C; and $Z_{11}$ is a nucleotide complementary to $Z_{12}$;

or, the sense strand of the siRNA comprises the nucleotide sequence shown in SEQ ID NO: 185, and the antisense strand of the siRNA comprises the nucleotide sequence shown in SEQ ID NO: 186:

```
                                  (SEQ ID NO: 185)
    5'-GGAUCUCUCUCAGAGUAUZ₁₅-3';
```

```
                                  (SEQ ID NO: 186)
    5'-Z₁₆AUACUCUGAGAGAGAUCCUG-3',
``` or, the sense strand of the siRNA comprises the nucleotide sequence shown in SEQ ID NO: 187, and the antisense strand of the siRNA comprises the nucleotide sequence shown in SEQ ID NO: 188:

```
                                  (SEQ ID NO: 187)
    5'-CAGGAUCUCUCUCAGAGUAUZ₁₅-3';
```

```
                                  (SEQ ID NO: 188)
    5'-Z₁₆AUACUCUGAGAGAGAUCCUGGG-3',
``` wherein, $Z_{16}$ is the first nucleotide from 5' terminal of the antisense strand; $Z_{16}$ is selected from A, U, G or C; and $Z_{15}$ is a nucleotide complementary to $Z_{16}$;

or, the sense strand of the siRNA comprises the nucleotide sequence shown in SEQ ID NO: 245, and the antisense strand of the siRNA comprises the nucleotide sequence shown in SEQ ID NO: 246:

```
                                  (SEQ ID NO: 245)
    5'-ACAUGGACAACUGCUAUAZ₁₉-3';
```

```
                                  (SEQ ID NO: 246)
    5'-Z₂₀UAUAGCAGUUGUCCAUGUGG-3',
``` or, the sense strand of the siRNA comprises the nucleotide sequence shown in SEQ ID NO: 247, and the antisense strand of the siRNA comprises the nucleotide sequence shown in SEQ ID NO: 248:

```
                                  (SEQ ID NO: 247)
    5'-CCACAUGGACAACUGCUAUAZ₁₉-3';
```

```
                                  (SEQ ID NO: 248)
    5'-Z₂₀UAUAGCAGUUGUCCAUGUGGAA-3',
``` wherein, $Z_{20}$ is the first nucleotide from 5' terminal of the antisense strand; $Z_{20}$ is selected from A, U, G or C; and $Z_{19}$ is a nucleotide complementary to $Z_{20}$;

or, the sense strand of the siRNA comprises the nucleotide sequence shown in SEQ ID NO: 305, and the antisense strand of the siRNA comprises the nucleotide sequence shown in SEQ ID NO: 306:

```
                                  (SEQ ID NO: 305)
    5'-UAGCAAGCUCUCAGUAUCZ₂₃-3';
```

```
                                  (SEQ ID NO: 306)
    5'-Z₂₄GAUACUGAGAGCUUGCUAGG-3',
``` or, the sense strand of the siRNA comprises the nucleotide sequence shown in SEQ ID NO: 307, and the antisense strand of the siRNA comprises the nucleotide sequence shown in SEQ ID NO: 308:

```
                                  (SEQ ID NO: 307)
    5'-CCUAGCAAGCUCUCAGUAUCZ₂₃-3';
```

```
                                  (SEQ ID NO: 308)
    5'-Z₂₄GAUACUGAGAGCUUGCUAGGCA-3',
``` wherein, $Z_{24}$ is the first nucleotide from 5' terminal of the antisense strand; $Z_{24}$ is selected from A, U, G or C; and $Z_{23}$ is a nucleotide complementary to $Z_{24}$;

or, the sense strand of the siRNA comprises the nucleotide sequence shown in SEQ ID NO: 365, and the antisense strand of the siRNA comprises the nucleotide sequence shown in SEQ ID NO: 366:

```
                                  (SEQ ID NO: 365)
    5'-AUAAGGUUACUUGUGUUGZ₂₇-3';
```

```
                                  (SEQ ID NO: 366)
    5'-Z₂₈CAACACAAGUAACCUUAUCC-3';
``` or, the sense strand of the siRNA comprises the nucleotide sequence shown in SEQ ID NO: 367, and the antisense strand comprises the nucleotide sequence shown in SEQ ID NO: 368:

```
                                  (SEQ ID NO: 367)
    5'-GGAUAAGGUUACUUGUGUUGZ₂₇-3';
```

```
                                  (SEQ ID NO: 368)
    5'-Z₂₈CAACACAAGUAACCUUAUCCUU-3';
``` wherein, $Z_{28}$ is the first nucleotide from 5' terminal of the antisense strand; $Z_{28}$ is selected from A, U, G or C; and $Z_{27}$ is a nucleotide complementary to $Z_{28}$;

or, the sense strand of the siRNA comprises the nucleotide sequence shown in SEQ ID NO: 425, and the antisense strand of the siRNA comprises the nucleotide sequence shown in SEQ ID NO: 426:

```
                                    (SEQ ID NO: 425)
     5'-GAAAAUCACCUAUGAAGAZ₃₁-3';
```

```
                                    (SEQ ID NO: 426)
     5'-Z₃₂UCUUCAUAGGUGAUUUUCAC-3',
``` or, the sense strand of the siRNA comprises the nucleotide sequence shown in SEQ ID NO: 427, and the antisense strand of the siRNA comprises the nucleotide sequence shown in SEQ ID NO: 428:

```
                                    (SEQ ID NO: 427)
     5'-GUGAAAAUCACCUAUGAAGAZ₃₁-3';
```

```
                                    (SEQ ID NO: 428)
     5'-Z₃₂UCUUCAUAGGUGAUUUUCACCC-3',
``` wherein, $Z_{32}$ is the first nucleotide from 5' terminal of the antisense strand; $Z_{32}$ is selected from A, U, G or C; and $Z_{31}$ is a nucleotide complementary to $Z_{32}$;
or, the sense strand of the siRNA comprises the nucleotide sequence shown in SEQ ID NO: 485, and the antisense strand of the siRNA comprises the nucleotide sequence shown in SEQ ID NO: 486:

```
                                    (SEQ ID NO: 485)
     5'-GAUGCUAUAAAGAACAACZ₃₅-3';
```

```
                                    (SEQ ID NO: 486)
     5'-Z₃₆GUUGUUCUUUAUAGCAUCCU-3',
``` or, the sense strand of the siRNA comprises the nucleotide sequence shown in SEQ ID NO: 487, and the antisense strand of the siRNA comprises the nucleotide sequence shown in SEQ ID NO: 488:

```
                                    (SEQ ID NO: 487)
     5'-AGGAUGCUAUAAAGAACAACZ₃₅-3';
```

```
                                    (SEQ ID NO: 488)
     5'-Z₃₆GUUGUUCUUUAUAGCAUCCUCA-3',
``` wherein, $Z_{36}$ is the first nucleotide from 5' terminal of the antisense strand; $Z_{36}$ is selected from A, U, G or C; and $Z_{35}$ is a nucleotide complementary to $Z_{36}$;
or, the sense strand of the siRNA comprises the nucleotide sequence shown in SEQ ID NO: 545, and the antisense strand of the siRNA comprises the nucleotide sequence shown in SEQ ID NO: 546:

```
                                    (SEQ ID NO: 545)
     5'-GAACAACUCCUUUUAUGGZ₃₉-3';
```

```
                                    (SEQ ID NO: 546)
     5'-Z₄₀CCAUAAAAGGAGUUGUUCUU-3',
``` or, the sense strand of the siRNA comprises the nucleotide sequence shown in SEQ ID NO: 547, and the antisense strand of the siRNA comprises the nucleotide sequence shown in SEQ ID NO: 548:

```
                                    (SEQ ID NO: 547)
     5'-AAGAACAACUCCUUUUAUGGZ₃₉-3';
```

-continued

```
                                    (SEQ ID NO: 548)
     5'-Z₄₀CCAUAAAAGGAGUUGUUCUUUA-3',
``` wherein, $Z_{40}$ is the first nucleotide from 5' terminal of the antisense strand; $Z_{40}$ is selected from A, U, G or C; and $Z_{39}$ is a nucleotide complementary to $Z_{40}$;
or, the sense strand of the siRNA comprises the nucleotide sequence shown in SEQ ID NO: 605, and the antisense strand of the siRNA comprises the nucleotide sequence shown in SEQ ID NO: 606:

```
                                    (SEQ ID NO: 605)
     5'-CUUGCUCUGAAGUAGAAAZ₄₃-3';
```

```
                                    (SEQ ID NO: 606)
     5'-Z₄₄UUUCUACUUCAGAGCAAGCC-3',
``` or, the sense strand of the siRNA comprises the nucleotide sequence shown in SEQ ID NO: 607, and the antisense strand of the siRNA comprises the nucleotide sequence shown in SEQ ID NO: 608:

```
                                    (SEQ ID NO: 607)
     5'-GGCUUGCUCUGAAGUAGAAAZ₄₃-3';
```

```
                                    (SEQ ID NO: 608)
     5'-5'-Z₄₄UUUCUACUUCAGAGCAAGCCAC-3',
``` wherein, $Z_{44}$ is the first nucleotide from 5' terminal of the antisense strand; $Z_{44}$ is selected from A, U, G or C; and $Z_{43}$ is a nucleotide complementary to $Z_{44}$;
or, the sense strand of the siRNA comprises the nucleotide sequence shown in SEQ ID NO: 665, and the antisense strand of the siRNA comprises the nucleotide sequence shown in SEQ ID NO: 666:

```
                                    (SEQ ID NO: 665)
     5'-CUUCUUUGCCAUCAAAGAZ₄₇-3';
```

```
                                    (SEQ ID NO: 666)
     5'-Z₄₈UCUUUGAUGGCAAAGAAGAU-3',
``` or, the sense strand of the siRNA comprises the nucleotide sequence shown in SEQ ID NO: 667, and the antisense strand of the siRNA comprises the nucleotide sequence shown in SEQ ID NO: 668:

```
                                    (SEQ ID NO: 667)
     5'-AUCUUCUUUGCCAUCAAAGAZ₄₇-3';
```

```
                                    (SEQ ID NO: 668)
     5'-Z₄₈UCUUUGAUGGCAAAGAAGAUAG-3',
``` wherein, $Z_{48}$ is the first nucleotide from 5' terminal of the antisense strand; $Z_{48}$ is selected from A, U, G or C; and $Z_{47}$ is a nucleotide complementary to $Z_{48}$.

7. The siRNA conjugate according to claim 1, wherein the siRNA is any one of siXOa1 of SEQ ID NOs: 9 and 10, siXOa2 of SEQ ID NOs: 11 and 12, siXOb1 of SEQ ID NOs: 69 and 70, siXOb2 of SEQ ID NOs: 71 and 72, siXOc1 of SEQ ID NOs: 129 and 130, siXOc2 of SEQ ID NOs: 131 and 132, siXOd1 of SEQ ID NOs: 189 and 190, siXOd2 of SEQ ID NOs: 191 and 192, siXOe1 of SEQ ID NOs: 249 and 250, siXOe2 of SEQ ID NOs: 251 and 252, siXOf1 of SEQ ID NOs: 309 and 310, siXOf2 of SEQ ID NOs: 311 and 312, siXOg1 of SEQ ID NOs: 369 and 370, siXOg2 of SEQ ID NOs: 371 and 372, siXOh1 of SEQ ID NOs: 429 and 430, siXOh2 of SEQ ID NOs: 431 and 432, siXOi1 of SEQ ID NOs: 489 and 490, siXOi2 of SEQ ID NOs: 491 and 492, siXOj1 of SEQ ID NOs: 549 and 550, siXOj2 of SEQ ID NOs: 551 and 552, siXOk1 of SEQ ID NOs: 609 and 610, siXOk2 of SEQ ID NOs: 611 and 612, siXO11 of SEQ ID NOs: 669 and 670, and siXO12 of SEQ ID NOs: 671 and 672.

8. The siRNA conjugate according to claim 1, wherein each nucleotide in the sense strand and the antisense strand is independently a fluoro modified nucleotide or a non-fluoro modified nucleotide; wherein the fluoro modified nucleotide is located in the nucleotide sequence I and the nucleotide sequence II; and in the direction from 5' terminal to 3' terminal, at least the nucleotides at positions 7, 8 and 9 of the nucleotide sequence I are fluoro modified nucleotides; and in the direction from 5' terminal to 3' terminal, at least the nucleotides at positions 2, 6, 14 and 16 of the nucleotide sequence II are fluoro modified nucleotides.

9. The siRNA conjugate according to claim 8, wherein each non-fluoro modified nucleotide is a methoxy modified nucleotide, and the methoxy modified nucleotide refers to a nucleotide formed by substituting the 2'-hydroxy of the ribose group of a nucleotide with a methoxy.

10. The siRNA conjugate according to claim 1, wherein in the direction from 5' terminal to 3' terminal, the nucleotides at positions 5, 7, 8 and 9 of the nucleotide sequence I in the sense strand are fluoro modified nucleotides, and the nucleotides at the rest of positions in the sense strand of the siRNA are methoxy modified nucleotides; and in the direction from 5' terminal to 3' terminal, the nucleotides at positions 2, 6, 8, 9, 14 and 16 of the nucleotide sequence II in the antisense strand of the siRNA are fluoro modified nucleotides, and the nucleotides at the rest of positions in the antisense strand of the siRNA are methoxy modified nucleotides;

or, in the direction from 5' terminal to 3' terminal, the nucleotides at positions 5, 7, 8 and 9 of the nucleotide sequence I in the sense strand of the siRNA are fluoro modified nucleotides, and the nucleotides at the rest of positions in the sense strand of the siRNA are methoxy modified nucleotides; and, in the direction from 5' terminal to 3' terminal, the nucleotides at positions 2, 6, 14 and 16 of the nucleotide sequence II in the antisense strand of the siRNA are fluoro modified nucleotides, and the nucleotides at the rest of positions in the antisense strand of the siRNA are methoxy modified nucleotides;

or, in the direction from 5' terminal to 3' terminal, the nucleotides at positions 7, 8 and 9 of the nucleotide sequence I in the sense strand are fluoro modified nucleotides, and the nucleotides at the rest of positions in the sense strand of the siRNA are methoxy modified nucleotides; and in the direction from 5' terminal to 3' terminal, the nucleotides at positions 2, 6, 14 and 16 of the nucleotide sequence II in the antisense strand of the siRNA are fluoro modified nucleotides, and the nucleotides at the rest of positions in the antisense strand of the siRNA are methoxy modified nucleotides.

11. The siRNA conjugate according to claim 1, wherein the siRNA is any one of siXOa1-M1 of SEQ ID NOs: 13 and 14, siXOa1-M2 of SEQ ID NOs: 15 and 16, siXOa1-M3 of SEQ ID NOs: 17 and 18, siXOa2-M1 of SEQ ID NOs: 19 and 20, siXOa2-M2 of SEQ ID NOs: 21 and 22, siXOa2-M3 of SEQ ID NOs: 23 and 24, siXOb1-M1 of SEQ ID NOs: 73 and 74, siXOb1-M2 of SEQ ID NOs: 75 and 76, siXOb1-M3 of SEQ ID NOs: 77 and 78, siXOb2-M1 of SEQ ID NOs: 79 and 80, siXOb2-M2 of SEQ ID NOs: 81 and 82, siXOb2-M3 of SEQ ID NOs: 83 and 84, siXOc1-M1 of SEQ ID NOs: 133 and 134, siXOc1-M2 of SEQ ID NOs: 135 and 136, siXOc1-M3 of SEQ ID NOs: 137 and 138, siXOc2-M1 of SEQ ID NOs: 139 and 140, siXOc2-M2 of SEQ ID NOs: 141 and 142, siXOc2-M3 of SEQ ID NOs: 143 and 144, siXOd1-M1 of SEQ ID NOs: 193 and 194, siXOd1-M2 of SEQ ID NOs: 195 and 196, siXOd1-M3 of SEQ ID NOs: 197 and 198, siXOd2-M1 of SEQ ID NOs: 199 and 200, siXOd2-M2 of SEQ ID NOs: 201 and 202, siXOd2-M3 of SEQ ID NOs: 203 and 204, siXOe1-M1 of SEQ ID NOs: 253 and 254, siXOe1-M2 of SEQ ID NOs: 255 and 256, siXOe1-M3 of SEQ ID NOs: 257 and 258, siXOe2-M1 of SEQ ID NOs: 259 and 260, siXOe2-M2 of SEQ ID NOs: 261 and 262, siXOe2-M3 of SEQ ID NOs: 263 and 264, siXOf1-M1 of SEQ ID NOs: 313 and 314, siXOf1-M2 of SEQ ID NOs: 315 and 316, siXOf1-M3 of SEQ ID NOs: 317 and 318, siXOf2-M1 of SEQ ID NOs: 319 and 320, siXOf2-M2 of SEQ ID NOs: 321 and 322, siXOf2-M3 of SEQ ID NOs: 323 and 324, siXOg1-M1 of SEQ ID NOs: 373 and 374, siXOg1-M2 of SEQ ID NOs: 375 and 376, siXOg1-M3 of SEQ ID NOs: 377 and 378, siXOg2-M1 of SEQ ID NOs: 379 and 380, siXOg2-M2 of SEQ ID NOs: 381 and 382, siXOg2-M3 of SEQ ID NOs: 383 and 384, siXOh1-M1 of SEQ ID NOs: 433 and 434, siXOh1-M2 of SEQ ID NOs: 435 and 436, siXOh1-M3 of SEQ ID NOs: 437 and 438, siXOh2-M1 of SEQ ID NOs: 439 and 440, siXOh2-M2 of SEQ ID NOs: 441 and 442, siXOh2-M3 of SEQ ID NOs: 443 and 444, siXOi1-M1 of SEQ ID NOs: 493 and 494, siXOi1-M2 of SEQ ID NOs: 495 and 496, siXOi1-M3 of SEQ ID NOs: 497 and 498, siXOi2-M1 of SEQ ID NOs: 499 and 500, siXOi2-M2 of SEQ ID NOs: 501 and 502, siXOi2-M3 of SEQ ID NOs: 503 and 504, siXOj1-M1 of SEQ ID NOs: 553 and 554, siXOj1-M2 of SEQ ID NOs: 555 and 556, siXOj1-M3 of SEQ ID NOs: 557 and 558, siXOj2-M1 of SEQ ID NOs: 559 and 560, siXOj2-M2 of SEQ ID NOs: 561 and 562, siXOj2-M3 of SEQ ID NOs: 563 and 564, siXOk1-M1 of SEQ ID NOs: 613 and 614, siXOk1-M2 of SEQ ID NOs: 615 and 616, siXOk1-M3 of SEQ ID NOs: 617 and 618, siXOk2-M1 of SEQ ID NOs: 619 and 620, siXOk2-M2 of SEQ ID NOs: 621 and 622, siXOk2-M3 of SEQ ID NOs: 623 and 624, siXO11-M1 of SEQ ID NOs: 673 and 674, siXO11-M2 of SEQ ID NOs: 675 and 676, siXO11-M3 of SEQ ID NOs: 677 and 678 siXO12-M1 of SEQ ID NOs: 679 and 680, siXO12-M2 of SEQ ID NOs: 681 and 682, and siXO12-M3 of SEQ ID NOs: 683 and 684.

12. The siRNA conjugate according to claim 11, wherein, in the siRNA, at least one phosphate group is a phosphoro-thioate group, and the phosphorothioate linkage exists in at least one of the following positions:

the position between the first nucleotide and the second nucleotide at 5' terminal of the sense strand;
the position between the second nucleotide and the third nucleotide at 5' terminal of the sense strand;
the position between the first nucleotide and the second nucleotide at 3' terminal of the sense strand;
the position between the second nucleotide and the third nucleotide at 3' terminal of the sense strand;
the position between the first nucleotide and the second nucleotide at 5' terminal of the antisense strand;
the position between the second nucleotide and the third nucleotide at 5' terminal of the antisense strand;
the position between the first nucleotide and the second nucleotide at 3' terminal of the antisense strand; and
the position between the second nucleotide and the third nucleotide at 3' terminal of the antisense strand.

13. The siRNA conjugate according to claim 1, wherein the siRNA is any one of siXOa1-M1S of SEQ ID NOs: 25 and 26, siXOa1-M2S of SEQ ID NOs: 27 and 28, siXOa1-M3S of SEQ ID NOs: 29 and 30, siXOa2-M1S of SEQ ID NOs: 31 and 32, siXOa2-M2S of SEQ ID NOs: 33 and 34, siXOa2-M3S of SEQ ID NOs: 35 and 36, siXOb1-M1S of SEQ ID NOs: 85 and 86, siXOb1-M2S of SEQ ID NOs: 87 and 88, siXOb1-M3S of SEQ ID NOs: 89 and 90, siXOb2-M1S of SEQ ID NOs: 91 and 92, siXOb2-M2S of SEQ ID NOs: 93 and 94, siXOb2-M3S of SEQ ID NOs: 95 and 96, siXOc1-M1S of SEQ ID NOs: 145 and 146, siXOc1-M2S of SEQ ID NOs: 147 and 148, siXOc1-M3S of SEQ ID NOs: 149 and 150, siXOc2-M1S of SEQ ID NOs: 151 and 152, siXOc2-M2S of SEQ ID NOs: 153 and 154, siXOc2-M3S of SEQ ID NOs: 155 and 156, siXOd1-M1S of SEQ ID NOs: 205 and 206, siXOd1-M2S of SEQ ID NOs: 207 and 208, siXOd1-M3S of SEQ ID NOs: 209 and 210, siXOd2-M1S of SEQ ID NOs: 211 and 212, siXOd2-M2S of SEQ ID NOs: 213 and 214, siXOd2-M3S of SEQ ID NOs: 215 and 216, siXOe1-M1S of SEQ ID NOs: 265 and 266, siXOe1-M2S of SEQ ID NOs: 267 and 268, siXOe1-M3S of SEQ ID NOs: 269 and 270, siXOe2-M1S of SEQ ID NOs: 271 and 272, siXOe2-M2S of SEQ ID NOs: 273 and 274, siXOe2-M3S of SEQ ID NOs: 275 and 276, siXOf1-M1S of SEQ ID NOs: 325 and 326, siXOf1-M2S of SEQ ID NOs: 327 and 328, siXOf1-M3S of SEQ ID NOs: 329 and 330, siXOf2-M1S of SEQ ID NOs: 331 and 332, siXOf2-M2S of SEQ ID NOs: 333 and 334, siXOf2-M3S of SEQ ID NOs: 335 and 336, siXOg1-M1S of SEQ ID NOs: 385 and 386, siXOg1-M2S of SEQ ID NOs: 387 and 388, siXOg1-M3S of SEQ ID NOs: 389 and 390, siXOg2-M1S of SEQ ID NOs: 391 and 392, siXOg2-M2S of SEQ ID NOs: 393 and 394, siXOg2-M3S of SEQ ID NOs: 395 and 396, siXOh1-M1S of SEQ ID NOs: 445 and 446, siXOh1-M2S of SEQ ID NOs: 447 and 448, siXOh1-M3S of SEQ ID NOs: 449 and 450, siXOh2-M1S of SEQ ID NOs: 451 and 452, siXOh2-M2S of SEQ ID NOs: 453 and 454, siXOh2-M3S of SEQ ID NOs: 455 and 456, siXOi1-M1S of SEQ ID NOs: 505 and 506, siXOi1-M2S of SEQ ID NOs: 507 and 508, siXOi1-M3S of SEQ ID NOs: 509 and 510, siXOi2-M1S of SEQ ID NOs: 511 and 512, siXOi2-M2S of SEQ ID NOs: 513 and 514, siXOi2-M3S of SEQ ID NOs: 515 and 516, siXOj1-M1S of SEQ ID NOs: 565 and 566, siXOj1-M2S of SEQ ID NOs: 567 and 568, siXOj1-M3S of SEQ ID NOs: 569 and 570, siXOj2-M1S of SEQ ID NOs: 571 and 572, siXOj2-M2S of SEQ ID NOs: 573 and 574, siXOj2-M3S of SEQ ID NOs: 575 and 576, siXOk1-M1S of SEQ ID NOs: 625 and 626, siXOk1-M2S of SEQ ID NOs: 627 and 628, siXOk1-M3S of SEQ ID NOs: 629 and 630, siXOk2-M1S of SEQ ID NOs: 631 and 632, siXOk2-M2S of SEQ ID NOs: 633 and 634, siXOk2-M3S of SEQ ID NOs: 635 and 636, siXOl1-M1S of SEQ ID NOs: 685 and 686, siXOl1-M2S of SEQ ID NOs: 687 and 688, siXOl1-M3S of SEQ ID NOs: 689 and 690, siXOl2-M1S of SEQ ID NOs: 691 and 692, siXOl2-M2S of SEQ ID NOs: 693 and 694 and siXOl2-M3S of SEQ ID NOs: 695 and 696;

or the siRNA is selected from the group consisting of: siXOa1-M1P1 of SEQ ID NOs: 37 and 38, siXOa1-M2P1 of SEQ ID NOs: 39 and 40, siXOa1-M3P1 of SEQ ID NOs: 41 and 42, siXOa2-M1P1 of SEQ ID NOs: 43 and 44, siXOa2-M2P1 of SEQ ID NOs: 45 and 46, siXOa2-M3P1 of SEQ ID NOs: 47 and 48, siXOa1-M1SP1 of SEQ ID NOs: 49 and 50, siXOa1-M2SP1 of SEQ ID NOs: 51 and 52, siXOa1-M3SP1 of SEQ ID NOs: 53 and 54, siXOa2-M1SP1 of SEQ ID NOs: 55 and 56, siXOa2-M2SP1 of SEQ ID NOs: 57 and 58, siXOa2-M3SP1 of SEQ ID NOs: 59 and 60, siXOb1-M1P1 of SEQ ID NOs: 97 and 98, siXOb1-M2P1 of SEQ ID NOs: 99 and 100, siXOb1-M3P1 of SEQ ID NOs: 101 and 102, siXOb2-M1P1 of SEQ ID NOs: 103 and 104, siXOb2-M2P1 of SEQ ID NOs: 105 and 106, siXOb2-M3P1 of SEQ ID NOs: 107 and 108, siXOb1-M1SP1 of SEQ ID NOs: 109 and 110, siXOb1-M2SP1 of SEQ ID NOs: 111 and 112, siXOb1-M3SP1 of SEQ ID NOs: 113 and 114, siXOb2-M1SP1 of SEQ ID NOs: 115 and 116, siXOb2-M2SP1 of SEQ ID NOs: 117 and 118, siXOb2-M3SP1 of SEQ ID NOs: 119 and 120, siXOc1-M1P1 of SEQ ID NOs: 157 and 158, siXOc1-M2P1 of SEQ ID NOs: 159 and 160, siXOc1-M3P1 of SEQ ID NOs: 161 and 162, siXOc2-M1P1 of SEQ ID NOs: 163 and 164, siXOc2-M2P1 of SEQ ID NOs: 165 and 166, siXOc2-M3P1 of SEQ ID NOs: 167 and 168, siXOc1-M1SP1 of SEQ ID NOs: 169 and 170, siXOc1-M2SP1 of SEQ ID NOs: 171 and 172, siXOc1-M3SP1 of SEQ ID NOs: 173 and 174, siXOc2-M1SP1 of SEQ ID NOs: 175 and 176, siXOc2-M2SP1 of SEQ ID NOs: 177 and 178, siXOc2-M3SP1 of SEQ ID NOs: 179 and 180, siXOd1-M1P1 of SEQ ID NOs: 217 and 218, siXOd1-M2P1 of SEQ ID NOs: 219 and 220, siXOd1-M3P1 of SEQ ID NOs: 221 and 222, siXOd2-M1P1 of SEQ ID NOs: 223 and 224, siXOd2-M2P1 of SEQ ID NOs: 225 and 226, siXOd2-M3P1 of SEQ ID NOs: 227 and 228, siXOd1-M1SP1 of SEQ ID NOs: 229 and 230, siXOd1-M2SP1 of SEQ ID NOs: 231 and 232, siXOd1-M3SP1 of SEQ ID NOs: 233 and 234, siXOd2-M1SP1 of SEQ ID NOs: 235 and 236, siXOd2-M2SP1 of SEQ ID NOs: 237 and 238, siXOd2-M3SP1 of SEQ ID NOs: 239 and 240, siXOe1-M1P1 of SEQ ID NOs: 277 and 278, siXOe1-M2P1 of SEQ ID NOs: 279 and 280, siXOe1-M3P1 of SEQ ID NOs: 281 and 282, siXOe2-M1P1 of SEQ ID NOs: 283 and 284, siXOe2-M2P1 of SEQ ID NOs: 285 and 286, siXOe2-M3P1 of SEQ ID NOs: 287 and 288, siXOe1-M1SP1 of SEQ ID NOs: 289 and 290, siXOe1-M2SP1 of SEQ ID NOs: 291 and 292, siXOe1-M3SP1 of SEQ ID NOs: 293 and 294, siXOe2-M1SP1 of SEQ ID NOs: 295 and 296, siXOe2-M2SP1 of SEQ ID NOs: 297 and 298, siXOe2-M3SP1 of SEQ ID NOs: 299 and 300, siXOf1-M1P1 of SEQ ID NOs: 337 and 338, sixOf1-M2P1 of SEQ ID NOs: 339 and 340, siXOf1-M3P1 of SEQ ID NOs: 341 and 342, siXOf2-M1P1 of SEQ ID NOs: 343 and 344, siXOf2-M2P1 of SEQ ID NOs: 345 and 346, siXOf2-M3P1 of SEQ ID NOs: 347 and 348, siXOf1-M1SP1 of SEQ ID NOs: 349 and 350, siXOf1-M2SP1 of SEQ ID NOs: 351 and 352, siXOf1-M3SP1 of SEQ ID NOs: 353 and 354, siXOf2-M1SP1 of SEQ ID NOs: 355 and 356, siXOf2-M2SP1 of SEQ ID NOs: 357 and 358, siXOf2-M3SP1 of SEQ ID NOs: 359 and 360, siXOg1-M1P1 of SEQ ID NOs: 397 and 398, siXOg1-M2P1 of SEQ ID NOs: 399 and 400, siXOg1-M3P1 of SEQ ID NOs: 401 and 402, siXOg2-M1P1 of SEQ ID NOs: 403 and 404, siXOg2-M2P1 of SEQ ID NOs: 405 and 406, siXOg2-M3P1 of SEQ ID NOs: 407 and 408, siXOg1-M1SP1 of SEQ ID NOs: 409 and 410, siXOg1-M2SP1 of SEQ ID NOs: 411 and 412, siXOg1-M3SP1 of SEQ ID NOs: 413 and 414, siXOg2-M1SP1 of SEQ ID NOs: 415 and 416, siXOg2-M2SP1 of SEQ ID NOs: 417 and 418, siXOg2-M3SP1 of SEQ ID NOs: 419 and 420, siXOh1-M1P1 of SEQ ID NOs: 457 and 458, siXOh1-M2P1 of SEQ ID NOs: 459 and 460, siXOh1-M3P1 of SEQ ID NOs: 461 and 462, siXOh2-M1P1 of SEQ ID NOs: 463 and 464, siXOh2-M2P1 of SEQ ID NOs: 465 and 466, siXOh2-M3P1 of SEQ ID NOs: 467 and 468, siXOh1-M1SP1 of SEQ ID NOs: 469 and 470, siXOh1-M2SP1 of SEQ ID NOs: 471 and 472, siXOh1-M3SP1 of SEQ ID NOs: 473 and 474, siXOh2-M1SP1 of SEQ ID NOs: 475 and 476, siXOh2-M2SP1 of SEQ ID NOs: 477 and 478, siXOh2-M3SP1 of SEQ ID NOs: 479 and 480, siXOi1-M1P1 of SEQ ID NOs: 517 and 518, siXOi1-M2P1 of SEQ ID NOs: 519 and 520, siXOi1-M3P1 of SEQ ID NOs: 521 and 522, siXOi2-M1P1 of SEQ ID NOs: 523 and 524, siXOi2-M2P1 of SEQ ID NOs: 525 and 526, siXOi2-M3P1 of SEQ ID NOs: 527 and 528, sixOi1-M1SP1 of SEQ ID NOs: 529 and 530, siXOi1-M2SP1 of SEQ ID NOs: 531 and 532, siXOi1-M3SP1 of SEQ ID NOs: 533 and 534, siXOi2-M1SP1 of SEQ ID NOs: 535 and 536, siXOi2-M2SP1 of SEQ ID NOs: 537 and 538, siXOi2-M3SP1 of SEQ ID NOs: 539 and 540, siXOj1-M1P1 of SEQ ID NOs: 577 and 578, siXOj1-M2P1 of SEQ ID NOs: 579 and 580, siXOj1-M3P1 of SEQ ID NOs: 581 and 582, siXOj2-M1P1 of SEQ ID NOs: 583 and 584, siXOj2-M2P1 of SEQ ID NOs: 585 and 586, siXOj2-M3P1 of SEQ ID NOs: 587 and 588, siXOk1-M1P1 of SEQ ID NOs: 637 and 638, siXOk1-M2P1 of SEQ ID NOs: 639 and 640, siXOk1-M3P1 of SEQ ID NOs: 641 and 642, siXOk2-M1P1 of SEQ ID NOs: 643 and 644, siXOk2-M2P1 of SEQ ID NOs: 645 and 646, siXOk2-M3P1 of SEQ ID NOs: 647 and 648, siXO11-M1P1 of SEQ ID NOs: 697 and 698, siXO11-M2P1 of SEQ ID NOs: 699 and 700, siXO11-M3P1 of SEQ ID NOs: 701 and 702, siXO12-M1P1 of SEQ ID NOs: 703 and 704, siXO12-M2P1 of SEQ ID NOs: 705 and 706, siXO12-M3P1 of SEQ ID NOs: 707 and 708, siXOj1-M1SP1 of SEQ ID NOs: 589 and 590, siXOj1-M2SP1 of SEQ ID NOs: 591 and 592, siXOj1-M3SP1 of SEQ ID NOs: 593 and 594, siXOj2-M1SP1 of SEQ ID NOs: 595 and 596, siXOj2-M2SP1 of SEQ ID NOs: 597 and 598, siXOj2-M3SP1 of SEQ ID NOs: 599 and 600, siXOk1-M1SP1 of SEQ ID NOs: 649 and 650, siXOk1-M2SP1 of SEQ ID NOs: 651 and 652, siXOk1-M3SP1 of SEQ ID NOs: 653 and 654, siXOk2-M1SP1 of SEQ ID NOs: 655 and 656, siXOk2-M2SP1 of SEQ ID NOs: 657 and 658, siXOk2-M3SP1 of SEQ ID NOs: 659 and 660, siXO11-M1SP1 of SEQ ID NOs: 709 and 710, siXO11-M2SP1 of SEQ ID NOs: 711 and 712, siXO11-M3SP1 of SEQ ID NOs: 713 and 714, siXO12-M1SP1 of SEQ ID NOs: 715 and 716, siXO12-M2SP1 of SEQ ID NOs: 717 and 718 and siXO12-M3SP1 of SEQ ID NOs: 719 and 720.

14. The siRNA conjugate according to claim 1, wherein each $L_1$ is independently selected from the group consisting of groups A1-A26 and any combinations thereof:

(A1)

(A2)

(A3)

(A4)

-continued (A5)

(A6)

(A7)

(A8)

(A9)

(A10)

(A11)

(A12)

(A13)

(A14)

(A15)

(A16)

(A17)

433

-continued

434

-continued (A18)

(A19)

(A20)

(A21)

(A22)

(A23)

(A24)

(A25)

(A26)

wherein, each j1 is independently an integer of 1-20;

each j2 is independently an integer of 1-20;

each R' is independently a $C_1$-$C_{10}$ alkyl; and each Ra is independently selected from the group consisting of groups A27-A45 and any combinations thereof:

(A27)

(A28)

(A29)

(A30)

(A31)

(A32)

(A33)

(A34)

(A35)

(A36)

(A37)

(A38)

US 12,577,565 B2

435

-continued (A39)

H₂N—C(=O), (A40)

(A41)

HO—C(=O), (A42)

HO—C(=O), (A43)

NH₂

436

-continued (A44)

or (A45)

each Rb is independently a $C_1$-$C_{10}$ alkyl; and
〜 represents a site where the group is covalently linked.

15. The siRNA conjugate according to claim 14, wherein $L_1$ is selected from the connection combinations of one or more of groups A1, A4, A5, A6, A8, A10, A11, and A13; or $L_1$ is the connection combinations of at least two of groups A1, A4, A8, A10, and A11.

16. The siRNA conjugate according to claim 1, wherein the length of $L_1$ is 3-25 atoms; or the length of $L_1$ is 4-15 atoms.

17. The siRNA conjugate according to claim 1, wherein each of m1, m2 and m3 is independently an integer of 2-5; or m1=m2=m3.

18. The siRNA conjugate according to claim 1, wherein each targeting group is independently a ligand that binds to an asialoglycoprotein receptor on a surface of a mammalian hepatocyte, or at least one or each targeting group is galactose or N-acetylgalactosamine.

19. The siRNA conjugate according to claim 1, wherein the siRNA conjugate has a structure as shown by Formula (403), (404), (405), (406), (407), (408), (409), (410), (411), (412), (413), (414), (415), (416), (417), (418), (419), (420), (421) or (422):

Formula (403)

-continued

Formula (404)

Formula (405)

439                                                                                          440

-continued

Formula (406)

Formula (407)

Formula (408)

Formula (409)

Formula (410)

-continued

Formula (411)

Formula (412)

443 444

-continued

Formula (413)

Formula (414)

Formula (415)

445 446

Formula (416)

Formula (417)

Formula (418)

Formula (419)

-continued

Formula (420)

Formula (421)

Formula (422)

20. The siRNA conjugate according to claim 1, wherein the P atom in Formula A59 is linked to a 3' terminal of the sense strand of the siRNA.

* * * * *

SEQUENCE LISTING

```
<160> NUMBER OF SEQ ID NOS: 742

<210> SEQ ID NO 1
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z1, and Z1 is A

<400> SEQUENCE: 1
gagaugaagu ucaagaaun                                              19

<210> SEQ ID NO 2
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z2, and Z2 is U

<400> SEQUENCE: 2
nauucuugaa cuucaucuc                                              19

<210> SEQ ID NO 3
```

-continued

```
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z3, Z3 is a nucleotide complementary to
      Z4, and Z4 is selected from A, U, G or C

<400> SEQUENCE: 3
gagaugaagu ucaagaaun                                                    19

<210> SEQ ID NO 4
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z4, and Z4 is selected from A, U, G or C

<400> SEQUENCE: 4
nauucuugaa cuucaucuc                                                    19

<210> SEQ ID NO 5
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z3, Z3 is a nucleotide complementary to
      Z4, and Z4 is selected from A, U, G or C

<400> SEQUENCE: 5
gagaugaagu ucaagaaun                                                    19

<210> SEQ ID NO 6
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z4, and Z4 is selected from A, U, G or C

<400> SEQUENCE: 6
nauucuugaa cuucaucuca a                                                 21

<210> SEQ ID NO 7
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z3, Z3 is a nucleotide complementary to
      Z4, and Z4 is selected from A, U, G or C

<400> SEQUENCE: 7
```

-continued uugagaugaa guucaagaau n                                                                      21

<210> SEQ ID NO 8
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z4, and Z4 is selected from A, U, G or C

<400> SEQUENCE: 8
nauucuugaa cuucaucuca aug                                                                    23

<210> SEQ ID NO 9
<211> LENGTH: 19
<212> TYPE: RNA
<213> ORGANISM: Artificial Sequence
<220> FEATURE:
<223> OTHER INFORMATION: siRNA

<400> SEQUENCE: 9
gagaugaagu ucaagaaua                                                                         19

<210> SEQ ID NO 10
<211> LENGTH: 21
<212> TYPE: RNA
<213> ORGANISM: Artificial Sequence
<220> FEATURE:
<223> OTHER INFORMATION: siRNA

<400> SEQUENCE: 10
uauucuugaa cuucaucuca a                                                                      21

<210> SEQ ID NO 11
<211> LENGTH: 21
<212> TYPE: RNA
<213> ORGANISM: Artificial Sequence
<220> FEATURE:
<223> OTHER INFORMATION: siRNA

<400> SEQUENCE: 11
uugagaugaa guucaagaau a                                                                      21

<210> SEQ ID NO 12
<211> LENGTH: 23
<212> TYPE: RNA
<213> ORGANISM: Artificial Sequence
<220> FEATURE:
<223> OTHER INFORMATION: siRNA

<400> SEQUENCE: 12
uauucuugaa cuucaucuca aug                                                                    23

<210> SEQ ID NO 13
<211> LENGTH: 19
<212> TYPE: RNA
<213> ORGANISM: Artificial Sequence
<220> FEATURE:
<223> OTHER INFORMATION: siRNA

<400> SEQUENCE: 13
gagaugaagu ucaagaaua                                                                         19

-continued

```
<210> SEQ ID NO 14
<211> LENGTH: 21
<212> TYPE: RNA
<213> ORGANISM: Artificial Sequence
<220> FEATURE:
<223> OTHER INFORMATION: siRNA

<400> SEQUENCE: 14
uauucuugaa cuucaucuca a                                               21

<210> SEQ ID NO 15
<211> LENGTH: 19
<212> TYPE: RNA
<213> ORGANISM: Artificial Sequence
<220> FEATURE:
<223> OTHER INFORMATION: siRNA

<400> SEQUENCE: 15
gagaugaagu ucaagaaua                                                  19

<210> SEQ ID NO 16
<211> LENGTH: 21
<212> TYPE: RNA
<213> ORGANISM: Artificial Sequence
<220> FEATURE:
<223> OTHER INFORMATION: siRNA

<400> SEQUENCE: 16
uauucuugaa cuucaucuca a                                               21

<210> SEQ ID NO 17
<211> LENGTH: 19
<212> TYPE: RNA
<213> ORGANISM: Artificial Sequence
<220> FEATURE:
<223> OTHER INFORMATION: siRNA

<400> SEQUENCE: 17
gagaugaagu ucaagaaua                                                  19

<210> SEQ ID NO 18
<211> LENGTH: 21
<212> TYPE: RNA
<213> ORGANISM: Artificial Sequence
<220> FEATURE:
<223> OTHER INFORMATION: siRNA

<400> SEQUENCE: 18
uauucuugaa cuucaucuca a                                               21

<210> SEQ ID NO 19
<211> LENGTH: 21
<212> TYPE: RNA
<213> ORGANISM: Artificial Sequence
<220> FEATURE:
<223> OTHER INFORMATION: siRNA

<400> SEQUENCE: 19
uugagaugaa guucaagaau a                                               21

<210> SEQ ID NO 20
<211> LENGTH: 23
<212> TYPE: RNA
<213> ORGANISM: Artificial Sequence
<220> FEATURE:
<223> OTHER INFORMATION: siRNA
```

-continued

```
<400> SEQUENCE: 20
uauucuugaa cuucaucuca aug                                        23

<210> SEQ ID NO 21
<211> LENGTH: 21
<212> TYPE: RNA
<213> ORGANISM: Artificial Sequence
<220> FEATURE:
<223> OTHER INFORMATION: siRNA

<400> SEQUENCE: 21
uugagaugaa guucaagaau a                                          21

<210> SEQ ID NO 22
<211> LENGTH: 23
<212> TYPE: RNA
<213> ORGANISM: Artificial Sequence
<220> FEATURE:
<223> OTHER INFORMATION: siRNA

<400> SEQUENCE: 22
uauucuugaa cuucaucuca aug                                        23

<210> SEQ ID NO 23
<211> LENGTH: 21
<212> TYPE: RNA
<213> ORGANISM: Artificial Sequence
<220> FEATURE:
<223> OTHER INFORMATION: siRNA

<400> SEQUENCE: 23
uugagaugaa guucaagaau a                                          21

<210> SEQ ID NO 24
<211> LENGTH: 23
<212> TYPE: RNA
<213> ORGANISM: Artificial Sequence
<220> FEATURE:
<223> OTHER INFORMATION: siRNA

<400> SEQUENCE: 24
uauucuugaa cuucaucuca aug                                        23

<210> SEQ ID NO 25
<211> LENGTH: 19
<212> TYPE: RNA
<213> ORGANISM: Artificial Sequence
<220> FEATURE:
<223> OTHER INFORMATION: siRNA

<400> SEQUENCE: 25
gagaugaagu ucaagaaua                                             19

<210> SEQ ID NO 26
<211> LENGTH: 21
<212> TYPE: RNA
<213> ORGANISM: Artificial Sequence
<220> FEATURE:
<223> OTHER INFORMATION: siRNA

<400> SEQUENCE: 26
uauucuugaa cuucaucuca a                                          21

<210> SEQ ID NO 27
<211> LENGTH: 19
```

-continued

```
<212> TYPE: RNA
<213> ORGANISM: Artificial Sequence
<220> FEATURE:
<223> OTHER INFORMATION: siRNA

<400> SEQUENCE: 27
gagaugaagu ucaagaaua                                                    19

<210> SEQ ID NO 28
<211> LENGTH: 21
<212> TYPE: RNA
<213> ORGANISM: Artificial Sequence
<220> FEATURE:
<223> OTHER INFORMATION: siRNA

<400> SEQUENCE: 28
uauucuugaa cuucaucuca a                                                 21

<210> SEQ ID NO 29
<211> LENGTH: 19
<212> TYPE: RNA
<213> ORGANISM: Artificial Sequence
<220> FEATURE:
<223> OTHER INFORMATION: siRNA

<400> SEQUENCE: 29
gagaugaagu ucaagaaua                                                    19

<210> SEQ ID NO 30
<211> LENGTH: 21
<212> TYPE: RNA
<213> ORGANISM: Artificial Sequence
<220> FEATURE:
<223> OTHER INFORMATION: siRNA

<400> SEQUENCE: 30
uauucuugaa cuucaucuca a                                                 21

<210> SEQ ID NO 31
<211> LENGTH: 21
<212> TYPE: RNA
<213> ORGANISM: Artificial Sequence
<220> FEATURE:
<223> OTHER INFORMATION: siRNA

<400> SEQUENCE: 31
uugagaugaa guucaagaau a                                                 21

<210> SEQ ID NO 32
<211> LENGTH: 23
<212> TYPE: RNA
<213> ORGANISM: Artificial Sequence
<220> FEATURE:
<223> OTHER INFORMATION: siRNA

<400> SEQUENCE: 32
uauucuugaa cuucaucuca aug                                               23

<210> SEQ ID NO 33
<211> LENGTH: 21
<212> TYPE: RNA
<213> ORGANISM: Artificial Sequence
<220> FEATURE:
<223> OTHER INFORMATION: siRNA

<400> SEQUENCE: 33
```

```
uugagaugaa guucaagaau a                                              21

<210> SEQ ID NO 34
<211> LENGTH: 23
<212> TYPE: RNA
<213> ORGANISM: Artificial Sequence
<220> FEATURE:
<223> OTHER INFORMATION: siRNA

<400> SEQUENCE: 34
uauucuugaa cuucaucuca aug                                            23

<210> SEQ ID NO 35
<211> LENGTH: 21
<212> TYPE: RNA
<213> ORGANISM: Artificial Sequence
<220> FEATURE:
<223> OTHER INFORMATION: siRNA

<400> SEQUENCE: 35
uugagaugaa guucaagaau a                                              21

<210> SEQ ID NO 36
<211> LENGTH: 23
<212> TYPE: RNA
<213> ORGANISM: Artificial Sequence
<220> FEATURE:
<223> OTHER INFORMATION: siRNA

<400> SEQUENCE: 36
uauucuugaa cuucaucuca aug                                            23

<210> SEQ ID NO 37
<211> LENGTH: 19
<212> TYPE: RNA
<213> ORGANISM: Artificial Sequence
<220> FEATURE:
<223> OTHER INFORMATION: siRNA

<400> SEQUENCE: 37
gagaugaagu ucaagaaua                                                 19

<210> SEQ ID NO 38
<211> LENGTH: 21
<212> TYPE: RNA
<213> ORGANISM: Artificial Sequence
<220> FEATURE:
<223> OTHER INFORMATION: siRNA

<400> SEQUENCE: 38
uauucuugaa cuucaucuca a                                              21

<210> SEQ ID NO 39
<211> LENGTH: 19
<212> TYPE: RNA
<213> ORGANISM: Artificial Sequence
<220> FEATURE:
<223> OTHER INFORMATION: siRNA

<400> SEQUENCE: 39
gagaugaagu ucaagaaua                                                 19

<210> SEQ ID NO 40
<211> LENGTH: 21
<212> TYPE: RNA
<213> ORGANISM: Artificial Sequence
```

-continued

```
<220> FEATURE:
<223> OTHER INFORMATION: siRNA

<400> SEQUENCE: 40
uauucuugaa cuucaucuca a                                              21

<210> SEQ ID NO 41
<211> LENGTH: 19
<212> TYPE: RNA
<213> ORGANISM: Artificial Sequence
<220> FEATURE:
<223> OTHER INFORMATION: siRNA

<400> SEQUENCE: 41
gagaugaagu ucaagaaua                                                 19

<210> SEQ ID NO 42
<211> LENGTH: 21
<212> TYPE: RNA
<213> ORGANISM: Artificial Sequence
<220> FEATURE:
<223> OTHER INFORMATION: siRNA

<400> SEQUENCE: 42
uauucuugaa cuucaucuca a                                              21

<210> SEQ ID NO 43
<211> LENGTH: 21
<212> TYPE: RNA
<213> ORGANISM: Artificial Sequence
<220> FEATURE:
<223> OTHER INFORMATION: siRNA

<400> SEQUENCE: 43
uugagaugaa guucaagaau a                                              21

<210> SEQ ID NO 44
<211> LENGTH: 23
<212> TYPE: RNA
<213> ORGANISM: Artificial Sequence
<220> FEATURE:
<223> OTHER INFORMATION: siRNA

<400> SEQUENCE: 44
uauucuugaa cuucaucuca aug                                            23

<210> SEQ ID NO 45
<211> LENGTH: 21
<212> TYPE: RNA
<213> ORGANISM: Artificial Sequence
<220> FEATURE:
<223> OTHER INFORMATION: siRNA

<400> SEQUENCE: 45
uugagaugaa guucaagaau a                                              21

<210> SEQ ID NO 46
<211> LENGTH: 23
<212> TYPE: RNA
<213> ORGANISM: Artificial Sequence
<220> FEATURE:
<223> OTHER INFORMATION: siRNA

<400> SEQUENCE: 46
uauucuugaa cuucaucuca aug                                            23
```

-continued

```
<210> SEQ ID NO 47
<211> LENGTH: 21
<212> TYPE: RNA
<213> ORGANISM: Artificial Sequence
<220> FEATURE:
<223> OTHER INFORMATION: siRNA

<400> SEQUENCE: 47
uugagaugaa guucaagaau a                                              21

<210> SEQ ID NO 48
<211> LENGTH: 23
<212> TYPE: RNA
<213> ORGANISM: Artificial Sequence
<220> FEATURE:
<223> OTHER INFORMATION: siRNA

<400> SEQUENCE: 48
uauucuugaa cuucaucuca aug                                            23

<210> SEQ ID NO 49
<211> LENGTH: 19
<212> TYPE: RNA
<213> ORGANISM: Artificial Sequence
<220> FEATURE:
<223> OTHER INFORMATION: siRNA

<400> SEQUENCE: 49
gagaugaagu ucaagaaua                                                 19

<210> SEQ ID NO 50
<211> LENGTH: 21
<212> TYPE: RNA
<213> ORGANISM: Artificial Sequence
<220> FEATURE:
<223> OTHER INFORMATION: siRNA

<400> SEQUENCE: 50
uauucuugaa cuucaucuca a                                              21

<210> SEQ ID NO 51
<211> LENGTH: 19
<212> TYPE: RNA
<213> ORGANISM: Artificial Sequence
<220> FEATURE:
<223> OTHER INFORMATION: siRNA

<400> SEQUENCE: 51
gagaugaagu ucaagaaua                                                 19

<210> SEQ ID NO 52
<211> LENGTH: 21
<212> TYPE: RNA
<213> ORGANISM: Artificial Sequence
<220> FEATURE:
<223> OTHER INFORMATION: siRNA

<400> SEQUENCE: 52
uauucuugaa cuucaucuca a                                              21

<210> SEQ ID NO 53
<211> LENGTH: 19
<212> TYPE: RNA
<213> ORGANISM: Artificial Sequence
<220> FEATURE:
<223> OTHER INFORMATION: siRNA
```

-continued

<400> SEQUENCE: 53
gagaugaagu ucaagaaua                                                                                    19

<210> SEQ ID NO 54
<211> LENGTH: 21
<212> TYPE: RNA
<213> ORGANISM: Artificial Sequence
<220> FEATURE:
<223> OTHER INFORMATION: siRNA

<400> SEQUENCE: 54
uauucuugaa cuucaucuca a                                                                                 21

<210> SEQ ID NO 55
<211> LENGTH: 21
<212> TYPE: RNA
<213> ORGANISM: Artificial Sequence
<220> FEATURE:
<223> OTHER INFORMATION: siRNA

<400> SEQUENCE: 55
uugagaugaa guucaagaau a                                                                                 21

<210> SEQ ID NO 56
<211> LENGTH: 23
<212> TYPE: RNA
<213> ORGANISM: Artificial Sequence
<220> FEATURE:
<223> OTHER INFORMATION: siRNA

<400> SEQUENCE: 56
uauucuugaa cuucaucuca aug                                                                               23

<210> SEQ ID NO 57
<211> LENGTH: 21
<212> TYPE: RNA
<213> ORGANISM: Artificial Sequence
<220> FEATURE:
<223> OTHER INFORMATION: siRNA

<400> SEQUENCE: 57
uugagaugaa guucaagaau a                                                                                 21

<210> SEQ ID NO 58
<211> LENGTH: 23
<212> TYPE: RNA
<213> ORGANISM: Artificial Sequence
<220> FEATURE:
<223> OTHER INFORMATION: siRNA

<400> SEQUENCE: 58
uauucuugaa cuucaucuca aug                                                                               23

<210> SEQ ID NO 59
<211> LENGTH: 21
<212> TYPE: RNA
<213> ORGANISM: Artificial Sequence
<220> FEATURE:
<223> OTHER INFORMATION: siRNA

<400> SEQUENCE: 59
uugagaugaa guucaagaau a                                                                                 21

<210> SEQ ID NO 60

-continued

```
<211> LENGTH: 23
<212> TYPE: RNA
<213> ORGANISM: Artificial Sequence
<220> FEATURE:
<223> OTHER INFORMATION: siRNA

<400> SEQUENCE: 60
uauucuugaa cuucaucuca aug                                            23

<210> SEQ ID NO 61
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z5, and Z5 is U

<400> SEQUENCE: 61
cauaacugga auuuguaan                                                 19

<210> SEQ ID NO 62
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z6, and Z6 is A

<400> SEQUENCE: 62
nuuacaaauu ccaguuaug                                                 19

<210> SEQ ID NO 63
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z7, Z7 is a nucleotide complementary to
     Z8, and Z8 is selected from A, U, G or C

<400> SEQUENCE: 63
cauaacugga auuuguaan                                                 19

<210> SEQ ID NO 64
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z8, and Z8 is selected from A, U, G or C

<400> SEQUENCE: 64
nuuacaaauu ccaguuaug                                                 19

<210> SEQ ID NO 65
<211> LENGTH: 19
<212> TYPE: RNA
```

-continued

```
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z7, Z7 is a nucleotide complementary to
      Z8, and Z8 is selected from A, U, G or C

<400> SEQUENCE: 65
cauaacugga auuuguaan                                                       19

<210> SEQ ID NO 66
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z8, and Z8 is selected from A, U, G or C

<400> SEQUENCE: 66
nuuacaaauu ccaguuaugu u                                                    21

<210> SEQ ID NO 67
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z7, Z7 is a nucleotide complementary to
      Z8, and Z8 is selected from A, U, G or C

<400> SEQUENCE: 67
aacauaacug gaauuuguaa n                                                    21

<210> SEQ ID NO 68
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z8, and Z8 is selected from A, U, G or C

<400> SEQUENCE: 68
nuuacaaauu ccaguuaugu uac                                                  23

<210> SEQ ID NO 69
<211> LENGTH: 19
<212> TYPE: RNA
<213> ORGANISM: Artificial Sequence
<220> FEATURE:
<223> OTHER INFORMATION: siRNA

<400> SEQUENCE: 69
cauaacugga auuuguaau                                                       19

<210> SEQ ID NO 70
<211> LENGTH: 21
<212> TYPE: RNA
<213> ORGANISM: Artificial Sequence
```

-continued

```
<220> FEATURE:
<223> OTHER INFORMATION: siRNA

<400> SEQUENCE: 70
auuacaaauu ccaguuaugu u                                                     21

<210> SEQ ID NO 71
<211> LENGTH: 21
<212> TYPE: RNA
<213> ORGANISM: Artificial Sequence
<220> FEATURE:
<223> OTHER INFORMATION: siRNA

<400> SEQUENCE: 71
aacauaacug gaauuuguaa u                                                     21

<210> SEQ ID NO 72
<211> LENGTH: 23
<212> TYPE: RNA
<213> ORGANISM: Artificial Sequence
<220> FEATURE:
<223> OTHER INFORMATION: siRNA

<400> SEQUENCE: 72
auuacaaauu ccaguuaugu uac                                                   23

<210> SEQ ID NO 73
<211> LENGTH: 19
<212> TYPE: RNA
<213> ORGANISM: Artificial Sequence
<220> FEATURE:
<223> OTHER INFORMATION: siRNA

<400> SEQUENCE: 73
cauaacugga auuuguaau                                                        19

<210> SEQ ID NO 74
<211> LENGTH: 21
<212> TYPE: RNA
<213> ORGANISM: Artificial Sequence
<220> FEATURE:
<223> OTHER INFORMATION: siRNA

<400> SEQUENCE: 74
auuacaaauu ccaguuaugu u                                                     21

<210> SEQ ID NO 75
<211> LENGTH: 19
<212> TYPE: RNA
<213> ORGANISM: Artificial Sequence
<220> FEATURE:
<223> OTHER INFORMATION: siRNA

<400> SEQUENCE: 75
cauaacugga auuuguaau                                                        19

<210> SEQ ID NO 76
<211> LENGTH: 21
<212> TYPE: RNA
<213> ORGANISM: Artificial Sequence
<220> FEATURE:
<223> OTHER INFORMATION: siRNA

<400> SEQUENCE: 76
auuacaaauu ccaguuaugu u                                                     21
```

```
<210> SEQ ID NO 77
<211> LENGTH: 19
<212> TYPE: RNA
<213> ORGANISM: Artificial Sequence
<220> FEATURE:
<223> OTHER INFORMATION: siRNA

<400> SEQUENCE: 77
cauaacugga auuuguaau                                                      19

<210> SEQ ID NO 78
<211> LENGTH: 21
<212> TYPE: RNA
<213> ORGANISM: Artificial Sequence
<220> FEATURE:
<223> OTHER INFORMATION: siRNA

<400> SEQUENCE: 78
auuacaaauu ccaguuaugu u                                                   21

<210> SEQ ID NO 79
<211> LENGTH: 21
<212> TYPE: RNA
<213> ORGANISM: Artificial Sequence
<220> FEATURE:
<223> OTHER INFORMATION: siRNA

<400> SEQUENCE: 79
aacauaacug gaauuuguaa u                                                   21

<210> SEQ ID NO 80
<211> LENGTH: 23
<212> TYPE: RNA
<213> ORGANISM: Artificial Sequence
<220> FEATURE:
<223> OTHER INFORMATION: siRNA

<400> SEQUENCE: 80
auuacaaauu ccaguuaugu uac                                                 23

<210> SEQ ID NO 81
<211> LENGTH: 21
<212> TYPE: RNA
<213> ORGANISM: Artificial Sequence
<220> FEATURE:
<223> OTHER INFORMATION: siRNA

<400> SEQUENCE: 81
aacauaacug gaauuuguaa u                                                   21

<210> SEQ ID NO 82
<211> LENGTH: 23
<212> TYPE: RNA
<213> ORGANISM: Artificial Sequence
<220> FEATURE:
<223> OTHER INFORMATION: siRNA

<400> SEQUENCE: 82
auuacaaauu ccaguuaugu uac                                                 23

<210> SEQ ID NO 83
<211> LENGTH: 21
<212> TYPE: RNA
<213> ORGANISM: Artificial Sequence
<220> FEATURE:
<223> OTHER INFORMATION: siRNA
```

-continued

<400> SEQUENCE: 83
aacauaacug gaauuuguaa u                                              21

<210> SEQ ID NO 84
<211> LENGTH: 23
<212> TYPE: RNA
<213> ORGANISM: Artificial Sequence
<220> FEATURE:
<223> OTHER INFORMATION: siRNA

<400> SEQUENCE: 84
auuacaaauu ccaguuaugu uac                                            23

<210> SEQ ID NO 85
<211> LENGTH: 19
<212> TYPE: RNA
<213> ORGANISM: Artificial Sequence
<220> FEATURE:
<223> OTHER INFORMATION: siRNA

<400> SEQUENCE: 85
cauaacugga auuuguaau                                                 19

<210> SEQ ID NO 86
<211> LENGTH: 21
<212> TYPE: RNA
<213> ORGANISM: Artificial Sequence
<220> FEATURE:
<223> OTHER INFORMATION: siRNA

<400> SEQUENCE: 86
auuacaaauu ccaguuaugu u                                              21

<210> SEQ ID NO 87
<211> LENGTH: 19
<212> TYPE: RNA
<213> ORGANISM: Artificial Sequence
<220> FEATURE:
<223> OTHER INFORMATION: siRNA

<400> SEQUENCE: 87
cauaacugga auuuguaau                                                 19

<210> SEQ ID NO 88
<211> LENGTH: 21
<212> TYPE: RNA
<213> ORGANISM: Artificial Sequence
<220> FEATURE:
<223> OTHER INFORMATION: sina

<400> SEQUENCE: 88
auuacaaauu ccaguuaugu u                                              21

<210> SEQ ID NO 89
<211> LENGTH: 19
<212> TYPE: RNA
<213> ORGANISM: Artificial Sequence
<220> FEATURE:
<223> OTHER INFORMATION: siRNA

<400> SEQUENCE: 89
cauaacugga auuuguaau                                                 19

<210> SEQ ID NO 90

-continued

```
<211> LENGTH: 21
<212> TYPE: RNA
<213> ORGANISM: Artificial Sequence
<220> FEATURE:
<223> OTHER INFORMATION: siRNA

<400> SEQUENCE: 90
auuacaaauu ccaguuaugu u                                           21

<210> SEQ ID NO 91
<211> LENGTH: 21
<212> TYPE: RNA
<213> ORGANISM: Artificial Sequence
<220> FEATURE:
<223> OTHER INFORMATION: siRNA

<400> SEQUENCE: 91
aacauaacug gaauuuguaa u                                           21

<210> SEQ ID NO 92
<211> LENGTH: 23
<212> TYPE: RNA
<213> ORGANISM: Artificial Sequence
<220> FEATURE:
<223> OTHER INFORMATION: siRNA

<400> SEQUENCE: 92
auuacaaauu ccaguuaugu uac                                         23

<210> SEQ ID NO 93
<211> LENGTH: 21
<212> TYPE: RNA
<213> ORGANISM: Artificial Sequence
<220> FEATURE:
<223> OTHER INFORMATION: siRNA

<400> SEQUENCE: 93
aacauaacug gaauuuguaa u                                           21

<210> SEQ ID NO 94
<211> LENGTH: 23
<212> TYPE: RNA
<213> ORGANISM: Artificial Sequence
<220> FEATURE:
<223> OTHER INFORMATION: siRNA

<400> SEQUENCE: 94
auuacaaauu ccaguuaugu uac                                         23

<210> SEQ ID NO 95
<211> LENGTH: 21
<212> TYPE: RNA
<213> ORGANISM: Artificial Sequence
<220> FEATURE:
<223> OTHER INFORMATION: siRNA

<400> SEQUENCE: 95
aacauaacug gaauuuguaa u                                           21

<210> SEQ ID NO 96
<211> LENGTH: 23
<212> TYPE: RNA
<213> ORGANISM: Artificial Sequence
<220> FEATURE:
<223> OTHER INFORMATION: siRNA

<400> SEQUENCE: 96
```

```
auuacaaauu ccaguuaugu uac                                   23

<210> SEQ ID NO 97
<211> LENGTH: 19
<212> TYPE: RNA
<213> ORGANISM: Artificial Sequence
<220> FEATURE:
<223> OTHER INFORMATION: siRNA

<400> SEQUENCE: 97
cauaacugga auuuguaau                                        19

<210> SEQ ID NO 98
<211> LENGTH: 21
<212> TYPE: RNA
<213> ORGANISM: Artificial Sequence
<220> FEATURE:
<223> OTHER INFORMATION: siRNA

<400> SEQUENCE: 98
auuacaaauu ccaguuaugu u                                     21

<210> SEQ ID NO 99
<211> LENGTH: 19
<212> TYPE: RNA
<213> ORGANISM: Artificial Sequence
<220> FEATURE:
<223> OTHER INFORMATION: siRNA

<400> SEQUENCE: 99
cauaacugga auuuguaau                                        19

<210> SEQ ID NO 100
<211> LENGTH: 21
<212> TYPE: RNA
<213> ORGANISM: Artificial Sequence
<220> FEATURE:
<223> OTHER INFORMATION: siRNA

<400> SEQUENCE: 100
auuacaaauu ccaguuaugu u                                     21

<210> SEQ ID NO 101
<211> LENGTH: 19
<212> TYPE: RNA
<213> ORGANISM: Artificial Sequence
<220> FEATURE:
<223> OTHER INFORMATION: siRNA

<400> SEQUENCE: 101
cauaacugga auuuguaau                                        19

<210> SEQ ID NO 102
<211> LENGTH: 21
<212> TYPE: RNA
<213> ORGANISM: Artificial Sequence
<220> FEATURE:
<223> OTHER INFORMATION: siRNA

<400> SEQUENCE: 102
auuacaaauu ccaguuaugu u                                     21

<210> SEQ ID NO 103
<211> LENGTH: 21
<212> TYPE: RNA
<213> ORGANISM: Artificial Sequence
<220> FEATURE:
```

<223> OTHER INFORMATION: siRNA

<400> SEQUENCE: 103
aacauaacug gaauuuguaa u                                    21

<210> SEQ ID NO 104
<211> LENGTH: 23
<212> TYPE: RNA
<213> ORGANISM: Artificial Sequence
<220> FEATURE:
<223> OTHER INFORMATION: siRNA

<400> SEQUENCE: 104
auuacaaauu ccaguuaugu uac                                  23

<210> SEQ ID NO 105
<211> LENGTH: 21
<212> TYPE: RNA
<213> ORGANISM: Artificial Sequence
<220> FEATURE:
<223> OTHER INFORMATION: siRNA

<400> SEQUENCE: 105
aacauaacug gaauuuguaa u                                    21

<210> SEQ ID NO 106
<211> LENGTH: 23
<212> TYPE: RNA
<213> ORGANISM: Artificial Sequence
<220> FEATURE:
<223> OTHER INFORMATION: siRNA

<400> SEQUENCE: 106
auuacaaauu ccaguuaugu uac                                  23

<210> SEQ ID NO 107
<211> LENGTH: 21
<212> TYPE: RNA
<213> ORGANISM: Artificial Sequence
<220> FEATURE:
<223> OTHER INFORMATION: siRNA

<400> SEQUENCE: 107
aacauaacug gaauuuguaa u                                    21

<210> SEQ ID NO 108
<211> LENGTH: 23
<212> TYPE: RNA
<213> ORGANISM: Artificial Sequence
<220> FEATURE:
<223> OTHER INFORMATION: siRNA

<400> SEQUENCE: 108
auuacaaauu ccaguuaugu uac                                  23

<210> SEQ ID NO 109
<211> LENGTH: 19
<212> TYPE: RNA
<213> ORGANISM: Artificial Sequence
<220> FEATURE:
<223> OTHER INFORMATION: siRNA

<400> SEQUENCE: 109
cauaacugga uuuguaau                                        19

-continued

```
<210> SEQ ID NO 110
<211> LENGTH: 21
<212> TYPE: RNA
<213> ORGANISM: Artificial Sequence
<220> FEATURE:
<223> OTHER INFORMATION: siRNA

<400> SEQUENCE: 110
auuacaaauu ccaguuaugu u                                                    21

<210> SEQ ID NO 111
<211> LENGTH: 19
<212> TYPE: RNA
<213> ORGANISM: Artificial Sequence
<220> FEATURE:
<223> OTHER INFORMATION: siRNA

<400> SEQUENCE: 111
cauaacugga auuuguaau                                                       19

<210> SEQ ID NO 112
<211> LENGTH: 21
<212> TYPE: RNA
<213> ORGANISM: Artificial Sequence
<220> FEATURE:
<223> OTHER INFORMATION: siRNA

<400> SEQUENCE: 112
auuacaaauu ccaguuaugu u                                                    21

<210> SEQ ID NO 113
<211> LENGTH: 19
<212> TYPE: RNA
<213> ORGANISM: Artificial Sequence
<220> FEATURE:
<223> OTHER INFORMATION: siRNA

<400> SEQUENCE: 113
cauaacugga auuuguaau                                                       19

<210> SEQ ID NO 114
<211> LENGTH: 21
<212> TYPE: RNA
<213> ORGANISM: Artificial Sequence
<220> FEATURE:
<223> OTHER INFORMATION: siRNA

<400> SEQUENCE: 114
auuacaaauu ccaguuaugu u                                                    21

<210> SEQ ID NO 115
<211> LENGTH: 21
<212> TYPE: RNA
<213> ORGANISM: Artificial Sequence
<220> FEATURE:
<223> OTHER INFORMATION: siRNA

<400> SEQUENCE: 115
aacauaacug gaauuuguaa u                                                    21

<210> SEQ ID NO 116
<211> LENGTH: 23
<212> TYPE: RNA
<213> ORGANISM: Artificial Sequence
<220> FEATURE:
<223> OTHER INFORMATION: siRNA
```

-continued

```
<400> SEQUENCE: 116
auuacaaauu ccaguuaugu uac                                            23

<210> SEQ ID NO 117
<211> LENGTH: 21
<212> TYPE: RNA
<213> ORGANISM: Artificial Sequence
<220> FEATURE:
<223> OTHER INFORMATION: siRNA

<400> SEQUENCE: 117
aacauaacug gaauuuguaa u                                              21

<210> SEQ ID NO 118
<211> LENGTH: 23
<212> TYPE: RNA
<213> ORGANISM: Artificial Sequence
<220> FEATURE:
<223> OTHER INFORMATION: siRNA

<400> SEQUENCE: 118
auuacaaauu ccaguuaugu uac                                            23

<210> SEQ ID NO 119
<211> LENGTH: 21
<212> TYPE: RNA
<213> ORGANISM: Artificial Sequence
<220> FEATURE:
<223> OTHER INFORMATION: siRNA

<400> SEQUENCE: 119
aacauaacug gaauuuguaa u                                              21

<210> SEQ ID NO 120
<211> LENGTH: 23
<212> TYPE: RNA
<213> ORGANISM: Artificial Sequence
<220> FEATURE:
<223> OTHER INFORMATION: siRNA

<400> SEQUENCE: 120
auuacaaauu ccaguuaugu uac                                            23

<210> SEQ ID NO 121
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z9, and Z9 is U

<400> SEQUENCE: 121
cauuaucaca auugaggan                                                 19

<210> SEQ ID NO 122
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z10, and Z10 is A
```

-continued

```
<400> SEQUENCE: 122
nuccucaauu gugauaaug                                                     19

<210> SEQ ID NO 123
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z11, Z11 is a nucleotide complementary to
      Z12, and Z12 is selected from A, U, G or C

<400> SEQUENCE: 123
cauuaucaca auugaggan                                                     19

<210> SEQ ID NO 124
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z12, and Z12 is selected from A, U, G or C

<400> SEQUENCE: 124
nuccucaauu gugauaaug                                                     19

<210> SEQ ID NO 125
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z11, Z11 is a nucleotide complementary to
      Z12, and Z12 is selected from A, U, G or C

<400> SEQUENCE: 125
cauuaucaca auugaggan                                                     19

<210> SEQ ID NO 126
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z12, and Z12 is selected from A, U, G or C

<400> SEQUENCE: 126
nuccucaauu gugauaaugg c                                                  21

<210> SEQ ID NO 127
<211> LENGTH: 21
<212> TYPE: RNA
<213> ORGANISM: Artificial Sequence
<220> FEATURE:
<223> OTHER INFORMATION: siRNA
<220> FEATURE:
```

-continued

```
<221> NAME/KEY: misc_feature
<222> LOCATION: (21)..(21)
<223> OTHER INFORMATION: n is Z11, Z11 is a nucleotide complementary to
      Z12, and Z12 is selected from A, U, G or C

<400> SEQUENCE: 127
gccauuauca caauugagga n                                              21

<210> SEQ ID NO 128
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z12, and Z12 is selected from A, U, G or C

<400> SEQUENCE: 128
nuccucaauu gugauaaugg cug                                            23

<210> SEQ ID NO 129
<211> LENGTH: 19
<212> TYPE: RNA
<213> ORGANISM: Artificial Sequence
<220> FEATURE:
<223> OTHER INFORMATION: siRNA

<400> SEQUENCE: 129
cauuaucaca auugaggau                                                 19

<210> SEQ ID NO 130
<211> LENGTH: 21
<212> TYPE: RNA
<213> ORGANISM: Artificial Sequence
<220> FEATURE:
<223> OTHER INFORMATION: siRNA

<400> SEQUENCE: 130
auccucaauu gugauaaugg c                                              21

<210> SEQ ID NO 131
<211> LENGTH: 21
<212> TYPE: RNA
<213> ORGANISM: Artificial Sequence
<220> FEATURE:
<223> OTHER INFORMATION: siRNA

<400> SEQUENCE: 131
gccauuauca caauugagga u                                              21

<210> SEQ ID NO 132
<211> LENGTH: 23
<212> TYPE: RNA
<213> ORGANISM: Artificial Sequence
<220> FEATURE:
<223> OTHER INFORMATION: siRNA

<400> SEQUENCE: 132
auccucaauu gugauaaugg cug                                            23

<210> SEQ ID NO 133
<211> LENGTH: 19
<212> TYPE: RNA
<213> ORGANISM: Artificial Sequence
<220> FEATURE:
```

```
<223> OTHER INFORMATION: siRNA

<400> SEQUENCE: 133
cauuaucaca auugaggau                                                19

<210> SEQ ID NO 134
<211> LENGTH: 21
<212> TYPE: RNA
<213> ORGANISM: Artificial Sequence
<220> FEATURE:
<223> OTHER INFORMATION: siRNA

<400> SEQUENCE: 134
auccucaauu gugauaaugg c                                             21

<210> SEQ ID NO 135
<211> LENGTH: 19
<212> TYPE: RNA
<213> ORGANISM: Artificial Sequence
<220> FEATURE:
<223> OTHER INFORMATION: siRNA

<400> SEQUENCE: 135
cauuaucaca auugaggau                                                19

<210> SEQ ID NO 136
<211> LENGTH: 21
<212> TYPE: RNA
<213> ORGANISM: Artificial Sequence
<220> FEATURE:
<223> OTHER INFORMATION: siRNA

<400> SEQUENCE: 136
auccucaauu gugauaaugg c                                             21

<210> SEQ ID NO 137
<211> LENGTH: 19
<212> TYPE: RNA
<213> ORGANISM: Artificial Sequence
<220> FEATURE:
<223> OTHER INFORMATION: siRNA

<400> SEQUENCE: 137
cauuaucaca auugaggau                                                19

<210> SEQ ID NO 138
<211> LENGTH: 21
<212> TYPE: RNA
<213> ORGANISM: Artificial Sequence
<220> FEATURE:
<223> OTHER INFORMATION: siRNA

<400> SEQUENCE: 138
auccucaauu gugauaaugg c                                             21

<210> SEQ ID NO 139
<211> LENGTH: 21
<212> TYPE: RNA
<213> ORGANISM: Artificial Sequence
<220> FEATURE:
<223> OTHER INFORMATION: siRNA

<400> SEQUENCE: 139
gccauuauca caauugagga u                                             21
```

-continued

```
<210> SEQ ID NO 140
<211> LENGTH: 23
<212> TYPE: RNA
<213> ORGANISM: Artificial Sequence
<220> FEATURE:
<223> OTHER INFORMATION: siRNA

<400> SEQUENCE: 140
auccucaauu gugauaaugg cug                                         23

<210> SEQ ID NO 141
<211> LENGTH: 21
<212> TYPE: RNA
<213> ORGANISM: Artificial Sequence
<220> FEATURE:
<223> OTHER INFORMATION: siRNA

<400> SEQUENCE: 141
gccauuauca caauugagga u                                           21

<210> SEQ ID NO 142
<211> LENGTH: 23
<212> TYPE: RNA
<213> ORGANISM: Artificial Sequence
<220> FEATURE:
<223> OTHER INFORMATION: siRNA

<400> SEQUENCE: 142
auccucaauu gugauaaugg cug                                         23

<210> SEQ ID NO 143
<211> LENGTH: 21
<212> TYPE: RNA
<213> ORGANISM: Artificial Sequence
<220> FEATURE:
<223> OTHER INFORMATION: siRNA

<400> SEQUENCE: 143
gccauuauca caauugagga u                                           21

<210> SEQ ID NO 144
<211> LENGTH: 23
<212> TYPE: RNA
<213> ORGANISM: Artificial Sequence
<220> FEATURE:
<223> OTHER INFORMATION: siRNA

<400> SEQUENCE: 144
auccucaauu gugauaaugg cug                                         23

<210> SEQ ID NO 145
<211> LENGTH: 19
<212> TYPE: RNA
<213> ORGANISM: Artificial Sequence
<220> FEATURE:
<223> OTHER INFORMATION: siRNA

<400> SEQUENCE: 145
cauuaucaca auugaggau                                              19

<210> SEQ ID NO 146
<211> LENGTH: 21
<212> TYPE: RNA
<213> ORGANISM: Artificial Sequence
<220> FEATURE:
<223> OTHER INFORMATION: siRNA
```

-continued

```
<400> SEQUENCE: 146
auccucaauu gugauaaugg c                                              21

<210> SEQ ID NO 147
<211> LENGTH: 19
<212> TYPE: RNA
<213> ORGANISM: Artificial Sequence
<220> FEATURE:
<223> OTHER INFORMATION: siRNA

<400> SEQUENCE: 147
cauuaucaca auugaggau                                                 19

<210> SEQ ID NO 148
<211> LENGTH: 21
<212> TYPE: RNA
<213> ORGANISM: Artificial Sequence
<220> FEATURE:
<223> OTHER INFORMATION: siRNA

<400> SEQUENCE: 148
auccucaauu gugauaaugg c                                              21

<210> SEQ ID NO 149
<211> LENGTH: 19
<212> TYPE: RNA
<213> ORGANISM: Artificial Sequence
<220> FEATURE:
<223> OTHER INFORMATION: siRNA

<400> SEQUENCE: 149
cauuaucaca auugaggau                                                 19

<210> SEQ ID NO 150
<211> LENGTH: 21
<212> TYPE: RNA
<213> ORGANISM: Artificial Sequence
<220> FEATURE:
<223> OTHER INFORMATION: siRNA

<400> SEQUENCE: 150
auccucaauu gugauaaugg c                                              21

<210> SEQ ID NO 151
<211> LENGTH: 21
<212> TYPE: RNA
<213> ORGANISM: Artificial Sequence
<220> FEATURE:
<223> OTHER INFORMATION: siRNA

<400> SEQUENCE: 151
gccauuauca caauugagga u                                              21

<210> SEQ ID NO 152
<211> LENGTH: 23
<212> TYPE: RNA
<213> ORGANISM: Artificial Sequence
<220> FEATURE:
<223> OTHER INFORMATION: siRNA

<400> SEQUENCE: 152
auccucaauu gugauaaugg cug                                            23

<210> SEQ ID NO 153
<211> LENGTH: 21
```

<212> TYPE: RNA
<213> ORGANISM: Artificial Sequence
<220> FEATURE:
<223> OTHER INFORMATION: siRNA

<400> SEQUENCE: 153
gccauuauca caauugagga u                                          21

<210> SEQ ID NO 154
<211> LENGTH: 23
<212> TYPE: RNA
<213> ORGANISM: Artificial Sequence
<220> FEATURE:
<223> OTHER INFORMATION: siRNA

<400> SEQUENCE: 154
auccucaauu gugauaaugg cug                                        23

<210> SEQ ID NO 155
<211> LENGTH: 21
<212> TYPE: RNA
<213> ORGANISM: Artificial Sequence
<220> FEATURE:
<223> OTHER INFORMATION: siRNA

<400> SEQUENCE: 155
gccauuauca caauugagga u                                          21

<210> SEQ ID NO 156
<211> LENGTH: 23
<212> TYPE: RNA
<213> ORGANISM: Artificial Sequence
<220> FEATURE:
<223> OTHER INFORMATION: siRNA

<400> SEQUENCE: 156
auccucaauu gugauaaugg cug                                        23

<210> SEQ ID NO 157
<211> LENGTH: 19
<212> TYPE: RNA
<213> ORGANISM: Artificial Sequence
<220> FEATURE:
<223> OTHER INFORMATION: siRNA

<400> SEQUENCE: 157
cauuaucaca auugaggau                                             19

<210> SEQ ID NO 158
<211> LENGTH: 21
<212> TYPE: RNA
<213> ORGANISM: Artificial Sequence
<220> FEATURE:
<223> OTHER INFORMATION: siRNA

<400> SEQUENCE: 158
auccucaauu gugauaaugg c                                          21

<210> SEQ ID NO 159
<211> LENGTH: 19
<212> TYPE: RNA
<213> ORGANISM: Artificial Sequence
<220> FEATURE:
<223> OTHER INFORMATION: siRNA

<400> SEQUENCE: 159

-continued cauuaucaca auugaggau                                              19

<210> SEQ ID NO 160
<211> LENGTH: 21
<212> TYPE: RNA
<213> ORGANISM: Artificial Sequence
<220> FEATURE:
<223> OTHER INFORMATION: siRNA

<400> SEQUENCE: 160
auccucaauu gugauaaugg c                                          21

<210> SEQ ID NO 161
<211> LENGTH: 19
<212> TYPE: RNA
<213> ORGANISM: Artificial Sequence
<220> FEATURE:
<223> OTHER INFORMATION: siRNA

<400> SEQUENCE: 161
cauuaucaca auugaggau                                              19

<210> SEQ ID NO 162
<211> LENGTH: 21
<212> TYPE: RNA
<213> ORGANISM: Artificial Sequence
<220> FEATURE:
<223> OTHER INFORMATION: siRNA

<400> SEQUENCE: 162
auccucaauu gugauaaugg c                                          21

<210> SEQ ID NO 163
<211> LENGTH: 21
<212> TYPE: RNA
<213> ORGANISM: Artificial Sequence
<220> FEATURE:
<223> OTHER INFORMATION: siRNA

<400> SEQUENCE: 163
gccauuauca caauugagga u                                          21

<210> SEQ ID NO 164
<211> LENGTH: 23
<212> TYPE: RNA
<213> ORGANISM: Artificial Sequence
<220> FEATURE:
<223> OTHER INFORMATION: siRNA

<400> SEQUENCE: 164
auccucaauu gugauaaugg cug                                        23

<210> SEQ ID NO 165
<211> LENGTH: 21
<212> TYPE: RNA
<213> ORGANISM: Artificial Sequence
<220> FEATURE:
<223> OTHER INFORMATION: siRNA

<400> SEQUENCE: 165
gccauuauca caauugagga u                                          21

<210> SEQ ID NO 166
<211> LENGTH: 23
<212> TYPE: RNA
<213> ORGANISM: Artificial Sequence -continued

```
<220> FEATURE:
<223> OTHER INFORMATION: siRNA

<400> SEQUENCE: 166
auccucaauu gugauaaugg cug                                    23

<210> SEQ ID NO 167
<211> LENGTH: 21
<212> TYPE: RNA
<213> ORGANISM: Artificial Sequence
<220> FEATURE:
<223> OTHER INFORMATION: siRNA

<400> SEQUENCE: 167
gccauuauca caauugagga u                                      21

<210> SEQ ID NO 168
<211> LENGTH: 23
<212> TYPE: RNA
<213> ORGANISM: Artificial Sequence
<220> FEATURE:
<223> OTHER INFORMATION: siRNA

<400> SEQUENCE: 168
auccucaauu gugauaaugg cug                                    23

<210> SEQ ID NO 169
<211> LENGTH: 19
<212> TYPE: RNA
<213> ORGANISM: Artificial Sequence
<220> FEATURE:
<223> OTHER INFORMATION: siRNA

<400> SEQUENCE: 169
cauuaucaca auugaggau                                         19

<210> SEQ ID NO 170
<211> LENGTH: 21
<212> TYPE: RNA
<213> ORGANISM: Artificial Sequence
<220> FEATURE:
<223> OTHER INFORMATION: siRNA

<400> SEQUENCE: 170
auccucaauu gugauaaugg c                                       21

<210> SEQ ID NO 171
<211> LENGTH: 19
<212> TYPE: RNA
<213> ORGANISM: Artificial Sequence
<220> FEATURE:
<223> OTHER INFORMATION: siRNA

<400> SEQUENCE: 171
cauuaucaca auugaggau                                         19

<210> SEQ ID NO 172
<211> LENGTH: 21
<212> TYPE: RNA
<213> ORGANISM: Artificial Sequence
<220> FEATURE:
<223> OTHER INFORMATION: siRNA

<400> SEQUENCE: 172
auccucaauu gugauaaugg c                                       21
```

-continued

<210> SEQ ID NO 173
<211> LENGTH: 19
<212> TYPE: RNA
<213> ORGANISM: Artificial Sequence
<220> FEATURE:
<223> OTHER INFORMATION: siRNA

<400> SEQUENCE: 173
cauuaucaca auugaggau                                                            19

<210> SEQ ID NO 174
<211> LENGTH: 21
<212> TYPE: RNA
<213> ORGANISM: Artificial Sequence
<220> FEATURE:
<223> OTHER INFORMATION: siRNA

<400> SEQUENCE: 174
auccucaauu gugauaaugg c                                                         21

<210> SEQ ID NO 175
<211> LENGTH: 21
<212> TYPE: RNA
<213> ORGANISM: Artificial Sequence
<220> FEATURE:
<223> OTHER INFORMATION: siRNA

<400> SEQUENCE: 175
gccauuauca caauugagga u                                                         21

<210> SEQ ID NO 176
<211> LENGTH: 23
<212> TYPE: RNA
<213> ORGANISM: Artificial Sequence
<220> FEATURE:
<223> OTHER INFORMATION: siRNA

<400> SEQUENCE: 176
auccucaauu gugauaaugg cug                                                       23

<210> SEQ ID NO 177
<211> LENGTH: 21
<212> TYPE: RNA
<213> ORGANISM: Artificial Sequence
<220> FEATURE:
<223> OTHER INFORMATION: siRNA

<400> SEQUENCE: 177
gccauuauca caauugagga u                                                         21

<210> SEQ ID NO 178
<211> LENGTH: 23
<212> TYPE: RNA
<213> ORGANISM: Artificial Sequence
<220> FEATURE:
<223> OTHER INFORMATION: siRNA

<400> SEQUENCE: 178
auccucaauu gugauaaugg cug                                                       23

<210> SEQ ID NO 179
<211> LENGTH: 21
<212> TYPE: RNA
<213> ORGANISM: Artificial Sequence
<220> FEATURE:
<223> OTHER INFORMATION: siRNA -continued

<400> SEQUENCE: 179
gccauuauca caauugagga u                                                     21

<210> SEQ ID NO 180
<211> LENGTH: 23
<212> TYPE: RNA
<213> ORGANISM: Artificial Sequence
<220> FEATURE:
<223> OTHER INFORMATION: siRNA

<400> SEQUENCE: 180
auccucaauu gugauaaugg cug                                                   23

<210> SEQ ID NO 181
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z13, and Z13 is U

<400> SEQUENCE: 181
ggaucucucu cagaguaun                                                        19

<210> SEQ ID NO 182
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z14, and Z14 is A

<400> SEQUENCE: 182
nauacucuga gagagaucc                                                        19

<210> SEQ ID NO 183
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z15, Z15 is a nucleotide complementary to
      Z16, and Z16 is selected from A, U, G or C

<400> SEQUENCE: 183
ggaucucucu cagaguaun                                                        19

<210> SEQ ID NO 184
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z16, and Z16 is selected from A, U, G or C

<400> SEQUENCE: 184
nauacucuga gagagaucc                                                         19

<210> SEQ ID NO 185
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z15, Z15 is a nucleotide complementary to
      Z16, and Z16 is selected from A, U, G or C

<400> SEQUENCE: 185
ggaucucucu cagaguaun                                                         19

<210> SEQ ID NO 186
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z16, and Z16 is selected from A, U, G or C

<400> SEQUENCE: 186
nauacucuga gagagauccu g                                                      21

<210> SEQ ID NO 187
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z15, Z15 is a nucleotide complementary to
      Z16, and Z16 is selected from A, U, G or C

<400> SEQUENCE: 187
caggaucucu cucagaguau n                                                      21

<210> SEQ ID NO 188
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z16, and Z16 is selected from A, U, G or C

<400> SEQUENCE: 188
nauacucuga gagagauccu ggg                                                    23

<210> SEQ ID NO 189
<211> LENGTH: 19
<212> TYPE: RNA
<213> ORGANISM: Artificial Sequence
<220> FEATURE:
<223> OTHER INFORMATION: siRNA

<400> SEQUENCE: 189
ggaucucucu cagaguauu                                                     19

<210> SEQ ID NO 190
<211> LENGTH: 21
<212> TYPE: RNA
<213> ORGANISM: Artificial Sequence
<220> FEATURE:
<223> OTHER INFORMATION: siRNA

<400> SEQUENCE: 190
aauacucuga gagagauccu g                                                  21

<210> SEQ ID NO 191
<211> LENGTH: 21
<212> TYPE: RNA
<213> ORGANISM: Artificial Sequence
<220> FEATURE:
<223> OTHER INFORMATION: siRNA

<400> SEQUENCE: 191
caggaucucu cucagaguau u                                                  21

<210> SEQ ID NO 192
<211> LENGTH: 23
<212> TYPE: RNA
<213> ORGANISM: Artificial Sequence
<220> FEATURE:
<223> OTHER INFORMATION: siRNA

<400> SEQUENCE: 192
aauacucuga gagagauccu ggg                                                23

<210> SEQ ID NO 193
<211> LENGTH: 19
<212> TYPE: RNA
<213> ORGANISM: Artificial Sequence
<220> FEATURE:
<223> OTHER INFORMATION: siRNA

<400> SEQUENCE: 193
ggaucucucu cagaguauu                                                     19

<210> SEQ ID NO 194
<211> LENGTH: 21
<212> TYPE: RNA
<213> ORGANISM: Artificial Sequence
<220> FEATURE:
<223> OTHER INFORMATION: siRNA

<400> SEQUENCE: 194
aauacucuga gagagauccu g                                                  21

<210> SEQ ID NO 195
<211> LENGTH: 19
<212> TYPE: RNA
<213> ORGANISM: Artificial Sequence
<220> FEATURE:
<223> OTHER INFORMATION: siRNA

<400> SEQUENCE: 195
ggaucucucu cagaguauu                                                     19

<210> SEQ ID NO 196
<211> LENGTH: 21
<212> TYPE: RNA
<213> ORGANISM: Artificial Sequence -continued

```
<220> FEATURE:
<223> OTHER INFORMATION: siRNA

<400> SEQUENCE: 196
aauacucuga gagagauccu g                                        21

<210> SEQ ID NO 197
<211> LENGTH: 19
<212> TYPE: RNA
<213> ORGANISM: Artificial Sequence
<220> FEATURE:
<223> OTHER INFORMATION: siRNA

<400> SEQUENCE: 197
ggaucucucu cagaguauu                                           19

<210> SEQ ID NO 198
<211> LENGTH: 21
<212> TYPE: RNA
<213> ORGANISM: Artificial Sequence
<220> FEATURE:
<223> OTHER INFORMATION: siRNA

<400> SEQUENCE: 198
aauacucuga gagagauccu g                                        21

<210> SEQ ID NO 199
<211> LENGTH: 21
<212> TYPE: RNA
<213> ORGANISM: Artificial Sequence
<220> FEATURE:
<223> OTHER INFORMATION: siRNA

<400> SEQUENCE: 199
caggaucucu cucagaguau u                                        21

<210> SEQ ID NO 200
<211> LENGTH: 23
<212> TYPE: RNA
<213> ORGANISM: Artificial Sequence
<220> FEATURE:
<223> OTHER INFORMATION: siRNA

<400> SEQUENCE: 200
aauacucuga gagagauccu ggg                                      23

<210> SEQ ID NO 201
<211> LENGTH: 21
<212> TYPE: RNA
<213> ORGANISM: Artificial Sequence
<220> FEATURE:
<223> OTHER INFORMATION: siRNA

<400> SEQUENCE: 201
caggaucucu cucagaguau u                                        21

<210> SEQ ID NO 202
<211> LENGTH: 23
<212> TYPE: RNA
<213> ORGANISM: Artificial Sequence
<220> FEATURE:
<223> OTHER INFORMATION: siRNA

<400> SEQUENCE: 202
aauacucuga gagagauccu ggg                                      23
```

-continued

```
<210> SEQ ID NO 203
<211> LENGTH: 21
<212> TYPE: RNA
<213> ORGANISM: Artificial Sequence
<220> FEATURE:
<223> OTHER INFORMATION: siRNA

<400> SEQUENCE: 203
caggaucucu cucagaguau u                                              21

<210> SEQ ID NO 204
<211> LENGTH: 23
<212> TYPE: RNA
<213> ORGANISM: Artificial Sequence
<220> FEATURE:
<223> OTHER INFORMATION: siRNA

<400> SEQUENCE: 204
aauacucuga gagagauccu ggg                                            23

<210> SEQ ID NO 205
<211> LENGTH: 19
<212> TYPE: RNA
<213> ORGANISM: Artificial Sequence
<220> FEATURE:
<223> OTHER INFORMATION: siRNA

<400> SEQUENCE: 205
ggaucucucu cagaguauu                                                 19

<210> SEQ ID NO 206
<211> LENGTH: 21
<212> TYPE: RNA
<213> ORGANISM: Artificial Sequence
<220> FEATURE:
<223> OTHER INFORMATION: siRNA

<400> SEQUENCE: 206
aauacucuga gagagauccu g                                              21

<210> SEQ ID NO 207
<211> LENGTH: 19
<212> TYPE: RNA
<213> ORGANISM: Artificial Sequence
<220> FEATURE:
<223> OTHER INFORMATION: siRNA

<400> SEQUENCE: 207
ggaucucucu cagaguauu                                                 19

<210> SEQ ID NO 208
<211> LENGTH: 21
<212> TYPE: RNA
<213> ORGANISM: Artificial Sequence
<220> FEATURE:
<223> OTHER INFORMATION: siRNA

<400> SEQUENCE: 208
aauacucuga gagagauccu g                                              21

<210> SEQ ID NO 209
<211> LENGTH: 19
<212> TYPE: RNA
<213> ORGANISM: Artificial Sequence
<220> FEATURE:
<223> OTHER INFORMATION: siRNA
```

-continued

<400> SEQUENCE: 209
ggaucucucu cagaguauu                                                                        19

<210> SEQ ID NO 210
<211> LENGTH: 21
<212> TYPE: RNA
<213> ORGANISM: Artificial Sequence
<220> FEATURE:
<223> OTHER INFORMATION: siRNA

<400> SEQUENCE: 210
aauacucuga gagagauccu g                                                                     21

<210> SEQ ID NO 211
<211> LENGTH: 21
<212> TYPE: RNA
<213> ORGANISM: Artificial Sequence
<220> FEATURE:
<223> OTHER INFORMATION: siRNA

<400> SEQUENCE: 211
caggaucucu cucagaguau u                                                                     21

<210> SEQ ID NO 212
<211> LENGTH: 23
<212> TYPE: RNA
<213> ORGANISM: Artificial Sequence
<220> FEATURE:
<223> OTHER INFORMATION: siRNA

<400> SEQUENCE: 212
aauacucuga gagagauccu ggg                                                                   23

<210> SEQ ID NO 213
<211> LENGTH: 21
<212> TYPE: RNA
<213> ORGANISM: Artificial Sequence
<220> FEATURE:
<223> OTHER INFORMATION: siRNA

<400> SEQUENCE: 213
caggaucucu cucagaguau u                                                                     21

<210> SEQ ID NO 214
<211> LENGTH: 23
<212> TYPE: RNA
<213> ORGANISM: Artificial Sequence
<220> FEATURE:
<223> OTHER INFORMATION: siRNA

<400> SEQUENCE: 214
aauacucuga gagagauccu ggg                                                                   23

<210> SEQ ID NO 215
<211> LENGTH: 21
<212> TYPE: RNA
<213> ORGANISM: Artificial Sequence
<220> FEATURE:
<223> OTHER INFORMATION: siRNA

<400> SEQUENCE: 215
caggaucucu cucagaguau u                                                                     21

<210> SEQ ID NO 216

-continued

```
<211> LENGTH: 23
<212> TYPE: RNA
<213> ORGANISM: Artificial Sequence
<220> FEATURE:
<223> OTHER INFORMATION: siRNA

<400> SEQUENCE: 216
aauacucuga gagagauccu ggg                                         23

<210> SEQ ID NO 217
<211> LENGTH: 19
<212> TYPE: RNA
<213> ORGANISM: Artificial Sequence
<220> FEATURE:
<223> OTHER INFORMATION: siRNA

<400> SEQUENCE: 217
ggaucucucu cagaguauu                                              19

<210> SEQ ID NO 218
<211> LENGTH: 21
<212> TYPE: RNA
<213> ORGANISM: Artificial Sequence
<220> FEATURE:
<223> OTHER INFORMATION: siRNA

<400> SEQUENCE: 218
aauacucuga gagagauccu g                                           21

<210> SEQ ID NO 219
<211> LENGTH: 19
<212> TYPE: RNA
<213> ORGANISM: Artificial Sequence
<220> FEATURE:
<223> OTHER INFORMATION: siRNA

<400> SEQUENCE: 219
ggaucucucu cagaguauu                                              19

<210> SEQ ID NO 220
<211> LENGTH: 21
<212> TYPE: RNA
<213> ORGANISM: Artificial Sequence
<220> FEATURE:
<223> OTHER INFORMATION: siRNA

<400> SEQUENCE: 220
aauacucuga gagagauccu g                                           21

<210> SEQ ID NO 221
<211> LENGTH: 19
<212> TYPE: RNA
<213> ORGANISM: Artificial Sequence
<220> FEATURE:
<223> OTHER INFORMATION: siRNA

<400> SEQUENCE: 221
ggaucucucu cagaguauu                                              19

<210> SEQ ID NO 222
<211> LENGTH: 21
<212> TYPE: RNA
<213> ORGANISM: Artificial Sequence
<220> FEATURE:
<223> OTHER INFORMATION: siRNA

<400> SEQUENCE: 222
```

```
aauacucuga gagagauccu g                                          21

<210> SEQ ID NO 223
<211> LENGTH: 21
<212> TYPE: RNA
<213> ORGANISM: Artificial Sequence
<220> FEATURE:
<223> OTHER INFORMATION: siRNA

<400> SEQUENCE: 223
caggaucucu cucagaguau u                                          21

<210> SEQ ID NO 224
<211> LENGTH: 23
<212> TYPE: RNA
<213> ORGANISM: Artificial Sequence
<220> FEATURE:
<223> OTHER INFORMATION: siRNA

<400> SEQUENCE: 224
aauacucuga gagagauccu ggg                                        23

<210> SEQ ID NO 225
<211> LENGTH: 21
<212> TYPE: RNA
<213> ORGANISM: Artificial Sequence
<220> FEATURE:
<223> OTHER INFORMATION: siRNA

<400> SEQUENCE: 225
caggaucucu cucagaguau u                                          21

<210> SEQ ID NO 226
<211> LENGTH: 23
<212> TYPE: RNA
<213> ORGANISM: Artificial Sequence
<220> FEATURE:
<223> OTHER INFORMATION: siRNA

<400> SEQUENCE: 226
aauacucuga gagagauccu ggg                                        23

<210> SEQ ID NO 227
<211> LENGTH: 21
<212> TYPE: RNA
<213> ORGANISM: Artificial Sequence
<220> FEATURE:
<223> OTHER INFORMATION: siRNA

<400> SEQUENCE: 227
caggaucucu cucagaguau u                                          21

<210> SEQ ID NO 228
<211> LENGTH: 23
<212> TYPE: RNA
<213> ORGANISM: Artificial Sequence
<220> FEATURE:
<223> OTHER INFORMATION: siRNA

<400> SEQUENCE: 228
aauacucuga gagagauccu ggg                                        23

<210> SEQ ID NO 229
<211> LENGTH: 19
<212> TYPE: RNA
```

```
<213> ORGANISM: Artificial Sequence
<220> FEATURE:
<223> OTHER INFORMATION: siRNA

<400> SEQUENCE: 229
ggaucucucu cagaguauu                                              19

<210> SEQ ID NO 230
<211> LENGTH: 21
<212> TYPE: RNA
<213> ORGANISM: Artificial Sequence
<220> FEATURE:
<223> OTHER INFORMATION: siRNA

<400> SEQUENCE: 230
aauacucuga gagagauccu g                                          21

<210> SEQ ID NO 231
<211> LENGTH: 19
<212> TYPE: RNA
<213> ORGANISM: Artificial Sequence
<220> FEATURE:
<223> OTHER INFORMATION: siRNA

<400> SEQUENCE: 231
ggaucucucu cagaguauu                                              19

<210> SEQ ID NO 232
<211> LENGTH: 21
<212> TYPE: RNA
<213> ORGANISM: Artificial Sequence
<220> FEATURE:
<223> OTHER INFORMATION: siRNA

<400> SEQUENCE: 232
aauacucuga gagagauccu g                                          21

<210> SEQ ID NO 233
<211> LENGTH: 19
<212> TYPE: RNA
<213> ORGANISM: Artificial Sequence
<220> FEATURE:
<223> OTHER INFORMATION: siRNA

<400> SEQUENCE: 233
ggaucucucu cagaguauu                                              19

<210> SEQ ID NO 234
<211> LENGTH: 21
<212> TYPE: RNA
<213> ORGANISM: Artificial Sequence
<220> FEATURE:
<223> OTHER INFORMATION: siRNA

<400> SEQUENCE: 234
aauacucuga gagagauccu g                                          21

<210> SEQ ID NO 235
<211> LENGTH: 21
<212> TYPE: RNA
<213> ORGANISM: Artificial Sequence
<220> FEATURE:
<223> OTHER INFORMATION: siRNA

<400> SEQUENCE: 235
caggaucucu cucagaguau u                                          21
```

```
<210> SEQ ID NO 236
<211> LENGTH: 23
<212> TYPE: RNA
<213> ORGANISM: Artificial Sequence
<220> FEATURE:
<223> OTHER INFORMATION: siRNA

<400> SEQUENCE: 236
aauacucuga gagagauccu ggg                                          23

<210> SEQ ID NO 237
<211> LENGTH: 21
<212> TYPE: RNA
<213> ORGANISM: Artificial Sequence
<220> FEATURE:
<223> OTHER INFORMATION: siRNA

<400> SEQUENCE: 237
caggaucucu cucagaguau u                                            21

<210> SEQ ID NO 238
<211> LENGTH: 23
<212> TYPE: RNA
<213> ORGANISM: Artificial Sequence
<220> FEATURE:
<223> OTHER INFORMATION: siRNA

<400> SEQUENCE: 238
aauacucuga gagagauccu ggg                                          23

<210> SEQ ID NO 239
<211> LENGTH: 21
<212> TYPE: RNA
<213> ORGANISM: Artificial Sequence
<220> FEATURE:
<223> OTHER INFORMATION: siRNA

<400> SEQUENCE: 239
caggaucucu cucagaguau u                                            21

<210> SEQ ID NO 240
<211> LENGTH: 23
<212> TYPE: RNA
<213> ORGANISM: Artificial Sequence
<220> FEATURE:
<223> OTHER INFORMATION: siRNA

<400> SEQUENCE: 240
aauacucuga gagagauccu ggg                                          23

<210> SEQ ID NO 241
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z17, and Z17 is A

<400> SEQUENCE: 241
acauggacaa cugcuauan                                               19

<210> SEQ ID NO 242
```

```
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z18, and Z18 is U

<400> SEQUENCE: 242
nuauagcagu uguccaugu                                              19

<210> SEQ ID NO 243
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z19, Z19 is a nucleotide complementary to
      Z20, and Z20 is selected from A, U, G or C

<400> SEQUENCE: 243
acauggacaa cugcuauan                                             19

<210> SEQ ID NO 244
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z20, and Z20 is selected from A, U, G or C

<400> SEQUENCE: 244
nuauagcagu uguccaugu                                              19

<210> SEQ ID NO 245
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z19, Z19 is a nucleotide complementary to
      Z20, and Z20 is selected from A, U, G or C

<400> SEQUENCE: 245
acauggacaa cugcuauan                                             19

<210> SEQ ID NO 246
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z20, and Z20 is selected from A, U, G or C

<400> SEQUENCE: 246
nuauagcagu uguccaugug g                                           21
```

```
<210> SEQ ID NO 247
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z19, Z19 is a nucleotide complementary to
      Z20, and Z20 is selected from A, U, G or C

<400> SEQUENCE: 247
ccacauggac aacugcuaua n                                                21

<210> SEQ ID NO 248
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z20, and Z20 is selected from A, U, G or C

<400> SEQUENCE: 248
nuauagcagu uguccaugug gaa                                              23

<210> SEQ ID NO 249
<211> LENGTH: 19
<212> TYPE: RNA
<213> ORGANISM: Artificial Sequence
<220> FEATURE:
<223> OTHER INFORMATION: siRNA

<400> SEQUENCE: 249
acauggacaa cugcuauaa                                                   19

<210> SEQ ID NO 250
<211> LENGTH: 21
<212> TYPE: RNA
<213> ORGANISM: Artificial Sequence
<220> FEATURE:
<223> OTHER INFORMATION: siRNA

<400> SEQUENCE: 250
uuauagcagu uguccaugug g                                                21

<210> SEQ ID NO 251
<211> LENGTH: 21
<212> TYPE: RNA
<213> ORGANISM: Artificial Sequence
<220> FEATURE:
<223> OTHER INFORMATION: siRNA

<400> SEQUENCE: 251
ccacauggac aacugcuaua a                                                21

<210> SEQ ID NO 252
<211> LENGTH: 23
<212> TYPE: RNA
<213> ORGANISM: Artificial Sequence
<220> FEATURE:
<223> OTHER INFORMATION: siRNA

<400> SEQUENCE: 252
```
uuauagcagu uguccaugug gaa                                                    23

<210> SEQ ID NO 253
<211> LENGTH: 19
<212> TYPE: RNA
<213> ORGANISM: Artificial Sequence
<220> FEATURE:
<223> OTHER INFORMATION: siRNA

<400> SEQUENCE: 253
acauggacaa cugcuauaa                                                         19

<210> SEQ ID NO 254
<211> LENGTH: 21
<212> TYPE: RNA
<213> ORGANISM: Artificial Sequence
<220> FEATURE:
<223> OTHER INFORMATION: siRNA

<400> SEQUENCE: 254
uuauagcagu uguccaugug g                                                      21

<210> SEQ ID NO 255
<211> LENGTH: 19
<212> TYPE: RNA
<213> ORGANISM: Artificial Sequence
<220> FEATURE:
<223> OTHER INFORMATION: siRNA

<400> SEQUENCE: 255
acauggacaa cugcuauaa                                                         19

<210> SEQ ID NO 256
<211> LENGTH: 21
<212> TYPE: RNA
<213> ORGANISM: Artificial Sequence
<220> FEATURE:
<223> OTHER INFORMATION: siRNA

<400> SEQUENCE: 256
uuauagcagu uguccaugug g                                                      21

<210> SEQ ID NO 257
<211> LENGTH: 19
<212> TYPE: RNA
<213> ORGANISM: Artificial Sequence
<220> FEATURE:
<223> OTHER INFORMATION: siRNA

<400> SEQUENCE: 257
acauggacaa cugcuauaa                                                         19

<210> SEQ ID NO 258
<211> LENGTH: 21
<212> TYPE: RNA
<213> ORGANISM: Artificial Sequence
<220> FEATURE:
<223> OTHER INFORMATION: siRNA

<400> SEQUENCE: 258
uuauagcagu uguccaugug g                                                      21

<210> SEQ ID NO 259
<211> LENGTH: 21
<212> TYPE: RNA

<213> ORGANISM: Artificial Sequence
<220> FEATURE:
<223> OTHER INFORMATION: siRNA

<400> SEQUENCE: 259
ccacauggac aacugcuaua a                                                    21

<210> SEQ ID NO 260
<211> LENGTH: 23
<212> TYPE: RNA
<213> ORGANISM: Artificial Sequence
<220> FEATURE:
<223> OTHER INFORMATION: siRNA

<400> SEQUENCE: 260
uuauagcagu uguccaugug gaa                                                  23

<210> SEQ ID NO 261
<211> LENGTH: 21
<212> TYPE: RNA
<213> ORGANISM: Artificial Sequence
<220> FEATURE:
<223> OTHER INFORMATION: siRNA

<400> SEQUENCE: 261
ccacauggac aacugcuaua a                                                    21

<210> SEQ ID NO 262
<211> LENGTH: 23
<212> TYPE: RNA
<213> ORGANISM: Artificial Sequence
<220> FEATURE:
<223> OTHER INFORMATION: siRNA

<400> SEQUENCE: 262
uuauagcagu uguccaugug gaa                                                  23

<210> SEQ ID NO 263
<211> LENGTH: 21
<212> TYPE: RNA
<213> ORGANISM: Artificial Sequence
<220> FEATURE:
<223> OTHER INFORMATION: siRNA

<400> SEQUENCE: 263
ccacauggac aacugcuaua a                                                    21

<210> SEQ ID NO 264
<211> LENGTH: 23
<212> TYPE: RNA
<213> ORGANISM: Artificial Sequence
<220> FEATURE:
<223> OTHER INFORMATION: siRNA

<400> SEQUENCE: 264
uuauagcagu uguccaugug gaa                                                  23

<210> SEQ ID NO 265
<211> LENGTH: 19
<212> TYPE: RNA
<213> ORGANISM: Artificial Sequence
<220> FEATURE:
<223> OTHER INFORMATION: siRNA

<400> SEQUENCE: 265
acauggacaa cugcuauaa                                                       19

```
<210> SEQ ID NO 266
<211> LENGTH: 21
<212> TYPE: RNA
<213> ORGANISM: Artificial Sequence
<220> FEATURE:
<223> OTHER INFORMATION: siRNA

<400> SEQUENCE: 266
uuauagcagu uguccaugug g                                                         21

<210> SEQ ID NO 267
<211> LENGTH: 19
<212> TYPE: RNA
<213> ORGANISM: Artificial Sequence
<220> FEATURE:
<223> OTHER INFORMATION: siRNA

<400> SEQUENCE: 267
acauggacaa cugcuauaa                                                            19

<210> SEQ ID NO 268
<211> LENGTH: 21
<212> TYPE: RNA
<213> ORGANISM: Artificial Sequence
<220> FEATURE:
<223> OTHER INFORMATION: siRNA

<400> SEQUENCE: 268
uuauagcagu uguccaugug g                                                         21

<210> SEQ ID NO 269
<211> LENGTH: 19
<212> TYPE: RNA
<213> ORGANISM: Artificial Sequence
<220> FEATURE:
<223> OTHER INFORMATION: siRNA

<400> SEQUENCE: 269
acauggacaa cugcuauaa                                                            19

<210> SEQ ID NO 270
<211> LENGTH: 21
<212> TYPE: RNA
<213> ORGANISM: Artificial Sequence
<220> FEATURE:
<223> OTHER INFORMATION: siRNA

<400> SEQUENCE: 270
uuauagcagu uguccaugug g                                                         21

<210> SEQ ID NO 271
<211> LENGTH: 21
<212> TYPE: RNA
<213> ORGANISM: Artificial Sequence
<220> FEATURE:
<223> OTHER INFORMATION: siRNA

<400> SEQUENCE: 271
ccacauggac aacugcuaua a                                                         21

<210> SEQ ID NO 272
<211> LENGTH: 23
<212> TYPE: RNA
<213> ORGANISM: Artificial Sequence
<220> FEATURE:
```

-continued

```
<223> OTHER INFORMATION: siRNA

<400> SEQUENCE: 272
uuauagcagu uguccaugug gaa                                          23

<210> SEQ ID NO 273
<211> LENGTH: 21
<212> TYPE: RNA
<213> ORGANISM: Artificial Sequence
<220> FEATURE:
<223> OTHER INFORMATION: siRNA

<400> SEQUENCE: 273
ccacauggac aacugcuaua a                                            21

<210> SEQ ID NO 274
<211> LENGTH: 23
<212> TYPE: RNA
<213> ORGANISM: Artificial Sequence
<220> FEATURE:
<223> OTHER INFORMATION: siRNA

<400> SEQUENCE: 274
uuauagcagu uguccaugug gaa                                          23

<210> SEQ ID NO 275
<211> LENGTH: 21
<212> TYPE: RNA
<213> ORGANISM: Artificial Sequence
<220> FEATURE:
<223> OTHER INFORMATION: siRNA

<400> SEQUENCE: 275
ccacauggac aacugcuaua a                                            21

<210> SEQ ID NO 276
<211> LENGTH: 23
<212> TYPE: RNA
<213> ORGANISM: Artificial Sequence
<220> FEATURE:
<223> OTHER INFORMATION: siRNA

<400> SEQUENCE: 276
uuauagcagu uguccaugug gaa                                          23

<210> SEQ ID NO 277
<211> LENGTH: 19
<212> TYPE: RNA
<213> ORGANISM: Artificial Sequence
<220> FEATURE:
<223> OTHER INFORMATION: siRNA

<400> SEQUENCE: 277
acauggacaa cugcuauaa                                               19

<210> SEQ ID NO 278
<211> LENGTH: 21
<212> TYPE: RNA
<213> ORGANISM: Artificial Sequence
<220> FEATURE:
<223> OTHER INFORMATION: siRNA

<400> SEQUENCE: 278
uuauagcagu uguccaugug g                                            21
```

-continued

```
<210> SEQ ID NO 279
<211> LENGTH: 19
<212> TYPE: RNA
<213> ORGANISM: Artificial Sequence
<220> FEATURE:
<223> OTHER INFORMATION: siRNA

<400> SEQUENCE: 279
acauggacaa cugcuauaa                                                    19

<210> SEQ ID NO 280
<211> LENGTH: 21
<212> TYPE: RNA
<213> ORGANISM: Artificial Sequence
<220> FEATURE:
<223> OTHER INFORMATION: siRNA

<400> SEQUENCE: 280
uuauagcagu uguccaugug g                                                 21

<210> SEQ ID NO 281
<211> LENGTH: 19
<212> TYPE: RNA
<213> ORGANISM: Artificial Sequence
<220> FEATURE:
<223> OTHER INFORMATION: siRNA

<400> SEQUENCE: 281
acauggacaa cugcuauaa                                                    19

<210> SEQ ID NO 282
<211> LENGTH: 21
<212> TYPE: RNA
<213> ORGANISM: Artificial Sequence
<220> FEATURE:
<223> OTHER INFORMATION: siRNA

<400> SEQUENCE: 282
uuauagcagu uguccaugug g                                                 21

<210> SEQ ID NO 283
<211> LENGTH: 21
<212> TYPE: RNA
<213> ORGANISM: Artificial Sequence
<220> FEATURE:
<223> OTHER INFORMATION: siRNA

<400> SEQUENCE: 283
ccacauggac aacugcuaua a                                                 21

<210> SEQ ID NO 284
<211> LENGTH: 23
<212> TYPE: RNA
<213> ORGANISM: Artificial Sequence
<220> FEATURE:
<223> OTHER INFORMATION: siRNA

<400> SEQUENCE: 284
uuauagcagu uguccaugug gaa                                               23

<210> SEQ ID NO 285
<211> LENGTH: 21
<212> TYPE: RNA
<213> ORGANISM: Artificial Sequence
<220> FEATURE:
<223> OTHER INFORMATION: siRNA
```

-continued

```
<400> SEQUENCE: 285
ccacauggac aacugcuaua a                                          21

<210> SEQ ID NO 286
<211> LENGTH: 23
<212> TYPE: RNA
<213> ORGANISM: Artificial Sequence
<220> FEATURE:
<223> OTHER INFORMATION: siRNA

<400> SEQUENCE: 286
uuauagcagu uguccaugug gaa                                        23

<210> SEQ ID NO 287
<211> LENGTH: 21
<212> TYPE: RNA
<213> ORGANISM: Artificial Sequence
<220> FEATURE:
<223> OTHER INFORMATION: siRNA

<400> SEQUENCE: 287
ccacauggac aacugcuaua a                                          21

<210> SEQ ID NO 288
<211> LENGTH: 23
<212> TYPE: RNA
<213> ORGANISM: Artificial Sequence
<220> FEATURE:
<223> OTHER INFORMATION: siRNA

<400> SEQUENCE: 288
uuauagcagu uguccaugug gaa                                        23

<210> SEQ ID NO 289
<211> LENGTH: 19
<212> TYPE: RNA
<213> ORGANISM: Artificial Sequence
<220> FEATURE:
<223> OTHER INFORMATION: siRNA

<400> SEQUENCE: 289
acauggacaa cugcuauaa                                             19

<210> SEQ ID NO 290
<211> LENGTH: 21
<212> TYPE: RNA
<213> ORGANISM: Artificial Sequence
<220> FEATURE:
<223> OTHER INFORMATION: siRNA

<400> SEQUENCE: 290
uuauagcagu uguccaugug g                                          21

<210> SEQ ID NO 291
<211> LENGTH: 19
<212> TYPE: RNA
<213> ORGANISM: Artificial Sequence
<220> FEATURE:
<223> OTHER INFORMATION: siRNA

<400> SEQUENCE: 291
acauggacaa cugcuauaa                                             19

<210> SEQ ID NO 292
<211> LENGTH: 21
```

-continued

```
<212> TYPE: RNA
<213> ORGANISM: Artificial Sequence
<220> FEATURE:
<223> OTHER INFORMATION: siRNA

<400> SEQUENCE: 292
uuauagcagu uguccaugug g                                             21

<210> SEQ ID NO 293
<211> LENGTH: 19
<212> TYPE: RNA
<213> ORGANISM: Artificial Sequence
<220> FEATURE:
<223> OTHER INFORMATION: siRNA

<400> SEQUENCE: 293
acauggacaa cugcuauaa                                                19

<210> SEQ ID NO 294
<211> LENGTH: 21
<212> TYPE: RNA
<213> ORGANISM: Artificial Sequence
<220> FEATURE:
<223> OTHER INFORMATION: siRNA

<400> SEQUENCE: 294
uuauagcagu uguccaugug g                                             21

<210> SEQ ID NO 295
<211> LENGTH: 21
<212> TYPE: RNA
<213> ORGANISM: Artificial Sequence
<220> FEATURE:
<223> OTHER INFORMATION: siRNA

<400> SEQUENCE: 295
ccacauggac aacugcuaua a                                             21

<210> SEQ ID NO 296
<211> LENGTH: 23
<212> TYPE: RNA
<213> ORGANISM: Artificial Sequence
<220> FEATURE:
<223> OTHER INFORMATION: siRNA

<400> SEQUENCE: 296
uuauagcagu uguccaugug gaa                                           23

<210> SEQ ID NO 297
<211> LENGTH: 21
<212> TYPE: RNA
<213> ORGANISM: Artificial Sequence
<220> FEATURE:
<223> OTHER INFORMATION: siRNA

<400> SEQUENCE: 297
ccacauggac aacugcuaua a                                             21

<210> SEQ ID NO 298
<211> LENGTH: 23
<212> TYPE: RNA
<213> ORGANISM: Artificial Sequence
<220> FEATURE:
<223> OTHER INFORMATION: siRNA

<400> SEQUENCE: 298
```
uuauagcagu uguccaugug gaa                                                                  23

<210> SEQ ID NO 299
<211> LENGTH: 21
<212> TYPE: RNA
<213> ORGANISM: Artificial Sequence
<220> FEATURE:
<223> OTHER INFORMATION: siRNA

<400> SEQUENCE: 299
ccacauggac aacugcuaua a                                                                    21

<210> SEQ ID NO 300
<211> LENGTH: 23
<212> TYPE: RNA
<213> ORGANISM: Artificial Sequence
<220> FEATURE:
<223> OTHER INFORMATION: siRNA

<400> SEQUENCE: 300
uuauagcagu uguccaugug gaa                                                                  23

<210> SEQ ID NO 301
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z21, and Z21 is A

<400> SEQUENCE: 301
uagcaagcuc ucaguaucn                                                                       19

<210> SEQ ID NO 302
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z22, and Z22 is U

<400> SEQUENCE: 302
ngauacugag agcuugcua                                                                       19

<210> SEQ ID NO 303
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z23, Z23 is a nucleotide complementary to
      Z24, and Z24 is selected from A, U, G or C

<400> SEQUENCE: 303
uagcaagcuc ucaguaucn                                                                       19

<210> SEQ ID NO 304
<211> LENGTH: 19
<212> TYPE: RNA

```
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z24, and Z24 is selected from A, U, G or C

<400> SEQUENCE: 304
ngauacugag agcuugcua                                                 19

<210> SEQ ID NO 305
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z23, Z23 is a nucleotide complementary to
      Z24, and Z24 is selected from A, U, G or C

<400> SEQUENCE: 305
uagcaagcuc ucaguaucn                                                 19

<210> SEQ ID NO 306
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z24, and Z24 is selected from A, U, G or C

<400> SEQUENCE: 306
ngauacugag agcuugcuag g                                              21

<210> SEQ ID NO 307
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z23, Z23 is a nucleotide complementary to
      Z24, and Z24 is selected from A, U, G or C

<400> SEQUENCE: 307
ccuagcaagc ucucaguauc n                                              21

<210> SEQ ID NO 308
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z24, and Z24 is selected from A, U, G or C

<400> SEQUENCE: 308
ngauacugag agcuugcuag gca                                            23
```

-continued

```
<210> SEQ ID NO 309
<211> LENGTH: 19
<212> TYPE: RNA
<213> ORGANISM: Artificial Sequence
<220> FEATURE:
<223> OTHER INFORMATION: siRNA

<400> SEQUENCE: 309
uagcaagcuc ucaguauca                                                          19

<210> SEQ ID NO 310
<211> LENGTH: 21
<212> TYPE: RNA
<213> ORGANISM: Artificial Sequence
<220> FEATURE:
<223> OTHER INFORMATION: siRNA

<400> SEQUENCE: 310
ugauacugag agcuugcuag g                                                       21

<210> SEQ ID NO 311
<211> LENGTH: 21
<212> TYPE: RNA
<213> ORGANISM: Artificial Sequence
<220> FEATURE:
<223> OTHER INFORMATION: siRNA

<400> SEQUENCE: 311
ccuagcaagc ucucaguauc a                                                       21

<210> SEQ ID NO 312
<211> LENGTH: 23
<212> TYPE: RNA
<213> ORGANISM: Artificial Sequence
<220> FEATURE:
<223> OTHER INFORMATION: siRNA

<400> SEQUENCE: 312
ugauacugag agcuugcuag gca                                                     23

<210> SEQ ID NO 313
<211> LENGTH: 19
<212> TYPE: RNA
<213> ORGANISM: Artificial Sequence
<220> FEATURE:
<223> OTHER INFORMATION: siRNA

<400> SEQUENCE: 313
uagcaagcuc ucaguauca                                                          19

<210> SEQ ID NO 314
<211> LENGTH: 21
<212> TYPE: RNA
<213> ORGANISM: Artificial Sequence
<220> FEATURE:
<223> OTHER INFORMATION: siRNA

<400> SEQUENCE: 314
ugauacugag agcuugcuag g                                                       21

<210> SEQ ID NO 315
<211> LENGTH: 19
<212> TYPE: RNA
<213> ORGANISM: Artificial Sequence
<220> FEATURE:
<223> OTHER INFORMATION: siRNA
```

```
<400> SEQUENCE: 315
uagcaagcuc ucaguauca                                        19

<210> SEQ ID NO 316
<211> LENGTH: 21
<212> TYPE: RNA
<213> ORGANISM: Artificial Sequence
<220> FEATURE:
<223> OTHER INFORMATION: siRNA

<400> SEQUENCE: 316
ugauacugag agcuugcuag g                                     21

<210> SEQ ID NO 317
<211> LENGTH: 19
<212> TYPE: RNA
<213> ORGANISM: Artificial Sequence
<220> FEATURE:
<223> OTHER INFORMATION: siRNA

<400> SEQUENCE: 317
uagcaagcuc ucaguauca                                        19

<210> SEQ ID NO 318
<211> LENGTH: 21
<212> TYPE: RNA
<213> ORGANISM: Artificial Sequence
<220> FEATURE:
<223> OTHER INFORMATION: siRNA

<400> SEQUENCE: 318
ugauacugag agcuugcuag g                                     21

<210> SEQ ID NO 319
<211> LENGTH: 21
<212> TYPE: RNA
<213> ORGANISM: Artificial Sequence
<220> FEATURE:
<223> OTHER INFORMATION: siRNA

<400> SEQUENCE: 319
ccuagcaagc ucucaguauc a                                     21

<210> SEQ ID NO 320
<211> LENGTH: 23
<212> TYPE: RNA
<213> ORGANISM: Artificial Sequence
<220> FEATURE:
<223> OTHER INFORMATION: siRNA

<400> SEQUENCE: 320
ugauacugag agcuugcuag gca                                   23

<210> SEQ ID NO 321
<211> LENGTH: 21
<212> TYPE: RNA
<213> ORGANISM: Artificial Sequence
<220> FEATURE:
<223> OTHER INFORMATION: siRNA

<400> SEQUENCE: 321
ccuagcaagc ucucaguauc a                                     21

<210> SEQ ID NO 322
<211> LENGTH: 23
```

-continued

```
<212> TYPE: RNA
<213> ORGANISM: Artificial Sequence
<220> FEATURE:
<223> OTHER INFORMATION: siRNA

<400> SEQUENCE: 322
ugauacugag agcuugcuag gca                                           23

<210> SEQ ID NO 323
<211> LENGTH: 21
<212> TYPE: RNA
<213> ORGANISM: Artificial Sequence
<220> FEATURE:
<223> OTHER INFORMATION: siRNA

<400> SEQUENCE: 323
ccuagcaagc ucucaguauc a                                             21

<210> SEQ ID NO 324
<211> LENGTH: 23
<212> TYPE: RNA
<213> ORGANISM: Artificial Sequence
<220> FEATURE:
<223> OTHER INFORMATION: siRNA

<400> SEQUENCE: 324
ugauacugag agcuugcuag gca                                           23

<210> SEQ ID NO 325
<211> LENGTH: 19
<212> TYPE: RNA
<213> ORGANISM: Artificial Sequence
<220> FEATURE:
<223> OTHER INFORMATION: siRNA

<400> SEQUENCE: 325
uagcaagcuc ucaguauca                                                19

<210> SEQ ID NO 326
<211> LENGTH: 21
<212> TYPE: RNA
<213> ORGANISM: Artificial Sequence
<220> FEATURE:
<223> OTHER INFORMATION: siRNA

<400> SEQUENCE: 326
ugauacugag agcuugcuag g                                             21

<210> SEQ ID NO 327
<211> LENGTH: 19
<212> TYPE: RNA
<213> ORGANISM: Artificial Sequence
<220> FEATURE:
<223> OTHER INFORMATION: siRNA

<400> SEQUENCE: 327
uagcaagcuc ucaguauca                                                19

<210> SEQ ID NO 328
<211> LENGTH: 21
<212> TYPE: RNA
<213> ORGANISM: Artificial Sequence
<220> FEATURE:
<223> OTHER INFORMATION: siRNA

<400> SEQUENCE: 328
```

-continued

```
ugauacugag agcuugcuag g                                              21

<210> SEQ ID NO 329
<211> LENGTH: 19
<212> TYPE: RNA
<213> ORGANISM: Artificial Sequence
<220> FEATURE:
<223> OTHER INFORMATION: siRNA

<400> SEQUENCE: 329
uagcaagcuc ucaguauca                                                 19

<210> SEQ ID NO 330
<211> LENGTH: 21
<212> TYPE: RNA
<213> ORGANISM: Artificial Sequence
<220> FEATURE:
<223> OTHER INFORMATION: siRNA

<400> SEQUENCE: 330
ugauacugag agcuugcuag g                                              21

<210> SEQ ID NO 331
<211> LENGTH: 21
<212> TYPE: RNA
<213> ORGANISM: Artificial Sequence
<220> FEATURE:
<223> OTHER INFORMATION: siRNA

<400> SEQUENCE: 331
ccuagcaagc ucucaguauc a                                              21

<210> SEQ ID NO 332
<211> LENGTH: 23
<212> TYPE: RNA
<213> ORGANISM: Artificial Sequence
<220> FEATURE:
<223> OTHER INFORMATION: siRNA

<400> SEQUENCE: 332
ugauacugag agcuugcuag gca                                            23

<210> SEQ ID NO 333
<211> LENGTH: 21
<212> TYPE: RNA
<213> ORGANISM: Artificial Sequence
<220> FEATURE:
<223> OTHER INFORMATION: siRNA

<400> SEQUENCE: 333
ccuagcaagc ucucaguauc a                                              21

<210> SEQ ID NO 334
<211> LENGTH: 23
<212> TYPE: RNA
<213> ORGANISM: Artificial Sequence
<220> FEATURE:
<223> OTHER INFORMATION: siRNA

<400> SEQUENCE: 334
ugauacugag agcuugcuag gca                                            23

<210> SEQ ID NO 335
<211> LENGTH: 21
<212> TYPE: RNA
<213> ORGANISM: Artificial Sequence
```

```
<220> FEATURE:
<223> OTHER INFORMATION: siRNA

<400> SEQUENCE: 335
ccuagcaagc ucucaguauc a                                           21

<210> SEQ ID NO 336
<211> LENGTH: 23
<212> TYPE: RNA
<213> ORGANISM: Artificial Sequence
<220> FEATURE:
<223> OTHER INFORMATION: siRNA

<400> SEQUENCE: 336
ugauacugag agcuugcuag gca                                         23

<210> SEQ ID NO 337
<211> LENGTH: 19
<212> TYPE: RNA
<213> ORGANISM: Artificial Sequence
<220> FEATURE:
<223> OTHER INFORMATION: siRNA

<400> SEQUENCE: 337
uagcaagcuc ucaguauca                                              19

<210> SEQ ID NO 338
<211> LENGTH: 21
<212> TYPE: RNA
<213> ORGANISM: Artificial Sequence
<220> FEATURE:
<223> OTHER INFORMATION: siRNA

<400> SEQUENCE: 338
ugauacugag agcuugcuag g                                           21

<210> SEQ ID NO 339
<211> LENGTH: 19
<212> TYPE: RNA
<213> ORGANISM: Artificial Sequence
<220> FEATURE:
<223> OTHER INFORMATION: siRNA

<400> SEQUENCE: 339
uagcaagcuc ucaguauca                                              19

<210> SEQ ID NO 340
<211> LENGTH: 21
<212> TYPE: RNA
<213> ORGANISM: Artificial Sequence
<220> FEATURE:
<223> OTHER INFORMATION: siRNA

<400> SEQUENCE: 340
ugauacugag agcuugcuag g                                           21

<210> SEQ ID NO 341
<211> LENGTH: 19
<212> TYPE: RNA
<213> ORGANISM: Artificial Sequence
<220> FEATURE:
<223> OTHER INFORMATION: siRNA

<400> SEQUENCE: 341
uagcaagcuc ucaguauca                                              19
```

```
<210> SEQ ID NO 342
<211> LENGTH: 21
<212> TYPE: RNA
<213> ORGANISM: Artificial Sequence
<220> FEATURE:
<223> OTHER INFORMATION: siRNA

<400> SEQUENCE: 342
ugauacugag agcuugcuag g                                                   21

<210> SEQ ID NO 343
<211> LENGTH: 21
<212> TYPE: RNA
<213> ORGANISM: Artificial Sequence
<220> FEATURE:
<223> OTHER INFORMATION: siRNA

<400> SEQUENCE: 343
ccuagcaagc ucucaguauc a                                                   21

<210> SEQ ID NO 344
<211> LENGTH: 23
<212> TYPE: RNA
<213> ORGANISM: Artificial Sequence
<220> FEATURE:
<223> OTHER INFORMATION: siRNA

<400> SEQUENCE: 344
ugauacugag agcuugcuag gca                                                 23

<210> SEQ ID NO 345
<211> LENGTH: 21
<212> TYPE: RNA
<213> ORGANISM: Artificial Sequence
<220> FEATURE:
<223> OTHER INFORMATION: siRNA

<400> SEQUENCE: 345
ccuagcaagc ucucaguauc a                                                   21

<210> SEQ ID NO 346
<211> LENGTH: 23
<212> TYPE: RNA
<213> ORGANISM: Artificial Sequence
<220> FEATURE:
<223> OTHER INFORMATION: siRNA

<400> SEQUENCE: 346
ugauacugag agcuugcuag gca                                                 23

<210> SEQ ID NO 347
<211> LENGTH: 21
<212> TYPE: RNA
<213> ORGANISM: Artificial Sequence
<220> FEATURE:
<223> OTHER INFORMATION: siRNA

<400> SEQUENCE: 347
ccuagcaagc ucucaguauc a                                                   21

<210> SEQ ID NO 348
<211> LENGTH: 23
<212> TYPE: RNA
<213> ORGANISM: Artificial Sequence
<220> FEATURE:
<223> OTHER INFORMATION: siRNA
```

-continued

<400> SEQUENCE: 348
ugauacugag agcuugcuag gca                                          23

<210> SEQ ID NO 349
<211> LENGTH: 19
<212> TYPE: RNA
<213> ORGANISM: Artificial Sequence
<220> FEATURE:
<223> OTHER INFORMATION: siRNA

<400> SEQUENCE: 349
uagcaagcuc ucaguauca                                               19

<210> SEQ ID NO 350
<211> LENGTH: 21
<212> TYPE: RNA
<213> ORGANISM: Artificial Sequence
<220> FEATURE:
<223> OTHER INFORMATION: siRNA

<400> SEQUENCE: 350
ugauacugag agcuugcuag g                                            21

<210> SEQ ID NO 351
<211> LENGTH: 19
<212> TYPE: RNA
<213> ORGANISM: Artificial Sequence
<220> FEATURE:
<223> OTHER INFORMATION: siRNA

<400> SEQUENCE: 351
uagcaagcuc ucaguauca                                               19

<210> SEQ ID NO 352
<211> LENGTH: 21
<212> TYPE: RNA
<213> ORGANISM: Artificial Sequence
<220> FEATURE:
<223> OTHER INFORMATION: siRNA

<400> SEQUENCE: 352
ugauacugag agcuugcuag g                                            21

<210> SEQ ID NO 353
<211> LENGTH: 19
<212> TYPE: RNA
<213> ORGANISM: Artificial Sequence
<220> FEATURE:
<223> OTHER INFORMATION: siRNA

<400> SEQUENCE: 353
uagcaagcuc ucaguauca                                               19

<210> SEQ ID NO 354
<211> LENGTH: 21
<212> TYPE: RNA
<213> ORGANISM: Artificial Sequence
<220> FEATURE:
<223> OTHER INFORMATION: siRNA

<400> SEQUENCE: 354
ugauacugag agcuugcuag g                                            21

<210> SEQ ID NO 355

```
<211> LENGTH: 21
<212> TYPE: RNA
<213> ORGANISM: Artificial Sequence
<220> FEATURE:
<223> OTHER INFORMATION: siRNA

<400> SEQUENCE: 355
ccuagcaagc ucucaguauc a                                                          21

<210> SEQ ID NO 356
<211> LENGTH: 23
<212> TYPE: RNA
<213> ORGANISM: Artificial Sequence
<220> FEATURE:
<223> OTHER INFORMATION: siRNA

<400> SEQUENCE: 356
ugauacugag agcuugcuag gca                                                        23

<210> SEQ ID NO 357
<211> LENGTH: 21
<212> TYPE: RNA
<213> ORGANISM: Artificial Sequence
<220> FEATURE:
<223> OTHER INFORMATION: siRNA

<400> SEQUENCE: 357
ccuagcaagc ucucaguauc a                                                          21

<210> SEQ ID NO 358
<211> LENGTH: 23
<212> TYPE: RNA
<213> ORGANISM: Artificial Sequence
<220> FEATURE:
<223> OTHER INFORMATION: siRNA

<400> SEQUENCE: 358
ugauacugag agcuugcuag gca                                                        23

<210> SEQ ID NO 359
<211> LENGTH: 21
<212> TYPE: RNA
<213> ORGANISM: Artificial Sequence
<220> FEATURE:
<223> OTHER INFORMATION: siRNA

<400> SEQUENCE: 359
ccuagcaagc ucucaguauc a                                                          21

<210> SEQ ID NO 360
<211> LENGTH: 23
<212> TYPE: RNA
<213> ORGANISM: Artificial Sequence
<220> FEATURE:
<223> OTHER INFORMATION: siRNA

<400> SEQUENCE: 360
ugauacugag agcuugcuag gca                                                        23

<210> SEQ ID NO 361
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
```

-continued

```
<222> LOCATION: (19)..(19)
<223> OTHER INFORMATION: n is Z25, and Z25is G

<400> SEQUENCE: 361
auaagguuac uuguguugn                                              19

<210> SEQ ID NO 362
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z26, and Z26 is C

<400> SEQUENCE: 362
ncaacacaag uaaccuuau                                              19

<210> SEQ ID NO 363
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z27, Z27 is a nucleotide complementary to
      Z28, and Z28 is selected from A, U, G or C

<400> SEQUENCE: 363
auaagguuac uuguguugn                                              19

<210> SEQ ID NO 364
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z28, and Z28 is selected from A, U, G or C

<400> SEQUENCE: 364
ncaacacaag uaaccuuau                                              19

<210> SEQ ID NO 365
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z27, Z27 is a nucleotide complementary to
      Z28, and Z28 is selected from A, U, G or C

<400> SEQUENCE: 365
auaagguuac uuguguugn                                              19

<210> SEQ ID NO 366
<211> LENGTH: 21
<212> TYPE: RNA
<213> ORGANISM: Artificial Sequence
<220> FEATURE:
```

```
<223> OTHER INFORMATION: siRNA
<220> FEATURE:
<221> NAME/KEY: misc_feature
<222> LOCATION: (1)..(1)
<223> OTHER INFORMATION: n is Z28, and Z28 is selected from A, U, G or C

<400> SEQUENCE: 366
ncaacacaag uaaccuuauc c                                                   21

<210> SEQ ID NO 367
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z27, Z27 is a nucleotide complementary to
      Z28, and Z28 is selected from A, U, G or C

<400> SEQUENCE: 367
ggauaagguu acuuguguug n                                                   21

<210> SEQ ID NO 368
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z28, and Z28 is selected from A, U, G or C

<400> SEQUENCE: 368
ncaacacaag uaaccuuauc c                                                   21

<210> SEQ ID NO 369
<211> LENGTH: 19
<212> TYPE: RNA
<213> ORGANISM: Artificial Sequence
<220> FEATURE:
<223> OTHER INFORMATION: siRNA

<400> SEQUENCE: 369
auaagguuac uuguguugg                                                      19

<210> SEQ ID NO 370
<211> LENGTH: 21
<212> TYPE: RNA
<213> ORGANISM: Artificial Sequence
<220> FEATURE:
<223> OTHER INFORMATION: siRNA

<400> SEQUENCE: 370
ccaacacaag uaaccuuauc c                                                   21

<210> SEQ ID NO 371
<211> LENGTH: 21
<212> TYPE: RNA
<213> ORGANISM: Artificial Sequence
<220> FEATURE:
<223> OTHER INFORMATION: siRNA

<400> SEQUENCE: 371
ggauaagguu acuuguguug g                                                   21
```

-continued

```
<210> SEQ ID NO 372
<211> LENGTH: 23
<212> TYPE: RNA
<213> ORGANISM: Artificial Sequence
<220> FEATURE:
<223> OTHER INFORMATION: siRNA

<400> SEQUENCE: 372
ccaacacaag uaaccuuauc cuu                                              23

<210> SEQ ID NO 373
<211> LENGTH: 19
<212> TYPE: RNA
<213> ORGANISM: Artificial Sequence
<220> FEATURE:
<223> OTHER INFORMATION: siRNA

<400> SEQUENCE: 373
auaagguuac uuguguugg                                                  19

<210> SEQ ID NO 374
<211> LENGTH: 21
<212> TYPE: RNA
<213> ORGANISM: Artificial Sequence
<220> FEATURE:
<223> OTHER INFORMATION: siRNA

<400> SEQUENCE: 374
ccaacacaag uaaccuuauc c                                               21

<210> SEQ ID NO 375
<211> LENGTH: 19
<212> TYPE: RNA
<213> ORGANISM: Artificial Sequence
<220> FEATURE:
<223> OTHER INFORMATION: siRNA

<400> SEQUENCE: 375
auaagguuac uuguguugg                                                  19

<210> SEQ ID NO 376
<211> LENGTH: 21
<212> TYPE: RNA
<213> ORGANISM: Artificial Sequence
<220> FEATURE:
<223> OTHER INFORMATION: siRNA

<400> SEQUENCE: 376
ccaacacaag uaaccuuauc c                                               21

<210> SEQ ID NO 377
<211> LENGTH: 19
<212> TYPE: RNA
<213> ORGANISM: Artificial Sequence
<220> FEATURE:
<223> OTHER INFORMATION: siRNA

<400> SEQUENCE: 377
auaagguuac uuguguugg                                                  19

<210> SEQ ID NO 378
<211> LENGTH: 21
<212> TYPE: RNA
<213> ORGANISM: Artificial Sequence
<220> FEATURE:
<223> OTHER INFORMATION: siRNA
```

-continued

```
<400> SEQUENCE: 378
ccaacacaag uaaccuuauc c                                           21

<210> SEQ ID NO 379
<211> LENGTH: 21
<212> TYPE: RNA
<213> ORGANISM: Artificial Sequence
<220> FEATURE:
<223> OTHER INFORMATION: siRNA

<400> SEQUENCE: 379
ggauaagguu acuuguguug g                                           21

<210> SEQ ID NO 380
<211> LENGTH: 23
<212> TYPE: RNA
<213> ORGANISM: Artificial Sequence
<220> FEATURE:
<223> OTHER INFORMATION: siRNA

<400> SEQUENCE: 380
ccaacacaag uaaccuuauc cuu                                         23

<210> SEQ ID NO 381
<211> LENGTH: 21
<212> TYPE: RNA
<213> ORGANISM: Artificial Sequence
<220> FEATURE:
<223> OTHER INFORMATION: siRNA

<400> SEQUENCE: 381
ggauaagguu acuuguguug g                                           21

<210> SEQ ID NO 382
<211> LENGTH: 23
<212> TYPE: RNA
<213> ORGANISM: Artificial Sequence
<220> FEATURE:
<223> OTHER INFORMATION: siRNA

<400> SEQUENCE: 382
ccaacacaag uaaccuuauc cuu                                         23

<210> SEQ ID NO 383
<211> LENGTH: 21
<212> TYPE: RNA
<213> ORGANISM: Artificial Sequence
<220> FEATURE:
<223> OTHER INFORMATION: siRNA

<400> SEQUENCE: 383
ggauaagguu acuuguguug g                                           21

<210> SEQ ID NO 384
<211> LENGTH: 23
<212> TYPE: RNA
<213> ORGANISM: Artificial Sequence
<220> FEATURE:
<223> OTHER INFORMATION: siRNA

<400> SEQUENCE: 384
ccaacacaag uaaccuuauc cuu                                         23

<210> SEQ ID NO 385
```

-continued

```
<211> LENGTH: 19
<212> TYPE: RNA
<213> ORGANISM: Artificial Sequence
<220> FEATURE:
<223> OTHER INFORMATION: siRNA

<400> SEQUENCE: 385
auaagguuac uuguguugg                                                    19

<210> SEQ ID NO 386
<211> LENGTH: 21
<212> TYPE: RNA
<213> ORGANISM: Artificial Sequence
<220> FEATURE:
<223> OTHER INFORMATION: siRNA

<400> SEQUENCE: 386
ccaacacaag uaaccuuauc c                                                 21

<210> SEQ ID NO 387
<211> LENGTH: 19
<212> TYPE: RNA
<213> ORGANISM: Artificial Sequence
<220> FEATURE:
<223> OTHER INFORMATION: siRNA

<400> SEQUENCE: 387
auaagguuac uuguguugg                                                    19

<210> SEQ ID NO 388
<211> LENGTH: 21
<212> TYPE: RNA
<213> ORGANISM: Artificial Sequence
<220> FEATURE:
<223> OTHER INFORMATION: siRNA

<400> SEQUENCE: 388
ccaacacaag uaaccuuauc c                                                 21

<210> SEQ ID NO 389
<211> LENGTH: 19
<212> TYPE: RNA
<213> ORGANISM: Artificial Sequence
<220> FEATURE:
<223> OTHER INFORMATION: siRNA

<400> SEQUENCE: 389
auaagguuac uuguguugg                                                    19

<210> SEQ ID NO 390
<211> LENGTH: 21
<212> TYPE: RNA
<213> ORGANISM: Artificial Sequence
<220> FEATURE:
<223> OTHER INFORMATION: siRNA

<400> SEQUENCE: 390
ccaacacaag uaaccuuauc c                                                 21

<210> SEQ ID NO 391
<211> LENGTH: 21
<212> TYPE: RNA
<213> ORGANISM: Artificial Sequence
<220> FEATURE:
<223> OTHER INFORMATION: siRNA

<400> SEQUENCE: 391
```

-continued

```
ggauaagguu acuuguguug g                                          21

<210> SEQ ID NO 392
<211> LENGTH: 23
<212> TYPE: RNA
<213> ORGANISM: Artificial Sequence
<220> FEATURE:
<223> OTHER INFORMATION: siRNA

<400> SEQUENCE: 392
ccaacacaag uaaccuuauc cuu                                        23

<210> SEQ ID NO 393
<211> LENGTH: 21
<212> TYPE: RNA
<213> ORGANISM: Artificial Sequence
<220> FEATURE:
<223> OTHER INFORMATION: siRNA

<400> SEQUENCE: 393
ggauaagguu acuuguguug g                                          21

<210> SEQ ID NO 394
<211> LENGTH: 23
<212> TYPE: RNA
<213> ORGANISM: Artificial Sequence
<220> FEATURE:
<223> OTHER INFORMATION: siRNA

<400> SEQUENCE: 394
ccaacacaag uaaccuuauc cuu                                        23

<210> SEQ ID NO 395
<211> LENGTH: 21
<212> TYPE: RNA
<213> ORGANISM: Artificial Sequence
<220> FEATURE:
<223> OTHER INFORMATION: siRNA

<400> SEQUENCE: 395
ggauaagguu acuuguguug g                                          21

<210> SEQ ID NO 396
<211> LENGTH: 23
<212> TYPE: RNA
<213> ORGANISM: Artificial Sequence
<220> FEATURE:
<223> OTHER INFORMATION: siRNA

<400> SEQUENCE: 396
ccaacacaag uaaccuuauc cuu                                        23

<210> SEQ ID NO 397
<211> LENGTH: 19
<212> TYPE: RNA
<213> ORGANISM: Artificial Sequence
<220> FEATURE:
<223> OTHER INFORMATION: siRNA

<400> SEQUENCE: 397
auaagguuac uuguguugg                                             19

<210> SEQ ID NO 398
<211> LENGTH: 21
<212> TYPE: RNA
```

```
<213> ORGANISM: Artificial Sequence
<220> FEATURE:
<223> OTHER INFORMATION: siRNA

<400> SEQUENCE: 398
ccaacacaag uaaccuuauc c                                          21

<210> SEQ ID NO 399
<211> LENGTH: 19
<212> TYPE: RNA
<213> ORGANISM: Artificial Sequence
<220> FEATURE:
<223> OTHER INFORMATION: siRNA

<400> SEQUENCE: 399
auaagguuac uuguguugg                                             19

<210> SEQ ID NO 400
<211> LENGTH: 21
<212> TYPE: RNA
<213> ORGANISM: Artificial Sequence
<220> FEATURE:
<223> OTHER INFORMATION: siRNA

<400> SEQUENCE: 400
ccaacacaag uaaccuuauc c                                          21

<210> SEQ ID NO 401
<211> LENGTH: 19
<212> TYPE: RNA
<213> ORGANISM: Artificial Sequence
<220> FEATURE:
<223> OTHER INFORMATION: siRNA

<400> SEQUENCE: 401
auaagguuac uuguguugg                                             19

<210> SEQ ID NO 402
<211> LENGTH: 21
<212> TYPE: RNA
<213> ORGANISM: Artificial Sequence
<220> FEATURE:
<223> OTHER INFORMATION: siRNA

<400> SEQUENCE: 402
ccaacacaag uaaccuuauc c                                          21

<210> SEQ ID NO 403
<211> LENGTH: 21
<212> TYPE: RNA
<213> ORGANISM: Artificial Sequence
<220> FEATURE:
<223> OTHER INFORMATION: siRNA

<400> SEQUENCE: 403
ggauaagguu acuuguguug g                                          21

<210> SEQ ID NO 404
<211> LENGTH: 23
<212> TYPE: RNA
<213> ORGANISM: Artificial Sequence
<220> FEATURE:
<223> OTHER INFORMATION: siRNA

<400> SEQUENCE: 404
ccaacacaag uaaccuuauc cuu                                        23
```

```
<210> SEQ ID NO 405
<211> LENGTH: 21
<212> TYPE: RNA
<213> ORGANISM: Artificial Sequence
<220> FEATURE:
<223> OTHER INFORMATION: siRNA

<400> SEQUENCE: 405
ggauaagguu acuuguguug g                                          21

<210> SEQ ID NO 406
<211> LENGTH: 23
<212> TYPE: RNA
<213> ORGANISM: Artificial Sequence
<220> FEATURE:
<223> OTHER INFORMATION: siRNA

<400> SEQUENCE: 406
ccaacacaag uaaccuuauc cuu                                        23

<210> SEQ ID NO 407
<211> LENGTH: 21
<212> TYPE: RNA
<213> ORGANISM: Artificial Sequence
<220> FEATURE:
<223> OTHER INFORMATION: siRNA

<400> SEQUENCE: 407
ggauaagguu acuuguguug g                                          21

<210> SEQ ID NO 408
<211> LENGTH: 23
<212> TYPE: RNA
<213> ORGANISM: Artificial Sequence
<220> FEATURE:
<223> OTHER INFORMATION: siRNA

<400> SEQUENCE: 408
ccaacacaag uaaccuuauc cuu                                        23

<210> SEQ ID NO 409
<211> LENGTH: 19
<212> TYPE: RNA
<213> ORGANISM: Artificial Sequence
<220> FEATURE:
<223> OTHER INFORMATION: siRNA

<400> SEQUENCE: 409
auaagguuac uuguguugg                                             19

<210> SEQ ID NO 410
<211> LENGTH: 21
<212> TYPE: RNA
<213> ORGANISM: Artificial Sequence
<220> FEATURE:
<223> OTHER INFORMATION: siRNA

<400> SEQUENCE: 410
ccaacacaag uaaccuuauc c                                          21

<210> SEQ ID NO 411
<211> LENGTH: 19
<212> TYPE: RNA
<213> ORGANISM: Artificial Sequence
<220> FEATURE:
```

<223> OTHER INFORMATION: siRNA

<400> SEQUENCE: 411
auaagguuac uuguguugg                                                                    19

<210> SEQ ID NO 412
<211> LENGTH: 21
<212> TYPE: RNA
<213> ORGANISM: Artificial Sequence
<220> FEATURE:
<223> OTHER INFORMATION: siRNA

<400> SEQUENCE: 412
ccaacacaag uaaccuuauc c                                                                  21

<210> SEQ ID NO 413
<211> LENGTH: 19
<212> TYPE: RNA
<213> ORGANISM: Artificial Sequence
<220> FEATURE:
<223> OTHER INFORMATION: siRNA

<400> SEQUENCE: 413
auaagguuac uuguguugg                                                                    19

<210> SEQ ID NO 414
<211> LENGTH: 21
<212> TYPE: RNA
<213> ORGANISM: Artificial Sequence
<220> FEATURE:
<223> OTHER INFORMATION: siRNA

<400> SEQUENCE: 414
ccaacacaag uaaccuuauc c                                                                  21

<210> SEQ ID NO 415
<211> LENGTH: 21
<212> TYPE: RNA
<213> ORGANISM: Artificial Sequence
<220> FEATURE:
<223> OTHER INFORMATION: siRNA

<400> SEQUENCE: 415
ggauaagguu acuuguguug g                                                                  21

<210> SEQ ID NO 416
<211> LENGTH: 23
<212> TYPE: RNA
<213> ORGANISM: Artificial Sequence
<220> FEATURE:
<223> OTHER INFORMATION: siRNA

<400> SEQUENCE: 416
ccaacacaag uaaccuuauc cuu                                                                23

<210> SEQ ID NO 417
<211> LENGTH: 21
<212> TYPE: RNA
<213> ORGANISM: Artificial Sequence
<220> FEATURE:
<223> OTHER INFORMATION: siRNA

<400> SEQUENCE: 417
ggauaagguu acuuguguug g                                                                  21

<210> SEQ ID NO 418
<211> LENGTH: 23
<212> TYPE: RNA
<213> ORGANISM: Artificial Sequence
<220> FEATURE:
<223> OTHER INFORMATION: siRNA

<400> SEQUENCE: 418
ccaacacaag uaaccuuauc cuu                                                    23

<210> SEQ ID NO 419
<211> LENGTH: 21
<212> TYPE: RNA
<213> ORGANISM: Artificial Sequence
<220> FEATURE:
<223> OTHER INFORMATION: siRNA

<400> SEQUENCE: 419
ggauaagguu acuuguguug g                                                      21

<210> SEQ ID NO 420
<211> LENGTH: 23
<212> TYPE: RNA
<213> ORGANISM: Artificial Sequence
<220> FEATURE:
<223> OTHER INFORMATION: siRNA

<400> SEQUENCE: 420
ccaacacaag uaaccuuauc cuu                                                    23

<210> SEQ ID NO 421
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z29, and Z29 is A

<400> SEQUENCE: 421
gaaaaucacc uaugaagan                                                         19

<210> SEQ ID NO 422
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z30, and Z30 is U

<400> SEQUENCE: 422
nucuucauag gugauuuuc                                                         19

<210> SEQ ID NO 423
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z31, Z31 is a nucleotide complementary to
      Z32, and Z32 is selected from A, U, G or C -continued

<400> SEQUENCE: 423
gaaaaucacc uaugaagan                                                          19

<210> SEQ ID NO 424
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z32, and Z32 is selected from A, U, G or C

<400> SEQUENCE: 424
nucuucauag gugauuuuc                                                          19

<210> SEQ ID NO 425
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z31, Z31 is a nucleotide complementary to
      Z32, and Z32 is selected from A, U, G or C

<400> SEQUENCE: 425
gaaaaucacc uaugaagan                                                          19

<210> SEQ ID NO 426
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z32, and Z32 is selected from A, U, G or C

<400> SEQUENCE: 426
nucuucauag gugauuuuca c                                                       21

<210> SEQ ID NO 427
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z31, Z31 is a nucleotide complementary to
      Z32, and Z32 is selected from A, U, G or C

<400> SEQUENCE: 427
gugaaaauca ccuaugaaga n                                                       21

<210> SEQ ID NO 428
<211> LENGTH: 23
<212> TYPE: RNA
<213> ORGANISM: Artificial Sequence
<220> FEATURE:
<223> OTHER INFORMATION: siRNA
<220> FEATURE:

-continued

```
<221> NAME/KEY: misc_feature
<222> LOCATION: (1)..(1)
<223> OTHER INFORMATION: n is Z32, and Z32 is selected from A, U, G or C

<400> SEQUENCE: 428
nucuucauag gugauuuuca ccc                                                    23

<210> SEQ ID NO 429
<211> LENGTH: 19
<212> TYPE: RNA
<213> ORGANISM: Artificial Sequence
<220> FEATURE:
<223> OTHER INFORMATION: siRNA

<400> SEQUENCE: 429
gaaaaucacc uaugaagaa                                                         19

<210> SEQ ID NO 430
<211> LENGTH: 21
<212> TYPE: RNA
<213> ORGANISM: Artificial Sequence
<220> FEATURE:
<223> OTHER INFORMATION: siRNA

<400> SEQUENCE: 430
uucuucauag gugauuuuca c                                                      21

<210> SEQ ID NO 431
<211> LENGTH: 21
<212> TYPE: RNA
<213> ORGANISM: Artificial Sequence
<220> FEATURE:
<223> OTHER INFORMATION: siRNA

<400> SEQUENCE: 431
gugaaaauca ccuaugaaga a                                                      21

<210> SEQ ID NO 432
<211> LENGTH: 23
<212> TYPE: RNA
<213> ORGANISM: Artificial Sequence
<220> FEATURE:
<223> OTHER INFORMATION: siRNA

<400> SEQUENCE: 432
uucuucauag gugauuuuca ccc                                                    23

<210> SEQ ID NO 433
<211> LENGTH: 19
<212> TYPE: RNA
<213> ORGANISM: Artificial Sequence
<220> FEATURE:
<223> OTHER INFORMATION: siRNA

<400> SEQUENCE: 433
gaaaaucacc uaugaagaa                                                         19

<210> SEQ ID NO 434
<211> LENGTH: 21
<212> TYPE: RNA
<213> ORGANISM: Artificial Sequence
<220> FEATURE:
<223> OTHER INFORMATION: siRNA

<400> SEQUENCE: 434
uucuucauag gugauuuuca c                                                      21
```

```
<210> SEQ ID NO 435
<211> LENGTH: 19
<212> TYPE: RNA
<213> ORGANISM: Artificial Sequence
<220> FEATURE:
<223> OTHER INFORMATION: siRNA

<400> SEQUENCE: 435
gaaaaucacc uaugaagaa                                                    19

<210> SEQ ID NO 436
<211> LENGTH: 21
<212> TYPE: RNA
<213> ORGANISM: Artificial Sequence
<220> FEATURE:
<223> OTHER INFORMATION: siRNA

<400> SEQUENCE: 436
uucuucauag gugauuuuca c                                                 21

<210> SEQ ID NO 437
<211> LENGTH: 19
<212> TYPE: RNA
<213> ORGANISM: Artificial Sequence
<220> FEATURE:
<223> OTHER INFORMATION: siRNA

<400> SEQUENCE: 437
gaaaaucacc uaugaagaa                                                    19

<210> SEQ ID NO 438
<211> LENGTH: 21
<212> TYPE: RNA
<213> ORGANISM: Artificial Sequence
<220> FEATURE:
<223> OTHER INFORMATION: siRNA

<400> SEQUENCE: 438
uucuucauag gugauuuuca c                                                 21

<210> SEQ ID NO 439
<211> LENGTH: 21
<212> TYPE: RNA
<213> ORGANISM: Artificial Sequence
<220> FEATURE:
<223> OTHER INFORMATION: siRNA

<400> SEQUENCE: 439
gugaaaauca ccuaugaaga a                                                 21

<210> SEQ ID NO 440
<211> LENGTH: 23
<212> TYPE: RNA
<213> ORGANISM: Artificial Sequence
<220> FEATURE:
<223> OTHER INFORMATION: siRNA

<400> SEQUENCE: 440
uucuucauag gugauuuuca ccc                                               23

<210> SEQ ID NO 441
<211> LENGTH: 21
<212> TYPE: RNA
<213> ORGANISM: Artificial Sequence
<220> FEATURE:
```

-continued

<223> OTHER INFORMATION: siRNA

<400> SEQUENCE: 441
gugaaaauca ccuaugaaga a                                                    21

<210> SEQ ID NO 442
<211> LENGTH: 23
<212> TYPE: RNA
<213> ORGANISM: Artificial Sequence
<220> FEATURE:
<223> OTHER INFORMATION: siRNA

<400> SEQUENCE: 442
uucuucauag gugauuuuca ccc                                                  23

<210> SEQ ID NO 443
<211> LENGTH: 21
<212> TYPE: RNA
<213> ORGANISM: Artificial Sequence
<220> FEATURE:
<223> OTHER INFORMATION: siRNA

<400> SEQUENCE: 443
gugaaaauca ccuaugaaga a                                                    21

<210> SEQ ID NO 444
<211> LENGTH: 23
<212> TYPE: RNA
<213> ORGANISM: Artificial Sequence
<220> FEATURE:
<223> OTHER INFORMATION: siRNA

<400> SEQUENCE: 444
uucuucauag gugauuuuca ccc                                                  23

<210> SEQ ID NO 445
<211> LENGTH: 19
<212> TYPE: RNA
<213> ORGANISM: Artificial Sequence
<220> FEATURE:
<223> OTHER INFORMATION: siRNA

<400> SEQUENCE: 445 gaaaucacc uaugaagaa                                                        19

<210> SEQ ID NO 446
<211> LENGTH: 21
<212> TYPE: RNA
<213> ORGANISM: Artificial Sequence
<220> FEATURE:
<223> OTHER INFORMATION: siRNA

<400> SEQUENCE: 446
uucuucauag gugauuuuca c                                                    21

<210> SEQ ID NO 447
<211> LENGTH: 19
<212> TYPE: RNA
<213> ORGANISM: Artificial Sequence
<220> FEATURE:
<223> OTHER INFORMATION: siRNA

<400> SEQUENCE: 447 gaaaucacc uaugaagaa                                                        19

-continued

```
<210> SEQ ID NO 448
<211> LENGTH: 21
<212> TYPE: RNA
<213> ORGANISM: Artificial Sequence
<220> FEATURE:
<223> OTHER INFORMATION: siRNA

<400> SEQUENCE: 448
uucuucauag gugauuuuca c                                            21

<210> SEQ ID NO 449
<211> LENGTH: 19
<212> TYPE: RNA
<213> ORGANISM: Artificial Sequence
<220> FEATURE:
<223> OTHER INFORMATION: siRNA

<400> SEQUENCE: 449
gaaaaucacc uaugaagaa                                               19

<210> SEQ ID NO 450
<211> LENGTH: 21
<212> TYPE: RNA
<213> ORGANISM: Artificial Sequence
<220> FEATURE:
<223> OTHER INFORMATION: siRNA

<400> SEQUENCE: 450
uucuucauag gugauuuuca c                                            21

<210> SEQ ID NO 451
<211> LENGTH: 21
<212> TYPE: RNA
<213> ORGANISM: Artificial Sequence
<220> FEATURE:
<223> OTHER INFORMATION: siRNA

<400> SEQUENCE: 451
gugaaaauca ccuaugaaga a                                            21

<210> SEQ ID NO 452
<211> LENGTH: 23
<212> TYPE: RNA
<213> ORGANISM: Artificial Sequence
<220> FEATURE:
<223> OTHER INFORMATION: siRNA

<400> SEQUENCE: 452
uucuucauag gugauuuuca ccc                                          23

<210> SEQ ID NO 453
<211> LENGTH: 21
<212> TYPE: RNA
<213> ORGANISM: Artificial Sequence
<220> FEATURE:
<223> OTHER INFORMATION: siRNA

<400> SEQUENCE: 453
gugaaaauca ccuaugaaga a                                            21

<210> SEQ ID NO 454
<211> LENGTH: 23
<212> TYPE: RNA
<213> ORGANISM: Artificial Sequence
<220> FEATURE:
<223> OTHER INFORMATION: siRNA
```

```
<400> SEQUENCE: 454
uucuucauag gugauuuuca ccc                                              23

<210> SEQ ID NO 455
<211> LENGTH: 21
<212> TYPE: RNA
<213> ORGANISM: Artificial Sequence
<220> FEATURE:
<223> OTHER INFORMATION: siRNA

<400> SEQUENCE: 455
gugaaaauca ccuaugaaga a                                                21

<210> SEQ ID NO 456
<211> LENGTH: 23
<212> TYPE: RNA
<213> ORGANISM: Artificial Sequence
<220> FEATURE:
<223> OTHER INFORMATION: siRNA

<400> SEQUENCE: 456
uucuucauag gugauuuuca ccc                                              23

<210> SEQ ID NO 457
<211> LENGTH: 19
<212> TYPE: RNA
<213> ORGANISM: Artificial Sequence
<220> FEATURE:
<223> OTHER INFORMATION: siRNA

<400> SEQUENCE: 457
gaaaaucacc uaugaagaa                                                   19

<210> SEQ ID NO 458
<211> LENGTH: 21
<212> TYPE: RNA
<213> ORGANISM: Artificial Sequence
<220> FEATURE:
<223> OTHER INFORMATION: siRNA

<400> SEQUENCE: 458
uucuucauag gugauuuuca c                                                21

<210> SEQ ID NO 459
<211> LENGTH: 19
<212> TYPE: RNA
<213> ORGANISM: Artificial Sequence
<220> FEATURE:
<223> OTHER INFORMATION: siRNA

<400> SEQUENCE: 459
gaaaaucacc uaugaagaa                                                   19

<210> SEQ ID NO 460
<211> LENGTH: 21
<212> TYPE: RNA
<213> ORGANISM: Artificial Sequence
<220> FEATURE:
<223> OTHER INFORMATION: siRNA

<400> SEQUENCE: 460
uucuucauag gugauuuuca c                                                21

<210> SEQ ID NO 461
<211> LENGTH: 19
```

-continued

```
<212> TYPE: RNA
<213> ORGANISM: Artificial Sequence
<220> FEATURE:
<223> OTHER INFORMATION: siRNA

<400> SEQUENCE: 461
gaaaaucacc uaugaagaa                                                      19

<210> SEQ ID NO 462
<211> LENGTH: 21
<212> TYPE: RNA
<213> ORGANISM: Artificial Sequence
<220> FEATURE:
<223> OTHER INFORMATION: siRNA

<400> SEQUENCE: 462
uucuucauag gugauuuuca c                                                   21

<210> SEQ ID NO 463
<211> LENGTH: 21
<212> TYPE: RNA
<213> ORGANISM: Artificial Sequence
<220> FEATURE:
<223> OTHER INFORMATION: siRNA

<400> SEQUENCE: 463
gugaaaauca ccuaugaaga a                                                   21

<210> SEQ ID NO 464
<211> LENGTH: 23
<212> TYPE: RNA
<213> ORGANISM: Artificial Sequence
<220> FEATURE:
<223> OTHER INFORMATION: siRNA

<400> SEQUENCE: 464
uucuucauag gugauuuuca ccc                                                 23

<210> SEQ ID NO 465
<211> LENGTH: 21
<212> TYPE: RNA
<213> ORGANISM: Artificial Sequence
<220> FEATURE:
<223> OTHER INFORMATION: siRNA

<400> SEQUENCE: 465
gugaaaauca ccuaugaaga a                                                   21

<210> SEQ ID NO 466
<211> LENGTH: 23
<212> TYPE: RNA
<213> ORGANISM: Artificial Sequence
<220> FEATURE:
<223> OTHER INFORMATION: siRNA

<400> SEQUENCE: 466
uucuucauag gugauuuuca ccc                                                 23

<210> SEQ ID NO 467
<211> LENGTH: 21
<212> TYPE: RNA
<213> ORGANISM: Artificial Sequence
<220> FEATURE:
<223> OTHER INFORMATION: siRNA

<400> SEQUENCE: 467
```

-continued gugaaaauca ccuaugaaga a                                                                               21

<210> SEQ ID NO 468
<211> LENGTH: 23
<212> TYPE: RNA
<213> ORGANISM: Artificial Sequence
<220> FEATURE:
<223> OTHER INFORMATION: siRNA

<400> SEQUENCE: 468
uucuucauag gugauuuuca ccc                                                                             23

<210> SEQ ID NO 469
<211> LENGTH: 19
<212> TYPE: RNA
<213> ORGANISM: Artificial Sequence
<220> FEATURE:
<223> OTHER INFORMATION: siRNA

<400> SEQUENCE: 469 gaaaucacc uaugaagaa                                                                                   19

<210> SEQ ID NO 470
<211> LENGTH: 21
<212> TYPE: RNA
<213> ORGANISM: Artificial Sequence
<220> FEATURE:
<223> OTHER INFORMATION: siRNA

<400> SEQUENCE: 470
uucuucauag gugauuuuca c                                                                               21

<210> SEQ ID NO 471
<211> LENGTH: 19
<212> TYPE: RNA
<213> ORGANISM: Artificial Sequence
<220> FEATURE:
<223> OTHER INFORMATION: siRNA

<400> SEQUENCE: 471 gaaaucacc uaugaagaa                                                                                   19

<210> SEQ ID NO 472
<211> LENGTH: 21
<212> TYPE: RNA
<213> ORGANISM: Artificial Sequence
<220> FEATURE:
<223> OTHER INFORMATION: siRNA

<400> SEQUENCE: 472
uucuucauag gugauuuuca c                                                                               21

<210> SEQ ID NO 473
<211> LENGTH: 19
<212> TYPE: RNA
<213> ORGANISM: Artificial Sequence
<220> FEATURE:
<223> OTHER INFORMATION: siRNA

<400> SEQUENCE: 473 gaaaucacc uaugaagaa                                                                                   19

<210> SEQ ID NO 474
<211> LENGTH: 21
<212> TYPE: RNA
<213> ORGANISM: Artificial Sequence -continued
<220> FEATURE:
<223> OTHER INFORMATION: siRNA

<400> SEQUENCE: 474
uucuucauag gugauuuuca c                                                                          21

<210> SEQ ID NO 475
<211> LENGTH: 21
<212> TYPE: RNA
<213> ORGANISM: Artificial Sequence
<220> FEATURE:
<223> OTHER INFORMATION: siRNA

<400> SEQUENCE: 475
gugaaaauca ccuaugaaga a                                                                          21

<210> SEQ ID NO 476
<211> LENGTH: 23
<212> TYPE: RNA
<213> ORGANISM: Artificial Sequence
<220> FEATURE:
<223> OTHER INFORMATION: siRNA

<400> SEQUENCE: 476
uucuucauag gugauuuuca ccc                                                                        23

<210> SEQ ID NO 477
<211> LENGTH: 21
<212> TYPE: RNA
<213> ORGANISM: Artificial Sequence
<220> FEATURE:
<223> OTHER INFORMATION: siRNA

<400> SEQUENCE: 477
gugaaaauca ccuaugaaga a                                                                          21

<210> SEQ ID NO 478
<211> LENGTH: 23
<212> TYPE: RNA
<213> ORGANISM: Artificial Sequence
<220> FEATURE:
<223> OTHER INFORMATION: siRNA

<400> SEQUENCE: 478
uucuucauag gugauuuuca ccc                                                                        23

<210> SEQ ID NO 479
<211> LENGTH: 21
<212> TYPE: RNA
<213> ORGANISM: Artificial Sequence
<220> FEATURE:
<223> OTHER INFORMATION: siRNA

<400> SEQUENCE: 479
gugaaaauca ccuaugaaga a                                                                          21

<210> SEQ ID NO 480
<211> LENGTH: 23
<212> TYPE: RNA
<213> ORGANISM: Artificial Sequence
<220> FEATURE:
<223> OTHER INFORMATION: siRNA

<400> SEQUENCE: 480
uucuucauag gugauuuuca ccc                                                                        23

-continued

```
<210> SEQ ID NO 481
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z33, and Z33 is U

<400> SEQUENCE: 481
gaugcuauaa agaacaacn                                                                           19

<210> SEQ ID NO 482
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z34, and Z34 is A

<400> SEQUENCE: 482
nguuguucuu uauagcauc                                                                           19

<210> SEQ ID NO 483
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z35, Z35 is a nucleotide complementary to
      Z36, and Z36 is selected from A, U, G or C

<400> SEQUENCE: 483
gaugcuauaa agaacaacn                                                                           19

<210> SEQ ID NO 484
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z36, and Z36 is selected from A, U, G or C

<400> SEQUENCE: 484
nguuguucuu uauagcauc                                                                           19

<210> SEQ ID NO 485
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z35, Z35 is a nucleotide complementary to
      Z36, and Z36 is selected from A, U, G or C

<400> SEQUENCE: 485
```

-continued

```
gaugcuauaa agaacaacn                                                19

<210> SEQ ID NO 486
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z36, and Z36 is selected from A, U, G or C

<400> SEQUENCE: 486
nguuguucuu uauagcaucc u                                              21

<210> SEQ ID NO 487
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z35, Z35 is a nucleotide complementary to
      Z36, and Z36 is selected from A, U, G or C

<400> SEQUENCE: 487
aggaugcuau aaagaacaac n                                              21

<210> SEQ ID NO 488
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z36, and Z36 is selected from A, U, G or C

<400> SEQUENCE: 488
nguuguucuu uauagcaucc uca                                            23

<210> SEQ ID NO 489
<211> LENGTH: 19
<212> TYPE: RNA
<213> ORGANISM: Artificial Sequence
<220> FEATURE:
<223> OTHER INFORMATION: siRNA

<400> SEQUENCE: 489
gaugcuauaa agaacaacu                                                 19

<210> SEQ ID NO 490
<211> LENGTH: 21
<212> TYPE: RNA
<213> ORGANISM: Artificial Sequence
<220> FEATURE:
<223> OTHER INFORMATION: siRNA

<400> SEQUENCE: 490
aguuguucuu uauagcaucc u                                              21

<210> SEQ ID NO 491
<211> LENGTH: 21
```

```
<212> TYPE: RNA
<213> ORGANISM: Artificial Sequence
<220> FEATURE:
<223> OTHER INFORMATION: siRNA

<400> SEQUENCE: 491
aggaugcuau aaagaacaac u                                              21

<210> SEQ ID NO 492
<211> LENGTH: 23
<212> TYPE: RNA
<213> ORGANISM: Artificial Sequence
<220> FEATURE:
<223> OTHER INFORMATION: siRNA

<400> SEQUENCE: 492
aguuguucuu uauagcaucc uca                                            23

<210> SEQ ID NO 493
<211> LENGTH: 19
<212> TYPE: RNA
<213> ORGANISM: Artificial Sequence
<220> FEATURE:
<223> OTHER INFORMATION: siRNA

<400> SEQUENCE: 493
gaugcuauaa agaacaacu                                                 19

<210> SEQ ID NO 494
<211> LENGTH: 21
<212> TYPE: RNA
<213> ORGANISM: Artificial Sequence
<220> FEATURE:
<223> OTHER INFORMATION: siRNA

<400> SEQUENCE: 494
aguuguucuu uauagcaucc u                                              21

<210> SEQ ID NO 495
<211> LENGTH: 19
<212> TYPE: RNA
<213> ORGANISM: Artificial Sequence
<220> FEATURE:
<223> OTHER INFORMATION: siRNA

<400> SEQUENCE: 495
gaugcuauaa agaacaacu                                                 19

<210> SEQ ID NO 496
<211> LENGTH: 21
<212> TYPE: RNA
<213> ORGANISM: Artificial Sequence
<220> FEATURE:
<223> OTHER INFORMATION: siRNA

<400> SEQUENCE: 496
aguuguucuu uauagcaucc u                                              21

<210> SEQ ID NO 497
<211> LENGTH: 19
<212> TYPE: RNA
<213> ORGANISM: Artificial Sequence
<220> FEATURE:
<223> OTHER INFORMATION: siRNA

<400> SEQUENCE: 497
```

-continued gaugcuauaa agaacaacu                                                     19

<210> SEQ ID NO 498
<211> LENGTH: 21
<212> TYPE: RNA
<213> ORGANISM: Artificial Sequence
<220> FEATURE:
<223> OTHER INFORMATION: siRNA

<400> SEQUENCE: 498
aguuguucuu uauagcaucc u                                                  21

<210> SEQ ID NO 499
<211> LENGTH: 21
<212> TYPE: RNA
<213> ORGANISM: Artificial Sequence
<220> FEATURE:
<223> OTHER INFORMATION: siRNA

<400> SEQUENCE: 499
aggaugcuau aaagaacaac u                                                  21

<210> SEQ ID NO 500
<211> LENGTH: 23
<212> TYPE: RNA
<213> ORGANISM: Artificial Sequence
<220> FEATURE:
<223> OTHER INFORMATION: siRNA

<400> SEQUENCE: 500
aguuguucuu uauagcaucc uca                                                23

<210> SEQ ID NO 501
<211> LENGTH: 21
<212> TYPE: RNA
<213> ORGANISM: Artificial Sequence
<220> FEATURE:
<223> OTHER INFORMATION: siRNA

<400> SEQUENCE: 501
aggaugcuau aaagaacaac u                                                  21

<210> SEQ ID NO 502
<211> LENGTH: 23
<212> TYPE: RNA
<213> ORGANISM: Artificial Sequence
<220> FEATURE:
<223> OTHER INFORMATION: siRNA

<400> SEQUENCE: 502
aguuguucuu uauagcaucc uca                                                23

<210> SEQ ID NO 503
<211> LENGTH: 21
<212> TYPE: RNA
<213> ORGANISM: Artificial Sequence
<220> FEATURE:
<223> OTHER INFORMATION: siRNA

<400> SEQUENCE: 503
aggaugcuau aaagaacaac u                                                  21

<210> SEQ ID NO 504
<211> LENGTH: 23
<212> TYPE: RNA
<213> ORGANISM: Artificial Sequence
<220> FEATURE:
<223> OTHER INFORMATION: siRNA

<400> SEQUENCE: 504
aguuguucuu uauagcaucc uca                                                    23

<210> SEQ ID NO 505
<211> LENGTH: 19
<212> TYPE: RNA
<213> ORGANISM: Artificial Sequence
<220> FEATURE:
<223> OTHER INFORMATION: siRNA

<400> SEQUENCE: 505
gaugcuauaa agaacaacu                                                         19

<210> SEQ ID NO 506
<211> LENGTH: 21
<212> TYPE: RNA
<213> ORGANISM: Artificial Sequence
<220> FEATURE:
<223> OTHER INFORMATION: siRNA

<400> SEQUENCE: 506
aguuguucuu uauagcaucc u                                                      21

<210> SEQ ID NO 507
<211> LENGTH: 19
<212> TYPE: RNA
<213> ORGANISM: Artificial Sequence
<220> FEATURE:
<223> OTHER INFORMATION: siRNA

<400> SEQUENCE: 507
gaugcuauaa agaacaacu                                                         19

<210> SEQ ID NO 508
<211> LENGTH: 21
<212> TYPE: RNA
<213> ORGANISM: Artificial Sequence
<220> FEATURE:
<223> OTHER INFORMATION: siRNA

<400> SEQUENCE: 508
aguuguucuu uauagcaucc u                                                      21

<210> SEQ ID NO 509
<211> LENGTH: 19
<212> TYPE: RNA
<213> ORGANISM: Artificial Sequence
<220> FEATURE:
<223> OTHER INFORMATION: siRNA

<400> SEQUENCE: 509
gaugcuauaa agaacaacu                                                         19

<210> SEQ ID NO 510
<211> LENGTH: 21
<212> TYPE: RNA
<213> ORGANISM: Artificial Sequence
<220> FEATURE:
<223> OTHER INFORMATION: siRNA

<400> SEQUENCE: 510
aguuguucuu uauagcaucc u                                                      21

-continued

```
<210> SEQ ID NO 511
<211> LENGTH: 21
<212> TYPE: RNA
<213> ORGANISM: Artificial Sequence
<220> FEATURE:
<223> OTHER INFORMATION: siRNA

<400> SEQUENCE: 511
aggaugcuau aaagaacaac u                                                     21

<210> SEQ ID NO 512
<211> LENGTH: 23
<212> TYPE: RNA
<213> ORGANISM: Artificial Sequence
<220> FEATURE:
<223> OTHER INFORMATION: siRNA

<400> SEQUENCE: 512
aguuguucuu uauagcaucc uca                                                   23

<210> SEQ ID NO 513
<211> LENGTH: 21
<212> TYPE: RNA
<213> ORGANISM: Artificial Sequence
<220> FEATURE:
<223> OTHER INFORMATION: siRNA

<400> SEQUENCE: 513
aggaugcuau aaagaacaac u                                                     21

<210> SEQ ID NO 514
<211> LENGTH: 23
<212> TYPE: RNA
<213> ORGANISM: Artificial Sequence
<220> FEATURE:
<223> OTHER INFORMATION: siRNA

<400> SEQUENCE: 514
aguuguucuu uauagcaucc uca                                                   23

<210> SEQ ID NO 515
<211> LENGTH: 21
<212> TYPE: RNA
<213> ORGANISM: Artificial Sequence
<220> FEATURE:
<223> OTHER INFORMATION: siRNA

<400> SEQUENCE: 515
aggaugcuau aaagaacaac u                                                     21

<210> SEQ ID NO 516
<211> LENGTH: 23
<212> TYPE: RNA
<213> ORGANISM: Artificial Sequence
<220> FEATURE:
<223> OTHER INFORMATION: siRNA

<400> SEQUENCE: 516
aguuguucuu uauagcaucc uca                                                   23

<210> SEQ ID NO 517
<211> LENGTH: 19
<212> TYPE: RNA
<213> ORGANISM: Artificial Sequence
<220> FEATURE:
<223> OTHER INFORMATION: siRNA
```

-continued

<400> SEQUENCE: 517
gaugcuauaa agaacaacu                                              19

<210> SEQ ID NO 518
<211> LENGTH: 21
<212> TYPE: RNA
<213> ORGANISM: Artificial Sequence
<220> FEATURE:
<223> OTHER INFORMATION: siRNA

<400> SEQUENCE: 518
aguuguucuu uauagcaucc u                                           21

<210> SEQ ID NO 519
<211> LENGTH: 19
<212> TYPE: RNA
<213> ORGANISM: Artificial Sequence
<220> FEATURE:
<223> OTHER INFORMATION: siRNA

<400> SEQUENCE: 519
gaugcuauaa agaacaacu                                              19

<210> SEQ ID NO 520
<211> LENGTH: 21
<212> TYPE: RNA
<213> ORGANISM: Artificial Sequence
<220> FEATURE:
<223> OTHER INFORMATION: siRNA

<400> SEQUENCE: 520
aguuguucuu uauagcaucc u                                           21

<210> SEQ ID NO 521
<211> LENGTH: 19
<212> TYPE: RNA
<213> ORGANISM: Artificial Sequence
<220> FEATURE:
<223> OTHER INFORMATION: siRNA

<400> SEQUENCE: 521
gaugcuauaa agaacaacu                                              19

<210> SEQ ID NO 522
<211> LENGTH: 21
<212> TYPE: RNA
<213> ORGANISM: Artificial Sequence
<220> FEATURE:
<223> OTHER INFORMATION: siRNA

<400> SEQUENCE: 522
aguuguucuu uauagcaucc u                                           21

<210> SEQ ID NO 523
<211> LENGTH: 21
<212> TYPE: RNA
<213> ORGANISM: Artificial Sequence
<220> FEATURE:
<223> OTHER INFORMATION: siRNA

<400> SEQUENCE: 523
aggaugcuau aaagaacaac u                                           21

<210> SEQ ID NO 524

<211> LENGTH: 23
<212> TYPE: RNA
<213> ORGANISM: Artificial Sequence
<220> FEATURE:
<223> OTHER INFORMATION: siRNA

<400> SEQUENCE: 524
aguuguucuu uauagcaucc uca                                                                                        23

<210> SEQ ID NO 525
<211> LENGTH: 21
<212> TYPE: RNA
<213> ORGANISM: Artificial Sequence
<220> FEATURE:
<223> OTHER INFORMATION: siRNA

<400> SEQUENCE: 525
aggaugcuau aaagaacaac u                                                                                          21

<210> SEQ ID NO 526
<211> LENGTH: 23
<212> TYPE: RNA
<213> ORGANISM: Artificial Sequence
<220> FEATURE:
<223> OTHER INFORMATION: siRNA

<400> SEQUENCE: 526
aguuguucuu uauagcaucc uca                                                                                        23

<210> SEQ ID NO 527
<211> LENGTH: 21
<212> TYPE: RNA
<213> ORGANISM: Artificial Sequence
<220> FEATURE:
<223> OTHER INFORMATION: siRNA

<400> SEQUENCE: 527
aggaugcuau aaagaacaac u                                                                                          21

<210> SEQ ID NO 528
<211> LENGTH: 23
<212> TYPE: RNA
<213> ORGANISM: Artificial Sequence
<220> FEATURE:
<223> OTHER INFORMATION: siRNA

<400> SEQUENCE: 528
aguuguucuu uauagcaucc uca                                                                                        23

<210> SEQ ID NO 529
<211> LENGTH: 19
<212> TYPE: RNA
<213> ORGANISM: Artificial Sequence
<220> FEATURE:
<223> OTHER INFORMATION: siRNA

<400> SEQUENCE: 529
gaugcuauaa agaacaacu                                                                                             19

<210> SEQ ID NO 530
<211> LENGTH: 21
<212> TYPE: RNA
<213> ORGANISM: Artificial Sequence
<220> FEATURE:
<223> OTHER INFORMATION: siRNA

<400> SEQUENCE: 530

-continued aguuguucuu uauagcaucc u                                                        21

<210> SEQ ID NO 531
<211> LENGTH: 19
<212> TYPE: RNA
<213> ORGANISM: Artificial Sequence
<220> FEATURE:
<223> OTHER INFORMATION: siRNA

<400> SEQUENCE: 531
gaugcuauaa agaacaacu                                                           19

<210> SEQ ID NO 532
<211> LENGTH: 21
<212> TYPE: RNA
<213> ORGANISM: Artificial Sequence
<220> FEATURE:
<223> OTHER INFORMATION: siRNA

<400> SEQUENCE: 532
aguuguucuu uauagcaucc u                                                        21

<210> SEQ ID NO 533
<211> LENGTH: 19
<212> TYPE: RNA
<213> ORGANISM: Artificial Sequence
<220> FEATURE:
<223> OTHER INFORMATION: siRNA

<400> SEQUENCE: 533
gaugcuauaa agaacaacu                                                           19

<210> SEQ ID NO 534
<211> LENGTH: 21
<212> TYPE: RNA
<213> ORGANISM: Artificial Sequence
<220> FEATURE:
<223> OTHER INFORMATION: siRNA

<400> SEQUENCE: 534
aguuguucuu uauagcaucc u                                                        21

<210> SEQ ID NO 535
<211> LENGTH: 21
<212> TYPE: RNA
<213> ORGANISM: Artificial Sequence
<220> FEATURE:
<223> OTHER INFORMATION: siRNA

<400> SEQUENCE: 535
aggaugcuau aaagaacaac u                                                        21

<210> SEQ ID NO 536
<211> LENGTH: 23
<212> TYPE: RNA
<213> ORGANISM: Artificial Sequence
<220> FEATURE:
<223> OTHER INFORMATION: siRNA

<400> SEQUENCE: 536
aguuguucuu uauagcaucc uca                                                      23

<210> SEQ ID NO 537
<211> LENGTH: 21
<212> TYPE: RNA

-continued

```
<213> ORGANISM: Artificial Sequence
<220> FEATURE:
<223> OTHER INFORMATION: siRNA

<400> SEQUENCE: 537
aggaugcuau aaagaacaac u                                         21

<210> SEQ ID NO 538
<211> LENGTH: 23
<212> TYPE: RNA
<213> ORGANISM: Artificial Sequence
<220> FEATURE:
<223> OTHER INFORMATION: siRNA

<400> SEQUENCE: 538
aguuguucuu uauagcaucc uca                                       23

<210> SEQ ID NO 539
<211> LENGTH: 21
<212> TYPE: RNA
<213> ORGANISM: Artificial Sequence
<220> FEATURE:
<223> OTHER INFORMATION: siRNA

<400> SEQUENCE: 539
aggaugcuau aaagaacaac u                                         21

<210> SEQ ID NO 540
<211> LENGTH: 23
<212> TYPE: RNA
<213> ORGANISM: Artificial Sequence
<220> FEATURE:
<223> OTHER INFORMATION: siRNA

<400> SEQUENCE: 540
aguuguucuu uauagcaucc uca                                       23

<210> SEQ ID NO 541
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z37, and Z37 is A

<400> SEQUENCE: 541
gaacaacucc uuuuauggn                                            19

<210> SEQ ID NO 542
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z38, and Z38 is U

<400> SEQUENCE: 542
nccauaaaag gaguuguuc                                            19

<210> SEQ ID NO 543
<211> LENGTH: 19
```

-continued

```
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z39, Z39 is a nucleotide complementary to
      Z40, and Z40 is selected from A, U, G or C

<400> SEQUENCE: 543
gaacaacucc uuuuauggn                                                    19

<210> SEQ ID NO 544
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z40, and Z40 is selected from A, U, G or C

<400> SEQUENCE: 544
nccauaaaag gaguuguuc                                                    19

<210> SEQ ID NO 545
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z39, Z39 is a nucleotide complementary to
      Z40, and Z40 is selected from A, U, G or C

<400> SEQUENCE: 545
gaacaacucc uuuuauggn                                                    19

<210> SEQ ID NO 546
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z40, and Z40 is selected from A, U, G or C

<400> SEQUENCE: 546
nccauaaaag gaguuguucu u                                                 21

<210> SEQ ID NO 547
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z39, Z39 is a nucleotide complementary to
      Z40, and Z40 is selected from A, U, G or C

<400> SEQUENCE: 547
aagaacaacu ccuuuuaugg n                                                 21
```

```
<210> SEQ ID NO 548
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z40, and Z40 is selected from A, U, G or C

<400> SEQUENCE: 548
nccauaaaag gaguuguucu u                                                       21

<210> SEQ ID NO 549
<211> LENGTH: 19
<212> TYPE: RNA
<213> ORGANISM: Artificial Sequence
<220> FEATURE:
<223> OTHER INFORMATION: siRNA

<400> SEQUENCE: 549
gaacaacucc uuuuaugga                                                          19

<210> SEQ ID NO 550
<211> LENGTH: 21
<212> TYPE: RNA
<213> ORGANISM: Artificial Sequence
<220> FEATURE:
<223> OTHER INFORMATION: siRNA

<400> SEQUENCE: 550
uccauaaaag gaguuguucu u                                                       21

<210> SEQ ID NO 551
<211> LENGTH: 21
<212> TYPE: RNA
<213> ORGANISM: Artificial Sequence
<220> FEATURE:
<223> OTHER INFORMATION: siRNA

<400> SEQUENCE: 551
aagaacaacu ccuuuuaugg a                                                       21

<210> SEQ ID NO 552
<211> LENGTH: 23
<212> TYPE: RNA
<213> ORGANISM: Artificial Sequence
<220> FEATURE:
<223> OTHER INFORMATION: siRNA

<400> SEQUENCE: 552
uccauaaaag gaguuguucu uua                                                     23

<210> SEQ ID NO 553
<211> LENGTH: 19
<212> TYPE: RNA
<213> ORGANISM: Artificial Sequence
<220> FEATURE:
<223> OTHER INFORMATION: siRNA

<400> SEQUENCE: 553
gaacaacucc uuuuaugga                                                          19

<210> SEQ ID NO 554
```

```
<211> LENGTH: 21
<212> TYPE: RNA
<213> ORGANISM: Artificial Sequence
<220> FEATURE:
<223> OTHER INFORMATION: siRNA

<400> SEQUENCE: 554
uccauaaaag gaguuguucu u                                              21

<210> SEQ ID NO 555
<211> LENGTH: 19
<212> TYPE: RNA
<213> ORGANISM: Artificial Sequence
<220> FEATURE:
<223> OTHER INFORMATION: siRNA

<400> SEQUENCE: 555
gaacaacucc uuuuaugga                                                 19

<210> SEQ ID NO 556
<211> LENGTH: 21
<212> TYPE: RNA
<213> ORGANISM: Artificial Sequence
<220> FEATURE:
<223> OTHER INFORMATION: siRNA

<400> SEQUENCE: 556
uccauaaaag gaguuguucu u                                              21

<210> SEQ ID NO 557
<211> LENGTH: 19
<212> TYPE: RNA
<213> ORGANISM: Artificial Sequence
<220> FEATURE:
<223> OTHER INFORMATION: siRNA

<400> SEQUENCE: 557
gaacaacucc uuuuaugga                                                 19

<210> SEQ ID NO 558
<211> LENGTH: 21
<212> TYPE: RNA
<213> ORGANISM: Artificial Sequence
<220> FEATURE:
<223> OTHER INFORMATION: siRNA

<400> SEQUENCE: 558
uccauaaaag gaguuguucu u                                              21

<210> SEQ ID NO 559
<211> LENGTH: 21
<212> TYPE: RNA
<213> ORGANISM: Artificial Sequence
<220> FEATURE:
<223> OTHER INFORMATION: siRNA

<400> SEQUENCE: 559
aagaacaacu ccuuuuaugg a                                              21

<210> SEQ ID NO 560
<211> LENGTH: 23
<212> TYPE: RNA
<213> ORGANISM: Artificial Sequence
<220> FEATURE:
<223> OTHER INFORMATION: siRNA

<400> SEQUENCE: 560
```
uccauaaaag gaguuguucu uua                                    23

<210> SEQ ID NO 561
<211> LENGTH: 21
<212> TYPE: RNA
<213> ORGANISM: Artificial Sequence
<220> FEATURE:
<223> OTHER INFORMATION: siRNA

<400> SEQUENCE: 561
aagaacaacu ccuuuuaugg a                                      21

<210> SEQ ID NO 562
<211> LENGTH: 23
<212> TYPE: RNA
<213> ORGANISM: Artificial Sequence
<220> FEATURE:
<223> OTHER INFORMATION: siRNA

<400> SEQUENCE: 562
uccauaaaag gaguuguucu uua                                    23

<210> SEQ ID NO 563
<211> LENGTH: 21
<212> TYPE: RNA
<213> ORGANISM: Artificial Sequence
<220> FEATURE:
<223> OTHER INFORMATION: siRNA

<400> SEQUENCE: 563
aagaacaacu ccuuuuaugg a                                      21

<210> SEQ ID NO 564
<211> LENGTH: 23
<212> TYPE: RNA
<213> ORGANISM: Artificial Sequence
<220> FEATURE:
<223> OTHER INFORMATION: siRNA

<400> SEQUENCE: 564
uccauaaaag gaguuguucu uua                                    23

<210> SEQ ID NO 565
<211> LENGTH: 19
<212> TYPE: RNA
<213> ORGANISM: Artificial Sequence
<220> FEATURE:
<223> OTHER INFORMATION: siRNA

<400> SEQUENCE: 565
gaacaacucc uuuuaugga                                         19

<210> SEQ ID NO 566
<211> LENGTH: 21
<212> TYPE: RNA
<213> ORGANISM: Artificial Sequence
<220> FEATURE:
<223> OTHER INFORMATION: siRNA

<400> SEQUENCE: 566
uccauaaaag gaguuguucu u                                      21

<210> SEQ ID NO 567
<211> LENGTH: 19
<212> TYPE: RNA

```
<213> ORGANISM: Artificial Sequence
<220> FEATURE:
<223> OTHER INFORMATION: siRNA

<400> SEQUENCE: 567
gaacaacucc uuuuaugga                                              19

<210> SEQ ID NO 568
<211> LENGTH: 21
<212> TYPE: RNA
<213> ORGANISM: Artificial Sequence
<220> FEATURE:
<223> OTHER INFORMATION: siRNA

<400> SEQUENCE: 568
uccauaaaag gaguuguucu u                                           21

<210> SEQ ID NO 569
<211> LENGTH: 19
<212> TYPE: RNA
<213> ORGANISM: Artificial Sequence
<220> FEATURE:
<223> OTHER INFORMATION: siRNA

<400> SEQUENCE: 569
gaacaacucc uuuuaugga                                              19

<210> SEQ ID NO 570
<211> LENGTH: 21
<212> TYPE: RNA
<213> ORGANISM: Artificial Sequence
<220> FEATURE:
<223> OTHER INFORMATION: siRNA

<400> SEQUENCE: 570
uccauaaaag gaguuguucu u                                           21

<210> SEQ ID NO 571
<211> LENGTH: 21
<212> TYPE: RNA
<213> ORGANISM: Artificial Sequence
<220> FEATURE:
<223> OTHER INFORMATION: siRNA

<400> SEQUENCE: 571
aagaacaacu ccuuuuaugg a                                           21

<210> SEQ ID NO 572
<211> LENGTH: 23
<212> TYPE: RNA
<213> ORGANISM: Artificial Sequence
<220> FEATURE:
<223> OTHER INFORMATION: siRNA

<400> SEQUENCE: 572
uccauaaaag gaguuguucu uua                                         23

<210> SEQ ID NO 573
<211> LENGTH: 21
<212> TYPE: RNA
<213> ORGANISM: Artificial Sequence
<220> FEATURE:
<223> OTHER INFORMATION: siRNA

<400> SEQUENCE: 573
aagaacaacu ccuuuuaugg a                                           21
```

```
<210> SEQ ID NO 574
<211> LENGTH: 23
<212> TYPE: RNA
<213> ORGANISM: Artificial Sequence
<220> FEATURE:
<223> OTHER INFORMATION: siRNA

<400> SEQUENCE: 574
uccauaaaag gaguuguucu uua                                                    23

<210> SEQ ID NO 575
<211> LENGTH: 21
<212> TYPE: RNA
<213> ORGANISM: Artificial Sequence
<220> FEATURE:
<223> OTHER INFORMATION: siRNA

<400> SEQUENCE: 575
aagaacaacu ccuuuuaugg a                                                      21

<210> SEQ ID NO 576
<211> LENGTH: 23
<212> TYPE: RNA
<213> ORGANISM: Artificial Sequence
<220> FEATURE:
<223> OTHER INFORMATION: siRNA

<400> SEQUENCE: 576
uccauaaaag gaguuguucu uua                                                    23

<210> SEQ ID NO 577
<211> LENGTH: 19
<212> TYPE: RNA
<213> ORGANISM: Artificial Sequence
<220> FEATURE:
<223> OTHER INFORMATION: siRNA

<400> SEQUENCE: 577
gaacaacucc uuuuaugga                                                         19

<210> SEQ ID NO 578
<211> LENGTH: 21
<212> TYPE: RNA
<213> ORGANISM: Artificial Sequence
<220> FEATURE:
<223> OTHER INFORMATION: siRNA

<400> SEQUENCE: 578
uccauaaaag gaguuguucu u                                                      21

<210> SEQ ID NO 579
<211> LENGTH: 19
<212> TYPE: RNA
<213> ORGANISM: Artificial Sequence
<220> FEATURE:
<223> OTHER INFORMATION: siRNA

<400> SEQUENCE: 579
gaacaacucc uuuuaugga                                                         19

<210> SEQ ID NO 580
<211> LENGTH: 21
<212> TYPE: RNA
<213> ORGANISM: Artificial Sequence
<220> FEATURE:
```

<223> OTHER INFORMATION: siRNA

<400> SEQUENCE: 580
uccauaaaag gaguuguucu u                                                                21

<210> SEQ ID NO 581
<211> LENGTH: 19
<212> TYPE: RNA
<213> ORGANISM: Artificial Sequence
<220> FEATURE:
<223> OTHER INFORMATION: siRNA

<400> SEQUENCE: 581
gaacaacucc uuuuaugga                                                                   19

<210> SEQ ID NO 582
<211> LENGTH: 21
<212> TYPE: RNA
<213> ORGANISM: Artificial Sequence
<220> FEATURE:
<223> OTHER INFORMATION: siRNA

<400> SEQUENCE: 582
uccauaaaag gaguuguucu u                                                                21

<210> SEQ ID NO 583
<211> LENGTH: 21
<212> TYPE: RNA
<213> ORGANISM: Artificial Sequence
<220> FEATURE:
<223> OTHER INFORMATION: siRNA

<400> SEQUENCE: 583
aagaacaacu ccuuuuaugg a                                                                21

<210> SEQ ID NO 584
<211> LENGTH: 23
<212> TYPE: RNA
<213> ORGANISM: Artificial Sequence
<220> FEATURE:
<223> OTHER INFORMATION: siRNA

<400> SEQUENCE: 584
uccauaaaag gaguuguucu uua                                                              23

<210> SEQ ID NO 585
<211> LENGTH: 21
<212> TYPE: RNA
<213> ORGANISM: Artificial Sequence
<220> FEATURE:
<223> OTHER INFORMATION: siRNA

<400> SEQUENCE: 585
aagaacaacu ccuuuuaugg a                                                                21

<210> SEQ ID NO 586
<211> LENGTH: 23
<212> TYPE: RNA
<213> ORGANISM: Artificial Sequence
<220> FEATURE:
<223> OTHER INFORMATION: siRNA

<400> SEQUENCE: 586
uccauaaaag gaguuguucu uua                                                              23

```
<210> SEQ ID NO 587
<211> LENGTH: 21
<212> TYPE: RNA
<213> ORGANISM: Artificial Sequence
<220> FEATURE:
<223> OTHER INFORMATION: siRNA

<400> SEQUENCE: 587
aagaacaacu ccuuuuaugg a                                              21

<210> SEQ ID NO 588
<211> LENGTH: 23
<212> TYPE: RNA
<213> ORGANISM: Artificial Sequence
<220> FEATURE:
<223> OTHER INFORMATION: siRNA

<400> SEQUENCE: 588
uccauaaaag gaguuguucu uua                                            23

<210> SEQ ID NO 589
<211> LENGTH: 19
<212> TYPE: RNA
<213> ORGANISM: Artificial Sequence
<220> FEATURE:
<223> OTHER INFORMATION: siRNA

<400> SEQUENCE: 589
gaacaacucc uuuuaugga                                                 19

<210> SEQ ID NO 590
<211> LENGTH: 21
<212> TYPE: RNA
<213> ORGANISM: Artificial Sequence
<220> FEATURE:
<223> OTHER INFORMATION: siRNA

<400> SEQUENCE: 590
uccauaaaag gaguuguucu u                                              21

<210> SEQ ID NO 591
<211> LENGTH: 19
<212> TYPE: RNA
<213> ORGANISM: Artificial Sequence
<220> FEATURE:
<223> OTHER INFORMATION: siRNA

<400> SEQUENCE: 591
gaacaacucc uuuuaugga                                                 19

<210> SEQ ID NO 592
<211> LENGTH: 21
<212> TYPE: RNA
<213> ORGANISM: Artificial Sequence
<220> FEATURE:
<223> OTHER INFORMATION: siRNA

<400> SEQUENCE: 592
uccauaaaag gaguuguucu u                                              21

<210> SEQ ID NO 593
<211> LENGTH: 19
<212> TYPE: RNA
<213> ORGANISM: Artificial Sequence
<220> FEATURE:
<223> OTHER INFORMATION: siRNA
```

-continued

<400> SEQUENCE: 593
gaacaacucc uuuuaugga                                                    19

<210> SEQ ID NO 594
<211> LENGTH: 21
<212> TYPE: RNA
<213> ORGANISM: Artificial Sequence
<220> FEATURE:
<223> OTHER INFORMATION: siRNA

<400> SEQUENCE: 594
uccauaaaag gaguuguucu u                                                 21

<210> SEQ ID NO 595
<211> LENGTH: 21
<212> TYPE: RNA
<213> ORGANISM: Artificial Sequence
<220> FEATURE:
<223> OTHER INFORMATION: siRNA

<400> SEQUENCE: 595
aagaacaacu ccuuuuaugg a                                                 21

<210> SEQ ID NO 596
<211> LENGTH: 23
<212> TYPE: RNA
<213> ORGANISM: Artificial Sequence
<220> FEATURE:
<223> OTHER INFORMATION: siRNA

<400> SEQUENCE: 596
uccauaaaag gaguuguucu uua                                               23

<210> SEQ ID NO 597
<211> LENGTH: 21
<212> TYPE: RNA
<213> ORGANISM: Artificial Sequence
<220> FEATURE:
<223> OTHER INFORMATION: siRNA

<400> SEQUENCE: 597
aagaacaacu ccuuuuaugg a                                                 21

<210> SEQ ID NO 598
<211> LENGTH: 23
<212> TYPE: RNA
<213> ORGANISM: Artificial Sequence
<220> FEATURE:
<223> OTHER INFORMATION: siRNA

<400> SEQUENCE: 598
uccauaaaag gaguuguucu uua                                               23

<210> SEQ ID NO 599
<211> LENGTH: 21
<212> TYPE: RNA
<213> ORGANISM: Artificial Sequence
<220> FEATURE:
<223> OTHER INFORMATION: siRNA

<400> SEQUENCE: 599
aagaacaacu ccuuuuaugg a                                                 21

<210> SEQ ID NO 600
<211> LENGTH: 23

-continued

```
<212> TYPE: RNA
<213> ORGANISM: Artificial Sequence
<220> FEATURE:
<223> OTHER INFORMATION: siRNA

<400> SEQUENCE: 600
uccauaaaag gaguuguucu uua                                            23

<210> SEQ ID NO 601
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z41, and Z41 is U

<400> SEQUENCE: 601
cuugcucuga aguagaaan                                                 19

<210> SEQ ID NO 602
<211> LENGTH: 20
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z42, and Z42 is A

<400> SEQUENCE: 602
nauuucuacu ucagagcaag                                                20

<210> SEQ ID NO 603
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z43, Z43 is a nucleotide complementary to
     Z44, and Z44 is selected from A, U, G or C

<400> SEQUENCE: 603
cuugcucuga aguagaaan                                                 19

<210> SEQ ID NO 604
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z44, and Z44 is selected from A, U, G or C

<400> SEQUENCE: 604
nuuucuacuu cagagcaag                                                 19

<210> SEQ ID NO 605
<211> LENGTH: 19
<212> TYPE: RNA
<213> ORGANISM: Artificial Sequence
```

```
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z43, Z43 is a nucleotide complementary to
      Z44, and Z44 is selected from A, U, G or C

<400> SEQUENCE: 605
cuugcucuga aguagaaan                                                  19

<210> SEQ ID NO 606
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z44, and Z44 is selected from A, U, G or C

<400> SEQUENCE: 606
nuuucuacuu cagagcaagc c                                               21

<210> SEQ ID NO 607
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (21)..(21)
<223> OTHER INFORMATION: n is Z43, Z43 is a nucleotide complementary to
      Z44, and Z44 is selected from A, U, G or C

<400> SEQUENCE: 607
ggcuugcucu gaaguagaaa n                                               21

<210> SEQ ID NO 608
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z44, and Z44 is selected from A, U, G or C

<400> SEQUENCE: 608
nuuucuacuu cagagcaagc cac                                             23

<210> SEQ ID NO 609
<211> LENGTH: 19
<212> TYPE: RNA
<213> ORGANISM: Artificial Sequence
<220> FEATURE:
<223> OTHER INFORMATION: siRNA

<400> SEQUENCE: 609
cuugcucuga aguagaaau                                                  19

<210> SEQ ID NO 610
<211> LENGTH: 21
<212> TYPE: RNA
<213> ORGANISM: Artificial Sequence
<220> FEATURE:
```

-continued

<223> OTHER INFORMATION: siRNA

<400> SEQUENCE: 610
auuucuacuu cagagcaagc c                                                    21

<210> SEQ ID NO 611
<211> LENGTH: 21
<212> TYPE: RNA
<213> ORGANISM: Artificial Sequence
<220> FEATURE:
<223> OTHER INFORMATION: siRNA

<400> SEQUENCE: 611
ggcuugcucu gaaguagaaa u                                                    21

<210> SEQ ID NO 612
<211> LENGTH: 23
<212> TYPE: RNA
<213> ORGANISM: Artificial Sequence
<220> FEATURE:
<223> OTHER INFORMATION: siRNA

<400> SEQUENCE: 612
auuucuacuu cagagcaagc cac                                                  23

<210> SEQ ID NO 613
<211> LENGTH: 19
<212> TYPE: RNA
<213> ORGANISM: Artificial Sequence
<220> FEATURE:
<223> OTHER INFORMATION: siRNA

<400> SEQUENCE: 613
cuugcucuga aguagaaau                                                       19

<210> SEQ ID NO 614
<211> LENGTH: 21
<212> TYPE: RNA
<213> ORGANISM: Artificial Sequence
<220> FEATURE:
<223> OTHER INFORMATION: siRNA

<400> SEQUENCE: 614
auuucuacuu cagagcaagc c                                                    21

<210> SEQ ID NO 615
<211> LENGTH: 19
<212> TYPE: RNA
<213> ORGANISM: Artificial Sequence
<220> FEATURE:
<223> OTHER INFORMATION: siRNA

<400> SEQUENCE: 615
cuugcucuga aguagaaau                                                       19

<210> SEQ ID NO 616
<211> LENGTH: 21
<212> TYPE: RNA
<213> ORGANISM: Artificial Sequence
<220> FEATURE:
<223> OTHER INFORMATION: siRNA

<400> SEQUENCE: 616
auuucuacuu cagagcaagc c                                                    21

-continued

```
<210> SEQ ID NO 617
<211> LENGTH: 19
<212> TYPE: RNA
<213> ORGANISM: Artificial Sequence
<220> FEATURE:
<223> OTHER INFORMATION: siRNA

<400> SEQUENCE: 617
cuugcucuga aguagaaau                                              19

<210> SEQ ID NO 618
<211> LENGTH: 21
<212> TYPE: RNA
<213> ORGANISM: Artificial Sequence
<220> FEATURE:
<223> OTHER INFORMATION: siRNA

<400> SEQUENCE: 618
auuucuacuu cagagcaagc c                                           21

<210> SEQ ID NO 619
<211> LENGTH: 21
<212> TYPE: RNA
<213> ORGANISM: Artificial Sequence
<220> FEATURE:
<223> OTHER INFORMATION: siRNA

<400> SEQUENCE: 619
ggcuugcucu gaaguagaaa u                                           21

<210> SEQ ID NO 620
<211> LENGTH: 23
<212> TYPE: RNA
<213> ORGANISM: Artificial Sequence
<220> FEATURE:
<223> OTHER INFORMATION: siRNA

<400> SEQUENCE: 620
auuucuacuu cagagcaagc cac                                         23

<210> SEQ ID NO 621
<211> LENGTH: 21
<212> TYPE: RNA
<213> ORGANISM: Artificial Sequence
<220> FEATURE:
<223> OTHER INFORMATION: siRNA

<400> SEQUENCE: 621
ggcuugcucu gaaguagaaa u                                           21

<210> SEQ ID NO 622
<211> LENGTH: 23
<212> TYPE: RNA
<213> ORGANISM: Artificial Sequence
<220> FEATURE:
<223> OTHER INFORMATION: siRNA

<400> SEQUENCE: 622
auuucuacuu cagagcaagc cac                                         23

<210> SEQ ID NO 623
<211> LENGTH: 21
<212> TYPE: RNA
<213> ORGANISM: Artificial Sequence
<220> FEATURE:
<223> OTHER INFORMATION: siRNA
```

-continued

<400> SEQUENCE: 623
ggcuugcucu gaaguagaaa u                                                          21

<210> SEQ ID NO 624
<211> LENGTH: 23
<212> TYPE: RNA
<213> ORGANISM: Artificial Sequence
<220> FEATURE:
<223> OTHER INFORMATION: siRNA

<400> SEQUENCE: 624
auuucuacuu cagagcaagc cac                                                        23

<210> SEQ ID NO 625
<211> LENGTH: 19
<212> TYPE: RNA
<213> ORGANISM: Artificial Sequence
<220> FEATURE:
<223> OTHER INFORMATION: siRNA

<400> SEQUENCE: 625
cuugcucuga aguagaaau                                                             19

<210> SEQ ID NO 626
<211> LENGTH: 21
<212> TYPE: RNA
<213> ORGANISM: Artificial Sequence
<220> FEATURE:
<223> OTHER INFORMATION: siRNA

<400> SEQUENCE: 626
auuucuacuu cagagcaagc c                                                          21

<210> SEQ ID NO 627
<211> LENGTH: 19
<212> TYPE: RNA
<213> ORGANISM: Artificial Sequence
<220> FEATURE:
<223> OTHER INFORMATION: siRNA

<400> SEQUENCE: 627
cuugcucuga aguagaaau                                                             19

<210> SEQ ID NO 628
<211> LENGTH: 21
<212> TYPE: RNA
<213> ORGANISM: Artificial Sequence
<220> FEATURE:
<223> OTHER INFORMATION: siRNA

<400> SEQUENCE: 628
auuucuacuu cagagcaagc c                                                          21

<210> SEQ ID NO 629
<211> LENGTH: 19
<212> TYPE: RNA
<213> ORGANISM: Artificial Sequence
<220> FEATURE:
<223> OTHER INFORMATION: siRNA

<400> SEQUENCE: 629
cuugcucuga aguagaaau                                                             19

<210> SEQ ID NO 630
<211> LENGTH: 21

```
<212> TYPE: RNA
<213> ORGANISM: Artificial Sequence
<220> FEATURE:
<223> OTHER INFORMATION: siRNA

<400> SEQUENCE: 630
auuucuacuu cagagcaagc c                                                    21

<210> SEQ ID NO 631
<211> LENGTH: 21
<212> TYPE: RNA
<213> ORGANISM: Artificial Sequence
<220> FEATURE:
<223> OTHER INFORMATION: siRNA

<400> SEQUENCE: 631
ggcuugcucu gaaguagaaa u                                                    21

<210> SEQ ID NO 632
<211> LENGTH: 23
<212> TYPE: RNA
<213> ORGANISM: Artificial Sequence
<220> FEATURE:
<223> OTHER INFORMATION: siRNA

<400> SEQUENCE: 632
auuucuacuu cagagcaagc cac                                                  23

<210> SEQ ID NO 633
<211> LENGTH: 21
<212> TYPE: RNA
<213> ORGANISM: Artificial Sequence
<220> FEATURE:
<223> OTHER INFORMATION: siRNA

<400> SEQUENCE: 633
ggcuugcucu gaaguagaaa u                                                    21

<210> SEQ ID NO 634
<211> LENGTH: 23
<212> TYPE: RNA
<213> ORGANISM: Artificial Sequence
<220> FEATURE:
<223> OTHER INFORMATION: siRNA

<400> SEQUENCE: 634
auuucuacuu cagagcaagc cac                                                  23

<210> SEQ ID NO 635
<211> LENGTH: 21
<212> TYPE: RNA
<213> ORGANISM: Artificial Sequence
<220> FEATURE:
<223> OTHER INFORMATION: siRNA

<400> SEQUENCE: 635
ggcuugcucu gaaguagaaa u                                                    21

<210> SEQ ID NO 636
<211> LENGTH: 23
<212> TYPE: RNA
<213> ORGANISM: Artificial Sequence
<220> FEATURE:
<223> OTHER INFORMATION: siRNA

<400> SEQUENCE: 636
```

-continued auuucuacuu cagagcaagc cac                                              23

<210> SEQ ID NO 637
<211> LENGTH: 19
<212> TYPE: RNA
<213> ORGANISM: Artificial Sequence
<220> FEATURE:
<223> OTHER INFORMATION: siRNA

<400> SEQUENCE: 637
cuugcucuga aguagaaau                                                   19

<210> SEQ ID NO 638
<211> LENGTH: 21
<212> TYPE: RNA
<213> ORGANISM: Artificial Sequence
<220> FEATURE:
<223> OTHER INFORMATION: siRNA

<400> SEQUENCE: 638
auuucuacuu cagagcaagc c                                                21

<210> SEQ ID NO 639
<211> LENGTH: 19
<212> TYPE: RNA
<213> ORGANISM: Artificial Sequence
<220> FEATURE:
<223> OTHER INFORMATION: siRNA

<400> SEQUENCE: 639
cuugcucuga aguagaaau                                                   19

<210> SEQ ID NO 640
<211> LENGTH: 21
<212> TYPE: RNA
<213> ORGANISM: Artificial Sequence
<220> FEATURE:
<223> OTHER INFORMATION: siRNA

<400> SEQUENCE: 640
auuucuacuu cagagcaagc c                                                21

<210> SEQ ID NO 641
<211> LENGTH: 19
<212> TYPE: RNA
<213> ORGANISM: Artificial Sequence
<220> FEATURE:
<223> OTHER INFORMATION: siRNA

<400> SEQUENCE: 641
cuugcucuga aguagaaau                                                   19

<210> SEQ ID NO 642
<211> LENGTH: 21
<212> TYPE: RNA
<213> ORGANISM: Artificial Sequence
<220> FEATURE:
<223> OTHER INFORMATION: siRNA

<400> SEQUENCE: 642
auuucuacuu cagagcaagc c                                                21

<210> SEQ ID NO 643
<211> LENGTH: 21
<212> TYPE: RNA
<213> ORGANISM: Artificial Sequence -continued

```
<220> FEATURE:
<223> OTHER INFORMATION: siRNA

<400> SEQUENCE: 643
ggcuugcucu gaaguagaaa u                                                          21

<210> SEQ ID NO 644
<211> LENGTH: 23
<212> TYPE: RNA
<213> ORGANISM: Artificial Sequence
<220> FEATURE:
<223> OTHER INFORMATION: siRNA

<400> SEQUENCE: 644
auuucuacuu cagagcaagc cac                                                        23

<210> SEQ ID NO 645
<211> LENGTH: 21
<212> TYPE: RNA
<213> ORGANISM: Artificial Sequence
<220> FEATURE:
<223> OTHER INFORMATION: siRNA

<400> SEQUENCE: 645
ggcuugcucu gaaguagaaa u                                                          21

<210> SEQ ID NO 646
<211> LENGTH: 23
<212> TYPE: RNA
<213> ORGANISM: Artificial Sequence
<220> FEATURE:
<223> OTHER INFORMATION: siRNA

<400> SEQUENCE: 646
auuucuacuu cagagcaagc cac                                                        23

<210> SEQ ID NO 647
<211> LENGTH: 21
<212> TYPE: RNA
<213> ORGANISM: Artificial Sequence
<220> FEATURE:
<223> OTHER INFORMATION: siRNA

<400> SEQUENCE: 647
ggcuugcucu gaaguagaaa u                                                          21

<210> SEQ ID NO 648
<211> LENGTH: 23
<212> TYPE: RNA
<213> ORGANISM: Artificial Sequence
<220> FEATURE:
<223> OTHER INFORMATION: siRNA

<400> SEQUENCE: 648
auuucuacuu cagagcaagc cac                                                        23

<210> SEQ ID NO 649
<211> LENGTH: 19
<212> TYPE: RNA
<213> ORGANISM: Artificial Sequence
<220> FEATURE:
<223> OTHER INFORMATION: siRNA

<400> SEQUENCE: 649
cuugcucuga aguagaaau                                                             19
```

-continued

```
<210> SEQ ID NO 650
<211> LENGTH: 21
<212> TYPE: RNA
<213> ORGANISM: Artificial Sequence
<220> FEATURE:
<223> OTHER INFORMATION: siRNA

<400> SEQUENCE: 650
auuucuacuu cagagcaagc c                                              21

<210> SEQ ID NO 651
<211> LENGTH: 19
<212> TYPE: RNA
<213> ORGANISM: Artificial Sequence
<220> FEATURE:
<223> OTHER INFORMATION: siRNA

<400> SEQUENCE: 651
cuugcucuga aguagaaau                                                 19

<210> SEQ ID NO 652
<211> LENGTH: 21
<212> TYPE: RNA
<213> ORGANISM: Artificial Sequence
<220> FEATURE:
<223> OTHER INFORMATION: siRNA

<400> SEQUENCE: 652
auuucuacuu cagagcaagc c                                              21

<210> SEQ ID NO 653
<211> LENGTH: 19
<212> TYPE: RNA
<213> ORGANISM: Artificial Sequence
<220> FEATURE:
<223> OTHER INFORMATION: siRNA

<400> SEQUENCE: 653
cuugcucuga aguagaaau                                                 19

<210> SEQ ID NO 654
<211> LENGTH: 21
<212> TYPE: RNA
<213> ORGANISM: Artificial Sequence
<220> FEATURE:
<223> OTHER INFORMATION: siRNA

<400> SEQUENCE: 654
auuucuacuu cagagcaagc c                                              21

<210> SEQ ID NO 655
<211> LENGTH: 21
<212> TYPE: RNA
<213> ORGANISM: Artificial Sequence
<220> FEATURE:
<223> OTHER INFORMATION: siRNA

<400> SEQUENCE: 655
ggcuugcucu gaaguagaaa u                                              21

<210> SEQ ID NO 656
<211> LENGTH: 23
<212> TYPE: RNA
<213> ORGANISM: Artificial Sequence
<220> FEATURE:
<223> OTHER INFORMATION: siRNA
```

-continued

```
<400> SEQUENCE: 656
auuucuacuu cagagcaagc cac                                        23

<210> SEQ ID NO 657
<211> LENGTH: 21
<212> TYPE: RNA
<213> ORGANISM: Artificial Sequence
<220> FEATURE:
<223> OTHER INFORMATION: siRNA

<400> SEQUENCE: 657
ggcuugcucu gaaguagaaa u                                          21

<210> SEQ ID NO 658
<211> LENGTH: 23
<212> TYPE: RNA
<213> ORGANISM: Artificial Sequence
<220> FEATURE:
<223> OTHER INFORMATION: siRNA

<400> SEQUENCE: 658
auuucuacuu cagagcaagc cac                                        23

<210> SEQ ID NO 659
<211> LENGTH: 21
<212> TYPE: RNA
<213> ORGANISM: Artificial Sequence
<220> FEATURE:
<223> OTHER INFORMATION: siRNA

<400> SEQUENCE: 659
ggcuugcucu gaaguagaaa u                                          21

<210> SEQ ID NO 660
<211> LENGTH: 23
<212> TYPE: RNA
<213> ORGANISM: Artificial Sequence
<220> FEATURE:
<223> OTHER INFORMATION: siRNA

<400> SEQUENCE: 660
auuucuacuu cagagcaagc cac                                        23

<210> SEQ ID NO 661
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z45, and Z45 is U

<400> SEQUENCE: 661
cuucuuugcc aucaaagan                                             19

<210> SEQ ID NO 662
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
```

-continued

```
<223> OTHER INFORMATION: n is Z46, and Z46  is A

<400> SEQUENCE: 662
nucuuugaug gcaaagaag                                               19

<210> SEQ ID NO 663
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z47, Z47 is a nucleotide complementary to
      Z48, and Z48 is selected from A, U, G or C

<400> SEQUENCE: 663
cuucuuugcc aucaaagan                                              19

<210> SEQ ID NO 664
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z48, and Z48 is selected from A, U, G or C

<400> SEQUENCE: 664
nucuuugaug gcaaagaag                                               19

<210> SEQ ID NO 665
<211> LENGTH: 19
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (19)..(19)
<223> OTHER INFORMATION: n is Z47, Z47 is a nucleotide complementary to
      Z48, and Z48 is selected from A, U, G or C

<400> SEQUENCE: 665
cuucuuugcc aucaaagan                                              19

<210> SEQ ID NO 666
<211> LENGTH: 21
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z48, and Z48 is selected from A, U, G or C

<400> SEQUENCE: 666
nucuuugaug gcaaagaaga u                                            21

<210> SEQ ID NO 667
<211> LENGTH: 21
<212> TYPE: RNA
<213> ORGANISM: Artificial Sequence
<220> FEATURE:
<223> OTHER INFORMATION: siRNA
```

-continued

```
<220> FEATURE:
<221> NAME/KEY: misc_feature
<222> LOCATION: (21)..(21)
<223> OTHER INFORMATION: n is Z47, Z47 is a nucleotide complementary to
      Z48, and Z48 is selected from A, U, G or C

<400> SEQUENCE: 667
aucuucuuug ccaucaaaga n                                              21

<210> SEQ ID NO 668
<211> LENGTH: 23
<212> TYPE: RNA
<213> ORGANISM: Artificial Sequence
<220> FEATURE:
<223> OTHER INFORMATION: siRNA
<220> FEATURE:
<221> NAME/KEY: misc_feature
<222> LOCATION: (1)..(1)
<223> OTHER INFORMATION: n is Z48, and Z48 is selected from A, U, G or C

<400> SEQUENCE: 668
nucuuugaug gcaaagaaga uag                                            23

<210> SEQ ID NO 669
<211> LENGTH: 19
<212> TYPE: RNA
<213> ORGANISM: Artificial Sequence
<220> FEATURE:
<223> OTHER INFORMATION: siRNA

<400> SEQUENCE: 669
cuucuuugcc aucaaagau                                                 19

<210> SEQ ID NO 670
<211> LENGTH: 21
<212> TYPE: RNA
<213> ORGANISM: Artificial Sequence
<220> FEATURE:
<223> OTHER INFORMATION: siRNA

<400> SEQUENCE: 670
aucuuugaug gcaaagaaga u                                              21

<210> SEQ ID NO 671
<211> LENGTH: 21
<212> TYPE: RNA
<213> ORGANISM: Artificial Sequence
<220> FEATURE:
<223> OTHER INFORMATION: siRNA

<400> SEQUENCE: 671
aucuucuuug ccaucaaaga u                                              21

<210> SEQ ID NO 672
<211> LENGTH: 23
<212> TYPE: RNA
<213> ORGANISM: Artificial Sequence
<220> FEATURE:
<223> OTHER INFORMATION: siRNA

<400> SEQUENCE: 672
aucuuugaug gcaaagaaga uag                                            23

<210> SEQ ID NO 673
<211> LENGTH: 19
<212> TYPE: RNA
<213> ORGANISM: Artificial Sequence
```

-continued

```
<220> FEATURE:
<223> OTHER INFORMATION: siRNA

<400> SEQUENCE: 673
cuucuuugcc aucaaagau                                          19

<210> SEQ ID NO 674
<211> LENGTH: 21
<212> TYPE: RNA
<213> ORGANISM: Artificial Sequence
<220> FEATURE:
<223> OTHER INFORMATION: siRNA

<400> SEQUENCE: 674
aucuuugaug gcaaagaaga u                                       21

<210> SEQ ID NO 675
<211> LENGTH: 19
<212> TYPE: RNA
<213> ORGANISM: Artificial Sequence
<220> FEATURE:
<223> OTHER INFORMATION: siRNA

<400> SEQUENCE: 675
cuucuuugcc aucaaagau                                          19

<210> SEQ ID NO 676
<211> LENGTH: 21
<212> TYPE: RNA
<213> ORGANISM: Artificial Sequence
<220> FEATURE:
<223> OTHER INFORMATION: siRNA

<400> SEQUENCE: 676
aucuuugaug gcaaagaaga u                                       21

<210> SEQ ID NO 677
<211> LENGTH: 19
<212> TYPE: RNA
<213> ORGANISM: Artificial Sequence
<220> FEATURE:
<223> OTHER INFORMATION: siRNA

<400> SEQUENCE: 677
cuucuuugcc aucaaagau                                          19

<210> SEQ ID NO 678
<211> LENGTH: 21
<212> TYPE: RNA
<213> ORGANISM: Artificial Sequence
<220> FEATURE:
<223> OTHER INFORMATION: siRNA

<400> SEQUENCE: 678
aucuuugaug gcaaagaaga u                                       21

<210> SEQ ID NO 679
<211> LENGTH: 21
<212> TYPE: RNA
<213> ORGANISM: Artificial Sequence
<220> FEATURE:
<223> OTHER INFORMATION: siRNA

<400> SEQUENCE: 679
aucuucuuug ccaucaaaga u                                       21
```

-continued

```
<210> SEQ ID NO 680
<211> LENGTH: 23
<212> TYPE: RNA
<213> ORGANISM: Artificial Sequence
<220> FEATURE:
<223> OTHER INFORMATION: siRNA

<400> SEQUENCE: 680
aucuuugaug gcaaagaaga uag                                                    23

<210> SEQ ID NO 681
<211> LENGTH: 21
<212> TYPE: RNA
<213> ORGANISM: Artificial Sequence
<220> FEATURE:
<223> OTHER INFORMATION: siRNA

<400> SEQUENCE: 681
aucuucuuug ccaucaaaga u                                                      21

<210> SEQ ID NO 682
<211> LENGTH: 23
<212> TYPE: RNA
<213> ORGANISM: Artificial Sequence
<220> FEATURE:
<223> OTHER INFORMATION: siRNA

<400> SEQUENCE: 682
aucuuugaug gcaaagaaga uag                                                    23

<210> SEQ ID NO 683
<211> LENGTH: 21
<212> TYPE: RNA
<213> ORGANISM: Artificial Sequence
<220> FEATURE:
<223> OTHER INFORMATION: siRNA

<400> SEQUENCE: 683
aucuucuuug ccaucaaaga u                                                      21

<210> SEQ ID NO 684
<211> LENGTH: 23
<212> TYPE: RNA
<213> ORGANISM: Artificial Sequence
<220> FEATURE:
<223> OTHER INFORMATION: siRNA

<400> SEQUENCE: 684
aucuuugaug gcaaagaaga uag                                                    23

<210> SEQ ID NO 685
<211> LENGTH: 19
<212> TYPE: RNA
<213> ORGANISM: Artificial Sequence
<220> FEATURE:
<223> OTHER INFORMATION: siRNA

<400> SEQUENCE: 685
cuucuuugcc aucaaagau                                                         19

<210> SEQ ID NO 686
<211> LENGTH: 21
<212> TYPE: RNA
<213> ORGANISM: Artificial Sequence
<220> FEATURE:
<223> OTHER INFORMATION: siRNA
```

-continued

```
<400> SEQUENCE: 686
aucuuugaug gcaaagaaga u                                          21

<210> SEQ ID NO 687
<211> LENGTH: 19
<212> TYPE: RNA
<213> ORGANISM: Artificial Sequence
<220> FEATURE:
<223> OTHER INFORMATION: siRNA

<400> SEQUENCE: 687
cuucuuugcc aucaaagau                                            19

<210> SEQ ID NO 688
<211> LENGTH: 21
<212> TYPE: RNA
<213> ORGANISM: Artificial Sequence
<220> FEATURE:
<223> OTHER INFORMATION: siRNA

<400> SEQUENCE: 688
aucuuugaug gcaaagaaga u                                          21

<210> SEQ ID NO 689
<211> LENGTH: 19
<212> TYPE: RNA
<213> ORGANISM: Artificial Sequence
<220> FEATURE:
<223> OTHER INFORMATION: siRNA

<400> SEQUENCE: 689
cuucuuugcc aucaaagau                                            19

<210> SEQ ID NO 690
<211> LENGTH: 21
<212> TYPE: RNA
<213> ORGANISM: Artificial Sequence
<220> FEATURE:
<223> OTHER INFORMATION: siRNA

<400> SEQUENCE: 690
aucuuugaug gcaaagaaga u                                          21

<210> SEQ ID NO 691
<211> LENGTH: 21
<212> TYPE: RNA
<213> ORGANISM: Artificial Sequence
<220> FEATURE:
<223> OTHER INFORMATION: siRNA

<400> SEQUENCE: 691
aucuucuuug ccaucaaaga u                                          21

<210> SEQ ID NO 692
<211> LENGTH: 23
<212> TYPE: RNA
<213> ORGANISM: Artificial Sequence
<220> FEATURE:
<223> OTHER INFORMATION: siRNA

<400> SEQUENCE: 692
aucuuugaug gcaaagaaga uag                                        23

<210> SEQ ID NO 693
```

-continued

```
<211> LENGTH: 21
<212> TYPE: RNA
<213> ORGANISM: Artificial Sequence
<220> FEATURE:
<223> OTHER INFORMATION: siRNA

<400> SEQUENCE: 693
aucuucuuug ccaucaaaga u                                        21

<210> SEQ ID NO 694
<211> LENGTH: 23
<212> TYPE: RNA
<213> ORGANISM: Artificial Sequence
<220> FEATURE:
<223> OTHER INFORMATION: siRNA

<400> SEQUENCE: 694
aucuuugaug gcaaagaaga uag                                      23

<210> SEQ ID NO 695
<211> LENGTH: 21
<212> TYPE: RNA
<213> ORGANISM: Artificial Sequence
<220> FEATURE:
<223> OTHER INFORMATION: siRNA

<400> SEQUENCE: 695
aucuucuuug ccaucaaaga u                                        21

<210> SEQ ID NO 696
<211> LENGTH: 23
<212> TYPE: RNA
<213> ORGANISM: Artificial Sequence
<220> FEATURE:
<223> OTHER INFORMATION: siRNA

<400> SEQUENCE: 696
aucuuugaug gcaaagaaga uag                                      23

<210> SEQ ID NO 697
<211> LENGTH: 19
<212> TYPE: RNA
<213> ORGANISM: Artificial Sequence
<220> FEATURE:
<223> OTHER INFORMATION: siRNA

<400> SEQUENCE: 697
cuucuuugcc aucaaagau                                           19

<210> SEQ ID NO 698
<211> LENGTH: 21
<212> TYPE: RNA
<213> ORGANISM: Artificial Sequence
<220> FEATURE:
<223> OTHER INFORMATION: siRNA

<400> SEQUENCE: 698
aucuuugaug gcaaagaaga u                                        21

<210> SEQ ID NO 699
<211> LENGTH: 19
<212> TYPE: RNA
<213> ORGANISM: Artificial Sequence
<220> FEATURE:
<223> OTHER INFORMATION: siRNA

<400> SEQUENCE: 699
```

-continued cuucuuugcc aucaaagau                                                                                  19

<210> SEQ ID NO 700
<211> LENGTH: 21
<212> TYPE: RNA
<213> ORGANISM: Artificial Sequence
<220> FEATURE:
<223> OTHER INFORMATION: siRNA

<400> SEQUENCE: 700
aucuuugaug gcaaagaaga u                                                                                21

<210> SEQ ID NO 701
<211> LENGTH: 19
<212> TYPE: RNA
<213> ORGANISM: Artificial Sequence
<220> FEATURE:
<223> OTHER INFORMATION: siRNA

<400> SEQUENCE: 701
cuucuuugcc aucaaagau                                                                                  19

<210> SEQ ID NO 702
<211> LENGTH: 21
<212> TYPE: RNA
<213> ORGANISM: Artificial Sequence
<220> FEATURE:
<223> OTHER INFORMATION: siRNA

<400> SEQUENCE: 702
aucuuugaug gcaaagaaga u                                                                                21

<210> SEQ ID NO 703
<211> LENGTH: 21
<212> TYPE: RNA
<213> ORGANISM: Artificial Sequence
<220> FEATURE:
<223> OTHER INFORMATION: siRNA

<400> SEQUENCE: 703
aucuucuuug ccaucaaaga u                                                                                21

<210> SEQ ID NO 704
<211> LENGTH: 23
<212> TYPE: RNA
<213> ORGANISM: Artificial Sequence
<220> FEATURE:
<223> OTHER INFORMATION: siRNA

<400> SEQUENCE: 704
aucuuugaug gcaaagaaga uag                                                                              23

<210> SEQ ID NO 705
<211> LENGTH: 21
<212> TYPE: RNA
<213> ORGANISM: Artificial Sequence
<220> FEATURE:
<223> OTHER INFORMATION: siRNA

<400> SEQUENCE: 705
aucuucuuug ccaucaaaga u                                                                                21

<210> SEQ ID NO 706
<211> LENGTH: 23
<212> TYPE: RNA

-continued

<213> ORGANISM: Artificial Sequence
<220> FEATURE:
<223> OTHER INFORMATION: siRNA

<400> SEQUENCE: 706
aucuuugaug gcaaagaaga uag                                                            23

<210> SEQ ID NO 707
<211> LENGTH: 21
<212> TYPE: RNA
<213> ORGANISM: Artificial Sequence
<220> FEATURE:
<223> OTHER INFORMATION: siRNA

<400> SEQUENCE: 707
aucuucuuug ccaucaaaga u                                                              21

<210> SEQ ID NO 708
<211> LENGTH: 23
<212> TYPE: RNA
<213> ORGANISM: Artificial Sequence
<220> FEATURE:
<223> OTHER INFORMATION: siRNA

<400> SEQUENCE: 708
aucuuugaug gcaaagaaga uag                                                            23

<210> SEQ ID NO 709
<211> LENGTH: 19
<212> TYPE: RNA
<213> ORGANISM: Artificial Sequence
<220> FEATURE:
<223> OTHER INFORMATION: siRNA

<400> SEQUENCE: 709
cuucuuugcc aucaaagau                                                                 19

<210> SEQ ID NO 710
<211> LENGTH: 21
<212> TYPE: RNA
<213> ORGANISM: Artificial Sequence
<220> FEATURE:
<223> OTHER INFORMATION: siRNA

<400> SEQUENCE: 710
aucuuugaug gcaaagaaga u                                                              21

<210> SEQ ID NO 711
<211> LENGTH: 19
<212> TYPE: RNA
<213> ORGANISM: Artificial Sequence
<220> FEATURE:
<223> OTHER INFORMATION: siRNA

<400> SEQUENCE: 711
cuucuuugcc aucaaagau                                                                 19

<210> SEQ ID NO 712
<211> LENGTH: 21
<212> TYPE: RNA
<213> ORGANISM: Artificial Sequence
<220> FEATURE:
<223> OTHER INFORMATION: siRNA

<400> SEQUENCE: 712
aucuuugaug gcaaagaaga u                                                              21

<210> SEQ ID NO 713
<211> LENGTH: 19
<212> TYPE: RNA
<213> ORGANISM: Artificial Sequence
<220> FEATURE:
<223> OTHER INFORMATION: siRNA

<400> SEQUENCE: 713
cuucuuugcc aucaaagau                                                    19

<210> SEQ ID NO 714
<211> LENGTH: 21
<212> TYPE: RNA
<213> ORGANISM: Artificial Sequence
<220> FEATURE:
<223> OTHER INFORMATION: siRNA

<400> SEQUENCE: 714
aucuuugaug gcaaagaaga u                                                 21

<210> SEQ ID NO 715
<211> LENGTH: 21
<212> TYPE: RNA
<213> ORGANISM: Artificial Sequence
<220> FEATURE:
<223> OTHER INFORMATION: siRNA

<400> SEQUENCE: 715
aucuucuuug ccaucaaaga u                                                 21

<210> SEQ ID NO 716
<211> LENGTH: 23
<212> TYPE: RNA
<213> ORGANISM: Artificial Sequence
<220> FEATURE:
<223> OTHER INFORMATION: siRNA

<400> SEQUENCE: 716
aucuuugaug gcaaagaaga uag                                               23

<210> SEQ ID NO 717
<211> LENGTH: 21
<212> TYPE: RNA
<213> ORGANISM: Artificial Sequence
<220> FEATURE:
<223> OTHER INFORMATION: siRNA

<400> SEQUENCE: 717
aucuucuuug ccaucaaaga u                                                 21

<210> SEQ ID NO 718
<211> LENGTH: 23
<212> TYPE: RNA
<213> ORGANISM: Artificial Sequence
<220> FEATURE:
<223> OTHER INFORMATION: siRNA

<400> SEQUENCE: 718
aucuuugaug gcaaagaaga uag                                               23

<210> SEQ ID NO 719
<211> LENGTH: 21
<212> TYPE: RNA
<213> ORGANISM: Artificial Sequence
<220> FEATURE:

-continued

<223> OTHER INFORMATION: siRNA

<400> SEQUENCE: 719
aucuucuuug ccaucaaaga u                                                          21

<210> SEQ ID NO 720
<211> LENGTH: 23
<212> TYPE: RNA
<213> ORGANISM: Artificial Sequence
<220> FEATURE:
<223> OTHER INFORMATION: siRNA

<400> SEQUENCE: 720
aucuuugaug gcaaagaaga uag                                                        23

<210> SEQ ID NO 721
<211> LENGTH: 19
<212> TYPE: RNA
<213> ORGANISM: Artificial Sequence
<220> FEATURE:
<223> OTHER INFORMATION: siRNA

<400> SEQUENCE: 721
uucuccgaac gugucacgu                                                             19

<210> SEQ ID NO 722
<211> LENGTH: 21
<212> TYPE: RNA
<213> ORGANISM: Artificial Sequence
<220> FEATURE:
<223> OTHER INFORMATION: siRNA

<400> SEQUENCE: 722
acgugacacg uucggagaac u                                                          21

<210> SEQ ID NO 723
<211> LENGTH: 19
<212> TYPE: RNA
<213> ORGANISM: Artificial Sequence
<220> FEATURE:
<223> OTHER INFORMATION: siRNA

<400> SEQUENCE: 723
gagaugaagu ucaagaaua                                                             19

<210> SEQ ID NO 724
<211> LENGTH: 19
<212> TYPE: RNA
<213> ORGANISM: Artificial Sequence
<220> FEATURE:
<223> OTHER INFORMATION: siRNA

<400> SEQUENCE: 724
uauucuugaa cuucaucuc                                                             19

<210> SEQ ID NO 725
<211> LENGTH: 19
<212> TYPE: RNA
<213> ORGANISM: Artificial Sequence
<220> FEATURE:
<223> OTHER INFORMATION: siRNA

<400> SEQUENCE: 725
acauggacaa cugcuauaa                                                             19

-continued

```
<210> SEQ ID NO 726
<211> LENGTH: 19
<212> TYPE: RNA
<213> ORGANISM: Artificial Sequence
<220> FEATURE:
<223> OTHER INFORMATION: siRNA

<400> SEQUENCE: 726
uuauagcagu uguccaugu                                                  19

<210> SEQ ID NO 727
<211> LENGTH: 19
<212> TYPE: RNA
<213> ORGANISM: Artificial Sequence
<220> FEATURE:
<223> OTHER INFORMATION: siRNA

<400> SEQUENCE: 727
uagcaagcuc ucaguauca                                                  19

<210> SEQ ID NO 728
<211> LENGTH: 19
<212> TYPE: RNA
<213> ORGANISM: Artificial Sequence
<220> FEATURE:
<223> OTHER INFORMATION: siRNA

<400> SEQUENCE: 728
ugauacugag agcuugcua                                                  19

<210> SEQ ID NO 729
<211> LENGTH: 19
<212> TYPE: RNA
<213> ORGANISM: Artificial Sequence
<220> FEATURE:
<223> OTHER INFORMATION: siRNA

<400> SEQUENCE: 729
cuagcaagcu cucaguauc                                                  19

<210> SEQ ID NO 730
<211> LENGTH: 19
<212> TYPE: DNA
<213> ORGANISM: Artificial Sequence
<220> FEATURE:
<223> OTHER INFORMATION: siRNA

<400> SEQUENCE: 730
gatactgaga gcttgctag                                                  19

<210> SEQ ID NO 731
<211> LENGTH: 19
<212> TYPE: DNA
<213> ORGANISM: Artificial Sequence
<220> FEATURE:
<223> OTHER INFORMATION: Target sequence of siXOa0

<400> SEQUENCE: 731
gagatgaagt tcaagaata                                                  19

<210> SEQ ID NO 732
<211> LENGTH: 19
<212> TYPE: DNA
<213> ORGANISM: Artificial Sequence
<220> FEATURE:
<223> OTHER INFORMATION: Target sequence of siXOe0
```

<400> SEQUENCE: 732
acatggacaa ctgctataa                                                          19

<210> SEQ ID NO 733
<211> LENGTH: 19
<212> TYPE: DNA
<213> ORGANISM: Artificial Sequence
<220> FEATURE:
<223> OTHER INFORMATION: Target sequence of siXOf0

<400> SEQUENCE: 733
tagcaagctc tcagtatca                                                          19

<210> SEQ ID NO 734
<211> LENGTH: 19
<212> TYPE: DNA
<213> ORGANISM: Artificial Sequence
<220> FEATURE:
<223> OTHER INFORMATION: Target sequence of CON-siXOf

<400> SEQUENCE: 734
ctagcaagct ctcagtatc                                                          19

<210> SEQ ID NO 735
<211> LENGTH: 20
<212> TYPE: DNA
<213> ORGANISM: Artificial Sequence
<220> FEATURE:
<223> OTHER INFORMATION: Upstream primer of human XO

<400> SEQUENCE: 735
gacccgacgg tatctccttt                                                         20

<210> SEQ ID NO 736
<211> LENGTH: 20
<212> TYPE: DNA
<213> ORGANISM: Artificial Sequence
<220> FEATURE:
<223> OTHER INFORMATION: Downstream primer of human XO

<400> SEQUENCE: 736
acgccacaga cttgacttgc                                                         20

<210> SEQ ID NO 737
<211> LENGTH: 19
<212> TYPE: DNA
<213> ORGANISM: Artificial Sequence
<220> FEATURE:
<223> OTHER INFORMATION: Upstream primer of human GAPDH

<400> SEQUENCE: 737
ggtcggagtc aacggattt                                                          19

<210> SEQ ID NO 738
<211> LENGTH: 19
<212> TYPE: DNA
<213> ORGANISM: Artificial Sequence
<220> FEATURE:
<223> OTHER INFORMATION: Downstream primer of human GAPDH

<400> SEQUENCE: 738
ccagcatcgc cccacttga                                                          19

<210> SEQ ID NO 739
<211> LENGTH: 23

```
<212> TYPE: DNA
<213> ORGANISM: Artificial Sequence
<220> FEATURE:
<223> OTHER INFORMATION: Upstream primer of mouse XO

<400> SEQUENCE: 739
aacagaattg tagtccgagt gaa                                          23

<210> SEQ ID NO 740
<211> LENGTH: 20
<212> TYPE: DNA
<213> ORGANISM: Artificial Sequence
<220> FEATURE:
<223> OTHER INFORMATION: Downstream primer of mouse XO

<400> SEQUENCE: 740
gtctgccacc agttatgagc                                              20

<210> SEQ ID NO 741
<211> LENGTH: 19
<212> TYPE: DNA
<213> ORGANISM: Artificial Sequence
<220> FEATURE:
<223> OTHER INFORMATION: Upstream primer of mouse GAPDH

<400> SEQUENCE: 741
tgcaccacca actgcttag                                               19

<210> SEQ ID NO 742
<211> LENGTH: 19
<212> TYPE: DNA
<213> ORGANISM: Artificial Sequence
<220> FEATURE:
<223> OTHER INFORMATION: Downstream primer of mouse GAPDH

<400> SEQUENCE: 742
ggatgcaggg atgatgttc                                               19
```